(12) United States Patent
Converso et al.

(10) Patent No.: US 12,258,329 B2
(45) Date of Patent: Mar. 25, 2025

(54) PYRIMIDONE DERIVATIVES AS SELECTIVE CYTOTOXIC AGENTS AGAINST HIV INFECTED CELLS

(71) Applicant: Merck Sharp & Dohme LLC, Rahway, NJ (US)

(72) Inventors: Antonella Converso, Elkins Park, PA (US); Cheng Wang, Fort Washington, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 776 days.

(21) Appl. No.: 17/413,882

(22) PCT Filed: Dec. 13, 2019

(86) PCT No.: PCT/US2019/066125
§ 371 (c)(1),
(2) Date: Jun. 14, 2021

(87) PCT Pub. No.: WO2020/131597
PCT Pub. Date: Jun. 25, 2020

(65) Prior Publication Data
US 2022/0064147 A1    Mar. 3, 2022

Related U.S. Application Data

(60) Provisional application No. 62/781,356, filed on Dec. 18, 2018.

(51) Int. Cl.
| | |
|---|---|
| C07D 239/52 | (2006.01) |
| A61K 31/505 | (2006.01) |
| A61K 45/06 | (2006.01) |
| A61P 31/18 | (2006.01) |
| C07D 403/06 | (2006.01) |

(52) U.S. Cl.
CPC ............ C07D 403/06 (2013.01); A61K 45/06 (2013.01)

(58) Field of Classification Search
CPC .. C07D 239/52; C07D 403/06; A61K 31/505; A61P 31/18
See application file for complete search history.

(56) References Cited

U.S. PATENT DOCUMENTS

| | | | |
|---|---|---|---|
| 7,166,738 B2 | 1/2007 | Dunn et al. | |
| 7,189,718 B2 | 3/2007 | Dunn et al. | |
| 8,486,975 B2 | 7/2013 | Burch et al. | |
| 9,469,634 B2 | 10/2016 | Han et al. | |
| 9,718,819 B2 | 8/2017 | Arrington et al. | |
| 10,189,831 B2 | 1/2019 | Arrington et al. | |
| 2013/0296382 A1 | 11/2013 | Burch et al. | |
| 2022/0017562 A1 | 1/2022 | Piazza et al. | |
| 2022/0064147 A1 | 3/2022 | Converso et al. | |

FOREIGN PATENT DOCUMENTS

| | | |
|---|---|---|
| WO | 2008076225 | 6/2008 |
| WO | 2008145562 A1 | 12/2008 |
| WO | 2009067166 A2 | 5/2009 |
| WO | 2011120133 A1 | 10/2011 |
| WO | 2014058747 A1 | 4/2014 |
| WO | 2015153304 A1 | 10/2015 |
| WO | 2020131597 A1 | 6/2020 |

OTHER PUBLICATIONS

Figueiredo, A. et al., Potent Nonnucleoside Reverse Transcriptase Inhibitors Target HIV-1 Gag-Pol, PLoS Pathogens, 2006, 1051-1059, 2(11).

International Search Report for PCT/US2019/066125, mailed Mar. 10, 2020; 13 pages.

Jochmans, Dirk et al., Selective killing of human immunodeficiency virus infected cells by non-nucleoside reverse transcriptase inhibitor-induced activation of HIV protease, Retrovirology, 2010, 1-14, 7:89.

Sudo, Sho et al., Efavirenz Enhances HIV-1 Gag Processing at the Plasma Membrane through Gag-Pol Dimerization, Journal of Virology, 2013, 3348-3360, 87(6).

Tachedjian, Gilda et al., Efavirenz enhances the proteolytic processing of an HIV-1 pol polyprotein precursor and reverse transcriptase homodimer formation, FEBS Letters, 2005, 379-384, 579.

Tachedjian, Gilda et al., Nonnucleoside reverse transcriptase inhibitors are chemical enhancers of dimerization of the HIV type 1 reverse transcriptase, PNAS, 2001, 7188-7193, 98(13).

Trinité, Benjamin et al., NNRTI-induced HIV-1 protease-mediated cytotoxicity induces rapid death of CD4 T cells during productive infection and latency reversal, Retrovirology, 2019, 1-11, 16(17).

Vanangamundi, M. et al., HIV-1 Non-Nucleoside Reverse Transcriptase Inhibitors: SAR and Lead Optimization Using CoMFA and CoMSIA Studies (1995-2016), Current Medicinal Chemistry, 2017, 3774-3812, 24(34).

(Continued)

*Primary Examiner* — Bruck Kifle
(74) *Attorney, Agent, or Firm* — Patricia A. Shatynski; John C. Todaro

(57) ABSTRACT

The present disclosure is directed to pyrimidone derivatives of Formula I and their use for selectively killing HIV infected GAG-POL expressing cells without concomitant cytotoxicity to HIV nave cells, and for the treatment or prophylaxis of infection by HIV, or for the treatment, prophylaxis or delay in the onset or progression of AIDS or AIDS Related Complex (ARC).

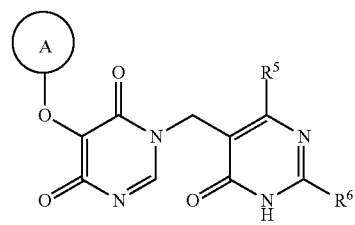

I

9 Claims, No Drawings

(56) References Cited

OTHER PUBLICATIONS

Zerbato, Jennifer et al., Nonnucleoside Reverse Transcriptase Inhibitors Reduce HIV-1 Production from latently Infected Resting CD4 + T Cells following latency Reversal, Antimicrobial Agents and Chemotherapy, 2017, 1-5, 61(3).

Chelur, Dattananda S. et al., Targeted cell killing by reconstituted caspases, PNAS, 2007, 2283-2288, 104(7).

PYRIMIDONE DERIVATIVES AS SELECTIVE CYTOTOXIC AGENTS AGAINST HIV INFECTED CELLS

CROSS-REFERENCE TO RELATED APPLICATIONS

This application is a National Stage application of International Patent Application No. PCT/US2019/066125, filed Dec. 13, 2019, which claims priority to U.S. Provisional Patent Application No. 62/781,356, filed Dec. 18, 2018.

BACKGROUND OF THE INVENTION

Human immunodeficiency virus (HIV) is the causative agent of acquired immunodeficiency syndrome (AIDS). In the absence of viral suppression, humans infected with HIV exhibit severe immunodeficiency which makes them highly susceptible to debilitating and ultimately fatal opportunistic infections. Multiple clinically approved antiretroviral drugs are available which demonstrate multi-log reductions in viral loads. Treated patients are at risk for acquiring mutations which render the virus in their bodies resistant to available therapies and rapid rebound of viremia is seen when therapy is removed, indicating that current regimens are not curative.

HIV is a retrovirus whose life cycle involves reverse transcription of a viral RNA genome into DNA via an enzyme known as reverse transcriptase and subsequent integration of the DNA copy into the host chromosomal DNA via the virally encoded integrase. Viral RNA is transcribed and viral proteins are translated using the host cellular machinery in conjunction with viral accessory proteins. Many viral proteins are contained within the GAG and GAG-POL proteins, with GAG containing structural proteins and GAG-POL resulting from a frameshift near the carboxy-terminus of GAG and containing protease (PR), reverse transcriptase (RT), and integrase (IN) viral enzymes, in addition to the structural proteins. GAG and GAG-POL are cleaved into individual proteins through the process of maturation which occurs during budding of virions from the infected cell. At this time GAG-POL dimerizes and the now dimeric HIV PR within the GAG-POL dimer forms an active enzyme which can cleave itself out of the polyprotein and catalyze further cleavage to form the remaining viral enzymes and structural proteins.

Available antiretroviral drugs act by blocking the virus at different stages in the viral life cycle. For example, reverse transcriptase inhibitors target the viral reverse transcriptase and prevent the RNA genome from being copied into DNA, integrase inhibitors block the ability of the copied DNA from being integrated into the host cell, and protease inhibitors prevent viral maturation so that virions produced from cells treated with protease inhibitors are immature and non-infectious. Once integration has occurred, a cell is infected until it dies through either normal cell death pathways, accelerated death due to viral factors, or is targeted by the immune system. While most infected cells are expected to die within ~2 days of being infected, the rapid rebound of viremia when therapy is removed is an indication that infected cells remain even after years on therapy (See, e.g., J. B. Dinoso et al., Proc. Natl. Acad. Sci. U.S.A., 2009, 106(23): 9403-9408). Thus, new therapies that can selectively kill the HIV infected cells would provide new treatment options for HIV infection. Treatment with compounds that can accelerate death of HIV infected cells and decrease the overall number of virally infected cells that persist within patients have the potential to decrease low-level viremia in suppressed patients and may also play a role in an HIV cure strategy.

SUMMARY OF THE INVENTION

The present disclosure is directed to pyrimidone derivatives and their use as HIV-Targeted Activator of Cell Kill agents which accelerate the death of HIV GAG-POL expressing cells without concomitant cytotoxicity to HIV naïve cells. Accordingly, the compounds disclosed herein are useful for the treatment or prophylaxis of infection by HIV, or for the treatment, prophylaxis or delay in the onset or progression of AIDS or AIDS Related Complex (ARC). Additionally, the compounds are useful for selectively killing HIV infected GAG-POL expressing cells in a subject infected with HIV. Compositions and methods of use comprising the compounds of this disclosure are also provided.

DETAILED DESCRIPTION OF THE INVENTION

The present disclosure is directed to pyrimidone derivative compounds and their use for accelerating the death of HIV GAG-POL expressing cells without concomitant cytotoxicity to HIV naïve cells. In the absence of compounds such as those from the present invention, protease (PR) activation takes place during viral maturation and the concentration of mature PR in the cytoplasm is limited. In contrast, the present compounds promote the desired phenotype by catalyzing GAG-POL dimerization inside the infected cell by binding to the immature RT binding site and triggering premature activation of the HIV PR enzyme inside the host infected cell prior to budding. As a result, PR cleaves host substrates within the cell, leading to cytotoxicity and cell death. This effect can be blocked in the presence of an HIV protease inhibitor such as indinavir or darunavir demonstrating the role of HIV protease in the process.

The compounds presently disclosed herein also have activity as Non-Nucleoside Reverse Transcriptase Inhibitors (NNRTIs), due to the homology between the mature and immature RT pocket in HIV that allows the compounds to bind to the mature hydrophobic pocket near the active site of the viral RT enzyme. Binding to mature RT results in inhibition of enzymatic activity and production of the DNA provirus, which prevents infection of naïve CD4+ T-cells.

While effects of NNRTIs on dimerization of RT and GAG-POL have been documented (Tachedjian et al. Proc. Natl. Acad. Sci. U.S.A. 2001, 98(13):7188; Tachedjian et al. FEBS Lett. 2005, 579:379; Figueiredo et al. PLOS Path. 2006, 2(11):1051; Sudo et al. J. Virol. 2013, 87(6):3348), selective killing of HIV infected cells as a result of enhanced dimerization was first reported by Jochmans et al. (Jochmans et al. Retrovirology 2010, 7:89). The authors generated data showing these effects in chronically infected MT-4 cells, PBMCs, and CD4+ cells. Based on the potencies of tested molecules they concluded that "These data present proof of concept for targeted drug induced elimination of HIV producing cells. While NNRTIs themselves may not be sufficiently potent for therapeutic application, the results provide a basis for the development of drugs exploiting this mechanism of action." More recently, Zerbato et al. (Zerbato et al. Antimicrob. Agents Chemother. 2017, 61(3)) measured the activity of NNRTIs in a primary cell model for HIV latency. They saw significant reduction in virus production for certain NNRTIs compared to other classes of antiretrovirals and inferred that this was due to these compounds' ability to eliminate cells expressing HIV GAG-POL proteins. More recently, Trinité et al. (Trinité et al., Retrovirology, 2019, 16(17)) documented how NNRTI-induced PR-activation triggers apoptotic cell death of productively HIV-infected resting or activated T-cells.

The present disclosure is directed to a compound of Formula I

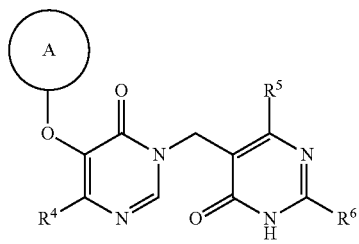

I or a pharmaceutically acceptable salt thereof, wherein:
Ring A is selected from:

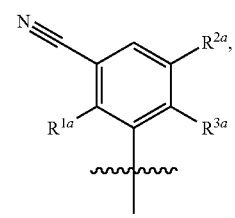

(Aa)

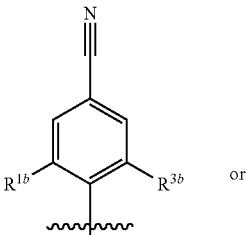

(Ab)

or

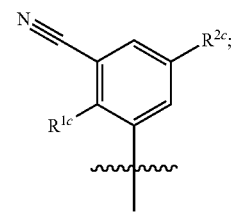

(Ac)

$R^{1a}$ is halo, —$C_{1-3}$alkyl unsubstituted or substituted with 1 to 7 of F; —$OC_{1-3}$alkyl unsubstituted or substituted with 1 to 7 of F; or —$NH_2$, —NH—$C_{1-3}$alkyl, —N($C_{1-3}$alkyl)$_2$, or —$C_{3-6}$cycloalkyl;

$R^{2a}$ is —H, halo, —$C_{1-3}$alkyl, —$CF_3$, —$CHF_2$, —$CH_2F$, —$NH_2$, —NH—$C_{1-3}$alkyl, —N($C_{1-3}$alkyl)$_2$, —$C_{3-6}$cycloalkyl or —$OC_{1-3}$alkyl unsubstituted or substituted with 1 to 3 of F;

$R^{3a}$ is —H or halo;

provided that $R^{2a}$ and $R^{3a}$ are not both —H;

$R^{1b}$ is halo, —$C_{1-3}$alkyl, —$CF_3$, —$CHF_2$, —$CH_2F$, —$NH_2$, —NH—$C_{1-3}$alkyl, —N($C_{1-3}$alkyl)$_2$, —$C_{3-6}$cycloalkyl, or —$OC_{1-3}$alkyl unsubstituted or substituted with 1 to 3 of F;

$R^{3b}$ is halo, —$C_{1-3}$alkyl, —$CF_3$, —$CHF_2$, —$CH_2F$, —$NH_2$, —NH—$C_{1-3}$alkyl, —N($C_{1-3}$alkyl)$_2$, —$C_{3-6}$cycloalkyl, or —$OC_{1-3}$ alkyl unsubstituted or substituted with 1 to 3 of F;

$R^{1c}$ is —H, halo, —$C_{1-3}$alkyl, —$CF_3$, —$CHF_2$, —$CH_2F$, —$NH_2$, —NH—$C_{1-3}$ alkyl, —N($C_{1-3}$alkyl)$_2$, —$C_{3-6}$cycloalkyl, or —$OC_{1-3}$alkyl unsubstituted or substituted with 1 to 3 of F;

$R^{2c}$ is —H, halo, —$C_{1-3}$ alkyl, —$CF_3$, —$CHF_2$—$CH_2F$, —$NH_2$, —NH—$C_{1-3}$alkyl, —N($C_{1-3}$alkyl)$_2$, —$C_{3-6}$cycloalkyl, or —$OC_{1-3}$alkyl unsubstituted or substituted with 1 to 3 of F;

provided that one of $R^{1c}$ or $R^{2c}$ is —H and the other is not —H;

$R^4$ is halo or —$C_{1-6}$alkyl substituted with 1 to 8 of —F;

$R^5$ is —H, —$NH_2$, —NH—$C_{1-3}$alkyl, —N($C_{1-3}$alkyl)$_2$, —$C_{3-6}$cycloalkyl, or —$C_{1-3}$alkyl unsubstituted or substituted with 1 to 7 of —F;

$R^6$ is —H, —$C_{1-4}$alkyl, —$C_{2-4}$alkenyl, —$NH_2$, —NH—$C_{1-3}$alkyl, —N($C_{1-3}$alkyl)$_2$, $C_{3-6}$cycloalkyl, -pyrazolyl unsubstituted or substituted with $C_{1-3}$alkyl, or —$C_{1-4}$alkyl substituted with $R^7$; and $R^7$ is —OH, —$OC_{1-3}$alkyl, —$C(O)OC_{1-3}$alkyl or —$CH_2O$-pyrimidinyl.

In Embodiment 1 of this disclosure are compounds of Formula I, or pharmaceutically acceptable salts thereof, wherein:
(i) $R^4$ is —$C_{1-6}$alkyl substituted with 1 to 8 of —F; or
(ii) $R^4$ is —$CF_3$, or —$C_{2-6}$alkyl substituted with 1 to 8 of —F; or
(iii) $R^4$ is —$C_{2-6}$alkyl substituted with 1 to 8 of —F; or
(iv) $R^4$ is —$C_{2-4}$alkyl substituted with 1 to 8 of —F; or
(v) $R^4$ is —CH(F)—$R^8$ or —C($F_2$)—$R^8$ wherein $R^8$ is (a) —$CH_3$ unsubstituted or substituted with 1 to 3 of —F, or (b) —$CH_2CH_3$ unsubstituted or substituted with 1 to 5 of —F; or
(vi) $R^4$ is —CH(F)$CH_3$, —CH(F)$CH_2F$, —CH(F)$CHF_2$, —CH(F)$CF_3$, —$CF_2CH_3$, —$CF_2CH_2F$, —$CF_2CHF_2$ or —$CF_2CF_3$.

In Embodiment 2 of this disclosure are compounds of Formula I or Embodiment 1, or pharmaceutically acceptable salts thereof, wherein:
(i) $R^5$ is —H, —$NH_2$, —$C_{3-4}$cycloalkyl, or —$C_{1-3}$alkyl unsubstituted or substituted with 1 to 7 of —F; or
(ii) $R^5$ is —H, —$NH_2$, -cyclopropyl, —$CH_3$ unsubstituted or substituted with 1 to 3 of —F, or —$CH_2CH_3$ substituted with 1 to 5 of —F; or
(iii) $R^5$ is —H or —$CH_3$ unsubstituted or substituted with 1 to 3 of —F.

In Embodiment 3 of this disclosure are compounds of Formula I, Embodiment 1 or Embodiment 2, or pharmaceutically acceptable salts thereof, wherein:
(i) $R^6$ is —H, —$C_{1-4}$alkyl, —CH=C($C_{1-3}$alkyl)$_2$, —$NH_2$, —NH—$C_{1-3}$ alkyl, —N($C_{1-3}$ alkyl)$_2$, or —$C_{1-4}$alkyl substituted with $R^7$; and $R^7$ is —OH, —$OC_{1-3}$alkyl or —$C(O)OC_{1-3}$alkyl; or
(ii) —H, —$C_{1-3}$alkyl (e.g., $CH_3$), —$C_{1-4}$alkyl-$OR^7$, —$C_{1-3}$alkyl-COOH, —$C_{2-4}$alkenyl, —$NH_2$ and pyrazolyl unsubstituted or substituted with $C_{1-3}$alkyl, wherein $R^7$ is —H, —$C_{1-3}$alkyl-$OCH_3$ or —$CH_2O$-pyrimidinyl; or
(iii) —$CH_3$, —$C_{1-4}$alkyl-OH, or —$C(O)OCH_3$.

In Embodiment 4 of this disclosure are compounds of Formula I, Embodiment 1, Embodiment 2, or Embodiment 3, wherein Ring A is (Aa) having the following Formula Ia:

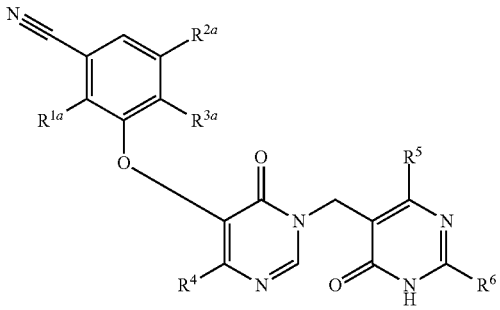

or a pharmaceutically acceptable salt thereof.

In Embodiment 4A of this disclosure are compounds of Formula I, Formula Ia, Embodiment 1, Embodiment 2, Embodiment 3, or Embodiment 4, or pharmaceutically acceptable salts thereof, wherein:
(i) $R^{1a}$ is —F, —Cl, Br, —$C_{1-3}$alkyl, —$CF_3$, —$CHF_2$, —$CH_2F$, —$NH_2$, —$C_{3-4}$cycloalkyl or —$OC_{1-3}$alkyl unsubstituted or substituted with 1 to 3 of F; and $R^{2a}$ is —H, —F, —Cl, Br, —$C_{1-3}$alkyl, —$CF_3$, —$CHF_2$, —$CH_2F$, —$NH_2$, —$C_{3-4}$cycloalkyl or —$OC_{1-3}$ alkyl unsubstituted or substituted with 1 to 3 of F; provided that $R^{2a}$ and $R^{3a}$ are not both —H; or
(ii) $R^{3a}$ is —H, —F, —Cl or Br, provided that $R^{2a}$ and $R^{3a}$ are not both —H; or
(iii) $R^{1a}$ and $R^{2a}$ are each independently —F, —Cl, Br, —$C_{1-3}$alkyl, —$CF_3$, —$CHF_2$, $CH_2F$, or —$OC_{1-3}$alkyl unsubstituted or substituted with 1 to 3 of F; and $R^{3a}$ is —H, —F, —Cl or Br, or $R^{3a}$ is H.

In Embodiment 4B of this disclosure are compounds of Formula I, Formula Ia, Embodiment 1, Embodiment 2, Embodiment 3, Embodiment 4, or Embodiment 4A, or pharmaceutically acceptable salts thereof, wherein:
$R^4$ is —CH(F)—$R^8$ or —C($F_2$)—$R^8$ wherein $R^8$ is (a) —$CH_3$ unsubstituted or substituted with 1 to 3 of F, or (b) —$CH_2CH_3$ unsubstituted or substituted with 1 to 5 of —F.

In Embodiment 5 of this disclosure are compounds of Formula I, Embodiment 1, Embodiment 2, or Embodiment 3, wherein Ring A is (Ab) having the following Formula Ib:

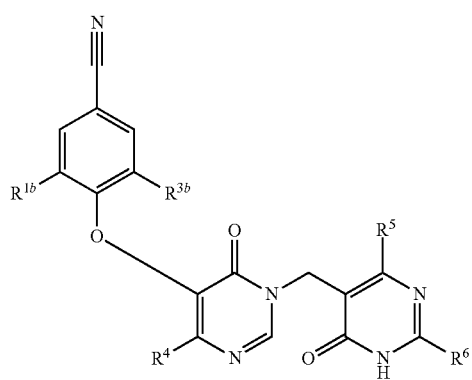

or a pharmaceutically acceptable salt thereof.

In Embodiment 5A of this disclosure are compounds of Formula I, Formula Ib, Embodiment 1, Embodiment 2, Embodiment 3, or Embodiment 5, or pharmaceutically acceptable salts thereof, wherein:
(i) $R^{1b}$ is halo, —$C_{1-3}$alkyl, —$CF_3$, —$CHF_2$, —$CH_2F$, —$C_{3-4}$cycloalkyl, or —$OC_{1-3}$alkyl unsubstituted or substituted with 1 to 3 of F; or
(ii) $R^{3b}$ is halo, —$C_{1-3}$alkyl, —$CF_3$, —$CHF_2$, —$CH_2F$, —$C_{3-4}$cycloalkyl, or —$OC_{1-3}$alkyl unsubstituted or substituted with 1 to 3 of F; or
(iii) $R^{1b}$ and $R^{3b}$ are each independently halo, —$C_{1-3}$alkyl, —$CF_3$, —$CHF_2$, —$CH_2F$, —$C_{3-4}$cycloalkyl, or —$OC_{1-3}$alkyl unsubstituted or substituted with 1 to 3 of F;
(iv) $R^{1b}$ and $R^{3b}$ are each independently —F, —Cl, —$CH_3$, —$CF_3$, —$CHF_2$—$CH_2F$, —$C_{3-4}$cycloalkyl, or —$OC_{1-3}$alkyl unsubstituted or substituted with 1 to 3 of F.

In Embodiment 5B of this disclosure are compounds of Formula I, Formula Ib, Embodiment 1, Embodiment 2, Embodiment 3, or Embodiment 5, or pharmaceutically acceptable salts thereof, wherein:
(i) $R^{1b}$ is —F, —Cl, —$CH_3$, —$CF_3$, —$CHF_2$, —$CH_2F$, —$OCH_3$ or cyclopropyl; or
(ii) $R^{3b}$ is —F, —Cl, —$CH_3$, —$CF_3$, —$CHF_2$, —$CH_2F$, —$OCH_3$ or cyclopropyl; or
(iii) $R^{1b}$ and $R^{3b}$ are each independently —F, —Cl, —$CH_3$, —$CF_3$, —$CHF_2$, —$CH_2F$, —$OCH_3$ or cyclopropyl.

In Embodiment 5C of this disclosure are compounds of Formula I, Formula Ib, Embodiment 1, Embodiment 2, Embodiment 3, Embodiment 5, or Embodiment 5A, or Embodiment 5B, or pharmaceutically acceptable salts thereof, wherein:
$R^4$ is —$CF_3$, —CH(F)—$R^8$ or —C($F_2$)—$R^8$ wherein $R^8$ is (a) —$CH_3$ unsubstituted or substituted with 1 to 3 of F, or (b) —$CH_2CH_3$ unsubstituted or substituted with 1 to 5 of —F.

In Embodiment 6 of this disclosure are compounds of Formula I, Embodiment 1, Embodiment 2, or Embodiment 3, wherein Ring A is (Ac) having the following Formula Ic:

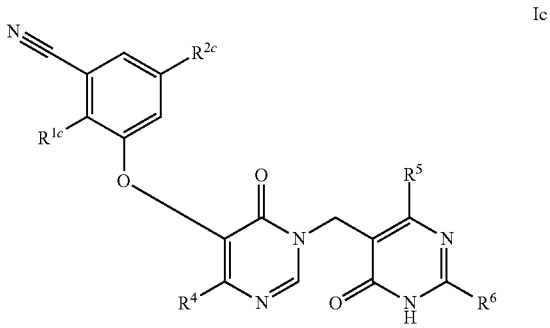

or a pharmaceutically acceptable salt thereof.

In Embodiment 6A of this disclosure are compounds of Formula I, Formula Ic, Embodiment 1, Embodiment 2, Embodiment 3 or Embodiment 6, or pharmaceutically acceptable salts thereof, wherein:
(i) $R^{1c}$ is —H, halo, —$CH_3$, —$CF_3$, —$CHF_2$ or —$CH_2F$; or
(ii) $R^{2c}$ is —H, halo, —$CH_3$, —$CF_3$, —$CHF_2$ or —$CH_2F$; or
(iii) $R^{1c}$ and $R^{2c}$ are each independently —H, halo, —$CH_3$, —$CF_3$, —$CHF_2$ or —$CH_2F$;

provided that one of R$^{1c}$ or R$^{2c}$ is —H and the other is not —H.

In Embodiment 6B of this disclosure are compounds of Formula I, Formula Ic, Embodiment 1, Embodiment 2, Embodiment 3, Embodiment 6, or Embodiment 6A, or pharmaceutically acceptable salts thereof, wherein:

R$^4$ is —CH(F)—R$^8$ or —C(F$_2$)—R$^8$ wherein R$^8$ is (a) —CH$_3$ unsubstituted or substituted with 1 to 3 of —F, or (b) —CH$_2$CH$_3$ unsubstituted or substituted with 1 to 5 of —F.

In Embodiment 7 are compounds of Formula I or a pharmaceutically acceptable salt thereof, wherein:

Ring A is selected from:

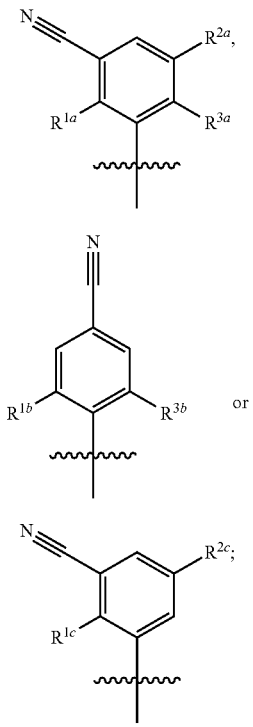

R$^{1a}$ is halo (e.g., F, Cl, Br), —C$_{1-3}$alkyl (e.g. —CH$_3$), —OC$_{1-3}$alkyl unsubstituted or substituted with 1-3 of F (e.g. —OCH$_3$), or —NH$_2$;

R$^{2a}$ is —H, halo (e.g., F, Cl, Br), —C$_{1-3}$alkyl unsubstituted or substituted with 1-6 of F (e.g., —CH$_3$, —CH$_2$CH$_3$, —CF$_3$, —CH$_2$F, —CHF$_2$);

R$^{3a}$ is —H or halo (e.g., F, Cl, Br);

provided that R$^{2a}$ and R$^{3a}$ are not both —H;

R$^{1b}$ is halo (e.g., F, Cl, Br), —C$_{1-3}$alkyl (e.g. —CH$_3$), —OC$_{1-3}$alkyl (e.g. —OCH$_3$), —CF$_3$, or —C$_{3-6}$cycloalkyl (e.g., cyclopropyl);

R$^{3b}$ is halo or —C$_{1-3}$alkyl unsubstituted or substituted with 1-6 of F (e.g., —CH$_3$, —CH$_2$CH$_3$, —CF$_3$, —CH$_2$F, —CHF$_2$);

R$^{1c}$ is —H, halo (e.g., F, Cl, Br) or —C$_{1-3}$alkyl (e.g., —CH$_3$, —CH$_2$CH$_3$);

R$^{2c}$ is —H, halo (e.g., F, Cl, Br), —C$_{1-3}$alkyl unsubstituted or substituted with 1 to 6 of —F (e.g., —CH$_3$, —CH$_2$CH$_3$, —CF$_3$, —CH$_2$F, —CHF$_2$);

provided that one of R$^{1c}$ or R$^{2c}$ is —H and the other is not —H;

R$^4$ is halo (e.g., F, Cl, Br), or —C$_{1-3}$alkyl substituted with 1 to 6 of —F (e.g., —CF$_3$, —CH$_2$F, —CHF$_2$, —CF$_2$CH$_3$, —CF$_2$CHF$_2$, —CF$_2$CF$_3$, —CH$_2$CH$_3$ substituted with 1-5 of F)

R$^5$ is —H, —NH$_2$, —C$_{3-6}$cycloalkyl (e.g., cyclopropyl), or —C$_{1-3}$alkyl unsubstituted or substituted with 1 to 6 of —F;

R$^6$ is —H, —C$_{1-3}$alkyl (e.g., CH$_3$), —C$_{1-4}$alkyl-OR$^7$, —C$_{1-3}$alkyl-COOH, —C$_{2-4}$alkenyl, —NH$_2$ and pyrazolyl unsubstituted or substituted with C$_{1-3}$alkyl, wherein R$^7$ is —H, —C$_{1-3}$alkyl-OCH$_3$ or —CH$_2$O-pyrimidinyl.

Reference to the compounds of Formula I herein encompasses the compounds of Formula I, Ia, Ib and Ic, and all embodiments, classes and sub-classes thereof and includes the compounds of the Examples herein. The compounds of Formula I encompass neutral compounds or salts thereof when such salts are possible, including pharmaceutically acceptable salts.

The term "e.g." means "for example." When the terms "e.g.," or "for example" are used herein, the example(s) recited are intended to be illustrative and are not intended to be an exhaustive list of all relevant examples.

As used herein, "alkyl" refers to both branched- and straight-chain saturated aliphatic hydrocarbon groups having the specified number of carbon atoms in a specified range. For example the term "C$_{1-6}$alkyl" means linear or branched chain alkyl groups, including all possible isomers, having 1, 2, 3, 4, 5 or 6 carbon atoms, and includes each of the hexyl and pentyl isomers as well as n-, iso-, sec- and tert-butyl (butyl, i-butyl, s-butyl, t-butyl, collectively "C$_4$alkyl"; Bu=butyl), n- and i-propyl (propyl, i-propyl, collectively "C$_3$alkyl"; Pr=propyl), ethyl (Et) and methyl (Me). "C$_{1-4}$alkyl" has 1, 2, 3 or 4 carbon atoms and includes each of n-, i-, s- and t-butyl, n- and i-propyl, ethyl and methyl. "C$_{1-3}$alkyl" has 1, 2 or 3 carbon atoms and includes each of n-propyl, i-propyl, ethyl and methyl.

"Cycloalkyl" refers to a cyclized alkyl ring having the indicated number of carbon atoms in a specified range. Thus, for example, "C$_{3-6}$cycloalkyl" includes each of cyclopropyl, cyclobutyl, cyclopentyl and cyclohexyl, and "C$_{3-4}$cycloalkyl" includes each of cyclopropyl and cyclobutyl.

"Halo" or "halogen" refers to chloro, fluoro, bromo or iodo. Chloro, fluoro and bromo are a class of halogens of interest, and more particularly fluoro.

"HIV naïve cell(s)" are cells that are not infected with HIV.

"Compatible anti-HIV agent(s)" are anti-HIV agents excluding HIV protease inhibitors.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present disclosure are limited to stable compounds embraced by Formula I and its embodiments. For example, certain moieties as defined in Formula I may be unsubstituted or substituted, and the latter is intended to encompass substitution patterns (i.e., number and kind of substituents) that are chemically possible for the moiety and that result in a stable compound.

This disclosure includes individual diastereomers, particularly epimers, i.e., compounds having the same chemical formula but which differ in the spatial arrangement around a single atom. This disclosure also includes mixtures of diastereomers, particularly mixtures of epimers, in all ratios.

This disclosure encompasses compounds of Formula I having either the (R) or (S) stereo-configuration at an asymmetric center and at any additional asymmetric centers that may be present in a compound of Formula I, as well as stereo-isomeric mixtures thereof. Embodiments of this disclosure also include a mixture of enantiomers enriched with 51% or more of one of the enantiomers, including for example 60% or more, 70% or more, 80% or more, or 90% or more of one enantiomer. A single epimer is preferred. An individual or single enantiomer refers to an enantiomer obtained by chiral synthesis and/or using generally known separation and purification techniques, and which may be 100% of one enantiomer or may contain small amounts (e.g., 10% or less) of the opposite enantiomer. Thus, individual enantiomers are a subject of this disclosure in pure form, both as levorotatory and as dextrorotatory antipodes, in the form of racemates and in the form of mixtures of the two enantiomers in all ratios. In the case of a cis/trans isomerism this disclosure includes both the cis form and the trans form as well as mixtures of these forms in all ratios.

The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present disclosure includes all such isomers, as well as salts, solvates (which includes hydrates). and solvated salts of such racemates, enantiomers, diastereomers and tautomers and mixtures thereof.

As would be recognized by one of ordinary skill in the art, certain compounds of the present disclosure may be able to exist as tautomers. All tautomeric forms of such compounds, whether isolated individually or in mixtures, are within the scope of the present disclosure. For example, in instances where an oxo (=O) substituent is permitted on a heteroaromatic ring and keto-enol tautomerism is possible, it is understood that the substituent might in fact be present, in whole or in part, in the —OH form.

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of Formula I; for example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). When the compounds of Formula I contain one or more acidic groups or basic groups, the invention includes the corresponding pharmaceutically acceptable salts.

Thus, the compounds of Formula I that contain acidic groups (e.g., —COOH) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I, which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

The instant disclosure encompasses any composition comprised of a compound of Formula I or a compound that is a salt thereof, including for example but not limited to, a composition comprised of said compound associated together with one or more additional molecular and/or ionic component(s) which may be referred to as a "co-crystal." The term "co-crystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals). There is no proton transfer between the dissimilar components and the solid phase is neither a simple salt nor a solvate. A discussion of co-crystals can be found, e.g., in S. Aitipamula et al., *Crystal Growth and Design,* 2012, 12 (5), pp. 2147-2152.

Furthermore, compounds of the present disclosure may exist in amorphous form and/or one or more crystalline forms, and as such all amorphous and crystalline forms and mixtures thereof of the compounds of Formula I and salts thereof are intended to be included within the scope of the present disclosure. In addition, some of the compounds of the instant disclosure may form solvates with water (i.e., a hydrate) or common organic solvents. Such solvates and hydrates, particularly the pharmaceutically acceptable solvates and hydrates, of the compounds of this disclosure are likewise encompassed within the scope of the compounds defined by Formula I and the pharmaceutically acceptable salts thereof, along with un-solvated and anhydrous forms of such compounds.

Accordingly, the compounds of Formula I or salts thereof including pharmaceutically acceptable salts thereof, embodiments thereof and specific compounds described and claimed herein, encompass all possible stereoisomers, tautomers, physical forms (e.g., amorphous and crystalline forms), co-crystal forms, solvate and hydrate forms, and any combination of the foregoing forms where such forms are possible.

Another embodiment of the present disclosure is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as, high performance liquid chromatography, and/or mass spectrometry or NMR techniques. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual stereoisomer.

The compounds of Formula I herein, and pharmaceutically acceptable salts thereof, are useful for eliciting GAG-POL dimerization in HIV-infected cells and thereby selectively killing HIV infected GAG-POL expressing cells without concomitant cytotoxicity to HIV naïve cells, referred to herein as TACK (Targeted Activator of Cell Kill) activity, or more specifically HIV TACK activity. HIV TACK or TACK have also been previously referred to as Small Molecule Activated Cell Kill (SMACK). Thus, the compounds of Formula I and pharmaceutically acceptable salts thereof are useful for:

(i) A method for the treatment or prophylaxis of infection by HIV, or for the treatment, prophylaxis, or delay in the onset or progression of AIDS or ARC in a human subject in need thereof which comprises administering to the human subject an effective amount of the compound according to Formula I, or a pharmaceutically acceptable salt thereof;

(ii) A method for eliciting GAG-POL dimerization in HIV-infected cells in a human subject in need thereof which comprises administering to the human subject an effective amount of the compound according to Formula I, or a pharmaceutically acceptable salt thereof; and/or (iii) A method for selectively killing HIV infected GAG-POL expressing cells without concomitant cytotoxicity to HIV naïve cells in a human subject which comprises administering to the human subject an effective amount of the compound according to Formula I, or a pharmaceutically acceptable salt thereof.

Additionally, the compounds of Formula I and pharmaceutically acceptable salts thereof are useful for any of the methods (i), (ii) or (iii) above, further comprising administering to the human subject an effective amount of one or more compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors and post-attachment inhibitors. In the methods of (i), (ii) or (iii) immediately above, the human subject can be treated with a compound Formula I or a pharmaceutically acceptable salt thereof in addition to treatment with one or more compatible HIV antiviral agents.

The compounds of Formula I and pharmaceutically acceptable salts thereof are also useful for a method for augmenting the suppression of HIV viremia in a human subject whose viremia is being suppressed by administration of one or more compatible HIV antiviral agents, which comprises additionally administering to the human subject an effective amount of the compound according to Formula I, or a pharmaceutically acceptable salt thereof.

Other embodiments of the present disclosure include the following:

(a) A pharmaceutical composition comprising an effective amount of a compound of Formula I or a pharmaceutically acceptable salt thereof, and a pharmaceutically acceptable carrier.

(b) A pharmaceutical composition which comprises the product prepared by combining (e.g., mixing) an effective amount of a compound of Formula I or a pharmaceutically acceptable salt thereof, and a pharmaceutically acceptable carrier.

(c) The pharmaceutical composition of (a) or (b), further comprising an effective amount of one or more compatible anti-HIV agents selected from the group consisting of HIV antiviral agents, immunomodulators, and anti-infective agents.

(d) The pharmaceutical composition of (c), wherein the compatible anti-HIV agent is selected from one or more of an antiviral selected from the group consisting of nucleoside or nucleotide HIV reverse transcriptase inhibitors, nucleoside HIV reverse transcriptase translocation inhibitors, non-nucleoside HIV reverse transcriptase inhibitors, HIV integrase inhibitors, HIV fusion inhibitors, HIV entry inhibitors, HIV maturation inhibitors and post attachment inhibitors.

(e) A combination which is (i) a compound of Formula I or a pharmaceutically acceptable salt thereof and (ii) one or more compatible anti-HIV agents selected from the group consisting of HIV antiviral agents, immunomodulators, and anti-infective agents; wherein the compound and the compatible anti-HIV agent are each employed in an amount that renders the combination effective for the treatment or prophylaxis of infection by HIV, or for the treatment, prophylaxis or delay in the onset or progression of AIDS or ARC.

(f) The combination of (e), wherein the compatible anti-HIV agent is an antiviral selected from the group consisting of nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors and post attachment inhibitors.

(g) A method for eliciting GAG-POL dimerization in HIV-infected cells, a method for selectively killing HIV infected GAG-POL expressing cells without concomitant cytotoxicity to HIV naïve cells, and/or a method for the treatment or prophylaxis of infection by HIV, or for the treatment, prophylaxis, or delay in the onset or progression of AIDS or ARC, comprising administering an effective amount of a compound of Formula I or a pharmaceutically acceptable salt thereof to a subject in need of such treatment.

(h) The method of (g), wherein the compound of Formula I or a pharmaceutically acceptable salt thereof is administered in combination with an effective amount of at least one other compatible HIV antiviral selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors and post attachment inhibitors.

(i) The method of (g) or (h) comprising administering to the subject the pharmaceutical composition of (a), (b), (c) or (d) or the combination of (e) or (f).

(j) Use of a compound of Formula I or a pharmaceutically acceptable salt thereof in the manufacture of a medicament for (1) eliciting GAG-POL dimerization in HIV-infected cells in a subject; (2) selectively killing HIV infected GAG-POL expressing cells without concomitant cytotoxicity to HIV naïve cells in a subject; (3) treatment or prophylaxis of infection by HIV in a subject; (4) treatment, prophylaxis or delay in the onset or progression of AIDS or ARC in a subject; (5) augmenting the suppression of HIV viremia in a subject undergoing treatment with a compatible anti-HIV agent, and/or (6) augmenting the suppression of HIV viremia in a subject whose viremia is being suppressed by administration of one or more compatible HIV antiviral agents.

(k) A compound of Formula I, or a pharmaceutically acceptable salt thereof, for use in (1) eliciting GAG-POL dimerization in HIV-infected cells; (2) selectively killing HIV infected GAG-POL expressing cells without concomitant cytotoxicity to HIV naïve cells; (3) treatment or prophylaxis of infection by HIV; (4) the treatment, prophylaxis or delay in the onset or progression of AIDS or ARC; and/or (5) augmenting the suppression of HIV viremia in a subject undergoing treatment with a compatible anti-HIV agent.

Additional embodiments of the present invention include each of the pharmaceutical compositions, methods and uses set forth in the preceding paragraphs, wherein the compound of Formula I or its salt employed therein in substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se.

In another embodiment of the present disclosure are the pharmaceutical compositions, methods and uses set forth above, wherein the HIV of interest is HIV-1.

An additional embodiment of the present invention includes the pharmaceutical compositions, methods, medicaments, uses and combinations set forth herein, wherein the HIV of interest is HIV-1. Thus, for example, in any of the pharmaceutical compositions, methods, medicaments, uses and combinations using the compounds of Formula I or pharmaceutically acceptable salts thereof, the compound or salt thereof is employed in an amount effective against HIV-1; and when used in combination with one or more compatible anti-HIV agent(s), each such additional agent is a compatible HIV-1 antiviral selected from one or more of nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors and post-attachment inhibitors.

The term "administration" and variants thereof (e.g., "administering" a compound) in reference to a compound of Formula I means providing the compound to the individual in need of treatment or prophylaxis and includes both self-administration and administration to the patient by another person or any other means. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

The term "subject" or "patient" as used herein refers to a human (or "person") who has been the object of treatment, observation or experiment. Examples of patients to be treated with an HIV TACK agent include but are not limited to, patients who have been infected with HIV, and/or HIV infected patients whose HIV viral load has been suppressed and/or is considered to be undetectable at time of HIV TACK treatment. Patients to be treated with an HIV TACK agent also include, but are not limited to, those using an HIV TACK agent for prophylaxis of HIV infection or for post-exposure prophylaxis after being potentially exposed to HIV to prevent becoming infected.

"Prophylaxis" includes each of pre-exposure prophylaxis (PrEP), i.e., using a compound of Formula I or a pharmaceutically acceptable salt thereof to prevent HIV infection in a person who does not have HIV, and post-exposure prophylaxis (PEP), i.e., using a compound of Formula I or a pharmaceutically acceptable salt thereof after being potentially exposed to HIV to prevent becoming infected with HIV.

The term "effective amount" as used herein means an amount of a compound sufficient to elicit GAG-POL dimerization in HIV-infected cells and selectively kill HIV infected GAG-POL expressing cells without concomitant cytotoxicity to HIV naïve cells; and/or exert a therapeutic effect, and/or a exert a prophylactic effect after administration. One embodiment of "effective amount" is a "therapeutically effective amount" which is an amount of a compound that is effective for selectively killing HIV infected GAG-POL expressing cells, effective for treating HIV infection, or effective for the treatment, prophylaxis or delay in the onset or progression of AIDS or ARC in a patient infected with HIV. Another embodiment of "effective amount" is a "prophylactically effective amount" which is an amount of the compound that is effective for prophylaxis of HIV infection, or prophylaxis of AIDS or ARC in an HIV-infected patient. It is understood that an effective amount can simultaneously be both a therapeutically effective amount, e.g., for treatment of HIV infection, and a prophylactically effective amount, e.g., for prevention or reduction of risk for developing AIDS or ARC in a subject infected with HIV.

In the combination therapies of the present invention, an effective amount can refer to each individual agent or to the combination as a whole, wherein the amounts of all agents administered in the combination are together effective, but wherein a component agent of the combination may or may not be present individually in an effective amount with reference to what is considered effective for that component agent if it were administered alone.

In the methods of the present invention, (i.e., selectively killing HIV infected GAG-POL expressing cells, the treatment of infection by HIV, prophylaxis of HIV infection or the treatment, prophylaxis or delay in the onset or progression of AIDS or ARC), the compounds of this invention, or salts thereof, can be administered by means that produce contact of the active agent with the agent's site of action. They can be administered by conventional means available for use in conjunction with pharmaceuticals, either as individual therapeutic agents or in a combination of therapeutic agents. The compound can be administered itself, but typically is administered with a pharmaceutical carrier selected on the basis of the chosen route of administration and standard pharmaceutical practice. The compounds of the invention can, for example, be administered orally (e.g., via tablet or capsule), parenterally (including subcutaneous injections, intravenous, intramuscular or intrasternal injection, or infusion techniques), by inhalation spray, or rectally, in the form of a unit dosage of a pharmaceutical composition containing an effective amount of the compound and conventional non-toxic pharmaceutically acceptable carriers, adjuvants and vehicles. The compound could also be administered via an implantable drug delivery device adapted to provide an effective amount of the compound or a pharmaceutical composition of the compound over an extended period of time.

Formulations

Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Implantable compositions can be prepared according to methods known in the art wherein the carrier comprises the active chemical ingredient with polymers and suitable excipients, or utilizing an implantable device for drug delivery. Further description of methods suitable for use in preparing pharmaceutical compositions for use in the present invention and of ingredients suitable for use in said compositions is provided in Remington—The Science and Practice of Pharmacy, 22nd Edition, published by Pharmaceutical Press and Philadelphia College of Pharmacy at University of the Sciences, 2012, ISBN 978 0 85711-062-6 and prior editions.

Formulations of compounds of Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are known in the art. For example, solid dispersions can be prepared using excipients and processes as described in reviews (e.g., A. T. M. Serajuddin, J Pharm Sci, 88:10, pp. 1058-1066 (1999)). Nanoparticulate systems based on both attrition and direct synthesis have also been described in reviews such as Wu et al (F. Kesisoglou, S. Panmai, Y. Wu, Advanced Drug Delivery Reviews, 59:7 pp. 631-644 (2007)).

The compounds of Formula I may be administered in a dosage range of, e.g., 1 to 20 mg/kg, or 1 to 10 mg/kg, or about 5 mg/kg of mammal (e.g., human) body weight per day, or at other time intervals as appropriate, in a single dose or in divided doses. The compounds of Formula I may be administered in a dosage range of 0.001 to 2000 mg. per day in a single dose or in divided doses. Examples of dosage ranges are 0.01 to 1500 mg per day, or 0.1 to 1000 mg per day, administered orally or via other routes of administration in a single dose or in divided doses.

For oral (e.g., tablets or capsules) or other routes of administration, the dosage units may contain 100 mg to 1500 mg of the active ingredient, for example but not limited to, 100, 150, 200, 250, 300, 350, 400, 450, 500, 600, 700, 800, 900, 1000, 1100, 1200, 1300, 1400 or 1500 milligrams of the active ingredient for the symptomatic adjustment of the dosage to the patient to be treated. Furthermore, the compound may be formulated in oral formulations for immediate or modified release such as extended or controlled release. When the compound of Formula I is administered as a salt, reference to an amount of the compound in milligrams or grams is based on the free form (i.e., the non-salt form) of the compound.

Daily administration can be via any suitable route of administration but is preferably via oral administration and can be a single dose or more than one dose at staggered times (divided daily doses) within each 24-hour period. Each dose may be administered using one or multiple dosage units as appropriate.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given dose. The amount and frequency of administration will be regulated according to the judgment of the attending clinician considering such factors.

An "anti-HIV agent" is any agent which is directly or indirectly effective in the inhibition of HIV, the treatment or prophylaxis of HIV infection, and/or the treatment, prophylaxis or delay in the onset or progression of AIDS or ARC. It is understood that an anti-HIV agent is effective in treating, preventing, or delaying the onset or progression of HIV infection or AIDS and/or diseases or conditions arising therefrom or associated therewith. The present disclosure is additionally directed to use of a compound of Formula I or pharmaceutically acceptable salts thereof, with one or more compatible anti-HIV agents, i.e., anti-HIV agents excluding HIV protease inhibitors. For example, the compounds of Formula I may be administered in combination with effective amounts of one or more compatible anti-HIV agents selected from HIV antiviral agents, immunomodulators, anti-infectives, or vaccines useful for treating HIV infection or AIDS. Suitable compatible HIV antivirals for use in combination with the compounds of the present disclosure include, but are not limited to, those listed in Table A as follows:

TABLE A

Antiviral Agents for Treating HIV infection or AIDS

| Name | Type |
|---|---|
| abacavir, ABC, ZIAGEN ® | NRTI |
| abacavir + lamivudine, EPZICOM ® | NRTI |
| abacavir + lamivudine + zidovudine, TRIZIVIR ® | NRTI |
| AZT, zidovudine, azidothymidine, RETROVIR ® | NRTI |
| bictegravir | InSTI |
| bictegravir + tenofovir alafenamide fumarate + emtricitabine, BIKTARVY ® | InSTI/NRTI/NRTI |
| capravirine | NNRTI |
| ddC, zalcitabine, dideoxycytidine, HIVID ® | NRTI |
| ddI, didanosine, dideoxyinosine, Videx ® | NRTI |
| ddI (enteric coated), VIDEX EC ® | NRTI |
| delavirdine, DLV, RESCRIPTOR ® | NNRTI |
| dolutegravir, TIVICAY ® | InSTI |
| dolutegravir + abacavir + lamivudine, TRIUMEQ ® | InSTI/NRTI/NRTI |
| doravirine, PIFELTRO ™ | NNRTI |
| doravirine/lamivudine/tenofovir disoproxil fumarate, DELSTRIGO ™ | NNRTI/NRTI/NRTI |
| efavirenz, EFV, SUSTIVA ®, STOCRIN ® | NNRTI |
| Efavirenz/emtricitabine/tenofovir disoproxil fumarate, ATRIPLA ® | NNRTI/NRTI/NRTI |
| EFdA (4'-ethynyl-2-fluoro-2'-deoxyadenosine) | NRTTI |
| Elvitegravir, VITEKTA ® | InSTI |
| emtricitabine, FTC, EMTRIVA ® | NRTI |
| emtricitabine + tenofovir disoproxil fumarate, TRUVADA ® | NRTI/NRTI |
| emivirine, COACTINON ® | NNRTI |
| enfuvirtide, FUZEON ® | FI |
| enteric coated didanosine, VIDEX EC ® | NRTI |
| etravirine, TMC-125 | NNRTI |
| Ibalizumab-uiyk (TROGARZO ®) | Post-Attachment Inhibitor or Monoclonal Antibody |
| lamivudine, 3TC, EPIVIR ® | NRTI |
| lamivudine + zidovudine, COMBIVIR ® | NRTI/NRTI |
| maraviroc, SELZENTRY ® | EI |
| nevirapine, NVP, VIRAMUNE ® | NNRTI |
| raltegravir, ISENTRESS ™ | InSTI |
| rilpivirine, EDURANT ® | NNRTI |
| stavudine, d4T, didehydrodeoxythymidine, ZERIT ® | NRTI |
| tenofovir disoproxil fumarate (TDF), VIREAD ® | NRTI |
| tenofovir alafenamide fumarate (TAF) | NRTI |
| vicriviroc | EI |

EI = entry inhibitor; FI = fusion inhibitor; InSTI = integrase inhibitor; NRTI = nucleoside or nucleotide reverse transcriptase inhibitor; NNRTI = non-nucleoside reverse transcriptase inhibitor; NRTTI = nucleoside reverse transcriptase translocation inhibitor. Some of the drugs listed in the table are used in a salt form; e.g., abacavir sulfate, delavirdine mesylate.

It is understood that the scope of combinations of the compounds of this invention with compatible anti-HIV agents is not limited to the HIV antivirals listed in Table A, but includes in principle any combination with any pharmaceutical composition useful for the treatment or prophylaxis of HIV AIDS, or ARC, with the exception of HIV protease inhibitors. The compatible HIV antiviral agents and other active agents will typically be employed in these combinations in their conventional dosage ranges and regimens as reported in the art, including, for example, the dosages described in the current Physicians' Desk Reference, Thomson P D R, 70th edition (2016), Montvale, NJ: PDR Network, or in prior editions thereof. The dosage ranges for a compound of the disclosure in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to the reverse transcriptase region within GAG-POL, e.g., by competitive inhibition.

The following acronyms and abbreviations have the indicated meanings:

| | |
|---|---|
| ACN = | acetonitrile |
| AcOH = | acetic acid |
| aq. = | aqueous |
| $B_2Pin_2$ = | bis(pinacolato)diboron |
| BPO = | benzoyl peroxide |
| CAN = | ceric amonium nitrate |
| cataCXium A Pd G2 precatalyst = | chloro[(di(1-adamantyl)-N-butylphosphine)-2-(2-aminobiphenyl)]palladium(II); |
| DAST = | (diethylamino)sulfur trifluoride |
| DCE = | 1,2-dichloroethane |
| DCM = | dichloromethane |
| DDQ = | 2,3-Dichloro-5,6-dicyano-1,4-benzoquinone |
| DIAD = | diisopropyl azodicarboxylate |
| DHP = | 3,4-dihydro-2H-pyran |
| DIBAL-H = | diisobutylaluminum hydride |
| DIPEA = | diisopropylethylamine |
| DME = | dimethoxyethane |
| DMF = | N,N-dimethylformamide |
| Dess-Martin periodinane = | 1,1,1-triacetoxy-1,1-dihydro-1,2-benziodoxol-3(1H)-one |
| DMSO = | dimethyl sulfoxide |
| DMSO-$d_6$ = | deuterated dimethyl sulfoxide |
| e.g. = | for example, but not limited to |
| EDC = | 1-Ethyl-3-(3-dimethylaminopropyl)carbodiimide |
| EDTA = | ethylenediaminetetraacetic acid |
| EtOAc = | ethyl acetate |
| EtOH = | ethanol |
| FBS = | fetal bovine serum |
| GFP = | Green fluorescent protein |
| HIV = | human immunodeficiency virus |
| HOBt = | hydroxybenzotriazole |
| HPLC = | high performance liquid chromatography |
| h = | hour |
| Int = | intermediate |
| Ir [(Ome) (1,5-COD)]$_2$ = | (1,5-Cyclooctadiene)(methoxy)iridium(I) dimer |
| LCAP = | liquid chromatography area percent |
| LC-MS = | liquid chromatography-mass spectroscopy |
| LDA = | lithium diisoproplyamide |
| LAH = | lithium aluminium hydride |
| m-CPBA = | 3-chloroperbenzoic acid |
| Me = | methyl |
| MeI = | methyl iodide |
| MeOH = | methanol |
| Me-THF = | 2-methyltetrahydrofuran |
| MTBE = | methyl tertiary-butyl ether |

| | |
|---|---|
| min = | minute |
| MS = | mass spectroscopy |
| MsCl = | methanesulfonyl chloride |
| NBS = | N-bromosuccinimide |
| n-BuLi = | n-butyl lithium |
| NCS = | N-chlorosuccinimide |
| NHS = | normal human serum |
| NMP = | N-methyl-2-pyrrolidinone |
| NMR = | nuclear magnetic resonance |
| PBMC = | peripheral blood mononuclear cell |
| PBS = | phosphate buffered saline |
| $Pd_2(dba)_3$ = | tris(dibenzylideneacetone)dipalladium(0) |
| $PdCl_2(dppf)$ = | [1,1'-bis(diphenylphosphino)ferrocene]dichloropalladium (II) |
| $Pd(OAc)_2$ = | palladium(II) acetate |
| $Pd(Ph_3P)_4$ = | tetrakis(triphenylphosphine)palladium(0) |
| P.E. = | petroleum ether |
| PHA = | phytoheagglutinin |
| PMB = | 4-methyoxybenzyl |
| PMBCl = | 4-methoxybenzyl chloride |
| PPTS = | 4-toluenesulfonic acid |
| RT = | room temperature |
| $SN_{Ar}$ = | nucleophilic aromatic substitution |
| TBAF = | tetrabutylammonium fluoride |
| Tc = | thiophene carboxylate |
| t-BuOH = | tert-butanol |
| t-BuOK = | potassium tert-butoxide |
| t-buXPhos Pd G3 precatalyst = | [(2-di-tert-butylphosphino-2',4',6'-triisopropyl-1,1'-biphenyl)-2-(2'-amino-1,1'-biphenyl)] palladium(II) methanesulfonate |
| TEA = | triethylamine |
| TFA = | trifluoroacetic acid |
| TFAA = | trifluoroacetic anhydride |
| THF = | tetrahydrofuran |
| TLC = | thin layer chromatography |
| TMS-Cl = | trimethylsilyl chloride |
| X-Phos = | 2-Dicyclohexylphosphino-2',4',6'-triisopropylbiphenyl |

Several methods for preparing the compounds of this invention are described in the following Schemes and Examples. Starting materials and intermediates are purchased or are made using known procedures, or as otherwise illustrated in the five Intermediate (A, B, C, AB and BC) sections that follow. A frequently applied route to the compounds of Formula I are described in the Schemes that follow.

SCHEME 1

Scheme 1

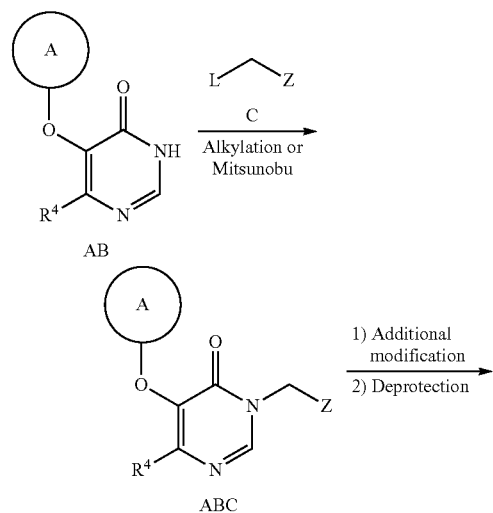

Scheme 1 depicts a method for preparing compounds of Formula I. Intermediate AB is prepared with procedures illustrated in the Intermediate AB section. Mitsunobu reaction or alkylation using an appropriate pyrimidone benzylic alcohol or halide (Intermediate C) provides Intermediate ABC. Intermediate C usually has a protected pyrimidone moiety shown as Z in Scheme 1. Synthesis of C is illustrated in the Intermediate C section. The resulting Intermediate ABC may optionally undergo additional modification, followed by a deprotection step to afford compounds of Formula I.

SCHEME 2

Scheme 2

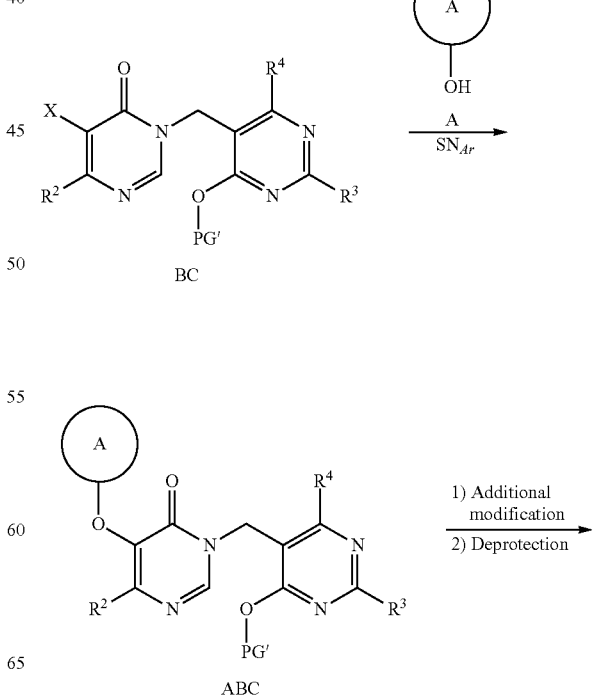

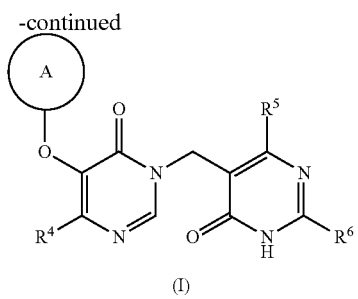

(I)

X = halogen: F or Br

Scheme 2 illustrates another method for preparing compounds of Formula I. An $SN_{Ar}$ reaction between a phenol A (either commercially available or prepared using procedures in the Intermediate A section) and an Intermediate BC (made by procedures illustrated in the Intermediate BC section) is used to make Intermediate ABC. The pyrimidone C ring is generally protected with a protecting group (PG') such as methyl or a PMB group. The resulting Intermediate ABC may then optionally undergo additional modification followed by a deprotection step to afford compounds of Formula I.

Reactions sensitive to moisture or air were performed under nitrogen or argon using anhydrous solvents and reagents. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure.

The progress of reactions was determined by either analytical thin layer chromatography (TLC) usually performed with E. Merck pre-coated TLC plates, silica gel 60E-254, layer thickness 0.25 mm or analytical liquid chromatography-mass spectrometry (LC-MS). Typically, the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 µm or a Waters Acquity UPLC® BEH C18 1.0×50 mm, 1.7 µm. The flow rate was 1 mL/min, and the injection volume was 10 µL. UV detection was in the range 210-400 nm. The mobile phase consisted of solvent A (water plus 0.05% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min. LC/MS determinations were carried out on a Waters Classing Aquity system equipped with TUV and MS detectors and a Waters SQD mass spectrometer, a Shimadzu 20 UV 254 and 220 nM with Shimadzu 2010 or 2020 mass spectrometer, or an Agilent 1200 HPLC quipped with DAD/ELSD and G6110 MSD using one of the following conditions: 1) Ascentis Express C18 (3×50 mm) 2.7 µm column using mobile phase containing A: 0.05% Trifluoroacetic acid in water and B: 0.05% Trifluoroacetic acid in acetonitrile with a gradient from 90:10 (A:B) to 5:95 (A:B) over 6 min at a flow rate of 1.8 mL/min, UV detection at 210 nm; 2) Aquity BEH C18, (1.0×50 mm) 1.7 µm column using mobile phase containing A: 0.05% Trifluoroacetic acid in water and B: 0.05% Trifluoroacetic acid in acetonitrile with a gradient from 90:10 (A:B) to 5:95 (A:B) over 2 min at a flow rate of 0.3 mL/min, UV detection at 215 nm; 3) Agilent YMC J'Sphere H-80 (3×50 mm) 5 µm column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer; 4) an Agilent TC-C18 (2.1×50 mm) 5 µm column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

Preparative HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. An alternate preparative HPLC system used was a Gilson Workstation consisting of: Gilson GX-281 Injector/Collector, Gilson UV/VIS-155 Detector, Gilson 333 and 334 Pumps, and equipped with a column selected from the following: Phenomenexd Synergi C18 (150 mm×30 mm×4 micron), YMC-Actus Pro C18 (150 mm×30 mm×5 micron), Xtimate C18 (150 mm×25 mm×5 micron), Boston Green ODS (150 mm×30 mm×5 micron), XSELECT C18 (150 mm×30 mm×5 micron), and Waters XSELECT C18 (150 mm×30 mm×5 micron). Conditions included either high pH (0-100% acetonitrile/water eluent comprising 0.1% v/v 10 mM $NH_4HCO_3$ or 0.05% $NH_4OH$) or low pH (0-95% acetonitrile/water eluent comprising 0.1% v/v TFA). The injection volume ranged from 1000-8000 µL, and the UV detection range was 210-400 nm. Mobile phase gradients were optimized for the individual compounds.

Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 µm, 60 Å pore size) in pre-packed cartridges of the size noted.

SFC chiral resolution was carried out on a Sepiate Prep SFC 100, Multigram II (MG II), THAR80 prep SFC, or a Waters SFC (80, 200, or 350) using the following conditions: Chiral Method A: AD-H column, 15% ethanol/CO2; Chiral Method B: AD-H column, 20% IPA/CO2; Chiral Method C: AS-H column, 20% MeOH/CO2; Chiral Method D: AD-H column, 20% ethanol/CO2; Chiral Method E: Lux Cellulose-4 column, 30% ethanol/CO2; Chiral Method F: IA column, 15% ethanol/CO2; Chiral Method G: IA column, 40% methanol/CO2; Chiral Method H: AD-H column, 10% methanol/CO2; Chiral Method I: AD-H column, 30% ethanol/CO2; Chiral Method J: AD-H column, 40% ethanol/CO2; and Chiral Method K: IG column, 12% methanol/CO2. Chiral analytical chromatography was most commonly performed on one of CHIRALPAK® AS, CHIRALPAK® AD, CHIRALCEL® OD, CHIRALCEL® IA, or CHIRALCEL® OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of CHIRALPAK AS, of CHIRALPAK AD, CHIRALCEL® OD, CHIRALCEL® IA, CHIRALCEL® OJ columns (20×250 mm) (Daicel Chemical Industries, Ltd.) with desired isocratic solvent systems identified on chiral analytical chromatography or by supercritical fluid (SFC) conditions.

Proton or $^1$H NMR was acquired using a Varian Unity-Inova 400 MHz NMR spectrometer equipped with a Varian 400 ATB PFG 5 mm, Nalorac DBG 400-5 or a Nalorac IDG 400-5 probe, a Varian-400 MHz MR spectrometer equipped with an Auto X ID PFG Probe 5 mm, a Varian 400 MHz VNMRS spectrometer equipped with a PFG 4Nuc Probe 5 mm, or a Bruker AvanceIII 500 MHz spectrometer equipped with a PABBO Probe 5 mm in accordance with standard analytical techniques, unless specified otherwise, and results of spectral analysis are reported. $^1$H NMR spectra were acquired in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz).

It is understood that a chiral center in a compound may exist in the "S" or "R" stereo-configuration, or as a mixture of both. Within a molecule, each bond drawn as a straight line from a chiral center encompasses each of the (R) and (S) stereoisomers as well as mixtures thereof unless otherwise noted. The compounds in Examples 17, 18, 28-36, 43, 44, 53 and 54 contain a chiral center. The isomer mixture made in each of Examples 17, 18, 28-36, 43, 44, 53 and 54 was separated, providing one or both of an isomer A (the faster eluting isomer) and an isomer B (the slower eluting isomer), based on their observed elution order resulting from the separation as performed in the Example. Elution time and/or order of separated isomers may differ if performed under conditions different than those employed herein. Absolute stereochemistry (R or 5) of the chiral center in each of the "A" and/or "B" separated stereoisomers in Examples 17, 18, 28-36, 43, 44, 53 and 54 was not determined, and "A" and "B" only refer to elution order resulting from the purification conditions as performed. An asterisk (*) may be used in the associated chemical structure drawings of the Example compounds to indicate a chiral center.

| Ex. | Purification conditions |
|---|---|
| 17 | SFC Chiralpak IC-H, 250 × 30 mm id, 5 μm, $IPA/CO_2$ = 45%, 80 mL/min. |
| 18 | SFC Chiralpak IC-H, 250 × 30 mm id, 5 μm, $EtOH/CO_2$ = 45%, 80 mL/min. |
| 32 | SFC Chiralpak IC-H, 250 × 30 mm id, 5 μm, $IPA/CO_2$ = 30%, 60 mL/min. |
| 33 | SFC Chiralpak IC-H, 250 × 30 mm id, 5 μm, $IPA/CO_2$ = 30%, 60 mL/min. |
| 34 | SFC Chiralpak IC-H, 250 × 30 mm id, 5 μm, $IPA/CO_2$ = 45%, 73 mL/min. |
| 35 | SFC Chiralpak IC-H, 250 × 30 mm id, 5 μm, $IPA/CO_2$ = 20%, 60 mL/min. |
| 36 | SFC Chiralpak IC-H, 250 × 30 mm id, 5 μm, $IPA/CO_2$ = 20%, 60 mL/min. |

INTERMEDIATE A SECTION

Intermediate A01

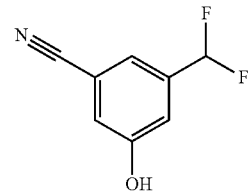 [SMILES: N#Cc1cc(O)cc(C(F)F)c1]

3-(difluoromethyl)-5-hydroxybenzonitrile

Step 1:
3-chloro-5-((4-methoxybenzyl)oxy)benzonitrile

To a solution of 3-chloro-5-hydroxybenzonitrile (30 g, 0.20 mol) in ACN (300 mL) was added PMBCl (34 g, 0.21 mol) and $K_2CO_3$ (55 g, 0.4 mmol), then the mixture was stirred at 70° C. for 4 h. The reaction mixture was filtered and concentrated in vacuum. The residue was purified by flash chromatography on silica (2% EtOAc/P.E.) to afford the title compound. $^1$H NMR (400 MHz, $CDCl_3$): δ 7.33 (d, J=8.0 Hz, 2H), 7.23 (s, 1H), 7.19 (s, 1H), 7.11 (s, 1H), 6.94 (d, J=8.0 Hz, 2H), 5.00 (s, 2H), 3.83 (s, 3H).

Step 2:
3-((4-methoxybenzyl)oxy)-5-vinylbenzonitrile

To a solution of 3-chloro-5-((4-methoxybenzyl)oxy)benzonitrile (50 g, 0.18 mol) in dioxane/$H_2O$ (400 mL/80 mL) was added potassium vinyltrifluoroborate (25 g, 0.18 mol), $K_2CO_3$ (50 g, 0.36 mol), X-Phos (17 g, 36 mmol) and $Pd(OAc)_2$ (4.1 g, 18 mmol) under $N_2$ atmosphere, the mixture was stirred at 80° C. for 2 h. After cooled to RT, the resulting mixture was filtered and extracted with EtOAc (3×400 mL). The combined organic layers were washed with brine, dried over $Na_2SO_4$, filtered and concentrated under reduced pressure. The residue was purified by flash chromatography on silica (1-2% EtOAc/P.E.) to afford the title compound. $^1$H NMR (400 MHz, $CDCl_3$): δ 7.34 (d, J=8.4 Hz, 2H), 7.28 (s, 1H), 7.20 (s, 1H), 7.09 (s, 1H), 6.93 (d, J=8.4 Hz, 2H), 6.63 (dd, J=17.6, 12.0 Hz, 1H), 5.78 (d, J=17.6 Hz, 1H), 5.38 (d, J=12.0 Hz, 1H), 5.01 (s, 2H), 3.82 (s, 3H).

Step 3:
3-formyl-5-((4-methoxybenzyl)oxy)benzonitrile

To a stirred solution of compound 3-((4-methoxybenzyl)oxy)-5-vinylbenzonitrile (28 g, 0.1 mol) in dioxane/$H_2O$ (180 mL/60 mL) was added 2,6-lutidine (22 g, 0.2 mol), $OsO_4$ (1.3 g, 5 mmol) and $NaIO_4$ (43 g, 0.2 mol), the mixture was stirred at RT for 3 h. Upon reaction completion, the mixture was diluted with water, extracted with EtOAc (3×200 mL). The organic layer was washed with water and brine, dried over $Na_2SO_4$, filtered and concentrated under reduced pressure. The residue was purified by flash chromatography on silica (2-10% EtOAc/P.E.) to afford the title compound. $^1$H NMR (400 MHz, DMSO-$d_6$): δ 9.95 (s, 1H), 7.90 (s, 1H), 7.82 (s, 1H), 7.76 (s, 1H), 7.37 (d, J=8.4 Hz, 2H), 6.93 (d, J=8.4 Hz, 2H), 5.14 (s, 2H), 3.73 (s, 3H).

Step 4: 3-(difluoromethyl)-5-((4-methoxybenzyl)oxy)benzonitrile

To a stirred solution of 3-formyl-5-((4-methoxybenzyl)oxy)benzonitrile (22 g, 82 mmol) in DCM (250 mL) was added DAST (106 g, 0.6 mol) at 0° C. under $N_2$ atmosphere, then the mixture was stirred for 3 h at RT. Upon reaction completion, the mixture was quenched with water, extracted with DCM (3×200 mL). The organic layer was washed with water and brine, dried over $Na_2SO_4$, filtered and concentrated under reduce pressure to give the title compound.

Step 5: 3-(difluoromethyl)-5-hydroxybenzonitrile

A solution of 3-(difluoromethyl)-5-((4-methoxybenzyl)oxy)benzonitrile (23.7 g, 82 mmol) in TFA/TFAA (100 mL/50 mL) was stirred at 110° C. for 3 h. When reaction was complete, the resulting mixture was quenched with saturated $NaHCO_3$ aq. (100 mL) and extracted with EtOAc (3×150 mL). The combined organic layers were washed with brine, dried over $Na_2SO_4$, filtered and concentrated under reduced pressure to afford the title compound. $^1$H NMR (400 MHz, DMSO-$d_6$): δ 10.66 (s, 1H), 7.41 (s, 1H), 7.28 (s, 1H), 7.23 (s, 1H), 6.97 (t, J=56.0 Hz, 1H).

Intermediate A02

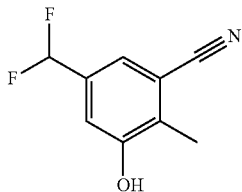

Step 1: 5-formyl-2-methylbenzonitrile

Into a 20-L 4-necked round-bottom flask purged and maintained with an inert atmosphere of nitrogen, was placed a solution of 5-bromo-2-methylbenzonitrile (750 g, 38.26 mol) in tetrahydrofuran (6 L), n-BuLi (1.54 L, 38.26 mol) was added dropwise at −78° C., the resulting solution was stirred for 30 min, the N,N-dimethylformamide (295 g, 4.04 mol, 1.05 equiv) was added dropwise. The reaction mixture was then stirred at −78° C. for 30 min in a liquid nitrogen bath, and then quenched by the addition of saturated $NH_4Cl$ aq. (5 L). The resulting solution was extracted with EtOAc (3×5 L). The organic layer was washed with brine, dried over $Na_2SO_4$, filtered and concentrated under reduced pressure to give the title compound.

Step 2: 3-bromo-5-formyl-2-methylbenzamide

Into a 3-L 4-necked round-bottom flask purged and maintained with an inert atmosphere of nitrogen, was placed a solution of 5-formyl-2-methylbenzonitrile (245 g, 1.69 mol) in sulfuric acid (980 mL), the reaction mixture was stirred at 60° C., 1-bromopyrrolidine-2,5-dione (300 g, 1.69 mol) was added in 3 batches. The resulting solution was stirred at 60° C. for 30 min. The reaction was then quenched by the addition of 5 L of water/ice, and stirred for 1 h. The solids were collected by filtration and dried under vacuum to afford the title compound and used as is in the next step.

Step 3: 3-bromo-5-formyl-2-methylbenzonitrile

Into a 20-L 4-necked round-bottom flask purged and maintained with an inert atmosphere of nitrogen, was placed a solution of 3-bromo-5-formyl-2-methylbenzamide (500 g, 2.07 mol) in dichloromethane (10 L), pyridine (524.5 g, 6.63 mol). While the resulting solution was stirred at 0° C., the 2,2,2-trifluoroacetate (1305 g, 6.21 mol) was added dropwise. The resulting solution was stirred for 30 min at RT, then quenched with water/ice (5 L), and extracted with DCM (3×5 L). The organic layers were combined and dried over anhydrous $Na_2SO_4$, filtered and concentrated under reduced pressure. The residue was purified with flash chromatography on silica (20% EtOAc/hexanes) to afford the title compound.

Step 4: 3-bromo-5-(difluoromethyl)-2-methylbenzonitrile

To a solution of 3-bromo-5-formyl-2-methylbenzonitrile (360 g, 1.61 mol) in dichloromethane (5.4 L), DAST (260 g, 1.61 mol, 1.00 equiv) was added dropwise at RT. The resulting solution was stirred at RT for 1 h, and then quenched with water/ice (3 L). The resulting solution was extracted with DCM (3×5 L). The organic layers were combined and dried over anhydrous $Na_2SO_4$, filtered and concentrated under reduced pressure to afford the title compound and used as is in the following step.

Step 5: 5-(difluoromethyl)-3-hydroxy-2-methylbenzonitrile

To a solution of 3-bromo-5-(difluoromethyl)-2-methylbenzonitrile (320 g, 1.30 mol) in 1,4-dioxane (1.6 L), was added solution of KOH (146 g, 2.60 mol) in water (1.6 L), $Pd_2(dba)_3$ (67 g, 64.92 mmol), and 2-di-tert-butylphosphino-2',4',6'-triisopropylbiphenyl (55 g, 129.53 mmol). The resulting mixture was purged by nitrogen (3×) and stirred at 90° C. for 1 h, and then partitioned between ice water (4 L) and EtOAc (3×2 L). The combined organic layers were washed with brine, dried over anhydrous $Na_2SO_4$, filtered and concentrated under reduced pressure. The residue was purified with flash chromatography on silica (33% EtOAc/hexanes) to afford the title compound. MS: 182 (M+1). 1H NMR (400 MHz, DMSO-$d_6$): δ 10.65 (s, 1H), 7.42 (d, J=1.6 Hz, 1H), 7.26 (d, J=1.5 Hz, 1H), 6.99 (s, 1H), 2.34 (d, J=1.3 Hz, 3H).

Intermediate A03

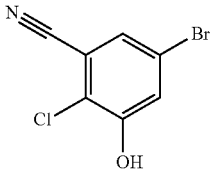 [SMILES: N#Cc1cc(Br)cc(O)c1Cl]

5-bromo-2-chloro-3-hydroxybenzonitrile

Step 1: 2-amino-5-bromo-3-fluorobenzonitrile

To a stirred solution of 2-amino-3-fluorobenzonitrile (10 g, 73.5 mmol) in DMF (10 mL) was added NBS (13.07 g, 73.5 mmol) and the resulting mixture was stirred at 0° C. for 12 h. Upon the reaction completion, the reaction mixture was diluted with water (50 mL). And the precipitate formed was removed by filtration, and the filtrate was concentrated under reduced pressure to give the title compound. MS: 215 and 217 (M+1).

Step 2: 5-bromo-2-chloro-3-fluorobenzonitrile

To a mixture of 2-amino-5-bromo-3-fluorobenzonitrile (9 g, 41.9 mmol), copper(I) chloride (12.43 g, 126 mmol) and copper(II) chloride (19.70 g, 146 mmol) in ACN (80 mL), was added tert-butyl nitrite (19.91 mL, 167 mmol) at 0° C. The resulting mixture was stirred at 25° C. for 6 h. The mixture was diluted with water (150 mL) and extracted with EtOAc (3×100 mL). The organic layer was washed with brine (3×50 mL), dried over $Na_2SO_4$, filtered and concentrated under reduced pressure. The residue was purified by flash chromatography on silica (10-100% EtOAc/P.E.) to give the title compound.

Step 3: 5-bromo-2-chloro-3-((4-methoxybenzyl)oxy)benzonitrile

To a stirred solution of (4-methoxyphenyl)methanol (2.475 g, 17.91 mmol) in DMF (100 mL) was added NaH (0.931 g, 23.29 mmol) at 0° C. After stirring for 20 min, was added 5-bromo-2-chloro-3-fluorobenzonitrile (4.2 g, 17.91 mmol). The reaction mixture was stirred at 25° C. for 3 h, then partitioned between water (50 mL) and EtOAc (3×50 mL). The organic layer was washed with brine, dried over anhydrous $Na_2SO_4$, filtered and concentrated under reduced pressure. The residue was purified by flash chromatography on silica (15-100% EtOAc/P.E.) to afford the title compound.

Step 4: 5-bromo-2-chloro-3-hydroxybenzonitrile

To a stirred solution of 5-bromo-2-chloro-3-((4-methoxybenzyl)oxy)benzonitrile (3.5 g, 9.93 mmol) in TFA (10 mL) and DCM (50 mL) was stirred at 25° C. for 3 h. Upon reaction completion, the mixture was concentrated under reduced pressure. The residue was purified by flash chromatography on silica (15-100% EtOAc/P.E.) to afford the title compound.

Intermediate A04

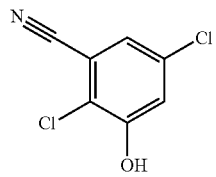

2,5-dichloro-3-hydroxybenzonitrile

Step 1: 2-amino-5-bromo-3-fluorobenzonitrile

To a stirred solution of 2-amino-3-fluorobenzonitrile (5 g, 36.7 mmol) in DMF (50 mL) was added 1-chloropyrrolidine-2,5-dione (5.15 g, 38.6 mmol) and the resulting mixture was stirred at 60° C. for 6 h. The mixture was partitioned between water (200 mL) and EtOAc (2×150 mL). The combined organic layers were washed with brine (3×300 mL), dried with anhydrous $Na_2SO_4$, filtered and concentrated under reduced pressure to give the title compound, which was used for the next step without purification. MS: 171.1 (M+1).

Step 2: 2,5-dichloro-3-fluorobenzonitrile

To a mixture of 2-amino-5-chloro-3-fluorobenzonitrile (6.217 g, 36.4 mmol), copper(I) chloride (10.82 g, 109 mmol) and copper(II) chloride (17.15 g, 128 mmol) in ACN (60 mL), was added tert-butyl nitrite (17.34 mL, 146 mmol) at 25° C. for 1 h. The reaction mixture was diluted with water (180 mL) and extracted with EtOAc (3×120 mL). The organic layer was washed with brine, dried over anhydrous $Na_2SO_4$, filtered and concentrated under reduced pressure. The residue was purified by flash chromatography on silica (10-100% EtOAc/P.E.) to afford the title compound. $^1$H NMR (400 MHz, chloroform-d): δ 7.51 (dd, J=2.26, 1.65 Hz, 1H), 7.44-7.47 (m, 1H).

Step 3: 2,5-dichloro-3-((4-methoxybenzyl)oxy)benzonitrile

To a stirred solution of (4-methoxyphenyl)methanol (2.75 g, 19.89 mmol) in DMF (40 mL) was added NaH (1.034 g, 25.9 mmol) at 0° C. The mixture was stirred at 0° C. for 30 min, then was added 2,5-dichloro-3-fluorobenzonitrile (3.78 g, 19.89 mmol), and then stirred at 25° C. for 2 h. The reaction mixture was diluted with water (200 mL) and extracted with EtOAc (3×150 mL). The organic layer was washed with brine, dried over anhydrous $Na_2SO_4$, filtered and concentrated to give the title compound. MS: 308.1 (M+1).

Step 4: 2,5-dichloro-3-hydroxybenzonitrile

To a stirred solution of 2,5-dichloro-3-((4-methoxybenzyl)oxy)benzonitrile (6.13 g, 19.89 mmol) in DCM (60 mL), TFA (20 mL) was and then stirred at 25° C. for 1 h. Upon the completion, the reaction mixture was poured into sat. $NaHCO_3$ aq. (30 mL), extracted with DCM (3×60 mL). The combined organic layers were washed with brine, dried over anhydrous $Na_2SO_4$, filtered and concentrated under reduced pressure to give the title compound, which was used directly without further purification. MS: 187.9 (M−1).

Intermediate A05

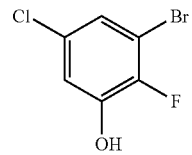

3-bromo-5-chloro-2-fluorophenol

Step 1: 2-(3-bromo-5-chloro-2-fluorophenyl)-4,4,5,5-tetramethyl-1,3,2-dioxaborolane To a solution of 2-bromo-4-chloro-1-fluorobenzene (300 g, 1.43 mol) in hexane (4.5 L), was added $B_2Pin_2$ (363.7 g,

Step 2: 3-bromo-5-chloro-2-fluorophenol

To a solution of 2-(3-bromo-5-chloro-2-fluorophenyl)-4,4,5,5-tetramethyl-1,3,2-dioxaborolane (385 g, 1.15 mol) in THF (3.85 L), was added a solution of sodium hydroxide (138 g, 3.45 mol) in water (3 L), 35% hydrogen peroxide aq. (390 g, 3.44 mol) at 0° C. The resulting solution was stirred at 0° C. for 2 h, and quenched by with sat. Na$_2$S$_2$O$_3$ aqueous solution. After the pH of the solution was adjusted to 3-4 with HCl (1 M), the resulting solution was extracted with EtOAc (3×3 L). The combined organic layers were washed with brine, then concentrated under reduced pressure. The residue was purified by flash chromatography on silica (0-90% EtOAc/P.E.) to afford the title compound. $^1$H NMR (400 MHz, CDCl$_3$): δ 11.31 (br. s., 1H), 7.47 (dd, J=2.4, 4.4 Hz, 1H), 7.30 (dd, J=2.4, 7.6 Hz, 1H).

Intermediate A06

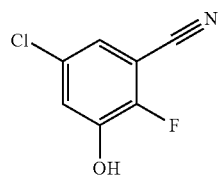 [SMILES: N#Cc1cc(Cl)cc(O)c1F]

5-chloro-2-fluoro-3-hydroxybenzonitrile

To a solution of 3-bromo-5-chloro-2-fluorophenol (86 g, 343 mmol) in NMP (860 mL), was added CuCN (154 g, 1.72 mol, 5.0 eq) in one portion. The resulting reaction mixture was stirred at 180° C. for 2 h, then partitioned between ice water (1 L) and EtOAc (3×800 mL). The combined organic layers were washed with brine, dried over anhydrous Na$_2$SO$_4$, filtered and concentrated under reduced pressure. The residue was purified by flash chromatography on silica (2-33% EtOAc/P.E.) to afford the title compound. $^1$H NMR (400 MHz, DMSO-d$_6$): δ 11.33 (br. s., 1H), 7.49 (dd, J=2.5, 4.5 Hz, 1H), 7.30 (dd, J=2.5, 7.6 Hz, 1H).

Intermediate A07

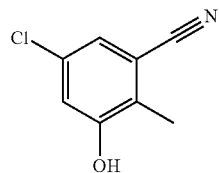

5-chloro-3-hydroxy-2-methylbenzonitrile

Step 1: 2,3-difluorobenzaldehyde

To a solution of 1,2-difluorobenzene (1668 g, 14.62 mol) in THF (16.7 L) cooled at −78° C., was added a THF solution of n-BuLi (6.44 L, 16.08 mol) dropwise with stirring over 60 min. Then to this mixture, was added N,N-dimethylformamide (5340 g, 73.06 mol) dropwise with stirring at −78° C. over 60 min. The resulting solution was stirred at −78° C. for 1 h. The reaction was then quenched with saturated NH$_4$Cl aq. (10 L), then extracted with EtOAc (3×10 L). The combined organic layers were washed with brine, dried over anhydrous Na$_2$SO$_4$, filtered and concentrated under reduced pressure. The residue was purified by flash chromatography on silica (2% EtOAc/P.E.) to afford the title compound.

Step 2: (E)-N-[(2,3-difluorophenyl)methylidene]hydroxylamine

A mixture of 2,3-difluorobenzaldehyde (2410 g, 16.96 mol) in a 70% solution of NH$_2$OH (672 g, 20.35 mol) in DMF (10 L) was stirred at 20° C. for 3 h, then partitioned between water (6 L) and EtOAc (3×8 L). The combined organic layers were washed with brine, dried over anhydrous Na$_2$SO$_4$, filtered and concentrated under reduced pressure. The residue was purified by flash chromatography on silica (2% EtOAc/P.E.) to afford the title compound.

Step 3: 2,3-difluorobenzonitrile

A solution of (E)-N-[(2,3-difluorophenyl)methylidene]hydroxylamine (2025 g, 12.89 mol) in DMF (11 L) was treated with POCl$_3$ (5688 g, 37.10 mol). The resulting solution was stirred at 25° C. for 3 h, then partitioned between water (6 L) and EtOAc (3×6 L). The combined organic layers were washed with brine, dried over anhydrous Na$_2$SO$_4$, filtered and concentrated under reduced pressure. The residue was purified by flash chromatography on silica (2% EtOAc/P.E.) to afford the title compound.

Step 4: 2-amino-3-fluorobenzonitrile

In a seal reactor, a solution of 2,3-difluorobenzonitrile (1273 g, 9.15 mol) in EtOH (13 L) was bubbled in NH$_3$(gas). The resulting solution was stirred at 140° C. for 8 h, cooled to RT then concentrated under reduced pressure. The residue was partitioned between water (5 L) and MTBE (3×8 L). The combined organic layers were washed with water, brine and dried over anhydrous Na$_2$SO$_4$, filtered and concentrated under reduced pressure to afford the title compound.

Step 5: 2-amino-5-chloro-3-fluorobenzonitrile

A solution of 2-amino-3-fluorobenzonitrile (934 g, 6.86 mol) in DMF (14 L) was treated with NCS (1008 g, 7.55 mol). The resulting solution was stirred at 45° C. for 2 h, then partitioned between ice water (20 L) and EtOAc (3×12 L). The organic layer was washed with brine, dried over anhydrous Na$_2$SO$_4$, filtered and concentrated under reduced pressure. The residue was purified by flash chromatography on silica (3% EtOAc/P.E.) to afford the title compound.

Step 6: 2-bromo-5-chloro-3-fluorobenzonitrile

To a mixture of t-BuONO (815 g, 7.88 mol) and CuBr$_2$ (1365 g, 6.13 mol) in ACN (8 L), was added a solution of 2-amino-5-chloro-3-fluorobenzonitrile (747 g, 4.38 mol) in ACN (7 L) dropwise with stirring over 90 min. The resulting mixture was stirred at RT for 10 h, and diluted with water (15 L), and then extracted with EtOAc (3×10 L). The organic layer was washed with brine, dried over anhydrous $Na_2SO_4$, filtered and concentrated under reduced pressure. The residue was purified by flash chromatography on silica (3% EtOAc/P.E.) to afford the title compound.

Step 7: 5-chloro-3-fluoro-2-methylbenzonitrile

A mixture of 2-bromo-5-chloro-3-fluorobenzonitrile (768 g, 3.28 mol), 1,4-methylboronic acid (297 g, 4.96 mol), potassium carbonate (913 g, 6.61 mol) and $PdCl_2(dppf)$ (213 g, 0.33 mol) in degassed 1,4-dioxane (4500 mL) and water (450 mL) was stirred at 100° C. for 60 min, and then diluted with water (4 L), and extracted with EtOAc (3×6 L). The organic layer was washed with brine, dried over anhydrous $Na_2SO_4$, filtered and concentrated under reduced pressure. The residue was purified by flash chromatography on silica (3% EtOAc/P.E.) to afford the title compound.

Step 8: 5-chloro-3-[(4-methoxyphenyl)methoxy]-2-methylbenzonitrile

Under atmosphere of nitrogen, to a solution of 4-Methoxybenzyl alcohol (410 g, 2.97 mol) in DMF (3200 mL), was added sodium hydride (128 g, 5.33 mol), followed by addition of a solution of 5-chloro-3-fluoro-2-methylbenzonitrile (418 g, 2.46 mol) in DMF (800 mL) drop wise. The resulting solution was stirred at 25° C. for 12 h, then diluted with ice water (2 L), and extracted with EtOAc (3×3 L). The organic layer was washed with brine, dried over anhydrous $Na_2SO_4$, filtered and concentrated under reduced pressure. The resulting solid was washed with petroleum ether and collected on top of a filter to afford the title compound.

Step 9: 5-chloro-3-hydroxy-2-methylbenzonitrile

A solution of 5-chloro-3-[(4-methoxyphenyl)methoxy]-2-methylbenzonitrile (518 g, 1.80 mol) in DCM (1500 mL) was treated with TFA (500 mL). The resulting solution was stirred at 25° C. for 1 h. The solids were collected on top of a filter to afford the title compound. MS: 166 (M−1). $^1$H NMR (400 MHz, DMSO-$d_6$): δ 10.67 (s, 1H), 7.32-7.33 (d, 1H), 7.07-7.08 (d, 1H), 2.24 (s, 3H).

Intermediate A08

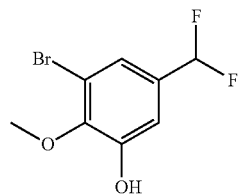

3-bromo-5-(difluoromethyl)-2-methoxyphenol

Step 1: 3-bromo-4,5-dihydroxybenzaldehyde

To a solution of 3-bromo-4-hydroxy-5-methoxybenzaldehyde (10 g, 43.3 mmol) in DCM (100 mL) was added a solution of $BBr_3$ (9.00 mL, 95 mmol) in DCM (100 mL) at 0° C., then the reaction mixture was stirred at 0° C. for 20 min and 25° C. for 2.5 h. Upon completion, the reaction was quenched by slow addition of MeOH (50 mL). The solvent was removed under reduced pressure. The residue was purified by flash chromatography on silica (0-20%, MeOH/DCM) to afford the title compound. MS: 216.9 (M+1).

Step 2: -bromo-5-hydroxy-4-methoxybenzaldehyde

To a solution of 3-bromo-4,5-dihydroxybenzaldehyde (6 g, 27.6 mmol) in DMF (80 mL) was added lithium carbonate (4.09 g, 55.3 mmol). After stirring at 45° C. for 1 h, the reaction mixture was treated with MeI (2.59 mL, 41.5 mmol). The reaction mixture was stirred at 45° C. for another 2 h, and then poured into ice water (400 mL), adjusted pH~6 with 1 N HCl, extracted with EtOAc (3×150 mL). The organic layer was washed with brine, dried over anhydrous $Na_2SO_4$, filtered and concentrated under reduced pressure. The residue was purified by flash chromatography on silica (5-33% EtOAc/P.E.) to afford the title compound. MS: 231.0 (M+1).

Step 3: 3-bromo-5-(difluoromethyl)-2-methoxyphenol

To a solution of 3-bromo-5-hydroxy-4-methoxybenzaldehyde (3.23 g, 13.98 mmol) in DCM (30 mL) was added DAST (18.47 mL, 140 mmol). The reaction mixture was stirred at 20° C. for 1 h, and then quenched by slow addition of sat. $NaHCO_3$ aq. (100 mL), extracted with DCM (3×50 mL). The organic layer was washed with brine, dried over anhydrous $Na_2SO_4$, filtered and concentrated under reduced pressure. The residue was purified by flash chromatography on silica (3-25% EtOAc/P.E.) to give the title compound. MS: 253.8 (M+1).

Intermediate A09

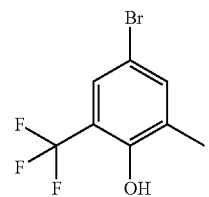

4-bromo-2-methyl-6-(trifluoromethyl)phenol

Step 1: 4-bromo-2-iodo-6-(trifluoromethyl)phenol

A solution of 4-bromo-2-(trifluoromethyl)phenol (4 g, 16.60 mmol), KI (16 g, 96 mmol) and $I_2$ (8.5 g, 33.5 mmol) in water (50 mL) was treated with $NH_3/H_2O$ (200 mL), and stirred at 30° C. for 16 h. Upon completion, the reaction mixture was neutralized with HCl (6 M) to pH of 7, then the precipitate was collected on top of a filter to afford the title compound. MS: 366.7 (M+1).

Step 2: 4-bromo-2-methyl-6-(trifluoromethyl)phenol

To a solution of 4-bromo-2-iodo-6-(trifluoromethyl)phenol (5 g, 13.63 mmol) in NMP (10 mL) was added $Pd_2(dba)_3$ (0.374 g, 0.409 mmol), triphenylphosphine (0.715 g, 2.73 mmol). The mixture was purged with N₂ and heated at 50° C. for 10 min, followed by addition of copper(I) iodide (0.260 g, 1.363 mmol). After the mixture was heated at 50° C. for another 10 min, tetramethylstannane (3.66 g, 20.44 mmol) was added into the reaction, and it was heated to 120° C. for 3 h. Upon complete conversion, the mixture was diluted with sat. KF aq. (50 mL) and extracted with EtOAc (3×40 mL). The organic layer was washed with water and brine, dried over anhydrous Na₂SO₄, filtered and concentrated. The residue was purified by reverse phase HPLC (ACN/water with 0.1% TFA modifier) to give the title compound. MS: 255 (M+1).

Intermediate A10

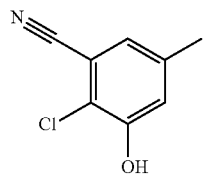

2-chloro-3-hydroxy-5-methylbenzonitrile

Step 1: 2-chloro-3-((4-methoxybenzyl)oxy)-5-methylbenzonitrile

To a solution of 5-bromo-2-chloro-3-((4-methoxybenzyl)oxy)benzonitrile (see Step 3 of Intermediate A03) (0.350 g, 0.993 mmol) in 1,4-dioxane (10 mL) was added K₂CO₃ (0.274 g, 1.985 mmol) and H₂O (1 mL), was added methylboronic acid (0.059 g, 0.993 mmol) and 1,1'-bis(diphenylphosphino)ferrocene-palladium(II)dichloride dichloromethane complex (0.081 g, 0.099 mmol). The resulting mixture was heated at 80° C. for 16 h, and then quenched with water and extracted with EtOAc. The organic layer was dried over anhydrous Na₂SO₄, filtered and concentrated under reduced pressure. The residue was purified by flash chromatography on silica (P.E. 100%) to afford the title compound.

Step 2: 2-chloro-3-hydroxy-5-methylbenzonitrile

To a solution of 2-chloro-3-((4-methoxybenzyl)oxy)-5-methylbenzonitrile (0.185 g, 0.643 mmol) in DCM (20 mL) was added TFA (0.050 ml, 0.643 mmol) at 0° C. The resulting mixture was stirred at RT for 2 h, and then was concentrated under reduced pressure. The residue was purified by flash chromatography on silica (EtOAc/P.E.=0-20%) to afford the title compound. MS: 168.0 (M+1).

The following intermediates in Table 1 were purchased from commercial sources.

TABLE 1

| INT | Structure | IUPAC Name | CAS# |
|---|---|---|---|
| A11 | 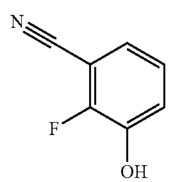 | 2-fluoro-3-hydroxybenzonitrile | 1000339-24-1 |
| A12 | 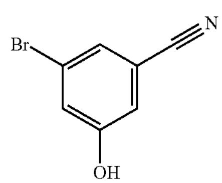 | 3-bromo-5-hydroxybenzonitrile | 770718-92-8 |
| A13 | 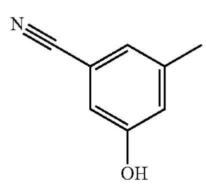 | 3-hydroxy-5-methylbenzonitrile | 95658-81-4 |
| A14 | 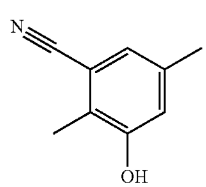 | 2,5-dimethyl-3-hydroxybenzonitrile | 90563-55-6 |

TABLE 1-continued

| INT | Structure | IUPAC Name | CAS# |
|---|---|---|---|
| A15 | 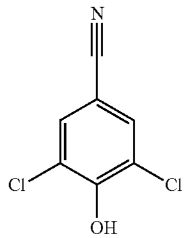 [SMILES: N#Cc1cc(Cl)c(O)c(Cl)c1] | 3,5-dichloro-4-hydroxybenzonitrile | 1891-95-8 |
| A16 | 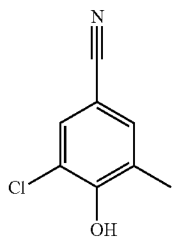 | 3-chloro-4-hydroxy-5-methylbenzonitrile | 173900-45-3 |
| A17 | 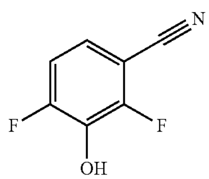 [SMILES: N#Cc1ccc(F)c(O)c1F] | 2,4-difluoro-3-hydroxybenzonitrile | 1214373-88-2 |
| A18 | 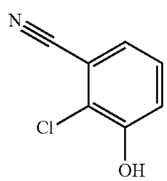 | 2-chloro-3-hydroxybenzonitrile | 51786-11-9 |
| A19 | 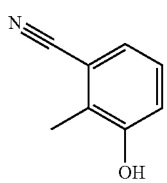 | 3-hydroxy-2-methylbenzonitrile | 55289-04-8 |
| A20 | 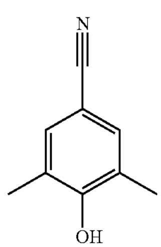 | 4-hydroxy-3,5-dimethylbenzonitrile | 4198-90-7 |
| A21 | 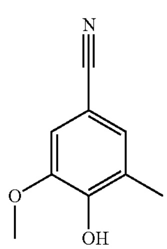 | 4-hydroxy-3-methoxy-5-methylbenzonitrile | 173900-47-5 |

INTERMEDIATE B SECTION

Intermediate B01

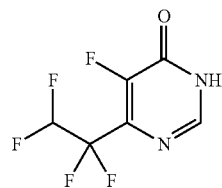 [SMILES: O=c1[nH]cnc(C(F)(F)C(F)F)c1F]

5-fluoro-6-(1,1,2,2-tetrafluoroethyl)-3,4-dihydropyrimidin-4-one

Step 1: 2,2,3,3-tetrafluoropropanoic Acid

To a solution of potassium heptaoxodichromium (1782 g, 6.06 mol) in sulfuric acid (2097 g, 21.38 mol) and water (2400 mL), was added of 2,2,3,3-tetrafluoropropan-1-ol (800 g, 6.06 mol) dropwise with stirring at 100° C. The resulting solution was stirred at 100° C. for 5 h with refluxing, and then extracted with MTBE (4×2 L). The organic layer was dried with anhydrous sodium sulfate and concentrated under reduced pressure to afford the title compound and used as is for the next step.

Step 2: 2,2,3,3-tetrafluoro-N-methoxy-N-methylpropanamide

To a solution of 2,2,3,3-tetrafluoropropanoic acid (crude product from previous step, 45% purity, 1007 g, 3.15 mol) in THF (4600 mL), was added sulfurooyl dichloride (787.2 g, 6.62 mol) dropwise at 0° C., followed by dropwise addition of DMF (753.4 g, 10.31 mol). After being stirred at RT for 45 min, the reaction mixture was cooled to 0° C., and then treated with methoxy(methyl)amine hydrochloride (1222.5 g, 12.53 mol), and TEA (1913 g, 18.91 mol) dropwise. The resulting mixture was stirred at RT for 5 h, and then quenched with ice water (2 L), and extracted with MTBE (3 L). The organic layer was washed with sat. NaHCO$_3$ aq, brine, dried over anhydrous sodium sulfate, filtered and distillated to afford the title compound.

Step 3: Ethyl 2,4,4,5,5-pentafluoro-3-oxopentanoate

To a solution of 2,2,3,3-tetrafluoro-N-methoxy-N-methylpropanamide (470 g, 2.49 mol) in THF (4700 mL), was added ethyl 2-fluoroacetate (316.2 g, 2.98 mol), 1M solution of LiHMDS in THF (3729 mL, 3.73 mol) at −78° C. The resulting mixture was stirred at −78° C. for 2 h, and then quenched with sat. NH$_4$Cl aq (1 L). After the pH value of the solution was adjusted to 3 with HCl (1M), the reaction mixture was extracted with MTBE (3×2 L). The organic layer was washed with brine, dried over anhydrous sodium sulfate, filtered and concentrated under reduced pressure to afford the title compound, which was used for the next step directly.

Step 4: 5-fluoro-6-(1,1,2,2-tetrafluoroethyl)-3,4-dihydropyrimidin-4-one

To a solution of ethyl 2,4,4,5,5-pentafluoro-3-oxopentanoate (533 g, 2.28 mol) in methanol (5330 mL), was added formamidine acetate (1185.1 g, 11.38 mol), and sodium methoxide (492 g, 9.11 mol). The resulting mixture was stirred at RT for 2 h, then quenched with ice water (1.5 L). After the pH value of the solution was adjusted to 3 with HCl (2M), the resulting mixture was extracted with MTBE (3×1 L). The combined organic layers was dried over anhydrous sodium sulfate, filtered and concentrated under reduced pressure. The residue was purified by re-crystallization from MTBE/P.E. (1:5) to afford the title compound. MS: 212.9 (M−1). $^1$HNMR: (300 MHz, CD$_3$OD): δ 8.10 (1H, s), 6.67~6.38 (1H, m).

The following intermediates in Table 2 were prepared according to scheme C using the procedure outlined in the synthesis of intermediate B01 using the relevant fluorinated alkyl alcohol or its corresponding acid/methyl ester.

TABLE 2

| INT | Structure | IUPAC Name | MS (M + 1) |
|---|---|---|---|
| B02 | ![structure] | 5-fluoro-6-(pentafluoroethyl)-3,4-dihydropyrimidin-4-one | 231.0 (M − 1) |
| B03 | ![structure] | 6-(1,1-difluoroethyl)-5-fluoropyrimidin-4(3H)-one | 177.1 (M − 1) |
| B04 | ![structure] | 5-fluoro-6-(trifluoromethyl)pyrimidin-4(3H)-one | 183.0 (M + 1) |

Intermediate B05

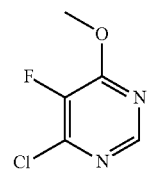

4-chloro-5-fluoro-6-methoxypyrimidine

To a solution of 4,6-dichloro-5-fluoropyrimidine (8.0 g, 47.9 mmol) in MeOH (80 mL) was added sodium methoxide (3.05 g, 56.5 mmol) at 0° C. The resulting reaction mixture was stirred at 20° C. for 2 h, then quenched with water (20 mL) and then extracted with EtOAc (3×20 mL). The organic layer was washed with brine, dried over anhydrous Na$_2$SO$_4$, filtrated and concentrated under reduced pressure to afford the title compound. MS: 163.1 (M+1). ¹H NMR (400 MHz, DMSO-$d_6$): δ 8.45 (s, 1H), 4.03 (s, 1H).

Intermediate B06

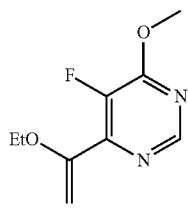

4-(1-ethoxyvinyl)-5-fluoro-6-methoxypyrimidine

To a solution of 4-chloro-5-fluoro-6-methoxypyrimidine (5.2 g, 28.8 mmol), tributyl (1-ethoxyvinyl) stannane (12.48 g, 34.5 mmol) in DMF (50 mL) was added Pd(Ph₃P)₄ (0.5 g, 0.433 mmol). The resulting reaction mixture was stirred at 100° C. for 4 h under $N_2$ atmosphere. Upon completion, the reaction was diluted with water (30 mL), extracted with EtOAc (3×100 mL). The combined organic layers were treated with sat. KF aq. (80 mL) and stirred at RT for 0.5 h, then passed through a CELITE® filter. The filtrate was washed with water, brine, and dried over anhydrous $Na_2SO_4$, filtrated and concentrated under reduced pressure. The residue purified by column chromatography on silica (10-90% EtOAc/P.E.) to afford the title compound. ¹H NMR (400 MHz, CDCl₃): δ 8.49 (s, 1H), 5.08 (d, J=2.8 Hz, 1H), 4.64 (d, J=3.2 Hz, 1H), 4.06 (s, 3H), 3.93 (m, 2H), 1.42 (m, 3H).

Intermediate B07

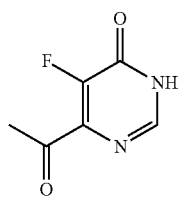

6-acetyl-5-fluoropyrimidin-4 (3H)-one

To a solution of 4-(1-ethoxyvinyl)-5-fluoro-6-methoxypyrimidine (4.5 g, 20.43 mmol) in THF (30 mL) was added 6M HCl aq. (20 mL, 120 mmol) dropwise at 0° C. The resulting reaction solution was stirred at 20° C. for 18 h, and then concentrated under reduced pressure while keeping the temperature of the bath at 40° C. to afford the title compound. ¹H NMR (400 MHz, DMSO-$d_6$): δ 8.15 (s, 1H), 2.50 (s, 3H).

Intermediate B08

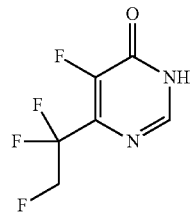

5-fluoro-6-(1,1,2-trifluoroethyl)pyrimidin-4 (3H)-one

Step 1: 2-fluoro-1-(5-fluoro-6-methoxypyrimidin-4-yl)ethanone

A solution of 4-(1-ethoxyvinyl)-5-fluoro-6-methoxypyrimidine, B06 (0.2 g, 0.86 mmol) in ACN (3 mL) was added dropwise to a suspension of 1-chloromethyl-4-fluoro-1,4-diazoniabicyclo[2.2.2]octane bis(tetrafluoroborate) (0.456 g, 1.29 mmol) in ACN (2 mL) and water (1 mL) over 4 h, maintaining the temperature below 15° C. The reaction mixture was then quenched with sat. NaHCO₃ aq. (10 mL) and left to stir for 10 min. After finished, the mixture was extracted with EA (3×10 mL). The combined organic layers were washed with brine, dried over MgSO₄, filtered and concentrated under reduced pressure to afford the title compound. MS: 189.1 (M+1).

Step 2: 5-fluoro-4-methoxy-6-(1,1,2-trifluoroethyl) pyrimidine

To a solution of 2-fluoro-1-(5-fluoro-6-methoxypyrimidin-4-yl)ethanone (0.15 g, 0.60 mmol) in DCM (2 mL) was added diethylaminosulfur trifluoride (0.578 g, 3.59 mmol). The resulting reaction mixture was stirred at 20° C. for 4 h, and then diluted with water, and extracted with EtOAc (3×50 mL). The combined organic layers were concentrated under reduced pressure. The residue was purified by preparative TLC (20% EtOAc/P.E.) to afford the title compound. ¹H NMR (400 MHz, CDCl₃) δ 8.56 (s, 1H), 4.99 (t, J=12.0 Hz, 1H), 4.88 (t, J=12.0 Hz, 1H), 4.12 (s, 3H).

Step 3: 5-fluoro-6-(1,1,2-trifluoroethyl)pyrimidin-4 (3H)-one

To a mixture of 5-fluoro-4-methoxy-6-(1,1,2-trifluoroethyl)pyrimidine (0.05 g, 0.238 mmol) and KI (0.119 g, 0.714 mmol) in ACN (15 mL), was added chlorotrimethylsilane (0.078 g, 0.714 mmol) at RT. The resulting mixture was stirred at 80° C. for 4 h, and then diluted with EtOAc, washed with aq. $Na_2S_2O_3$ and brine, dried over anhydrous $Na_2SO_4$, filtered and concentrated under reduced pressure to afford the title compound. MS: 197.1 (M+1).

Intermediate B09

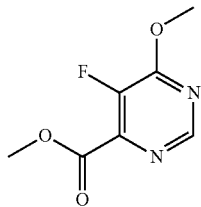

5-fluoro-6-methoxypyrimidine-4-carboxylate

Into a 20-L sealed tube purged with N2, was placed a solution of 4-chloro-5-fluoro-6-methoxypyrimidine, B05 (410 g, 2.52 mol) in MeOH (8.2 L), triethylamine (1.247 kg, 12.32 mol), PdCl$_2$dppf (201 g, 246.32 mmol). The solution was set up for carbonylation in a bomb with CO at 2 bar and heated at 50° C. for 16 h. The solids were filtered out. The filtrate was concentrated under reduced pressure to remove MeOH, and then diluted with EtOAc (4 L). The solids were filtered out. The filtrate was again concentrated under reduced pressure. The residue was purified with column chromatography on silica (10% EtOAc/hexanes) and then re-crystallized (propan-2-ol:H$_2$O=2:7) to afford the title compound MS: 187 (M+1). $^1$H NMR (400 MHz, CDCl$_3$): δ 5.587 (s, 1H), 4.109-4.075 (s, 3H), 4.003-3.935 (s, 3H).

Intermediate B10

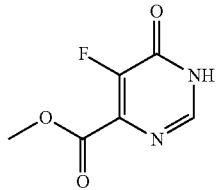

Methyl 5-fluoro-6-hydroxypyrimidine-4-carboxylate

Trimethylsilyl chloride (25.7 mL, 201 mmol) was slowly added to a stirring slurry of methyl 5-fluoro-6-methoxypyrimidine-4-carboxylate, B09 (25 g, 134 mmol) and potassium iodide (33.4 g, 201 mmol) in ACN (300 mL) at 25° C. The resulting mixture was stirred at 25° C. for 2 h. LC-MS indicated reaction was complete. The reaction was quenched with methanol (100 mL) and concentrated to afford the title compound, which was used in the next step without further purification. MS: 173.0 (M+1). $^1$H NMR (400 MHz, DMSO-dd6) 8.12 (s, 1H), 2.59 (s, 3H).

Intermediate B11

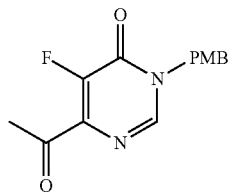

6-acetyl-5-fluoro-3-(4-methoxybenzyl)pyrimidin-4 (3H)-one

To a solution of 6-acetyl-5-fluoropyrimidin-4 (3H)-one, B07 (1.0 g, 5.44 mmol) in DMF (10 mL) was added K$_2$CO$_3$ (2.257 g, 16.33 mmol). The resulting reaction mixture was stirred at 20° C. for 10 min before 1-(chloromethyl)-4-methoxybenzene (1.023 g, 6.53 mmol) was added. The reaction mixture was stirred at 20° C. for another 6 h, and then diluted with water (50 mL) and extracted with EtOAc (3×50 mL). The combined organic layers were washed with water, brine, dried over anhydrous Na$_2$SO$_4$, filtrated and concentrated under reduced pressure. The residue was purified by column chromatography on silica (50% EtOAc/P.E.) to afford the title compound. MS: 277.1 (M+1). $^1$H NMR (400 MHz, CDCl$_3$): δ 8.01 (s, 1H), 7.29 (m, 2H), 6.89 (d, J=8.8, 2H), 5.09 (s, 2H), 3.81 (s, 2H), 2.58 (d, J=8.8, 3H).

The following intermediates in Table 3 were prepared under similar conditions as the above synthetic procedure outlined in the synthesis of intermediate B11 using a corresponding intermediate B that is prepared as described in the Intermediate B section.

TABLE 3

| INT | Structure | IUPAC Name | MS (M + 1) |
|---|---|---|---|
| B12 | ![structure] | 6-(1,1-difluoroethyl)-5-fluoro-3-(4-methoxybenzyl)pyrimidin-4(3H)-one | 299.0 |

TABLE 3-continued

| INT | Structure | IUPAC Name | MS (M + 1) |
|---|---|---|---|
| B13 | 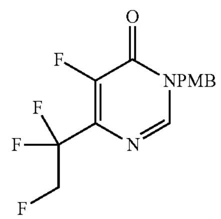 | 5-fluoro-3-(4-methoxybenzyl)-6-(1,1,2-trifluoroethyl)pyrimidin-4(3H)-one | 317.1 |
| B14 | 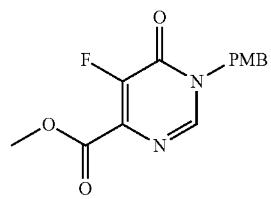 | Methyl 5-fluoro-1-(4-methoxybenzyl)-6-oxo-1,6-dihydropyrimidine-4-carboxylate | 293.0 |
| B15 | 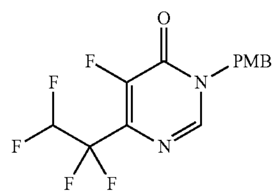 | 5-fluoro-3-(4-methoxybenzyl)-6-(1,1,2,2-tetrafluoroethyl)pyrimidin-4(3H)-one | 335.1 |
| B16 | 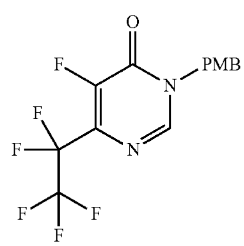 | 5-fluoro-3-(4-methoxybenzyl)-6-(perfluoroethyl)pyrimidin-4(3H)-one | 353.1 |

INTERMEDIATE C SECTION

Intermediate C01

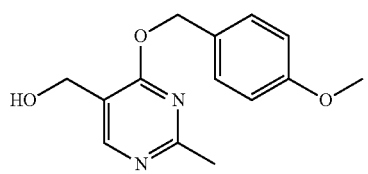 [SMILES: COc1ccc(COc2nc(C)ncc2CO)cc1]

[4-[(4-methoxyphenyl)methoxy]-2-methylpyrimidin-5-yl]methanol

Step 1: methyl 4-hydroxy-2-methylpyrimidine-5-carboxylate

Into a 10-L 4-necked round-bottom flask purged and maintained with an inert atmosphere of nitrogen, was placed 30% solution of NaOCH₃ in MeOH (883 mL), MeOH (5 L), 1,3-diethyl 2-(ethoxymethylidene)propanedioate (350 g, 1.62 mol), ethanimidamide hydrochloride (152.3 g, 1.61 mol). The resulting mixture was heated to reflux for 16 h. The solids were collected on top of a filter to afford the title compound.

Step 2: methyl 4-[(4-methoxyphenyl)methoxy]-2-methylpyrimidine-5-carboxylate Into a 20-L 4-necked round-bottom flask purged and maintained with an inert atmosphere of nitrogen, was placed a solution of methyl 4-hydroxy-2-methylpyrimidine-5-carboxylate (340 g, 2.02 mol) in 1,4-dioxane (8 L), 1-(chloromethyl)-4-methoxybenzene (378 g, 2.42 mol), Ag₂O (655.9 g, 2.83 mol). The resulting mixture was heated to reflux for 15 h. The solids were filtered out. The filtrate was concentrated under vacuum. The residue was purified by column chromatography on silica (10-50% EtOAc/P.E.) to afford the title compound.

Step 3: [4-[(4-methoxyphenyl)methoxy]-2-methylpyrimidin-5-yl]methanol

Into a 20-L 4-necked round-bottom flask purged and maintained with an inert atmosphere of nitrogen, was placed a solution of methyl 4-[(4-methoxyphenyl)methoxy]-2-methyl-pyrimidine-5-carboxylate (600, 2.08 mol) in THF (7500 mL), followed by the addition of LAH (2.5M) (835 mL) dropwise with stirring at −10° C. The resulting solution was stirred at −10° C. for 1 h, and then quenched with EtOAc (2500 mL), and MeOH (2500 mL). The resulting mixture was concentrated under reduced pressure. The residue was purified by column chromatography on silica (1-10% MeOH/DCM) to afford the title compound. MS: 261 (M+1). $^1$H NMR (300 MHz, CDCl$_3$): δ 8.332 (1H, s), 7.358-7.406 (2H, m), 6.888-6.936 (2H, m), 5.417 (2H, s), 4.615 (2H, s), 3.822 (2H, s), 2.641 (3H, s).

Intermediate C02

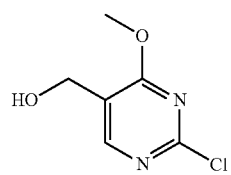

(2-chloro-4-methoxypyrimidin-5-yl)methanol

Step 1: 5-bromo-2-chloro-4-methoxypyrimidine

Into a 5000-mL 4-necked round-bottom flask purged and maintained with an inert atmosphere of nitrogen, was placed 5-bromo-2,4-dichloropyrimidine (160 g, 702.14 mmol) and MeOH (3200 mL), followed by dropwise addition of MeONa (126.8 g, 1.00 equiv) with stirring at 0° C. The resulting solution was stirred at 0° C. for 1 h, then concentrated under reduced pressure. The resulting solution was diluted with water (1 L). The solids were collected on top of a filter to afford the title compound.

Step 2: (2-chloro-4-methoxypyrimidin-5-yl)methanol

Into a 5000-mL 4-necked round-bottom flask purged and maintained with an inert atmosphere of nitrogen, was placed 5-bromo-2-chloro-4-methoxypyrimidine (136 g, 608.62 mmol) and toluene (2500 mL), followed by dropwise addition of n-BuLi (256 mL, 1.05 equiv) with stirring at −78° C. After 30 min stirring at −78° C., HCOOCH$_2$CH$_3$ (90 g, 1.22 mol) was added to the reaction mixture dropwise. The resulting solution was stirred at −78° C. for another 30 min, and then MeOH (218 mL) was added dropwise, followed by addition of NaBH$_4$ (30 g, 793.02 mmol). The reaction solution was stirred at −78° C. for another 10 min before quenched by slow addition of water (1000 mL), and warmed up to 10° C. The resulting mixture was extracted with EtOAc (2×2000 mL). The combined organic layers were washed with brine, dried over anhydrous sodium sulfate, filtered and concentrated under reduced pressure. The residue was washed with PE (1000 mL), and collected on top of a filter to afford the title compound. MS: 175 (M+1). $^1$H NMR (300 MHz, CDCL$_3$, ppm): δ 8.36 (d, J=0.9 Hz, 1H), 4.67 (d, J=0.9 Hz, 2H), 4.08 (s, 3H).

Intermediate C03

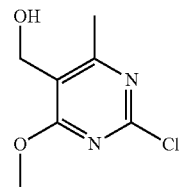

(2-chloro-4-methoxy-6-methylpyrimidin-5-yl)methanol

Intermediate C03 was prepared using a similar procedure outlined in the synthesis for intermediate C02 using 5-bromo-2-chloro-4-methoxy-6-methylpyrimidine. MS: 189 (M+1)

Intermediate C04

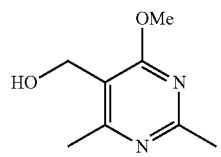

(4-methoxy-2,6-dimethylpyrimidin-5-yl)methanol

Step 1: 1,3-diethyl 2-(1-hydroxyethyl)propanedioate

Into a 50-L 4-necked round-bottom flask purged and maintained with an inert atmosphere of nitrogen, was placed a solution of 1,3-diethyl 2-acetylpropanedioate (5000 g, 24.73 mol) in AcOH (25 L). This was followed by the addition of NaBH$_4$ (1220 g, 32.25 mol) in several batches at 0° C. over 1 h. The resulting solution was stirred at 0° C. for 3 h, and then quenched with water (2 L), and extracted with DCM (3×5 L). The combined organic layers were concentrated under reduced pressure. The residue was purified by column chromatography on silica (50% EtOAc/hexanes) to afford the title compound.

Step 2: 1,3-diethyl 2-[1-(acetyloxy)ethyl]propanedioate

Into a 50-L 4-necked round-bottom flask purged and maintained with an inert atmosphere of nitrogen, was placed a solution of 1,3-diethyl 2-(1-hydroxyethyl)propanedioate (3800 g, 18.61 mol) in DCM (38 L), acetic anhydride (2280 g, 22.35 mol), TEA (3762 g, 37.18 mol), 4-dimethylaminopyridine (454 g, 3.72 mol). The resulting solution was stirred at 60° C. for 16 h, then quenched by the addition of water (4 L), and extracted with DCM (3×5 L). The combined organic layers were concentrated under reduced pressure. The residue was purified by column chromatography on silica (2% EtOAc/P.E.) to afford the title compound.

Step 3: 1,3-diethyl 2-ethylidenepropanedioate

Into a 10-L 4-necked round-bottom flask purged and maintained with an inert atmosphere of nitrogen, was placed 1,3-diethyl 2-[1-(acetyloxy)ethyl]propanedioate (3200 g, 12.99 mol). This was followed by dropwise addition of acetaldehyde (1716 g, 38.95 mol) with stirring at 80° C. over 40 min. The resulting solution was stirred at 80° C. for 16 h, then cooled to 20° C. and quenched by the addition of water (5 L), and then extracted with EtOAc (3×2 L). The combined organic layers were concentrated under reduced pressure. The residue was purified by column chromatography on silica (0.5% EtOAc/P.E.) to afford the title compound.

Step 4: Ethyl 2,4-dimethyl-6-oxo-1,4,5,6-tetrahydropyrimidine-5-carboxylate

Into a 50-L 4-necked round-bottom flask purged and maintained with an inert atmosphere of nitrogen, was placed a solution of ethanimidamide hydrochloride (1060 g, 11.21 mol) in ethanol (30 L), NaOEt (1380 g, 14.68 mol). This was followed by dropwise addition of a solution of 1,3-diethyl 2-ethylidenepropanedioate (1700 g, 9.13 mol) in ethanol (4 L) with stirring at 60° C. over 30 min. The resulting solution was stirred at 60° C. for 2 h, and then cooled to 20° C. The solid was filtered out. The filtrate was concentrated under reduced pressure to afford the title compound which was used as is in the next step.

Step 5: Ethyl 2,4-dimethyl-6-oxo-1,6-dihydropyrimidine-5-carboxylate

Into a 50-L 4-necked round-bottom flask purged and maintained with an inert atmosphere of nitrogen, was placed a solution of ethyl 2,4-dimethyl-6-oxo-1,4,5,6-tetrahydropyrimidine-5-carboxylate (2500 g, 12.61 mol) in 1,4-dioxane (25 L), potassium carbonate (7200 g, 52.09 mol), NBS (2300 g, 12.92 mol), BPO (78 g, 304.39 mmol). The resulting solution was stirred at 80° C. for 16 h. The reaction mixture was cooled to 20° C., and then quenched by the addition of water (10 L). The pH value of the solution was adjusted to 7 with HCl. The resulting solution was extracted with DCM (3×5 L). The combined organic layers were concentrated under reduced pressure. The residue was purified by column chromatography on silica (5% MeOH/DCM) to afford the title compound.

Step 6: Ethyl 4-chloro-2,6-dimethylpyrimidine-5-carboxylate

Into a 50-L 4-necked round-bottom flask purged and maintained with an inert atmosphere of nitrogen, was placed ethyl 2,4-dimethyl-6-oxo-1,6-dihydropyrimidine-5-carboxylate (1100 g, 5.61 mol) and POCl$_3$ (11 L). The resulting solution was stirred at 80° C. for 5 h, then concentrated under reduced pressure to afford the title compound, which was used in the next step as is.

Step 7: Ethyl 4-methoxy-2,6-dimethylpyrimidine-5-carboxylate

Into a 50-L 4-necked round-bottom flask purged and maintained with an inert atmosphere of nitrogen, was placed a solution of ethyl 4-chloro-2,6-dimethylpyrimidine-5-carboxylate (2000 g, 9.32 mol) in MeOH (20 L). The resulting solution was stirred at RT for 2 h, and concentrated under reduced pressure. The residue was dissolved in water (5 L). The resulting solution was extracted with DCM (3×2 L). The combined organic layers were concentrated under reduced pressure. The residue was purified by column chromatography on silica (10% EtOAc/P.E.) to afford the title compound.

Step 8: (4-methoxy-2,6-dimethylpyrimidin-5-yl)methanol

Into a 10-L 4-necked round-bottom flask purged and maintained with an inert atmosphere of nitrogen, was placed a solution of ethyl 4-methoxy-2,6-dimethylpyrimidine-5-carboxylate (270 g, 1.28 mol) in THF (2.7 L). This was followed by the addition of LAH (54 g, 1.42 mol) in several batches at 0° C. over 30 min. The resulting solution was stirred at 0° C. for 2 h, and then quenched by the addition of 15% NaOH (65 mL). After stirred for 1 h, the solids were filtered out. The filtrate was concentrated under reduced pressure to afford the title compound. MS: 169 (M+1). $^1$H NMR (400 MHz, CDCl$_3$): δ 4.678 (s, 2H), 3.988 (s, 3H), 2.562 (s, 3H), 2.493 (s, 3H).

Intermediate C05

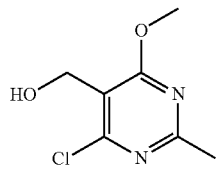

(4-chloro-6-methoxy-2-methylpyrimidin-5-yl)methanol

Step 1: 4,6-dichloro-2-methylpyrimidine-5-carbaldehyde

To a solution of POCl$_3$ (31.4 mL, 337 mmol) was added DMF (2.90 g, 39.6 mmol) at 0° C., then the resulting mixture was stirred at 25° C. for 0.5 h. Then 2-methylpyrimidine-4,6-diol (5 g, 39.6 mmol) was added. After being stirred at 25° C. for 1 h, the reaction mixture was heated at 120° C. for 10 h, and then poured onto ice (100 mL), and extracted with EtOAc (3×100 mL). The combined organic layers were washed with brine, dried over anhydrous Na$_2$SO$_4$, filtrated and concentrated under reduced pressure to afford the title compound which was used directly in the next step. MS: 190.9 (M+1).

Step 2: (4,6-dichloro-2-methylpyrimidin-5-yl)methanol

To a solution of 4,6-dichloro-2-methylpyrimidine-5-carbaldehyde (7.57 g, 39.6 mmol) in MeOH (75 mL) was added NaBH$_4$ (1.799 g, 47.6 mmol) at −40° C., then the mixture was stirred at 25° C. After 0.5 h, the reaction mixture was quenched with H$_2$O (100 mL), extracted with EtOAc (3×100 mL). The combined organic layers were dried over anhydrous Na$_2$SO$_4$, filtrated and concentrated under reduced pressure. The residue was purified by column chromatography on silica (5-33% EtOAc/P.E.) to afford the title compound. MS: 193.1 (M+1). $^1$H NMR (400 MHz, CDCl$_3$): δ 4.91 (s, 2H), 2.69 (s, 3H).

Step 3: (4-chloro-6-methoxy-2-methylpyrimidin-5-yl)methanol

To a solution of (4, 6-dichloro-2-methylpyrimidin-5-yl)methanol (1 g, 5.18 mmol) in MeOH (10 mL) was added sodium methoxide (0.280 g, 5.18 mmol), then the mixture was stirred at 25° C. for 4 h. The reaction mixture was then quenched with $H_2O$ (10 mL), extracted with EtOAc (3×10 mL). The combined organic layers were dried over anhydrous $Na_2SO_4$, filtrated and concentrated under reduced pressure to obtain the title compound. MS: 189.1 (M+1).

The following intermediates in Table 4 were prepared using a similar procedure as outlined in the synthesis of intermediate C05, but replacing the 4,6-dichloro-2-methylpyrimidine-5-carbaldehyde in Step 2 with the appropriate chloro substituted pyrimidine-5-carbaldehyde.

TABLE 4

| INT | Structure | IUPAC Name | MS (M + 1) |
|---|---|---|---|
| C06 | 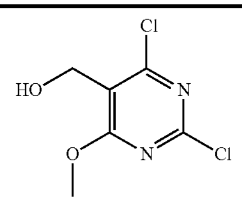 | (2,4-dichloro-6-methoxy-pyrimidin-5-yl)methanol | 211.4 |
| C07 | 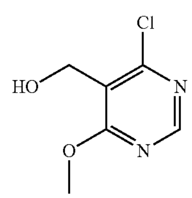 | (4-chloro-6-methoxy-pyrimidin-5-yl)methanol | 175.2 |

Intermediate C08

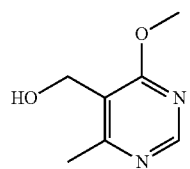

(4-methoxy-6-methylpyrimidin-5-yl)methanol

To a stirred solution of (4-chloro-6-methoxypyrimidin-5-yl)methanol (5 g, 28.6 mmol) in THF (100 mL) was added $Cs_2CO_3$ (18.66 g, 57.3 mmol) and trimethylboroxine (7.19 g, 57.3 mmol) in a sealed tube. After degassed with nitrogen for 5 min, 1,1'-bis(diphenyl phosphino)ferrocene-palladium (II)dichloride dichloromethane complex (2.339 g, 2.86 mmol) was added. The resulting mixture was heated at 70° C. for 7 h, and then filtered through CELITE®, washed with EtOAc and concentrated under reduced pressure. The residue was purified with column chromatography on silica (50-80% EtOAc/P.E.) to afford the title compound. MS: 155.2 (M+1). $^1$H NMR (300 MHz, $CDCl_3$): δ 8.332 (1H, s), 7.358-7.406 (2H, m), 6.888-6.936 (2H, m), 5.417 (2H, s), 4.615 (2H, s), 3.822 (2H, s), 2.641 (3H, s).

The following intermediates in Table 5 were prepared using a similar procedure as outlined in the synthesis of intermediate C08 but replacing the (4-chloro-6-methoxypyrimidin-5-yl)methanol with (2-chloro-4-methoxypyrimidin-5-yl)methanol and methylboronic acid or vinylboronic acid.

TABLE 5

| INT | Structure | IUPAC Name | MS (M + 1) |
|---|---|---|---|
| C09 | 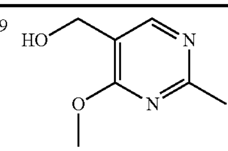 | (4-methoxy-2-methyl-pyrimidin-5-yl)methanol | 155.0 |
| C10 | 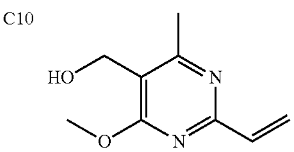 | (4-methoxy-6-methyl-2-vinylpyrimidin-5-yl)methanol | 181.3 |

Intermediate C11

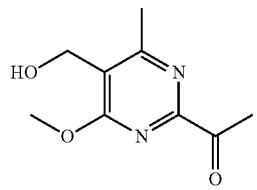

1-(5-(hydroxymethyl)-4-methoxy-6-methylpyrimidin-2-yl)ethan-1-one

Step 1: (2-(1-ethoxyvinyl)-4-methoxy-6-methylpyrimidin-5-yl)methanol

To a stirred solution of (2-chloro-4-methoxy-6-methylpyrimidin-5-yl)methanol (80 mg, 0.424 mmol) in DMF (1 mL) was added $Pd(Ph_3P)_4$ (49.0 mg, 0.042 mmol) under $N_2$ and the resulting mixture was stirred at 100° C. for 2 h. Then the mixture was diluted in water (10 mL) extracted with EtOAc (3×20 mL). The combined organic layers were treated with sat. KF aq. (20 mL) and stirred at 20° C. for 30 min before filtering over CELITE®. The filtrate was washed with water, brine, and dried over anhydrous $Na_2SO_4$, filtrated and concentrated under reduced pressure. The residue was purified by Preparative TLC plate (50% EtOAc/P.E.) to afford the title compound. $^1$H NMR (400 MHz, $CDCl_3$): δ 4.71 (br s, 2H), 4.58 (d, J=1.47 Hz, 1H), 3.94-4.11 (m, 5H), 2.59 (s, 3H), 1.49 (t, J=7.03 Hz, 3H).

Step 2: 1-(5-(hydroxymethyl)-4-methoxy-6-methylpyrimidin-2-yl)ethan-1-one

To a solution of (2-(1-ethoxyvinyl)-4-methoxy-6-methylpyrimidin-5-yl)methanol (130 mg, 0.580 mmol) in EtOAc (10 mL) was added 4N solution of HCl in EtOAc (5 mL). The resulting reaction mixture was stirred at 20° C. for 1 h, and then concentrated under reduced pressure to afford the title compound which was used into next step without purification. ¹H NMR (400 MHz, DMSO-d₆): δ 4.52 (s, 2H), 3.99 (s, 3H), 2.62 (s, 3H), 2.55 (s, 3H).

Intermediate C12

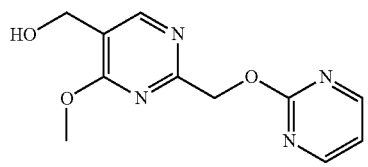 [SMILES: COc1nc(COc2ncccn2)ncc1CO]

(4-methoxy-6-methyl-2-((pyrimidin-2-yloxy)methyl)pyrimidin-5-yl)methanol

Step 1: 5-(((tert-butyldiphenylsilyl)oxy)methyl)-2-chloro-4-methoxy-6-methylpyrimidine To a solution of (2-chloro-4-methoxy-6-methylpyrimidin-5-yl)methanol (0.8 g, 4.24 mmol) in THF (14 mL) was added 1H-imidazole (0.866 g, 12.72 mmol) and tertbutyl-chloro-diphenylsilane (1.749 g, 6.36 mmol). The resulting mixture was stirred at 20° C. for 2 h, and then quenched with water and extracted with EtOAc (3×20 mL). The combined organic layers were washed with brine, dried over anhydrous Na₂SO₄, filtered and concentrated under reduced pressure. The residue was purified by column chromatography on silica (1.25% EtOAc/P.E.) to afford the title compound. MS: 472.2 (M+1). ¹H NMR (400 MHz, CDCl₃) δ 1.03 (s, 9H) 2.54 (s, 3H) 3.80 (s, 3H) 4.70 (s, 2H) 7.34-7.49 (m, 6H) 7.66 (dd, J=7.95, 1.34 Hz, 4H).

Step 2: 5-(((tert-butyldiphenylsilyl)oxy)methyl)-4-methoxy-6-methyl-2-vinylpyrimidine To a solution of 5-(((tert-butyldiphenylsilyl)oxy)methyl)-2-chloro-4-methoxy-6-methylpyrimidine (1.4 g, 3.28 mmol) in 1,4-dioxane (20 mL) and water (4 mL) was added K₂CO₃ (0.906 g, 6.56 mmol) and 4,4,5,5-tetramethyl-2-vinyl-1,3,2-dioxaborolane (1.010 g, 6.56 mmol) and PdCl₂(dppf) (0.240 g, 0.328 mmol). The resulting mixture was stirred at 100° C. for 2 h, and then diluted with water and extracted with EtOAc (3×30 mL). The combined organic layers were washed with brine, dried over anhydrous Na₂SO₄, filtered and concentrated under reduced pressure. The residue was purified by column chromatography on silica (2% EtOAc/P.E.) to afford the title compound. MS: 419.3 (M+1). ¹H NMR (400 MHz, CDCl₃) δ 1.04 (s, 9H) 2.56 (s, 3H) 3.83 (s, 3H) 4.74 (s, 2H) 5.67 (dd, J=10.30, 1.97 Hz, 1H) 6.51-6.62 (m, 1H) 6.71-6.82 (m, 1H) 7.34-7.48 (m, 6H) 7.69 (dd, J=7.89, 1.32 Hz, 4H).

Step 3: 5-(((tert-butyldiphenylsilyl)oxy)methyl)-4-methoxy-6-methylpyrimidine-2-carbaldehyde To a solution of 5-(((tert-butyldiphenylsilyl)oxy)methyl)-4-methoxy-6-methyl-2-vinylpyrimidine (1.2 g, 2.87 mmol) in 1,4-Dioxane (30 mL) and water (10 mL) was added osmium(VIII) oxide (0.018 g, 0.072 mmol) and 2,6-dimethylpyridine (0.860 g, 8.03 mmol). The resulting mixture was stirred at 20° C. for 30 min before sodium periodate (2.269 g, 10.61 mmol) was added. The reaction mixture was stirred at 20° C. for 10 h, and then quenched with saturated aqueous solution of Na₂SO₃ (10 mL) and extracted with EtOAc (3×20 mL). The combined organic layers were washed with 1M HCl, brine, and dried over anhydrous Na₂SO₄, filtered and concentrated under reduced pressure to afford the title compound, which was used for the next step without further purification. MS: 421.3 (M+1). ¹H NMR (400 MHz, CDCl₃) δ 1.03 (s, 9H) 2.68 (s, 2H) 3.86-3.93 (m, 2H) 4.79 (s, 2H) 7.34-7.49 (m, 6H) 7.61-7.70 (m, 4H) 9.95 (s, 1H).

Step 4: (5-(((tert-butyldiphenyl silyl)oxy)methyl)-4-methoxy-6-methylpyrimidin-2-yl)methanol To a solution of 5-(((tert-butyldiphenylsilyl)oxy)methyl)-4-methoxy-6-methylpyrimidine-2-carbaldehyde (0.65 g, 1.545 mmol) in EtOH (40 mL) was added Zn(BH₄)₂ (0.386 mL, 0.386 mmol) at −10-0° C. The resulting solution was stirred at this temperature for 30 min before quenched with 4N HCl (5 mL), diluted with water (50 mL) and extracted with EtOAc (3×50 mL). The combined organic layers were washed with brine, dried over anhydrous Na₂SO₄, filtered and concentrated under reduced pressure to afford the title compound. MS: 423.3 (M+1). ¹H NMR (400 MHz, CDCl₃) δ 0.99-1.11 (m, 13H) 2.59 (s, 3H) 3.81 (s, 3H) 4.68 (s, 2H) 4.74 (s, 2H) 7.33-7.49 (m, 8H) 7.63-7.70 (m, 5H).

Step 5: 5-(((tert-butyldiphenylsilyl)oxy)methyl)-4-methoxy-6-methyl-2-((pyrimidin-2-yloxy)methyl)pyrimidine To a solution of (5-(((tert-butyldiphenylsilyl)oxy)methyl)-4-methoxy-6-methylpyrimidin-2-yl)methanol (90 mg, 0.213 mmol) in t-BuOH (5 mL) was added 2-chloropyrimidine (24.39 mg, 0.213 mmol) and t-BuOK (59.7 mg, 0.532 mmol) at 50° C. The resulting reaction mixture was stirred at 50° C. for 2 h before diluted with water (20 mL) and extracted with EtOAc (3×20 mL). The combined organic layers were washed with brine, dried over anhydrous Na₂SO₄, filtered and concentrated under reduced pressure to afford the title compound, which was used to next step without purification. MS: 501.3 (M+1).

Step 6: (4-methoxy-6-methyl-2-((pyrimidin-2-yloxy)methyl)pyrimidin-5-yl)methanol To a solution of 5-(((tert-butyldiphenylsilyl)oxy)methyl)-4-methoxy-6-methyl-2-((pyrimidin-2-yloxy)methyl)pyrimidine (130 mg, 0.260 mmol) in THF (3 mL) was added TBAF (82 mg, 0.260 mmol) at 20° C. The resulting reaction mixture was stirred at 20° C. for 2 hrs before being diluted with water (50 mL) and extracted with EtOAc (3×50 mL). The combined organic extracts were washed with brine, dried over anhydrous Na₂SO₄, filtered and concentrated under reduced pressure. The residue was purified by preparative TLC plate (100% EtOAc) to afford the title compound. MS: 263.1 (M+1).

Intermediate C13

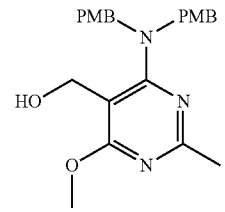

(4-(Bis(4-methoxybenzyl)amino)-6-methoxy-2-methylpyrimidin-5-yl)methanol

Step 1: 4-(Bis(4-methoxybenzyl)amino)-6-chloro-2-methylpyrimidine-5-carbaldehyde 4,6-dichloro-2-methylpyrimidine-5-carbaldehyde (600 mg, 3.14 mmol) was dissolved in DCM (15.7 mL) and chilled to 0° C. where Hunig's base (1207 µl, 6.91 mmol) was added followed by the addition of bis(4-methoxybenzyl)amine (889 mg, 3.46 mmol). The solution was stirred at 0° C. for 4 h. The reaction was added to DCM (20 mL). The solution was washed with water (2×10 mL) and concentrated under reduced pressure. The residue was purified by column chromatography on silica (0-50% EtOAc/hexanes) to afford title compound. MS: 412.2 (M+1).

Step 2: (4-(Bis(4-methoxybenzyl)amino)-6-methoxy-2-methylpyrimidin-5-yl)methanol 4-(Bis(4-methoxybenzyl)amino)-6-chloro-2-methylpyrimidine-5-carbaldehyde (1.2 g, 2.91 mmol) was added to a flask and was dissolved in THF (14.57 mL) and chilled to −78° C. where sodium methoxide (25% by weight in MeOH) (1.382 mL, 5.83 mmol) was added and stirred at 0° C. for 50 min. NaBH₄ (0.110 g, 2.91 mmol) was added at 0° C. and stirred for an additional 1 h. Water (1000 µL) was added to the solution at 0° C. and stirred for 10 min. Then the solution was taken into DCM (20 mL) and washed with water (2×10 mL) and the organic was concentrated under reduced pressure to isolate the title compound. MS: 410.3 (M+1).

Intermediate C14

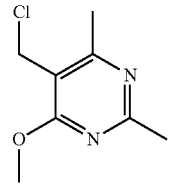

5-(chloromethyl)-4-methoxy-2,6-dimethylpyrimidine

To a stirred solution of (4-methoxy-2,6-dimethylpyrimidin-5-yl)methanol, C04 (1 g, 5.95 mmol) in DCM (15 mL) was added DIPEA (3.12 mL, 17.84 mmol) and MSCl (1.390 mL, 17.84 mmol) at 0° C. under N₂. The resulting reaction mixture was stirred at 15° C. for 2 h before diluted with water (15 mL) and extracted with DCM (3×20 mL). The combined organic layers were dried over anhydrous Na₂SO₄, filtered and concentrated under reduced pressure. The residue was purified by column chromatography on silica (1-33% EtOAc/P.E.) to afford the title compound. MS: 187 (M+1). ¹H NMR (400 MHz, CDCl₃): δ4.63 (s, 1H) 4.01 (s, 1H) 2.58 (s, 1H) 2.52 (s, 1H).

The following intermediates in Table 6 were prepared using a similar procedure as outlined in the synthesis of intermediate C14 but replacing the (4-methoxy-2,6-dimethylpyrimidin-5-yl)methanol with a corresponding pyrimidin-5-ylmethanol that is listed as starting material in Table 6.

TABLE 6

| NT | Starting material | Structure | IUPAC Name | MS (M + 1) |
|---|---|---|---|---|
| C15 | C09 | 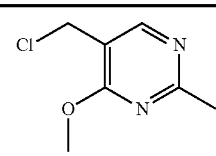 | 5-(chloromethyl)-4-methoxy-2-methylpyrimidine | 173.0 |
| C16 | C08 | 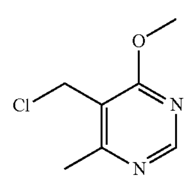 | 5-(chloromethyl)-4-methoxy-6-methylpyrimidine | 173.2 |
| C20 | C03 | 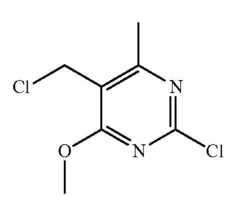 | 2-chloro-5-(chloromethyl)-4-methoxy-6-methylpyrimidine | 207.0 |
| C21 | C11 | 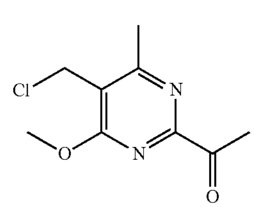 | 1-(5-(chloromethyl)-4-methoxy-6-methylpyrimidin-2-yl)ethanone | 215.1 |

TABLE 6-continued

| NT | Starting material | Structure | IUPAC Name | MS (M + 1) |
|---|---|---|---|---|
| C22 | C05 | 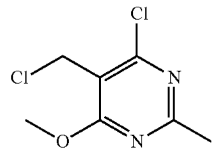 | 4-chloro-5-(chloromethyl)-6-methoxy-2-methylpyrimidine | 207.0 |
| C23 | C06 | 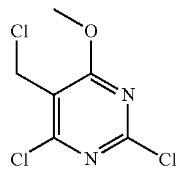 | 2,4-dichloro-5-(chloromethyl)-6-methoxypyrimidine | 226.9 |
| C24 | C10 | 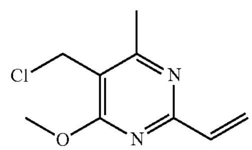 | 5-(chloromethyl)-4-methoxy-6-methyl-2-vinylpyrimidine | 199.0 |
| C25 | C12 | 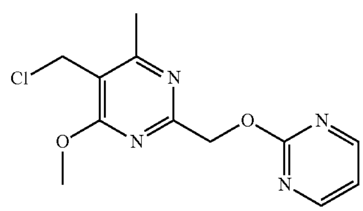 [SMILES: COc1nc(COc2ncccn2)nc(C)c1CCl] | 5-(chloromethyl)-4-methoxy-6-methyl-2-((pyrimidin-2-yloxy)methyl)pyrimidine | 281.1 |

INTERMEDIATE AB SECTION

Intermediate AB01

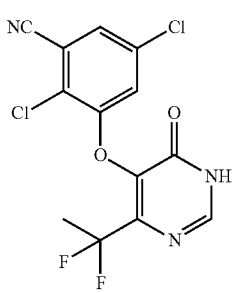 [SMILES: CC(F)(F)c1nc[nH]c(=O)c1Oc1cc(Cl)cc(C#N)c1Cl]

2,5-dichloro-3-((4-(1,1-difluoroethyl)-6-oxo-1,6-dihydropyrimidin-5-yl)oxy)benzonitrile Step 1: 3-bromo-5-((4-(1,1-difluoroethyl)-1-(4-methoxybenzyl)-6-oxo-1,6-dihydropyrimidin-5-yl)oxy)benzonitrile To a solution of 5-bromo-6-(1,1-difluoroethyl)-3-(4-methoxybenzyl)pyrimidin-4 (3H)-one (MK8507 case) (100 mg, 0.28 mmol)) in NMP (0.5 mL) was added 2,5-dichloro-3-hydroxybenzonitrile, A04 (105 mg, 0.56 mmol) and $K_2CO_3$ (192 mg, 1.39 mmol). The resulting reaction mixture was stirred at 140° C. for 2 h, and then filtered and purified by reverse phase HPLC (ACN/water with 0.1% TFA modifier) to afford the title compound as the TFA salt. MS: 477 (M+1).

Step 2: 2,5-dichloro-3-((4-(1,1-difluoroethyl)-6-oxo-1,6-dihydropyrimidin-5-yl)oxy)benzonitrile To a mixture of 2, 5-dichloro-3-((4-(1,1-difluoroethyl)-1-(4-methoxybenzyl)-6-oxo-1, 6-dihydropyrimidin-5-yl) oxy) benzonitrile (50 mg, 0.107 mmol) in TFA (2 mL), was add TFAA (0.227 mL, 1.609 mmol). The resulting solution was heated to 110° C. for 2 h, and then concentrated under the reduced pressure to afford the crude title compound, which was used directly in the next step without further purification. MS: 346.1 (M+1).

The following intermediates in Table 7 were prepared in an analogous manner as for the synthesis of intermediate AB01 described above and summarized as follows: $SN_{Ar}$ reaction between 5-bromo-6-(1,1-difluoroethyl)-3-(4-methoxybenzyl)pyrimidin-4 (3H)-one and a corresponding phenol from the intermediate A section, followed by deprotection to remove PMB group using TFA/TFAA.

TABLE 7

| INT | Structure | IUPAC Name | MS (M + 1) |
|---|---|---|---|
| AB02 | 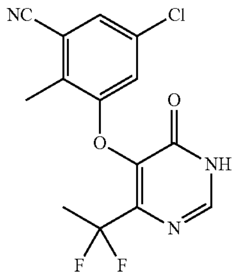 [SMILES: Cc1c(C#N)cc(Cl)cc1Oc1c(C(C)(F)F)nc[nH]c1=O] | 5-chloro-3-((4-(1,1-difluoroethyl)-6-oxo-1,6-dihydropyrimidin-5-yl)oxy)-2-methylbenzonitrile | 326 |
| AB03 | 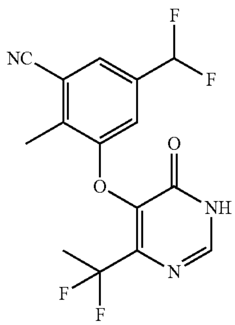 [SMILES: Cc1c(C#N)cc(C(F)F)cc1Oc1c(C(C)(F)F)nc[nH]c1=O] | 3-((4-(1,1-difluoroethyl)-6-oxo-1,6-dihydropyrimidin-5-yl)oxy)-5-(difluoromethyl)-2-methylbenzonitrile | 342 |

Intermediate AB04

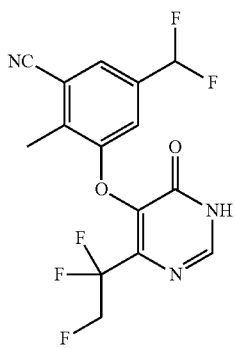 [SMILES: Cc1c(C#N)cc(C(F)F)cc1Oc1c(C(F)(F)CF)nc[nH]c1=O]

5-(difluoromethyl)-2-methyl-3-((6-oxo-4-(1,1,2-trifluoroethyl)-1,6-dihydropyrimidin-5-yl)oxy)benzonitrile Step 1: 5-(difluoromethyl)-3-((1-(4-methoxybenzyl)-6-oxo-4-(1,1,2-trifluoroethyl)-1,6-dihydropyrimidin-5-yl)oxy)-2-methylbenzonitrile To a mixture of 5-fluoro-3-(4-methoxybenzyl)-6-(1,1,2-trifluoroethyl)pyrimidin-4 (3H)-one, B13 (0.075 g, 0.237 mmol) and $K_2CO_3$ (0.066 g, 0.474 mmol) in DMA (2 mL) was added 5-(difluoromethyl)-3-hydroxy-2-methylbenzonitrile, A02 (0.043 g, 0.237 mmol) in one portion at 15° C. under $N_2$. The mixture was stirred at 100° C. for 16 h. The mixture was concentrated and diluted with EtOAc (5 mL), washed with $H_2O$ and brine, dried over anhydrous $Na_2SO_4$, filtered and concentrated The residue was purified by preparative TLC plates (100% EtOAc) to afford the title compound. MS: 480.2 (M+1).

Step 2: 5-(difluoromethyl)-2-methyl-3-((6-oxo-4-(1,1,2-trifluoroethyl)-1,6-dihydropyrimidin-5-yl)oxy) benzonitrile To a solution of 5-(difluoromethyl)-3-((1-(4-methoxybenzyl)-6-oxo-4-(1,1,2-trifluoroethyl)-1,6-dihydropyrimidin-5-yl)oxy)-2-methylbenzonitrile (70 mg, 0.146 mmol) in TFA (1 mL), was added TFAA (1 mL) and the mixture was stirred at 100° C. for 4 h. The mixture was concentrated and diluted with EtOAc (5 mL), washed with $H_2O$, saturated aqueous solution of $NaHCO_3$ and brine, dried over anhydrous $Na_2SO_4$, filtered and concentrated to give the crude title compound. MS: 360.1 (M+1).

The following intermediates in Table 8 were prepared in an analogous manner as for the synthesis of intermediate AB04 described above and summarized as follows: $SN_{Ar}$ reaction using a phenol from intermediate A section and a pyrimidone from intermediate B section, then deprotection to remove PMB group using TFA/TFAA.

TABLE 8

| INTERMEDIATE | Structure | IUPAC Name | MS (M + 1) |
|---|---|---|---|
| AB05 | 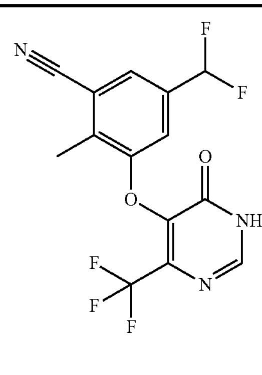 | 5-(difluoromethyl)-2-methyl-3-((6-oxo-4-(trifluoromethyl)-1,6-dihydropyrimidin-5-yl)oxy)benzonitrile | 346.1 |

TABLE 8-continued

| INTER-MEDIATE | Structure | IUPAC Name | MS (M + 1) |
|---|---|---|---|
| AB06 | 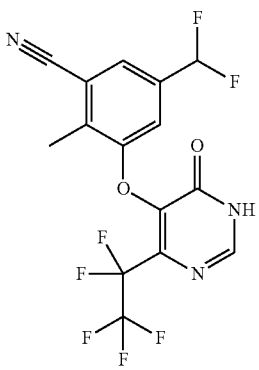 [SMILES: Cc1c(C#N)cc(C(F)F)cc1Oc1c(C(F)(F)C(F)(F)F)nc[nH]c1=O] | 5-(difluoromethyl)-2-methyl-3-((6-oxo-4-(perfluoroethyl)-1,6-dihydropyrimidin-5-yl)oxy)benzonitrile | 396.1 |
| AB07 | 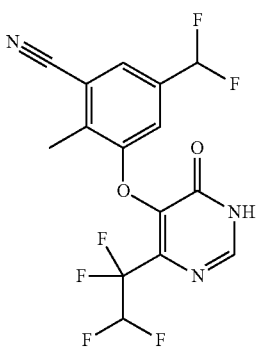 [SMILES: Cc1c(C#N)cc(C(F)F)cc1Oc1c(C(F)(F)C(F)F)nc[nH]c1=O] | 5-(difluoromethyl)-2-methyl-3-((6-oxo-4-(1,1,2,2-tetrafluoroethyl)-1,6-dihydropyrimidin-5-yl)oxy)benzonitrile | 378.1 |
| AB08 | 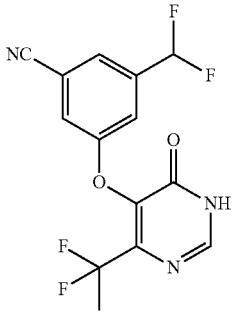 [SMILES: CC(F)(F)c1nc[nH]c(=O)c1Oc1cc(C#N)cc(C(F)F)c1] | 3-((4-(1,1-difluoroethyl)-6-oxo-1,6-dihydropyrimidin-5-yl)oxy)-5-(difluoromethyl)benzonitrile | 328 |
| AB09 | 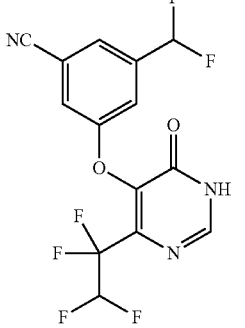 | 3-(difluoromethyl)-5-((6-oxo-4-(1,1,2,2-tetrafluoroethyl)-1,6-dihydropyrimidin-5-yl)oxy)benzonitrile | 364.0 |

TABLE 8-continued
| INTER-MEDIATE | Structure | IUPAC Name | MS (M + 1) |
|---|---|---|---|
| AB10 | 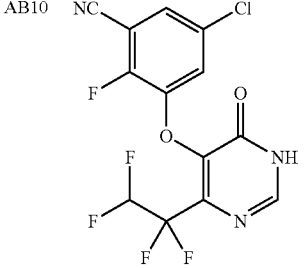 | 5-chloro-2-fluoro-3-((6-oxo-4-(1,1,2,2-tetrafluoroethyl)-1,6-dihydropyrimidin-5-yl)oxy)benzonitrile | 366.1 |
| AB11 | 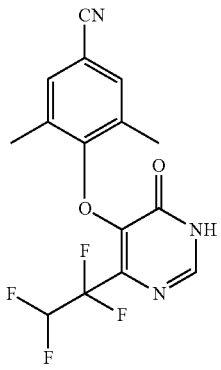 | 3,5-dimethyl-4-((6-oxo-4-(1,1,2,2-tetrafluoroethyl)-1,6-dihydropyrimidin-5-yl)oxy)benzonitrile | 341.9 |
| AB12 | 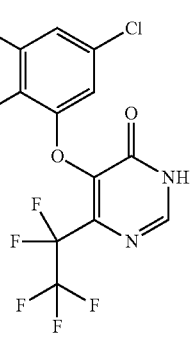 | 5-chloro-2-fluoro-3-((6-oxo-4-(perfluoroethyl)-1,6-dihydropyrimidin-5-yl)oxy)benzonitrile | 384.0 |
| AB13 | 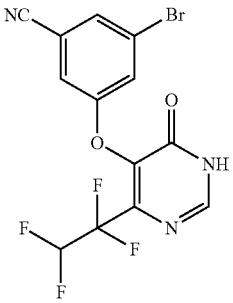 [SMILES: N#Cc1cc(Br)cc(Oc2c(C(F)(F)C(F)F)nc[nH]c2=O)c1] | 3-bromo-5-((6-oxo-4-(1,1,2,2-tetrafluoroethyl)-1,6-dihydropyrimidin-5-yl)oxy)benzonitrile | 392.0 |

Intermediate AB14

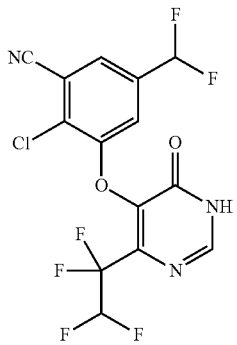 [SMILES: N#Cc1cc(C(F)F)cc(Oc2c(C(F)(F)C(F)F)nc[nH]c2=O)c1Cl]

2-chloro-5-(difluoromethyl)-3-((6-oxo-4-(1,1,2,2-tetrafluoroethyl)-1,6-dihydropyrimidin-5-yl)oxy)benzonitrile Step 1: 5-bromo-2-chloro-3-((1-(4-methoxybenzyl)-6-oxo-4-(1,1,2,2-tetrafluoroethyl)-1,6-dihydropyrimidin-5-yl)oxy)benzonitrile To a stirred solution of 5-fluoro-3-(4-methoxybenzyl)-6-(1,1,2,2-tetrafluoroethyl)-pyrimidin-4 (3H)-one, B15 (2 g, 5.98 mmol), 5-bromo-2-chloro-3-hydroxybenzonitrile, A03 (1.391 g, 5.98 mmol) in sulfolane (75 mL) was added $K_2CO_3$ (1.654 g, 11.97 mmol) and the mixture solution was stirred at 130° C. for 16 h. The mixture was diluted with water (4×50 mL) and extracted with EtOAc (3×50 mL). The combined organic layer was washed with brine, dried over anhydrous $Na_2SO_4$, filtered and concentrated under reduced pressure. The residue was purified by column chromatography on silica (25-100% EtOAc/P.E.) to afford the title compound. MS: 548.0 (M+1).

Step 2: 2-chloro-3-((1-(4-methoxybenzyl)-6-oxo-4-(1,1,2,2-tetrafluoroethyl)-1,6-dihydropyrimidin-5-yl)oxy)-5-vinylbenzonitrile To a stirred solution of 5-bromo-2-chloro-3-((1-(4-methoxybenzyl)-6-oxo-4-(1,1,2,2-tetrafluoroethyl)-1,6-dihydropyrimidin-5-yl)oxy)benzonitrile (1.45 g, 2.65 mmol) in 1,4-dioxane (24.07 mL) and water (4.93 mL), was added potassium vinyltrifluoroborate (0.426 g, 3.18 mmol), $K_2CO_3$ (0.733 g, 5.30 mmol) and $PdCl_2(dppf)$ (0.194 g, 0.265 mmol) under $N_2$. The resulting mixture was heated to 100° C. for 2 h, and then diluted with water (50 mL) and extracted with EtOAc (3×30 mL). The combined organic layer was washed with brine, dried over anhydrous $Na_2SO_4$, filtered and concentrated under reduced pressure. The residue was purified by column chromatography on silica (25-100% EtOAc/P.E.) to give the title compound. MS: 494.1 (M+1).

Step 3: 2-chloro-5-formyl-3-((1-(4-methoxybenzyl)-6-oxo-4-(1,1,2,2-tetrafluoroethyl)-1,6-dihydropyrimidin-5-yl)oxy)benzonitrile To a solution of 2-chloro-3-((1-(4-methoxybenzyl)-6-oxo-4-(1,1,2,2-tetrafluoroethyl)-1,6-dihydropyrimidin-5-yl)oxy)-5-vinylbenzonitrile (950 mg, 1.924 mmol) in 1,4-dioxane (15 mL) and water (5 mL), was added osmium (VIII) oxide (98 mg, 0.385 mmol), 2,6-dimethylpyridine (206 mg, 1.924 mmol). The resulting mixture was stirred for 15 min before sodium periodate (1234 mg, 5.77 mmol) was added. The resulting mixture was stirred at 25° C. for 12 h, and then was quenched with saturate aqueous $Na_2SO_3$, diluted with water (50 mL) and extracted with EtOAc (3×30 mL). The combined organic layers were washed with brine, dried over anhydrous $Na_2SO_4$, filtered and concentrated under reduced pressure to give the title compound. MS: 496.1 (M+1).

Step 4: 2-chloro-5-(difluoromethyl)-3-((1-(4-methoxybenzyl)-6-oxo-4-(1,1,2,2-tetrafluoroethyl)-1,6-dihydropyrimidin-5-yl)oxy)benzonitrile To a stirred solution of 2-chloro-5-formyl-3-((1-(4-methoxybenzyl)-6-oxo-4-(1,1,2,2-tetrafluoroethyl)-1,6-dihydropyrimidin-5-yl)oxy)benzonitrile (950 mg, 1.916 mmol) in DCM (20 mL) was added DAST (2532 µL, 19.16 mmol) and the mixture solution was stirred at 0° C. for 12 h. The mixture was diluted with water (40 mL) and extracted with DCM (3×30 mL). The combined organic layers were dried over anhydrous $Na_2SO_4$, filtered and concentrated under reduced pressure. The residue was purified by column chromatography on silica (25-100% EtOAc/P.E.) to give the title compound. MS: 518.1 (M+1).

Step 5: 2-chloro-5-(difluoromethyl)-3-((6-oxo-4-(1,1,2,2-tetrafluoroethyl)-1,6-dihydropyrimidin-5-yl)oxy)benzonitrile A solution of 2-chloro-5-(difluoromethyl)-3-((1-(4-methoxybenzyl)-6-oxo-4-(1,1,2,2-tetrafluoroethyl)-1,6-dihydropyrimidin-5-yl)oxy)benzonitrile (80 mg, 0.154 mmol) in TFA (1 mL) and TFAA (0.5 mL) was stirred at 110° C. for 1 h. The mixture was concentrated under reduced pressure. The residue was taken up with saturated aqueous $NaHCO_3$ (0.5 mL) and water (30 mL), and extracted with EtOAc (3×15 mL). The combined organic layers were washed with brine, dried over anhydrous $Na_2SO_4$, filtered and concentrated under reduced pressure to afford the title compound. MS: 398.0 (M+1).

Intermediate AB15

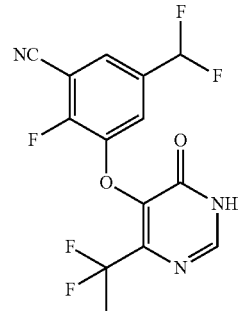 [SMILES: CC(F)(F)c1nc[nH]c(=O)c1Oc1cc(C(F)F)cc(C#N)c1F]

3-((4-(1,1-difluoroethyl)-6-oxo-1,6-dihydropyrimidin-5-yl)oxy)-5-(difluoromethyl)-2-fluorobenzonitrile Intermediate AB15 was prepared in an analogous manner as that described for intermediate AB14 using a corresponding intermediate A and intermediate B. MS: 346.1 (M+1).

Intermediate AB16

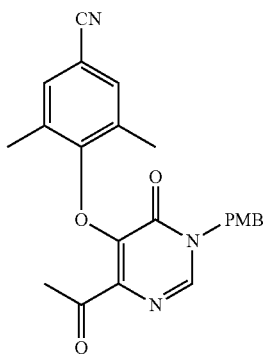

4-((4-acetyl-1-(4-methoxybenzyl)-6-oxo-1,6-dihydropyrimidin-5-yl)oxy)-3,5-dimethylbenzonitrile To a solution of 6-acetyl-5-fluoro-3-(4-methoxybenzyl) pyrimidin-4 (3H)-one, B11 (150 mg, 0.489 mmol) in DMA (1.000 mL) was added 4-hydroxy-3, 5-dimethylbenzonitrile (144 mg, 0.977 mmol) and $K_2CO_3$ (135 mg, 0.977 mmol). The resulting reaction mixture was stirred at 80° C. for 40 min, and then diluted with water (5 mL), extracted with EtOAc (3×10 mL). The combined organic layers were washed with water, brine, filtrated and concentrated under reduced pressure. The residue was purified by preparative TLC plate (50% EtOAc/P.E.) to give the title compound. $^1$H NMR (400 MHz, $CDCl_3$) δ 7.88 (s, 1H), 7.24 (s, 2H), 7.15 (s, 1H), 7.13 (s, 1H), 6.80 (d, J=8.8, 2H), 5.23 (s, 2H), 3.73 (s, 2H), 2.51 (s, 3H), 2.11 (s, 6H).

Intermediate AB17

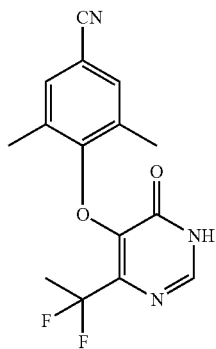 [SMILES: Cc1cc(C#N)cc(C)c1Oc1c(C(C)(F)F)nc[nH]c1=O]

3-chloro-4-((4-(1,1-difluoroethyl)-6-oxo-1,6-dihydropyrimidin-5-yl)oxy)-5-methylbenzonitrile Step 1: 4-((4-(1,1-difluoroethyl)-1-(4-methoxybenzyl)-6-oxo-1,6-dihydropyrimidin-5-yl)oxy)-3,5-dimethylbenzonitrile To a solution of 4-((4-acetyl-1-(4-methoxybenzyl)-6-oxo-1, 6-dihydropyrimidin-5-yl) oxy)-3, 5-dimethylbenzonitrile (160 mg, 0.357 mmol) in DCM (3.0 mL) was added DAST (0.472 mL, 3.57 mmol) at 20° C. The resulting reaction mixture was stirred at 50° C. for 18 h, and then diluted with water (3.0 mL), and extracted with DCM (3×5 mL). The combined organic layers were washed with brine, dried over anhydrous $Na_2SO_4$, filtrated and concentrated under reduced pressure. The residue was purified by preparative TLC plate (50% EtOAc/P.E.) to afford the title compound. $^1$H NMR (400 MHz, DMSO-$d_6$) δ 8.61 (s, 1H), 7.52 (s, 2H), 7.24 (d, J=8.4, 2H), 6.89 (d, J=8.4, 2H), 4.99 (s, 2H), 3.72 (s, 3H), 2.06 (s, 6H), 1.99 (m, 3H).

Step 3: 4-((4-(1,1-difluoroethyl)-6-oxo-1,6-dihydropyrimidin-5-yl)oxy)-3,5-dimethylbenzonitrile A suspension of 4-((4-(1,1-difluoroethyl)-1-(4-methoxybenzyl)-6-oxo-1,6-dihydropyrimidin-5-yl)oxy)-3, 5-dimethylbenzonitrile (100 mg, 0.212 mmol) in TFA (0.8 mL, 10.38 mmol) and TFAA (0.4 mL, 2.83 mmol) was stirred at 110° C. for 4 h. The reaction mixture was concentrated under reduced pressure. The residue was taken up with saturated aqueous $NaHCO_3$ adjusting pH to 9, and then extracted with DCM (3×10 mL). The combined organic layers were washed with brine, dried over anhydrous $Na_2SO_4$, filtrated and concentrated under reduced pressure to give the title compound. MS: 306.1 (M+1).

Intermediate AB18

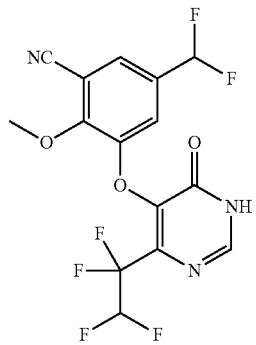 [SMILES: COc1c(C#N)cc(C(F)F)cc1Oc1c(C(F)(F)C(F)F)nc[nH]c1=O]

5-(difluoromethyl)-2-methoxy-3-((6-oxo-4-(1,1,2,2-tetrafluoroethyl)-1,6-dihydropyrimidin-5-yl)oxy)benzonitrile Step 1: 5-(3-bromo-5-(difluoromethyl)-2-methoxyphenoxy)-3-(4-methoxybenzyl)-6-(1,1,2,2-tetrafluoroethyl)pyrimidin-4 (3H)-one To a solution of 5-fluoro-3-(4-methoxybenzyl)-6-(1,1,2, 2-tetrafluoroethyl)pyrimidin-4 (3H)-one, B15 (300 mg, 0.898 mmol) in DMF (5 mL) was added 3-bromo-5-(difluoromethyl)-2-methoxyphenol, A08 (227 mg, 0.898 mmol) and $K_2CO_3$ (372 mg, 2.69 mmol). The reaction mixture was stirred at 80° C. for 2 h, and poured into $H_2O$ (30 mL), extracted with EtOAc (3×20 mL). The combined organic layers were washed with brine, filtered and concentrated under reduced pressure. The residue was purified by preparative TLC plate (33% EtOAc/P.E.) to afford the title compound. MS: 567.0 (M+1). $^1$H NMR (400 MHz, $CDCl_3$): δ 8.10 (s, 1H), 7.45 (s, 1H), 7.25-7.27 (m, 2H), 6.88-6.92 (m, 2H), 6.79 (s, 1H), 6.14-6.65 (m, 2H), 5.06 (s, 2H), 3.95 (s, 3H), 3.80-3.83 (m, 3H).

Step 2: 5-(difluoromethyl)-2-methoxy-3-((1-(4-methoxybenzyl)-6-oxo-4-(1,1,2,2-tetrafluoroethyl)-1,6-dihydropyrimidin-5-yl)oxy)benzonitrile To a solution of 5-(3-bromo-5-(difluoromethyl)-2-methoxyphenoxy)-3-(4-methoxybenzyl)-6-(1,1,2,2-tetrafluoroethyl)pyrimidin-4 (3H)-one (140 mg, 0.247 mmol) in DMF (2 mL) was added dicyanozinc (145 mg, 1.234 mmol), zinc (32.3 mg, 0.494 mmol) and bis(tri-tert-butylphosphine)palladium(0) (25.2 mg, 0.049 mmol) under $N_2$. The resulting mixture was stirred at 110° C. for 12 h, and then filtered. The filtrate was diluted with $H_2O$ (10 mL), extracted with EtOAc (3×10 mL). The combined organic layers were washed with brine, dried over anhydrous $Na_2SO_4$, filtered and concentrated under reduced pressure to give the title compound. MS: 514.0 (M+1).

Step 3: 5-(difluoromethyl)-2-methoxy-3-((6-oxo-4-(1,1,2,2-tetrafluoroethyl)-1,6-dihydropyrimidin-5-yl)oxy)benzonitrile To a solution of 5-(difluoromethyl)-2-methoxy-3-((1-(4-methoxybenzyl)-6-oxo-4-(1,1,2,2-tetrafluoroethyl)-1,6-dihydropyrimidin-5-yl)oxy)benzonitrile (80 mg, 0.156 mmol) in TFA (1 mL) was added trifluoroacetic anhydride (0.440 mL, 3.12 mmol). The resulting reaction mixture was stirred at 110° C. for 1 h, and then concentrated under reduced pressure. The residue was purified by preparative TLC plate (33% EtOAc/P.E.) to give the title compound. MS: 394.1 (M+1).

Intermediate AB19

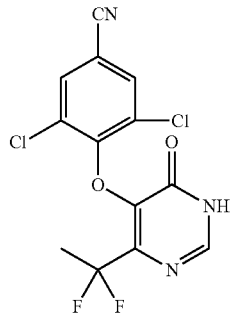 [SMILES: CC(F)(F)c1nc[nH]c(=O)c1Oc1c(Cl)cc(C#N)cc1Cl]

3,5-dichloro-4-((4-(1,1-difluoroethyl)-6-oxo-1,6-dihydropyrimidin-5-yl)oxy)benzonitrile

Step 1: 5-(4-bromo-2,6-dichlorophenoxy)-6-(1,1-difluoroethyl)-3-(4-methoxybenzyl)pyrimidin-4 (3H)-one A mixture of 5-bromo-6-(1,1-difluoroethyl)-3-(4-methoxybenzyl)pyrimidin-4 (3H)-one (MK8507 case) (400 mg, 1.114 mmol) and 4-bromo-2,6-dichlorophenol (808 mg, 3.34 mmol) and $K_2CO_3$ (770 mg, 5.57 mmol) in NMP (10 mL) was stirred at 140° C. for 27 h, and then diluted with $H_2O$ (50 mL) and extracted with EtOAc (2×50 mL). The combined organic layers were washed with brine, dried over anhydrous $Na_2SO_4$, filtered and concentrated under reduced pressure. The residue was purified by preparative TLC plate (50% EtOAc/P.E.) to afford the title compound. MS: 521 (M+1).

Step 2: 3,5-dichloro-4-((4-(1,1-difluoroethyl)-1-(4-methoxybenzyl)-6-oxo-1,6-dihydropyrimidin-5-yl)oxy)benzonitrile A mixture of 5-(4-bromo-2,6-dichlorophenoxy)-6-(1,1-difluoroethyl)-3-(4-methoxybenzyl) pyrimidin-4 (3H)-one (200 mg, 0.385 mmol) and cyanocopper (172 mg, 1.923 mmol) in NMP (10 mL) was stirred at 180° C. for 5 h. The reaction mixture was diluted with $H_2O$ (40 mL) and extracted with EtOAc (2×30 mL). The combined organic layers were washed with brine, dried over anhydrous $Na_2SO_4$, filtered and concentrated under reduced pressure. The residue was purified by preparative TLC plate (33% EtOAc/P.E.) to afford the title compound. MS: 647 (M+1).

Step 3: 3,5-dichloro-4-((4-(1,1-difluoroethyl)-6-oxo-1,6-dihydropyrimidin-5-yl)oxy)benzonitrile A solution of 3,5-dichloro-4-((4-(1,1-difluoroethyl)-1-(4-methoxybenzyl)-6-oxo-1,6-dihydropyrimidin-5-yl)oxy) benzonitrile (100 mg, 0.214 mmol) in TFA (2 mL, 0.214 mmol) and 2,2,2-trifluoroacetic anhydride (1 mL, 0.214 mmol) was stirred at 100° C. for 4 h, and then concentrated under reduced pressure. The residue was taken up with saturated aqueous $NaHCO_3$ solution resulting in a solution with pH=7-8, and then extracted with EtOAc (2×20 mL). The combined organic layers were washed with brine, dried over anhydrous $Na_2SO_4$, filtered and concentrated under reduced pressure to give the title compound, which was used for the next step without further purification. MS: 346 (M+1).

Intermediate AB20

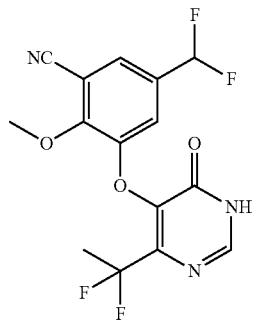 [SMILES: COc1c(C#N)cc(C(F)F)cc1Oc1c(C(C)(F)F)nc[nH]c1=O]

3-((4-(1,1-difluoroethyl)-6-oxo-1,6-dihydropyrimidin-5-yl)oxy)-5-(difluoromethyl)-2-methoxybenzonitrile

Step 1: 6-acetyl-5-(3-bromo-5-(difluoromethyl)-2-methoxyphenoxy)-3-(4-methoxybenzyl)pyrimidin-4 (3H)-one A solution of 6-acetyl-5-fluoro-3-(4-methoxybenzyl)pyrimidin-4 (3H)-one, B11 (546 mg, 1.976 mmol), $K_2CO_3$ (819 mg, 5.93 mmol) and 3-bromo-5-(difluoromethyl)-2-methoxyphenol, A08 (500 mg, 1.976 mmol) in DMF (10 mL) was stirred at 80° C. for 2 h, and then poured into water (50 mL), and extracted with EtOAc (3×30 mL). The combined organic layers were washed with brine, dried over anhydrous Na₂SO₄, filtered and concentrated under reduced pressure. The residue was purified by column chromatography on silica (5-20% EtOAc/P.E.) to give the title compound. MS: 509.0 (M+1).

Step 2: 5-(3-bromo-5-(difluoromethyl)-2-methoxyphenoxy)-6-(1,1-difluoroethyl)-3-(4-methoxybenzyl)pyrimidin-4 (3H)-one To a solution of 6-acetyl-5-(3-bromo-5-(difluoromethyl)-2-methoxyphenoxy)-3-(4-methoxybenzyl)pyrimidin-4 (3H)-one (470 mg, 0.923 mmol) in DCM (10 mL) was added DAST (1.219 mL, 9.23 mmol). The resulting reaction mixture was stirred at 20° C. for 1 h, and then poured into saturated aqueous NaHCO₃ (50 mL) dropwise, extracted with DCM (3×30 mL). The combined organic layers were washed with brine, dried over anhydrous Na₂SO₄, filtered and concentrated under reduced pressure. The residue was purified by column chromatography on silica (3.3-25% EtOAc/P.E.) to afford the title compound. MS: 531.0 (M+1).

Step 3: 3-((4-(1,1-difluoroethyl)-1-(4-methoxybenzyl)-6-oxo-1,6-dihydropyrimidin-5-yl)oxy)-5-(difluoromethyl)-2-methoxybenzonitrile To a solution of 5-(3-bromo-5-(difluoromethyl)-2-methoxyphenoxy)-6-(1,1-difluoroethyl)-3-(4-methoxybenzyl)pyrimidin-4 (3H)-one (335.6 mg, 0.632 mmol) in DMF (5 mL) was added dicyanozinc (371 mg, 3.16 mmol), zinc (83 mg, 1.263 mmol) and Pd(tBu₃P)₂ (97 mg, 0.189 mmol) under N₂. The resulting mixture was stirred at 110° C. for 12 h, and then diluted with H₂O (25 mL), and extracted with EtOAc (3×15 mL). The combined organic layers were washed with brine, dried over anhydrous Na₂SO₄, filtered and concentrated under reduced pressure to give the title compound. MS: 478.4 (M+1).

Step 4: 3-((4-(1,1-difluoroethyl)-6-oxo-1,6-dihydropyrimidin-5-yl)oxy)-5-(difluoromethyl)-2-methoxybenzonitrile To a solution of 3-((4-(1,1-difluoroethyl)-1-(4-methoxybenzyl)-6-oxo-1,6-dihydropyrimidin-5-yl)oxy)-5-(difluoromethyl)-2-methoxybenzonitrile (141 mg, 0.295 mmol) in TFA (2 mL) was added TFAA (1 mL, 7.08 mmol). The resulting reaction mixture was stirred at 110° C. for 0.5 h, then carefully poured into ice water (5 mL), extracted with EtOAc (3×3 mL). The combined organic layers were washed with brine, dried over anhydrous Na₂SO₄, filtered and concentrated under reduced pressure. The residue was purified by preparative TLC plate (50% EtOAc/P.E.) to afford the title compound. MS: 358.0 (M+1).

The following intermediates in Table 9 were prepared in an analogous manner as for the synthesis of intermediate AB20 using a corresponding phenol from Intermediate A section.

TABLE 9

| INT | Structure | IUPAC Name | MS (M + 1) |
|-----|-----------|------------|------------|
| AB21 | 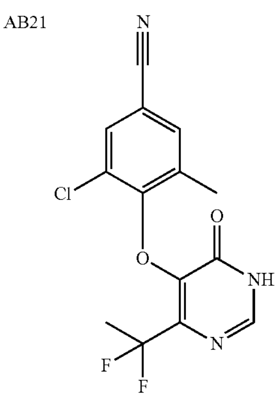 | 3-chloro-4-((4-(1,1-difluoroethyl)-6-oxo-1,6-dihydropyrimidin-5-yl)oxy)-5-methylbenzonitrile | 325.7 |
| AB22 | 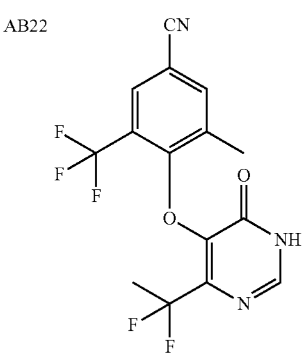 | 4-((4-(1,1-difluoroethyl)-6-oxo-1,6-dihydropyrimidin-5-yl)oxy)-3-methyl-5-(trifluoromethyl)benzonitrile | 360.1 |

TABLE 9-continued

| INT | Structure | IUPAC Name | MS (M + 1) |
|---|---|---|---|
| AB23 | NC, F, F, F, O, O, NH, N (3-((4-(1,1-difluoroethyl)-6-oxo-1,6-dihydropyrimidin-5-yl)oxy)-2,4,5-trifluorobenzonitrile structure) | 3-((4-(1,1-difluoroethyl)-6-oxo-1,6-dihydropyrimidin-5-yl)oxy)-2,4,5-trifluorobenzonitrile | 332.1 |

Intermediate AB24

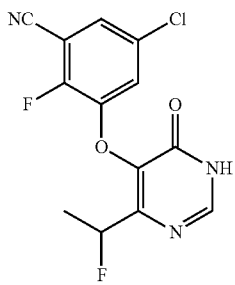

5-chloro-2-fluoro-3-((4-(1-fluoroethyl)-6-oxo-1,6-dihydropyrimidin-5-yl)oxy)benzonitrile Step 1: 6-acetyl-5-(3-bromo-5-chloro-2-fluorophenoxy)-3-(4-methoxybenzyl)pyrimidin-4 (3H)-one To a solution of 6-acetyl-5-fluoro-3-(4-methoxybenzyl)pyrimidin-4 (3H)-one, B11 (2 g, 7.24 mmol) in DMF (10 mL) was added 3-bromo-5-chloro-2-fluorophenol, A05 (1.959 g, 8.69 mmol) and K₂CO₃ (2.001 g, 14.48 mmol). The resulting mixture was stirred at 60° C. for 4 h, and then poured into H₂O (100 mL), extracted with EtOAc (3×50 mL). The combined organic layers were dried over anhydrous Na₂SO₄, filtered and concentrated under reduced pressure. The residue was purified by column chromatography on silica (2-3.3% MeOH/DCM) to give the title compound.

Step 2: 5-(3-bromo-5-chloro-2-fluorophenoxy)-6-(1-hydroxyethyl)-3-(4-methoxybenzyl)pyrimidin-4 (3H)-one To a solution of 6-acetyl-5-(3-bromo-5-chloro-2-fluorophenoxy)-3-(4-methoxybenzyl)pyrimidin-4 (3H)-one (300 mg, 0.623 mmol) in THF (2 mL) was added 0.1 M solution of Zn(BH₄)₂ in THF (0.934 mL, 0.093 mmol) at −30° C. and the mixture was stirred for 10 min. The reaction mixture was added water (1 drop) and then concentrated under reduced pressure to afford the title compound.

Step 3: 5-(3-bromo-5-chloro-2-fluorophenoxy)-6-(1-fluoroethyl)-3-(4-methoxybenzyl)pyrimidin-4 (3H)-one To a solution of 5-(3-bromo-5-chloro-2-fluorophenoxy)-6-(1-hydroxyethyl)-3-(4-methoxybenzyl)pyrimidin-4 (3H)-one (680 mg, 1.406 mmol) in DCM (10 mL) was added DAST (0.427 mL, 3.23 mmol) at 0° C. The resulting reaction mixture was stirred at 0° C. for 1 h, and then diluted with water (5 mL), extracted with DCM (3×10 mL). The combined organic layers were washed with brine, dried over anhydrous Na₂SO₄, filtrated and concentrated under reduced pressure to give the title compound.

Step 4: 5-chloro-2-fluoro-3-((4-(1-fluoroethyl)-1-(4-methoxybenzyl)-6-oxo-1,6-dihydropyrimidin-5-yl)oxy)benzonitrile To a stirred solution of 5-(3-bromo-5-chloro-2-fluorophenoxy)-6-(1-fluoroethyl)-3-(4-methoxybenzyl)pyrimidin-4 (3H)-one (340 mg, 0.700 mmol) in NMP (3 mL) was added cyanocopper (217 mg, 2.423 mmol) under N₂. The resulting mixture was stirred at 170° C. for 12 h, and then diluted with H₂O (30 mL) and EtOAc (30 mL). The mixture was filtered through CELITE®. The filtrate was extracted with EA (3×30 mL). The combined organic layers were washed with brine, dried over anhydrous Na₂SO₄, filtered and concentrated under reduced pressure. The residue was triturated with MeOH (20 mL) to afford the title compound.

Step 5: 5-chloro-2-fluoro-3-((4-(1-fluoroethyl)-6-oxo-1,6-dihydropyrimidin-5-yl)oxy)benzonitrile To a solution of 5-chloro-2-fluoro-3-((4-(1-fluoroethyl)-1-(4-methoxybenzyl)-6-oxo-1,6-dihydropyrimidin-5-yl)oxy)benzonitrile (0.217 g, 0.503 mmol) in TFA (1.5 mL) was added TFAA (0.75 mL). The resulting mixture was stirred at 100° C. for 6 h, and then diluted with DCM (10 mL), and concentrated under reduced pressure to afford the title compound.

The following intermediate in Table 10 was prepared in an analogous manner to that described above for intermediate AB24 except using 4-bromo-2,6-dichlorophenol in place of 3-bromo-5-chloro-2-fluorophenol in Step 1.

TABLE 10

| INT | Structure | IUPAC Name | MS (M + 1) |
|---|---|---|---|
| AB25 | (structure shown) | 3,5-dichloro-4-((4-(1-fluoroethyl)-6-oxo-1,6-dihydro-pyrimidin-5-yl)oxy)benzonitrile | 328.0 |

Intermediate AB26

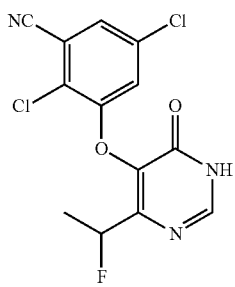 [SMILES: CC(F)c1nc[nH]c(=O)c1Oc1cc(Cl)cc(C#N)c1Cl]

2,5-dichloro-3-((4-(1-fluoroethyl)-6-oxo-1,6-dihydropyrimidin-5-yl)oxy)benzonitrile Step 1: 3-((4-acetyl-1-(4-methoxybenzyl)-6-oxo-1,6-dihydropyrimidin-5-yl)oxy)-2,5-dichlorobenzonitrile To a solution of 6-acetyl-5-fluoro-3-(4-methoxybenzyl)pyrimidin-4 (3H)-one, B11 (1.5 g, 5.43 mmol) in sulfolane (15 mL) was added 2,5-dichloro-3-hydroxybenzonitrile, A04 (1.531 g, 8.14 mmol) and $K_2CO_3$ (1.876 g, 13.57 mmol). The resulting mixture was stirred at 60° C. for 2 h, and then diluted with water (60 mL) and extracted with EtOAc (3×45 mL). The combined organic layers were washed with brine, dried over anhydrous $Na_2SO_4$, filtered and concentrated under reduced pressure. The residue was purified by column chromatography on silica (50-100% EtOAc/P.E.) to afford the title compound. MS: 444.1 (M+1).

Step 2: 2,5-dichloro-3-((6-(1-hydroxyethyl)-3-(4-methoxybenzyl)-4-oxo-1,2,3,4-tetrahydropyrimidin-5-yl)oxy)benzonitrile To a solution of 3-((4-acetyl-1-(4-methoxybenzyl)-6-oxo-1,6-dihydropyrimidin-5-yl)oxy)-2,5-dichlorobenzonitrile (800 mg, 1.801 mmol) in THF (10 mL), was added $NaBH_4$ (68.1 mg, 1.801 mmol). The resulting mixture was stirred at 25° C. for 0.5 h, and then quenched with water (30 mL), extracted with EtOAc (3×25 mL). The combined organic layers were washed with brine, dried over anhydrous $Na_2SO_4$, filtered and concentrated under reduced pressure. The residue was purified by column chromatography on silica (33% EtOAc/P.E.) to afford the title compound. MS: 448.1 (M+1).

Step 3: 2,5-dichloro-3-((4-(1-hydroxyethyl)-1-(4-methoxybenzyl)-6-oxo-1,6-dihydropyrimidin-5-yl)oxy)benzonitrile To a solution of 2,5-dichloro-3-((6-(1-hydroxyethyl)-3-(4-methoxybenzyl)-4-oxo-1,2,3,4-tetrahydropyrimidin-5-yl)oxy)benzonitrile (300 mg, 0.669 mmol) in $H_2O$ (1 mL) and ACN (4 mL), was added CAN (734 mg, 1.338 mmol). The resulting mixture was stirred at 25° C. for 0.5 h, and then quenched with water (16 mL), extracted with EtOAc (3×12 mL). The combined organic layers were washed with brine, dried over anhydrous $Na_2SO_4$, filtered and concentrated under reduced pressure to afford the title compound. MS: 446.1 (M+1).

Step 4: 2,5-dichloro-3-((4-(1-fluoroethyl)-1-(4-methoxybenzyl)-6-oxo-1,6-dihydropyrimidin-5-yl)oxy)benzonitrile To a solution of 2,5-dichloro-3-((4-(1-hydroxyethyl)-1-(4-methoxybenzyl)-6-oxo-1,6-dihydropyrimidin-5-yl)oxy)benzonitrile (173.3 mg, 0.388 mmol) in DCM (4 mL) was added DAST (0.513 mL, 3.88 mmol). The resulting mixture was stirred at 25° C. for 1 h, and then carefully quenched with saturated aqueous $NaHCO_3$ (16 mL), extracted with DCM (3×12 mL). The combined organic layers were washed with brine, dried over anhydrous $Na_2SO_4$, filtered and concentrated under reduced pressure. The residue was purified by column chromatography on silica (20% EtOAc/P.E.) to afford the title compound. MS: 448.3 $[M]^+$.

Step 5: 2,5-dichloro-3-((4-(1-fluoroethyl)-6-oxo-1,6-dihydropyrimidin-5-yl)oxy)benzonitrile To a solution of 2,5-dichloro-3-((4-(1-fluoroethyl)-1-(4-methoxybenzyl)-6-oxo-1,6-dihydropyrimidin-5-yl)oxy)benzonitrile (380 mg, 0.848 mmol) in TFA (5 mL) was added TFAA (5 mL, 35.4 mmol). The resulting mixture was stirred at 100° C. for 0.5 h, and then carefully quenched with saturated aqueous $NaHCO_3$ solution (20 mL), extracted with EtOAc (3×15 mL). The combined organic layers were washed with brine, dried over anhydrous $Na_2SO_4$, filtered and concentrated under reduced pressure to afford the title compound, which was used for the next step without further purification. MS: 382.2 $[M]^+$.

Intermediate AB27

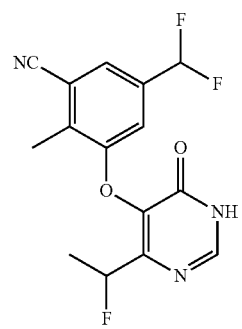 [SMILES: Cc1c(C#N)cc(C(F)F)cc1Oc1c(C(C)F)nc[nH]c1=O]

5-(difluoromethyl)-3-((4-(1-fluoroethyl)-6-oxo-1,6-dihydropyrimidin-5-yl)oxy)-2-methylbenzonitrile Step 1: 3-((4-acetyl-1-(4-methoxybenzyl)-6-oxo-1,6-dihydropyrimidin-5-yl)oxy)-5-(difluoromethyl)-2-methylbenzonitrile To a solution of 5-(difluoromethyl)-3-hydroxy-2-methylbenzonitrile, A02 (0.663 g, 3.62 mmol) and 6-acetyl-5-fluoro-3-(4-methoxybenzyl)pyrimidin-4 (3H)-one, B11 (1.0 g, 3.62 mmol) in DMF (10 mL) was added $K_2CO_3$ (1.001 g, 7.24 mmol). The resulting mixture was stirred at 60° C. for 2 h, and then diluted with water (30 mL), extracted with EtOAc (3×20 mL). The combined organic layers were washed with brine, dried over anhydrous $Na_2SO_4$, filtered and concentrated under reduced pressure to give the title compound. MS: 440.2 (M+1).

Step 2: 5-(difluoromethyl)-3-((6-(1-hydroxyethyl)-3-(4-methoxybenzyl)-4-oxo-1,2,3,4-tetrahydropyrimidin-5-yl)oxy)-2-methylbenzonitrile To a solution of 3-((4-acetyl-1-(4-methoxybenzyl)-6-oxo-1,6-dihydropyrimidin-5-yl)oxy)-5-(difluoromethyl)-2-methylbenzonitrile (1.5 g, 3.41 mmol) in MeOH (8 mL), was added $NaBH_4$ (0.129 g, 3.41 mmol). The resulting mixture was stirred at 25° C. for 0.5 h, and then quenched with water (30 mL), extracted with EtOAc (3×25 mL). The combined organic layers were washed with brine, dried over anhydrous $Na_2SO_4$, filtered and concentrated under reduced pressure to afford the title compound. MS: 444.1 (M+1).

Step 3: 5-(difluoromethyl)-3-((4-(1-hydroxyethyl)-1-(4-methoxybenzyl)-6-oxo-1,6-dihydropyrimidin-5-yl)oxy)-2-methylbenzonitrile To a stirred solution of 5-(difluoromethyl)-3-((6-(1-hydroxyethyl)-3-(4-methoxybenzyl)-4-oxo-1,2,3,4-tetrahydropyrimidin-5-yl)oxy)-2-methylbenzonitrile (1 g, 2.255 mmol) in THF (12 mL) was added DDQ (0.563 g, 2.481 mmol). The resulting mixture was stirred at 25° C. for 12 h, and then diluted with water (30 mL), extracted with EtOAc (3×20 mL). The combined organic layers were washed with brine, dried over anhydrous $Na_2SO_4$, filtered and concentrated under reduced pressure. The residue was purified by column chromatography on silica (50-100% EtOAc/P.E.) to afford the title compound. MS: 442.1 (M+1).

Step 4: 5-(difluoromethyl)-3-((4-(1-fluoroethyl)-1-(4-methoxybenzyl)-6-oxo-1,6-dihydropyrimidin-5-yl)oxy)-2-methylbenzonitrile To a stirred solution of 5-(difluoromethyl)-3-((4-(1-hydroxyethyl)-1-(4-methoxybenzyl)-6-oxo-1,6-dihydropyrimidin-5-yl)oxy)-2-methylbenzonitrile (900 mg, 1.631 mmol) in DCM (8 mL) was added DAST (2.155 mL, 16.31 mmol). The resulting mixture was stirred at 0° C. for 4 h, and then diluted with water (20 mL), extracted with EtOAc (3×20 mL). The combined organic layers were washed with brine, dried over anhydrous $Na_2SO_4$, filtered and concentrated under reduced pressure. The residue was purified by column chromatography on silica (50-100% EtOAc/P.E.) to afford the title compound. MS: 444.2 (M+1).

Step 5: 5-(difluoromethyl)-3-((4-(1-fluoroethyl)-6-oxo-1,6-dihydropyrimidin-5-yl)oxy)-2-methylbenzonitrile A solution of 5-(difluoromethyl)-3-((4-(1-fluoroethyl)-1-(4-methoxybenzyl)-6-oxo-1,6-dihydropyrimidin-5-yl)oxy)-2-methylbenzonitrile (300 mg, 0.677 mmol) in TFA (2 mL) and TFAA (1 mL) was stirred at 110° C. for 0.5 h, and then concentrated under reduced pressure. Then mixture was diluted with EtOAc (2 mL) and quenched with saturated aqueous $NaHCO_3$ solution (5 mL). The aqueous layer was further extracted with EtOAc (20 mL). The combined organic layers were washed with brine, dried over anhydrous $Na_2SO_4$, filtered and concentrated under reduced pressure to afford the title compound. MS: 324.1 (M+1).

Intermediate AB28

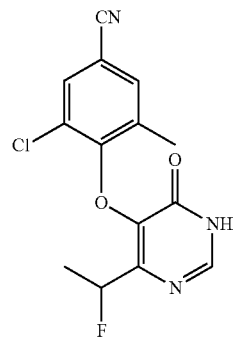 [SMILES: Cc1cc(C#N)cc(Cl)c1Oc1c(C(C)F)nc[nH]c1=O]

3-chloro-4-((4-(1-fluoroethyl)-6-oxo-1,6-dihydropyrimidin-5-yl)oxy)-5-methylbenzonitrile Step 1: 6-acetyl-5-(4-bromo-2-chloro-6-methylphenoxy)-3-(4-methoxybenzyl)pyrimidin-4 (3H)-one To a solution of 6-acetyl-5-fluoro-3-(4-methoxybenzyl)pyrimidin-4 (3H)-one, B11 (1.1 g, 3.98 mmol) in DMF (15 mL) was added 4-bromo-2-chloro-6-methylphenol (1.058 g, 4.78 mmol) and potassium carbonate (1.101 g, 7.96 mmol). The resulting mixture was stirred at 60° C. for 2 h, and then concentrated under reduced pressure. The residue was diluted with water (10 mL), and extracted with EtOAc (3×20 mL). The combined organic layers were dried over anhydrous $Na_2SO_4$, filtered and concentrated under reduced pressure. The residue was purified by column chromatography on silica (0-50% EtOAc/P.E.) to afford the title compound. MS: 478.8 (M+1).

Step 2: 5-(4-bromo-2-chloro-6-methylphenoxy)-6-(1-hydroxyethyl)-3-(4-methoxybenzyl)-2,3-dihydropyrimidin-4 (1H)-one To a solution of 6-acetyl-5-(4-bromo-2-chloro-6-methylphenoxy)-3-(4-methoxybenzyl)pyrimidin-4 (3H)-one (1.2 g, 2.51 mmol) in EtOAc (6 mL) and THF (9 mL), added 0.1 M solution of $Zn(BH_4)_2$ in THF (0.50 mL, 0.05 mmol) at −30° C. The resulting mixture was stirred at −30° C. for 5 min, and then diluted by water (50 mL), extracted with EtOAc (3×50 mL). The combined organic layers were dried over anhydrous $Na_2SO_4$, filtered and concentrated under reduced pressure to afford the title compound. MS: 483.0 (M+1).

Step 3: 5-(4-bromo-2-chloro-6-methylphenoxy)-6-(1-hydroxyethyl)-3-(4-methoxybenzyl)pyrimidin-4 (3H)-one To a solution of 5-(4-bromo-2-chloro-6-methylphenoxy)-6-(1-hydroxyethyl)-3-(4-methoxybenzyl)-2,3-dihydropyrimidin-4 (1H)-one (1 g, 2.08 mmol) in THF (10 mL) was added 4,5-dichloro-3,6-dioxocyclohexa-1,4-diene-1,2-dicarbonitrile (0.236 g, 1.04 mmol). The resulting reaction mixture was stirred at 25° C. for 0.5 h, and then diluted with water (50 mL), extracted with EA (3×50 mL). The combined organic layers were dried over anhydrous $Na_2SO_4$, filtered and concentrated under reduced pressure. The residue was purified by column chromatography on silica (0-50% EtOAc/P.E.) to afford the title compound. MS: 481.0 (M+1).

Step 4: 5-(4-bromo-2-chloro-6-methylphenoxy)-6-(1-fluoroethyl)-3-(4-methoxybenzyl)pyrimidin-4 (3H)-one To a solution of 5-(4-bromo-2-chloro-6-methylphenoxy)-6-(1-hydroxyethyl)-3-(4-methoxybenzyl)pyrimidin-4 (3H)-one (550 mg, 1.15 mmol) in DCM (11 mL) was added DAST (0.757 mL, 5.73 mmol) at 0° C. The resulting reaction mixture was stirred at 0° C. for 1 h, and then carefully quenched with water (15 mL), and extracted with DCM (3×20 mL). The combined organic layers were washed with brine, dried over anhydrous $Na_2SO_4$, filtrated and concentrated under reduced pressure. The residue was purified by column chromatography on silica (0-20% EtOAc/P.E.) to afford the title compound. MS: 483.0 (M+1). $^1H$ NMR (400 MHz, DMSO-$d_6$) δ ppm 1.51-1.66 (m, 3H) 2.18 (s, 3H) 3.72 (s, 3H) 4.92-5.04 (m, 2H) 5.89-6.16 (m, 1H) 6.89 (d, J=8.82 Hz, 2H) 7.23 (br d, J=7.28 Hz, 2H) 7.46 (br d, J=18.74 Hz, 2H) 8.57 (s, 1H).

Step 5: 3-chloro-4-((4-(1-fluoroethyl)-1-(4-methoxybenzyl)-6-oxo-1,6-dihydropyrimidin-5-yl) oxy)-5-methylbenzonitrile To a stirred solution of 5-(4-bromo-2-chloro-6-methylphenoxy)-6-(1-fluoroethyl)-3-(4-methoxybenzyl)pyrimidin-4 (3H)-one (383 mg, 0.80 mmol) in NMP (6 mL) was added cyanocopper (712 mg, 7.95 mmol) under $N_2$. The resulting mixture was stirred at 180° C. for 7 h, and then cooled to 25° C., diluted with $H_2O$ (20 mL) and EtOAc (20 mL), then filtered over CELITE®. The filtrate was extracted with EA (3×20 mL). The combined organic layers were washed with brine, dried over anhydrous $Na_2SO_4$, filtered and concentrated under reduced pressure to afford the title compound. MS: 428.0 (M+1).

Step 6: 3-chloro-4-((4-(1-fluoroethyl)-6-oxo-1,6-dihydropyrimidin-5-yl)oxy)-5-methylbenzonitrile A mixture of 3-chloro-4-((4-(1-fluoroethyl)-1-(4-methoxybenzyl)-6-oxo-1,6-dihydropyrimidin-5-yl)oxy)-5-methylbenzonitrile (600 mg, 1.40 mmol) in TFA (10 mL) and TFAA (5 mL) was heated at 100° C. for 16 h. The resulting mixture was concentrated under reduced pressure to afford the title compound, which was used in following steps directly without further purification. MS: 308.1 (M+1).

Intermediate AB29

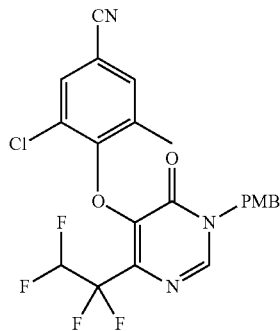

3-cyclopropyl-5-methyl-4-((6-oxo-4-(1,1,2,2-tetrafluoroethyl)-1,6-dihydropyrimidin-5-yl)oxy)benzonitrile

Step 1: 5-(4-bromo-2-chloro-6-methylphenoxy)-3-(4-methoxybenzyl)-6-(1,1,2,2-tetrafluoroethyl)pyrimidin-4 (3H)-one To a stirred solution of 5-fluoro-3-(4-methoxybenzyl)-6-(1,1,2,2-tetrafluoroethyl) pyrimidin-4 (3H)-one, B15 (700 mg, 2.094 mmol) in NMP (10 mL) was added 4-bromo-2-chloro-6-methylphenol (696 mg, 3.14 mmol) and potassium carbonate (868 mg, 6.28 mmol). The resulting mixture was stirred at 120° C. for 2 h, and then diluted with $H_2O$ (15 mL) and extracted with EtOAc (3×15 mL). The combined organic layers were washed with $H_2O$ and brine, dried over anhydrous $Na_2SO_4$, filtered and concentrated under reduced pressure. The residue was purified by column chromatography on silica (10-50% EtOAc/P.E.) to afford the title compound. $^1$HNMR (400 MHz, CDCl$_3$): δ7.94 (s, 1H) 7.32 (d, J=2.08 Hz, 1H) 7.28 (d, J=2.08 Hz, 1H) 7.22 (d, J=8.56 Hz, 2H) 6.90 (d, J=8.68 Hz, 2H) 6.21-6.55 (m, 1H) 4.99 (d, J=2.45 Hz, 2H) 3.81 (s, 3H) 2.29 (s, 3H).

Step 2: 3-chloro-4-((1-(4-methoxybenzyl)-6-oxo-4-(1,1,2,2-tetrafluoroethyl)-1,6-dihydropyrimidin-5-yl) oxy)-5-methylbenzonitrile To a stirred solution of 5-(4-bromo-2-chloro-6-methylphenoxy)-3-(4-methoxybenzyl)-6-(1,1,2,2-tetrafluoroethyl)pyrimidin-4 (3H)-one (800 mg, 1.49 mmol) in DMF (25 mL) was added dicyanozinc (193 mg, 1.64 mmol) and Pd(Ph$_3$P)$_4$ (173 mg, 0.15 mmol) under $N_2$. The resulting mixture was stirred at 80° C. for 2 h, and then diluted with EtOAc (25 mL). The mixture was washed with $H_2O$ and brine, dried over anhydrous $Na_2SO_4$, filtered and concentrated under reduced pressure. The residue was purified by column chromatography on silica (10-50% EtOAc/P.E.) to afford the title compound. $^1$H NMR (400 MHz, CDCl$_3$): δ 7.98 (s, 1H) 7.43-7.50 (m, 2H) 7.22 (d, J=8.68 Hz, 2H) 6.87-6.93 (m, 2H) 6.19-6.52 (m, 1H) 4.94-5.05 (m, 2H) 3.82 (s, 3H) 2.35 (s, 3H).

Intermediate AB30

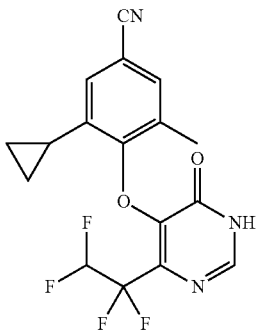 [SMILES: Cc1cc(C#N)cc(C2CC2)c1Oc1c(C(F)(F)C(F)F)nc[nH]c1=O]

3-cyclopropyl-5-methyl-4-((6-oxo-4-(1,1,2,2-tetrafluoroethyl)-1,6-dihydropyrimidin-5-yl)oxy)benzonitrile

Step 1: 3-cyclopropyl-4-((1-(4-methoxybenzyl)-6-oxo-4-(1,1,2,2-tetrafluoroethyl)-1,6-dihydropyrimidin-5-yl)oxy)-5-methylbenzonitrile To a stirred solution of 3-chloro-4-((1-(4-methoxybenzyl)-6-oxo-4-(1,1,2,2-tetrafluoroethyl)-1, 6-dihydropyrimidin-5-yl)oxy)-5-methylbenzonitrile, AB29 (150 mg, 0.31 mmol), cyclopropylboronic acid (134 mg, 1.56 mmol), potassium phosphate tribasic (396 mg, 1.868 mmol) and di((3S,5S,7S)-adamantan-1-yl)(butyl)phosphine (67.0 mg, 0.19 mmol) in toluene (5 mL) and H$_2$O (1 mL), was added Pd(OAc)$_2$ (20.97 mg, 0.093 mmol) under N$_2$. The resulting mixture was stirred at 130° C. for 16 h, and then passed through CELITE®. The filter cake was washed with DCM (10 mL) and MeOH (10 mL). The filtrate was concentrated under reduced pressure. The residue was purified by preparative TLC plate (33% EtOAc/P.E.) to afford the title compound. $^1$H NMR (400 MHz, CDCl$_3$): δ 7.89 (s, 1H) 7.27 (s, 1H) 7.14 (d, J=8.56 Hz, 2H) 7.01 (s, 1H) 6.81 (d, J=8.56 Hz, 2H) 6.14-6.48 (m, 1H) 4.78-5.00 (m, 2H) 3.74 (s, 3H) 2.17 (s, 3H) 1.65-1.73 (m, 1H) 0.64-0.79 (m, 2H) 0.39-0.51 (m, 1H) 0.20 (br dd, J=9.90, 4.16 Hz, 1H).

Step 4: 3-cyclopropyl-5-methyl-4-((6-oxo-4-(1,1,2,2-tetrafluoroethyl)-1,6-dihydropyrimidin-5-yl)oxy)benzonitrile A solution of 3-cyclopropyl-4-((1-(4-methoxybenzyl)-6-oxo-4-(1,1,2,2-tetrafluoroethyl)-1, 6-dihydropyrimidin-5-yl)oxy)-5-methylbenzonitrile (130 mg, 0.27 mmol) in TFA (2 mL) and TFAA (1 mL) was stirred at 110° C. for 3 h, and then cooled to RT, carefully quenched by adding saturated aqueous NaHCO$_3$ solution (10 mL), and extracted with EtOAc (3×5 mL). The combined organic layers were washed with brine, dried over anhydrous Na$_2$SO$_4$, filtered and concentrated under reduced pressure to afford the title compound. MS: 368.1 (M+1). $^1$H NMR (400 MHz, CDCl$_3$): δ0.80 (s, 1H) 7.78-7.83 (m, 1H) 7.33 (s, 1H) 7.11 (s, 1H) 6.28-6.57 (m, 1H) 2.26 (s, 3H) 1.80-1.86 (m, 1H) 0.86-0.92 (m, 1H) 0.68-0.84 (m, 2H) 0.39-0.52 (m, 1H).

Intermediate AB31

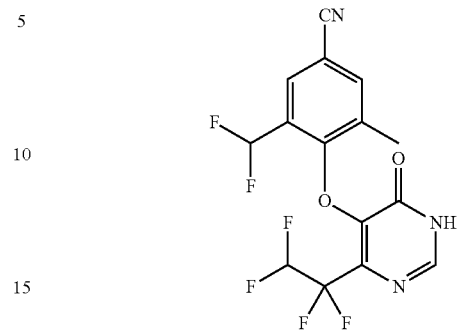

3-(difluoromethyl)-5-methyl-4-((6-oxo-4-(1,1,2,2-tetrafluoroethyl)-1,6-dihydropyrimidin-5-yl)oxy)benzonitrile

Step 1: 4-((1-(4-methoxybenzyl)-6-oxo-4-(1,1,2,2-tetrafluoroethyl)-1,6-dihydropyrimidin-5-yl)oxy)-3-methyl-5-vinylbenzonitrile To a stirred solution of 3-chloro-4-((1-(4-methoxybenzyl)-6-oxo-4-(1,1,2,2-tetrafluoroethyl)-1, 6-dihydropyrimidin-5-yl)oxy)-5-methylbenzonitrile, AB29 (370 mg, 0.77 mmol) in 1,4-dioxane (5 mL) and H$_2$O (1 mL) was added potassium trifluoro(vinyl)-borate (514 mg, 3.84 mmol), K$_2$CO$_3$ (637 mg, 4.61 mmol), dicyclohexyl(2',4',6'-triisopropyl-[1,1'-biphenyl]-2-yl)phosphine (146 mg, 0.307 mmol) and diacetoxypalladium (34.5 mg, 0.154 mmol) under N$_2$. The resulting mixture was stirred at 120° C. for 18 h, and then filtered over CELITE®. The filter cake was washed with MeOH (10 mL) and DCM (10 mL). The filtrate was concentrated under reduced pressure. The residue was purified by column chromatography on silica (10-50% EtOAc/P.E.) to afford the title compound. $^1$H NMR (400 MHz, CDCl$_3$): δ7.95 (s, 1H) 7.54 (d, J=2.08 Hz, 1H) 7.41 (d, J=1.83 Hz, 1H) 7.16-7.19 (m, 2H) 6.86-6.89 (m, 2H) 6.69 (dd, J=17.48, 11.00 Hz, 1H) 6.19-6.54 (m, 1H) 5.53 (d, J=17.48 Hz, 1H) 5.17-5.28 (m, 1H) 4.81-5.04 (m, 2H) 3.81 (s, 3H) 2.24 (s, 3H).

Step 2: 3-formyl-4-((1-(4-methoxybenzyl)-6-oxo-4-(1,1,2,2-tetrafluoroethyl)-1,6-dihydropyrimidin-5-yl)oxy)-5-methylbenzonitrile To a stirred solution of 4-((1-(4-methoxybenzyl)-6-oxo-4-(1,1,2,2-tetrafluoroethyl)-1, 6-dihydropyrimidin-5-yl)oxy)-3-methyl-5-vinylbenzonitrile (100 mg, 0.21 mmol) in 1,4-dioxane (1 mL) and water (0.33 mL), was added 2,6-dimethylpyridine (45.3 mg, 0.42 mmol), sodium periodate (136 mg, 0.63 mmol) and osmium(VIII) oxide (2.69 mg, 10.56 μmol). The resulting mixture was stirred at 15° C. for 1 h, and then quenched with saturated aqueous Na$_2$SO$_3$ solution (15 mL) and extracted with EtOAc (3×10 mL). The combined organic layers were washed with brine, dried over anhydrous Na$_2$SO$_4$, filtered and concentrated under reduced pressure. The residue was purified by preparative TLC plates (50% EtOAc/P.E.) to afford the title compound. $^1$H NMR (400 MHz, CDCl$_3$): δ10.16 (s, 1H) 7.99 (s, 1H) 7.68 (s, 1H) 7.42-7.46 (m, 1H) 7.17-7.20 (m, 2H) 6.88-6.91 (m, 2H) 6.13-6.55 (m, 1H) 4.95 (d, J=3.18 Hz, 2H) 3.81 (s, 3H) 2.25 (s, 3H).

Step 3: 3-(difluoromethyl)-4-((1-(4-methoxybenzyl)-6-oxo-4-(1,1,2,2-tetrafluoroethyl)-1,6-dihydropyrimidin-5-yl)oxy)-5-methylbenzonitrile To a stirred solution of 3-formyl-4-((1-(4-methoxybenzyl)-6-oxo-4-(1,1,2,2-tetrafluoroethyl)-1, 6-dihydropyrimidin-5-yl)oxy)-5-methylbenzonitrile (90 mg, 0.19 mmol) in DCM (1.5 mL) was added diethylaminosulfurtrifluoride (30.429 mg, 1.89 mmol) under $N_2$. The resulting mixture was stirred at 15° C. for 2 h, and then carefully poured into saturated aqueous solution of $NaHCO_3$ (20 mL), extracted with DCM (3×20 mL). The combined organic layers were dried over anhydrous $Na_2SO_4$, filtered and concentrated under reduced pressure. The residue was purified by preparative TLC plates (50% EtOAc/P.E.) to afford the title compound. MS: 498 (M+1).

Step 4: 3-(difluoromethyl)-5-methyl-4-((6-oxo-4-(1,1,2,2-tetrafluoroethyl)-1,6-dihydropyrimidin-5-yl)oxy)benzonitrile A solution of 3-(difluoromethyl)-4-((1-(4-methoxybenzyl)-6-oxo-4-(1,1,2,2-tetrafluoroethyl)-1, 6-dihydropyrimidin-5-yl)oxy)-5-methylbenzonitrile (60 mg, 0.072 mmol) in TFA (2 mL) and TFAA (1 mL) was stirred at 110° C. for 1 h. The mixture was quenched by adding saturated aqueous solution of $NaHCO_3$ (15 mL) and extracted with EtOAc (3×10 mL). The combined organic layers were washed with brine, dried over anhydrous $Na_2SO_4$, filtered and concentrated under reduced pressure to the title compound. MS: 378 (M+1).

Intermediate AB32

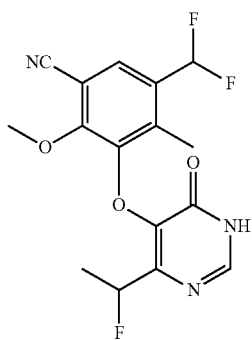 [SMILES: COc1c(C#N)cc(C(F)F)c(C)c1Oc1c(C(C)F)nc[nH]c1=O]

5-(difluoromethyl)-3-((4-(1-fluoroethyl)-6-oxo-1,6-dihydropyrimidin-5-yl)oxy)-2-methoxybenzonitrile Step 1: 6-acetyl-5-(3-bromo-5-(difluoromethyl)-2-methoxyphenoxy)-3-(4-methoxybenzyl) pyrimidin-4 (3H)-one To a solution of 6-acetyl-5-fluoro-3-(4-methoxybenzyl) pyrimidin-4 (3H)-one, B11 (460 mg, 1.67 mmol) in DMF (5 mL) was added 3-bromo-5-(difluoromethyl)-2-methoxyphenol, A08 (463 mg, 1.83 mmol) and $K_2CO_3$ (460 mg, 3.33 mmol). The resulting reaction mixture was stirred at 60° C. for 4 h, and then quenched with saturated $NH_4Cl$ solution, extracted with EtOAc (3×25 mL). The combined organic layers were dried over anhydrous sodium sulfate, filtered and concentrated under reduced pressure to afford the title compound. MS: 511.1 (M+1).

Step 2: 6-acetyl-5-(3-bromo-5-(difluoromethyl)-2-methoxyphenoxy)-3-(4-methoxybenzyl)-2,3-dihydropyrimidin-4 (1H)-one To a solution of 6-acetyl-5-(3-bromo-5-(difluoromethyl)-2-methoxyphenoxy)-3-(4-methoxybenzyl)pyrimidin-4 (3H)-one (650 mg, 1.28 mmol) in MeOH (3 mL) was added $NaBH_4$ (121 mg, 3.19 mmol) at 0° C. for 10 min, and then quenched with saturated aqueous $NH_4Cl$ solution, extracted with EtOAc (3×25 mL). The combined organic layers were dried over anhydrous $Na_2SO_4$, filtered and concentrated under reduced pressure to afford the title compound. MS: 513.2 (M+1).

Step 3: 5-(3-bromo-5-(difluoromethyl)-2-methoxyphenoxy)-6-(1-hydroxyethyl)-3-(4-methoxybenzyl) pyrimidin-4 (3H)-one To a solution of 5-(3-bromo-5-(difluoromethyl)-2-methoxyphenoxy)-6-(1-hydroxyethyl)-3-(4-methoxybenzyl)-2,3-dihydropyrimidin-4 (1H)-one (480 mg, 0.94 mmol) in THF (2 mL) was added DDQ (425 mg, 1.87 mmol) at 25° C. for 1 h, TLC (50% EtOAc/P.E.) showed the reaction was completed. The reaction mixture was diluted with $H_2O$ (20 mL), extracted with EtOAc (3×20 mL). The combined organic layers were washed with brine, dried over anhydrous $Na_2SO_4$, filtered and concentrated under reduced pressure to give the title compound, which was used in following step directly without further purification. MS: 513.2 (M+1).

Step 4: 5-(3-bromo-5-(difluoromethyl)-2-methoxyphenoxy)-6-(1-fluoroethyl)-3-(4-methoxybenzyl) pyrimidin-4 (3H)-one To a solution of 5-(3-bromo-5-(difluoromethyl)-2-methoxyphenoxy)-6-(1-hydroxyethyl)-3-(4-methoxybenzyl)pyrimidin-4 (3H)-one (280 mg, 0.55 mmol) in DCM (4 mL) was added DAST (0.739 mL, 5.59 mmol) at 25° C. The resulting mixture was stirred at 25° C. for 1 h, and then carefully quenched with water (100 mL), extracted with EtOAc (3×100 mL). The combined organic layers were washed with water, dried over anhydrous $Na_2SO_4$ and concentrated under reduced pressure. The residue was purified by column chromatography on silica (50% EtOAc/P.E.) to afford the title compound. MS: 513.2 (M+1).

Step 5: 5-(difluoromethyl)-3-((4-(1-fluoroethyl)-1-(4-methoxybenzyl)-6-oxo-1,6-dihydropyrimidin-5-yl)oxy)-2-methoxybenzonitrile To a solution of 5-(3-bromo-5-(difluoromethyl)-2-methoxyphenoxy)-6-(1-fluoroethyl)-3-(4-methoxybenzyl) pyrimidin-4 (3H)-one (60 mg, 0.12 mmol) in DMF (2 mL) was added dicyanozinc (68.6 mg, 0.58 mmol), zinc (22.93 mg, 0.35 mmol) and bis(tri-tert-butylphosphine)palladium (0) (59.7 mg, 0.12 mmol) under $N_2$. The resulting mixture was stirred at 140° C. for 16 h. TLC (50% EtOAc/P.E.) showed the starting material was consumed. The mixture was diluted with water (40 mL) and extracted with EtOAc (3×20 mL). The combined organic layers were washed with brine, dried over anhydrous $Na_2SO_4$, filtered and concentrated under reduced pressure. The residue was purified by preparative TLC plates (50% EtOAc/P.E.) to afford the title compound. MS: 460.2 (M+1).

Step 6: 5-(difluoromethyl)-3-((4-(1-fluoroethyl)-6-oxo-1,6-dihydropyrimidin-5-yl)oxy)-2-methoxybenzonitrile A solution of 5-(3-bromo-5-(difluoromethyl)-2-methoxyphenoxy)-3-(4-methoxybenzyl)-6-(1,1,2,2-tetrafluoroethyl) pyrimidin-4 (3H)-one (50 mg, 0.088 mmol) in TFAA (0.5 mL, 3.54 mmol) and TFA (1 mL) was stirred at 110° C. for 2 h. TLC (50% EtOAc/P.E.) showed the reaction was completed. The reaction mixture was diluted with H₂O (10 mL), and extracted with EtOAc (3×10 mL). The combined organic was washed with brine, dried over anhydrous Na₂SO₄, filtered and concentrated under reduced pressure to afford the title compound. MS: 340.2 (M+1).

Intermediate AB33

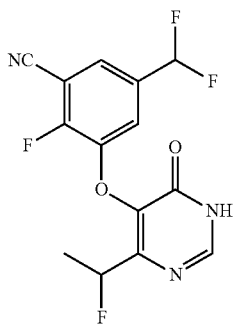 [SMILES: CC(F)c1nc[nH]c(=O)c1Oc1cc(C(F)F)cc(C#N)c1F]

5-(difluoromethyl)-2-fluoro-3-((4-(1-fluoroethyl)-6-oxo-1,6-dihydropyrimidin-5-yl)oxy)benzonitrile Step 1: 6-acetyl-5-(3-bromo-5-chloro-2-fluorophenoxy)-3-(4-methoxybenzyl)pyrimidin-4 (3H)-one A solution of 6-acetyl-5-fluoro-3-(4-methoxybenzyl)pyrimidin-4 (3H)-one, B11 (3 g, 10.86 mmol), 3-bromo-5-chloro-2-fluorophenol, A05 (3.37 g, 11.95 mmol), and K₂CO₃ (4.50 g, 32.6 mmol) in DMF (30 mL) was stirred at 50° C. for 1 h, and then diluted with water (50 mL) and extracted with EtOAc (3×50 mL). The combined organic layers were washed with brine, dried over Na₂SO₄, filtered and concentrated under reduced pressure. The residue was purified by column chromatography on silica (0-50% EtOAc/P.E.) to afford the title compound. ¹H NMR (400 MHz, DMSO-d₆): δ 2.49 (s, 3H) 2.49-2.49 (m, 1H) 3.73 (s, 3H) 5.08 (s, 2H) 6.91 (d, J=8.68 Hz, 2H) 7.21 (dd, J=6.91, 2.38 Hz, 1H) 7.33 (br d, J=8.68 Hz, 2H) 7.54 (dd, J=5.14, 2.45 Hz, 1H) 8.78 (s, 1H)

Step 2: 5-(3-bromo-5-chloro-2-fluorophenoxy)-6-(1-hydroxyethyl)-3-(4-methoxybenzyl)-2,3-dihydropyrimidin-4 (1H)-one To a solution of 6-acetyl-5-(3-bromo-5-chloro-2-fluorophenoxy)-3-(4-methoxy benzyl)pyrimidin-4 (3H)-one (3 g, 6.23 mmol) in MeOH (10 mL) and THF (20 mL), was added NaBH₄ (0.236 g, 6.23 mmol). The resulting mixture was stirred at 20° C. for 1 h. TLC (50% EtOAc/P.E.) and LC-MS show there was desired product. The reaction mixture was diluted with water (50 mL) and extracted with EtOAc (3×50 mL). The combined organic layers were washed with brine, dried over anhydrous Na₂SO₄, filtered and concentrated under reduced pressure to give the title compound, which was used in following step directly without further purification. MS: 487.1 (M+1).

Step 3: 5-(3-bromo-5-chloro-2-fluorophenoxy)-6-(1-hydroxyethyl)-3-(4-methoxybenzyl)pyrimidin-4 (3H)-one A mixture of 5-(3-bromo-5-chloro-2-fluorophenoxy)-6-(1-hydroxyethyl)-3-(4-methoxybenzyl)-2,3-dihydropyrimidin-4 (1H)-one (2.7 g, 5.56 mmol), and CAN (6.09 g, 11.12 mmol) in ACN (20 mL) and water (5 mL) was stirred at 20° C. for 20 min. TLC (50% EtOAc/P.E.) showed there was the desired product. The reaction mixture was diluted with water (50 mL), and extracted with EtOAc (3×50 mL). The combined organic layers were washed with brine, dried over anhydrous Na₂SO₄, filtered and concentrated under reduced pressure. The residue was purified by column chromatography on silica (0-50% EtOAc/P.E.) to afford the title compound. MS: 485.0 (M+1).

Step 4: 5-(3-bromo-5-chloro-2-fluorophenoxy)-6-(1-fluoroethyl)-3-(4-methoxybenzyl)pyrimidin-4 (3H)-one To a solution of 5-(3-bromo-5-chloro-2-fluorophenoxy)-6-(1-hydroxyethyl)-3-(4-methoxybenzyl)pyrimidin-4 (3H)-one (1.7 g, 3.51 mmol), and DAST (4.64 mL, 35.1 mmol) in DCM (17 mL) was stirred at 20° C. for 1 h. TLC (100% EtOAc) showed there was desired product. The reaction mixture was diluted with water (50 mL) and extracted with EtOAc (3×50 mL). The combined organic layers were washed with brine, dried over anhydrous Na₂SO₄, filtered and concentrated under reduced pressure. The residue was purified by column chromatography on silica (0-20% EtOAc/P.E.) to afford the title compound. ¹H NMR (400 MHz, DMSO-d₆): δ 1.49-1.59 (m, 3H) 3.73 (s, 3H) 5.06 (d, J=2.87 Hz, 2H) 5.65-5.84 (m, 1H) 6.90 (d, J=8.60 Hz, 2H) 7.15 (dd, J=6.84, 2.21 Hz, 1H) 7.32 (d, J=8.60 Hz, 2H) 7.55 (dd, J=5.07, 2.43 Hz, 1H) 8.74 (s, 1H).

Step 5: 5-chloro-2-fluoro-3-((4-(1-fluoroethyl)-1-(4-methoxybenzyl)-6-oxo-1,6-dihydropyrimidin-5-yl)oxy)benzonitrile To a solution of 5-(3-bromo-5-chloro-2-fluorophenoxy)-6-(1-fluoroethyl)-3-(4-methoxybenzyl)pyrimidin-4 (3H)-one (1.4 g, 2.88 mmol), and cyanocopper (2.58 g, 28.8 mmol) in NMP (25 mL) was stirred at 180° C. for 3.5 h. TLC (50% EtOAc/P.E.) and LC-MS showed there was desired product. The reaction mixture was diluted with EtOAc (50 mL), and passed through a filter. The filter cake was washed with EtOAc (20 mL) and H₂O (50 mL). The filtrate was extracted with EtOAc (3×50 mL). The combined organic layers were washed with brine, dried over anhydrous Na₂SO₄, filtered and concentrated under reduced pressure. The residue was purified by column chromatography on silica (0-50% EtOAc/P.E.) to afford the title compound. MS: 432.1 (M+1).

Step 6: 2-fluoro-3-((4-(1-fluoroethyl)-1-(4-methoxybenzyl)-6-oxo-1,6-dihydropyrimidin-5-yl)oxy)-5-vinylbenzonitrile To a stirred solution of 5-chloro-2-fluoro-3-((4-(1-fluoroethyl)-1-(4-methoxybenzyl)-6-oxo-1,6-dihydropyrimidin-5- yl)oxy)benzonitrile (200 mg, 0.46 mmol) in 1.4-dioxane (4 mL) and water (0.8 mL) was added potassium trifluoro (vinyl)borate (93 mg, 0.70 mmol), di((3S,5S,7S)-adamantan-1-yl)(butyl)phosphine (66.4 mg, 0.185 mmol), $K_3PO_4$ (197 mg, 0.926 mmol), diacetoxypalladium (20.80 mg, 0.093 mmol) was added under $N_2$. The resulting mixture was stirred at 110° C. for 2 h. TLC (50% EtOAc/P.E.) and LC-MS showed the completion of the reaction. The mixture was diluted with water (25 mL) and extracted with EtOAc (3×25 mL). The combined organic layers were washed with brine, dried over anhydrous $Na_2SO_4$, filtered and concentrated under reduced pressure. The residue was purified by preparative TLC plates (1% MeOH/DCM) to afford the title compound. MS: 424.2 (M+1).

Step 7: 2-fluoro-3-((4-(1-fluoroethyl)-1-(4-methoxybenzyl)-6-oxo-1,6-dihydropyrimidin-5-yl)oxy)-5-formylbenzonitrile To a solution of 2-fluoro-3-((4-(1-fluoroethyl)-1-(4-methoxybenzyl)-6-oxo-1,6-dihydropyrimidin-5-yl)oxy)-5-vinylbenzonitrile (300 mg, 0.71 mmol) in 1,4-dioxane (10 mL) and water (3 mL), was added osmium(VIII) oxide (4.50 mg, 0.018 mmol) and 2,6-dimethylpyridine (213 mg, 1.98 mmol). The resulting mixture was stirred at 20° C. for 0.5 h, then sodium periodate (561 mg, 2.62 mmol) was added. The mixture was stirred at 20° C. for another 3 h. TLC (50% EtOAc/P.E.) and LC-MS showed the complete conversion. The reaction was quenched with saturated aqueous $Na_2SO_3$ solution (10 mL) and extracted with EtOAc (3×20 mL). The combined organic layers were washed with brine, dried over anhydrous $Na_2SO_4$, filtered and concentrated. The residue was purified by preparative TLC plates (2% MeOH/DCM) to give the title compound. MS: 426.2 (M+1).

Step 8: 5-(difluoromethyl)-2-fluoro-3-((4-(1-fluoroethyl)-1-(4-methoxybenzyl)-6-oxo-1,6-dihydropyrimidin-5-yl)oxy)benzonitrile To a solution of 2-fluoro-3-((4-(1-fluoroethyl)-1-(4-methoxybenzyl)-6-oxo-1,6-dihydropyrimidin-5-yl)oxy)-5-formylbenzonitrile (300 mg, 0.71 mmol) in DCM (0.5 mL) was added DAST (0.932 mL, 7.05 mmol). The resulting mixture was stirred at 20° C. for 2 h when TLC (50% EtOAc/P.E.) and LC-MS showed complete conversion. The reaction was quenched with saturated aqueous $NaHCO_3$ solution (10 mL) and extracted with EtOAc (3×20 mL). The combined organic layers were washed with brine, dried over anhydrous $Na_2SO_4$, filtered and concentrated under reduced pressure. The residue was purified by preparative TLC plates (50% EtOAc/P.E.) to afford the title compound. MS: 448.2 (M+1). $^1$H NMR (400 MHz, DMSO-$d_6$): δ 1.51-1.62 (m, 3H) 3.73 (s, 3H) 4.98-5.15 (m, 2H) 5.67-5.93 (m, 1H) 6.80-7.12 (m, 3H) 7.31 (d, J=8.68 Hz, 2H) 7.57 (br d, J=6.48 Hz, 1H) 7.91 (br d, J=3.55 Hz, 1H) 8.79 (s, 1H).

Step 9: 5-(difluoromethyl)-2-fluoro-3-((4-(1-fluoroethyl)-6-oxo-1,6-dihydropyrimidin-5-yl)oxy)benzonitrile-notebook Page To a solution of 5-(difluoromethyl)-2-fluoro-3-((4-(1-fluoroethyl)-1-(4-methoxybenzyl)-6-oxo-1,6-dihydropyrimidin-5-yl)oxy)benzonitrile (160 mg, 0.36 mmol) in TFA (7 mL) and TFAA (3.5 mL) was stirred at 100° C. for 3 h. TLC (50% EtOAc/P.E.) and LC-MS showed complete conversion. The reaction mixture was concentrated under reduced pressure to dryness. The residual was diluted in EtOAc (2 mL), and then washed with saturated aqueous $NaHCO_3$ solution and brine, and concentrated under reduced pressure to afford the title compound, which was used in the next step directly without further purification. MS: 328.0 (M+1).

Intermediate AB34

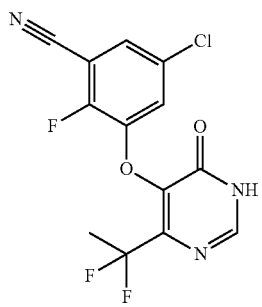 [SMILES: CC(F)(F)c1nc[nH]c(=O)c1Oc1cc(Cl)cc(C#N)c1F]

5-Chloro-3-((4-(1,1-difluoroethyl)-6-oxo-1,6-dihydropyrimidin-5-yl)oxy)-2-fluorobenzonitrile Step 1: Methyl 5-fluoro-1-(4-methoxybenzyl)-6-oxo-1,6-dihydropyrimidine-4-carboxylate Potassium carbonate (16.11 g, 117 mmol) was added to a mixture of methyl 5-fluoro-1-(4-methoxybenzyl)-6-oxo-1,6-dihydropyrimidine-4-carboxylate, B14 (21.29 g, 72.9 mmol) and 5-chloro-2-fluoro-3-hydroxybenzonitrile, A06 (10 g, 58.3 mmol) in dimethylacetamide (350 mL) at 25° C. The resulting mixture was stirred at 90° C. overnight. LC-MS showed desired product and clean reaction. Water (500 mL) was added and a precipitate was formed. The mixture was filtered and the solid was washed with water (100 mL) and hexanes (200 mL) and dried overnight under high vacuum to provide the title compound. MS: 444 (M+1).

Step 2: 5-(5-Chloro-3-cyano-2-fluorophenoxy)-1-(4-methoxybenzyl)-6-oxo-1,6-dihydropyrimidine-4-carboxylic Acid Potassium trimethylsilanolate (9.97 g, 78 mmol) was added to a stirring mixture of methyl 5-(5-chloro-3-cyano-2-fluorophenoxy)-1-(4-methoxybenzyl)-6-oxo-1,6-dihydropyrimidine-4-carboxylate (23 g, 51.8 mmol) in THF (345 mL). The resulting mixture was stirred at 25° C. for 1 h. LC-MS showed only desired product. HCl (1N aq., 300 mL) was added slowly and a white solid was formed. The mixture was concentrated under reduced pressure to remove THF. The mixture was filtered and the white solid was washed with water and dried under vacuum to provide the title compound. MS: 430.0 (M+1).

Step 3: 5-(5-Chloro-3-cyano-2-fluorophenoxy)-N-methoxy-1-(4-methoxybenzyl)-N-methyl-6-oxo-1,6-dihydropyrimidine-4-carboxamide To a flask containing 5-(5-chloro-3-cyano-2-fluorophenoxy)-1-(4-methoxybenzyl)-6-oxo-1,6-dihydropyrimidine-4-carboxylic acid (20 g, 46.5 mmol) and N,O-dimethylhydroxylamine hydrochloride (4.99 g, 51.2 mmol) in DMF (200 mL), was added triethylamine (25.9 mL, 186 mmol)

followed by EDC (9.81 g, 51.2 mmol) and HOBt (7.84 g, 51.2 mmol) at 25° C. The resulting mixture was stirred at 25° C. overnight. LC-MS indicated the completion of the reaction. Water (300 mL) was added and the resulting precipitate was filtered and washed with water, dried under vacuum to provide the title compound. MS: 473.1 (M+1).

Step 4: 3-((4-Acetyl-1-(4-methoxybenzyl)-6-oxo-1,6-dihydropyrimidin-5-yl)oxy)-5-chloro-2-fluorobenzonitrile Methylmagnesium bromide (3M in THF, 40 mL, 120 mmol) was added dropwise to a cooled (−78° C.) mixture of 5-(5-chloro-3-cyano-2-fluorophenoxy)-N-methoxy-1-(4-methoxybenzyl)-N-methyl-6-oxo-1,6-dihydropyrimidine-4-carboxamide (16.5 g, 34.9 mmol) in THF (350 mL). The resulting mixture was stirred at −78° C. for 3 h. LC-MS showed desired product but still starting material. The reaction mixture was then warmed up to 0° C. and stirred for 30 min. LC-MS indicated completion of the reaction. The reaction was quenched with saturated aqueous NH₄Cl solution (500 mL) and diluted with EtOAc (200 mL). The organic layer was separated and the aqueous layer was extracted with EtOAc (2×200 mL). The combined organic layers were washed with brine (500 mL), dried over anhydrous MgSO₄, filtered and concentrated under reduced pressure. The residue was purified by column chromatography on silica (0-100% EtOAc/hexanes) to afford the title compound. MS: 428.0 (M+1).

Step 5: 5-Chloro-3-((4-(1,1-difluoroethyl)-1-(4-methoxybenzyl)-6-oxo-1,6-dihydropyrimidin-5-yl)oxy)-2-fluorobenzonitrile DEOXOFLUOR® (15.08 mL, 82 mmol) was added to vial containing 3-((4-acetyl-1-(4-methoxybenzyl)-6-oxo-1,6-dihydropyrimidin-5-yl)oxy)-5-chloro-2-fluorobenzonitrile (7 g, 16.36 mmol) and dichloroethane (9.35 mL) at 25° C. The resulting vial was sealed and stirred at 70° C. for 3 h. LC-MS showed desired product. The reaction was cooled to room temperature and poured into a saturated NaHCO₃ solution very slowly and carefully. Then, the organic layer was separated and the aqueous layer was extracted with dichloromethane (2×100 mL). The combined organic layers were dried over MgSO4, filtered and concentrated. The residue was purified by column chromatography on silica (0-100% EtOAc/hexanes) to afford the title compound. MS: 450.0 (M+1).

Step 6: 5-Chloro-3-((4-(1,1-difluoroethyl)-6-oxo-1,6-dihydropyrimidin-5-yl)oxy)-2-fluorobenzonitrile A flask containing a mixture of 5-chloro-3-((4-(1,1-difluoroethyl)-1-(4-methoxybenzyl)-6-oxo-1,6-dihydropyrimidin-5-yl)oxy)-2-fluorobenzonitrile (7 g, 15.56 mmol) in trifluoroacetic acid (58.4 mL) and trifluoroacetic anhydride (19.45 mL) was stirred at 80° C. for 4 h. After cooling to room temperature, the mixture was concentrated under reduced pressure. The residue was dissolved in dichloromethane (50 mL) and hexanes (100 mL) were added slowly until the formation of a white solid. After stirring for 30 min, the white solid was collected on top of a filter, and dried under vacuum to provide the title compound. MS: 330.0 (M+1).

Intermediate AB35

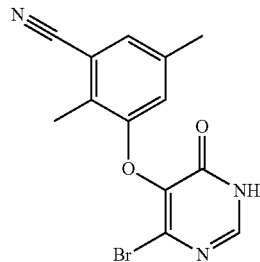 [SMILES: Cc1cc(C#N)c(C)c(Oc2c(Br)nc[nH]c2=O)c1]

3-((4-bromo-1-((2,4-dimethyl-6-oxo-1,6-dihydropyrimidin-5-yl)methyl)-6-oxo-1,6-dihydropyrimidin-5-yl)oxy)-2,5-dimethylbenzonitrile Step 1: Dimethyl 2-(5-chloro-3-cyano-2-methylphenoxy)malonate To a solution of 5-chloro-3-hydroxy-2-methylbenzonitrile, A07 (12 g, 71.6 mmol) was added potassium carbonate (19.79 g, 143 mmol). The resulting mixture was stirred for 15 minutes before dimethyl 2-chloromalonate (13.12 g, 79 mmol) was added. The reaction mixture was heated at 80° C. for 16 h. After cooled to room temperature, reaction mixture was concentrated under reduced pressure, then diluted with water and extracted with EtOAc. The organic layer was dried over anhydrous sodium sulfate, filtered and concentrated under reduced pressure. The residue was purified by column chromatography on silica (6% EtOAc/P.E.) to afford the title compound.

Step 2: 5-chloro-3-((4-hydroxy-6-oxo-1,6-dihydropyrimidin-5-yl)oxy)-2-methylbenzonitrile To a solution of formamidine acetate (9.09 g, 87 mmol) in MeOH (120 mL) was added sodium methoxide (9.44 g, 175 mmol) and the reaction mixture was stirred at RT for 5 minutes, and then was added dimethyl 2-(5-chloro-3-cyano-2-methylphenoxy)malonate (13 g, 43.7 mmol) portion wise. The reaction mixture was heated at 80° C. for 1 h. After cooled to room temperature, the reaction mixture was concentrated under reduced pressure to remove MeOH. The residue was dissolved in water (50 mL) and acidified to pH=5 by using 1.5M HCl. The precipitate was collected on top of a filter, washed with EtOAc to afford the crude title compound which was used as is in the next step.

Step 3: 5-chloro-3-((1-(4-methoxybenzyl)-4-((4-methoxybenzyl)oxy)-6-oxo-1,6-dihydropyrimidin-5-yl)oxy)-2-methylbenzonitrile To a solution of 5-chloro-3-((4-hydroxy-6-oxo-1,6-dihydropyrimidin-5-yl)oxy)-2-methylbenzonitrile (9 g, 32.4 mmol) in DMF (300 mL) was added potassium carbonate (13.44 g, 97 mmol) followed by addition of 1-(chloromethyl)-4-methoxybenzene (12.69 g, 81 mmol) after 15 minute initial stirring at room temperature. The reaction mixture was heated at 80° C. for 2 h, and then concentrated under reduced pressure. The residue was partitioned between ice water and EtOAc (3×). The combined organic layers were dried over anhydrous sodium sulfate, filtered and concentrated under reduced pressure. The residue was purified by column chromatography on silica (0-40% EtOAc/P.E.) to afford the title compound. MS: 518.4 (M+1).

Step 4: 5-chloro-3-((4-hydroxy-1-(4-methoxybenzyl)-6-oxo-1,6-dihydropyrimidin-5-yl)oxy)-2-methylbenzonitrile To a solution of 5-chloro-3-((1-(4-methoxybenzyl)-4-((4-methoxybenzyl)oxy)-6-oxo-1,6-dihydropyrimidin-5-yl)oxy)-2-methylbenzonitrile (10.2 g, 19.69 mmol) in DCM (85 mL) was added TFA (7.59 mL, 98 mmol) dropwise at 0° C. and the reaction mixture was stirred at room temperature for 30 minutes, and then concentrated under reduced pressure. The residue was triturated with methanol and the solid was collected on top of a filter to afford the title compound. MS: 398.2 (M+1).

Step 5: 3-((4-hydroxy-1-(4-methoxybenzyl)-6-oxo-1,6-dihydropyrimidin-5-yl)oxy)-2,5-dimethylbenzonitrile To a solution of 5-chloro-3-((4-hydroxy-1-(4-methoxybenzyl)-6-oxo-1,6-dihydropyrimidin-5-yl)oxy)-2-methylbenzonitrile (1.45 g, 3.64 mmol) in THF (15 mL) and water (2 mL) was added methylboronic acid (0.436 g, 7.29 mmol), potassium phosphate (2.321 g, 10.93 mmol). After purged with $N_2$, chloro(2-dicyclohexylphosphino-2',4',6'-tri-i-propyl-1,1'-biphenyl)(2'-amino-1,1'-biphenyl-2-yl) palladium (II) (0.287 g, 0.364 mmol) was added, then the reaction mixture was stirred at 100° C. for 16 h. The reaction mixture was passed through a filter, and the filtrate was concentrated under reduced pressure. The residue was purified by column chromatography on silica (3% MeOH/DCM.) to afford the title compound. MS: 378.2 (M+1).

Step 6: 3-((4-hydroxy-6-oxo-1,6-dihydropyrimidin-5-yl)oxy)-2,5-dimethylbenzonitrile To a solution of 3-((4-hydroxy-1-(4-methoxybenzyl)-6-oxo-1,6-dihydropyrimidin-5-yl)oxy)-2,5-dimethylbenzonitrile (1.0 g, 2.65 mmol) in trifluoroacetic acid (10 mL, 130 mmol) at 0° C., was added trifluoroacetic anhydride (5 mL, 35.4 mmol) and anisole (0.289 mL, 2.65 mmol). The reaction mixture was stirred at 100° C. for 3 h, and then concentrated under reduced pressure. The residue was purified by column chromatography on silica (3% MeOH/DCM) to afford the title compound.

Step 7: 3-((4,6-dibromopyrimidin-5-yl)oxy)-2,5-dimethylbenzonitrile

To a solution of 3-((4-hydroxy-6-oxo-1,6-dihydropyrimidin-5-yl)oxy)-2,5-dimethylbenzonitrile (500 mg, 1.944 mmol) in ACN (10 mL) at 0° C., was added phosphorus oxybromide (2229 mg, 7.77 mmol) followed by addition of triethylamine (0.542 mL, 3.89 mmol). The reaction mixture was stirred at 80° C. for 16 h, and then concentrated under reduced pressure. The residue was partitioned between water and EtOAc. The organic layer was washed with saturated sodium bicarbonate aqueous solution, brine and dried over anhydrous sodium sulfate, filtered and concentrated under reduced pressure. The residue was purified by column chromatography on silica (7% EtOAc/P.E.) to afford the title compound.

Step 8: 3-((4-bromo-6-oxo-1,6-dihydropyrimidin-5-yl)oxy)-2,5-dimethylbenzonitrile To a solution of 3-((4,6-dibromopyrimidin-5-yl)oxy)-2,5-dimethylbenzonitrile (530 mg, 1.384 mmol) in ACN (7 mL) and NMP (1.5 mL) was added potassium acetate (272 mg, 2.77 mmol). The reaction mixture was stirred at 80° C. for 16 h, and then concentrated under reduced pressure. The residue was partitioned between water and EtOAc. The organic layer was washed with water, brine and dried over anhydrous sodium sulfate, filtered and concentrated under reduced pressure. The residue was purified by column chromatography on silica (50% EtOAc/P.E.) to afford the title compound. MS: 639.0 (2M+1).

INTERMEDIATE BC SECTION

Intermediate BC01

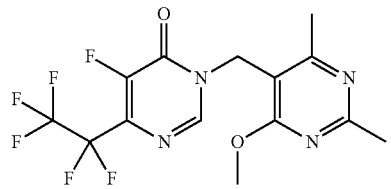 [SMILES: COc1nc(C)nc(C)c1Cn1cnc(C(F)(F)C(F)(F)F)c(F)c1=O]

5-fluoro-3-((4-methoxy-2,6-dimethylpyrimidin-5-yl)methyl)-6-(perfluoroethyl)pyrimidin-4 (3H)-one A mixture of 5-fluoro-6-(perfluoroethyl)pyrimidin-4 (3H)-one, B02 (420 mg, 1.81 mmol), potassium carbonate (625 mg, 4.52 mmol) and 5-(chloromethyl)-4-methoxy-2,6-dimethylpyrimidine, C14 (405 mg, 2.17 mmol) in DMA (9 mL) was stirred at RT for 16 h. LC-MS showed good for the conversion of starting material to product. The mixture was filtered. The filtrate was taken up by EtOAc (200 mL), and washed with water (3×50 mL), brine (50 mL), dried over anhydrous $MgSO_4$, filtered and concentrated under reduced pressure. The residue was purified with column chromatography on silica (0-10% MeOH/DCM) to isolate the title compound. MS: 383.1 (M+1). $^1$H NMR (600 MHz, DMSO-$d_6$) δ 8.79 (s, 1H), 4.86 (s, 2H), 2.35 (s, 3H), 2.27 (s, 3H), 2.18 (s, 3H).

Intermediate BC02

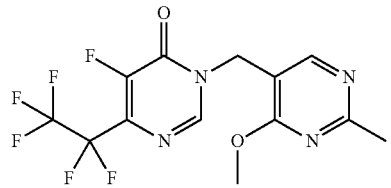 [SMILES: COc1nc(C)ncc1Cn1cnc(C(F)(F)C(F)(F)F)c(F)c1=O]

Methyl 5-fluoro-1-(4-methoxybenzyl)-6-oxo-1,6-dihydropyrimidine-4-carboxylate

A mixture of 5-fluoro-6-(perfluoroethyl)pyrimidin-4 (3H)-one, B02 (50 mg, 0.22 mmol), 5-(chloromethyl)-4-methoxy-2-methylpyrimidine, C15 (55.8 mg, 0.32 mmol) and potassium carbonate (89 mg, 0.65 mmol) in NMP (431 μl) was stirred at 23° C. for 16 h. LC-MS showed reaction is complete. The reaction mixture was diluted with water and the precipitate was collected on top of a filter and washed with water (3×), air dried to afford the title compound. MS: 369.1 (M+1).

The following intermediates in Table 11 were prepared under similar conditions as the above synthetic procedure outlined in the synthesis of intermediate BC02 using a corresponding intermediate B that is described in section B.

TABLE 11

| INT | Structure | IUPAC Name | MS (M + 1) |
|---|---|---|---|
| BC03 | 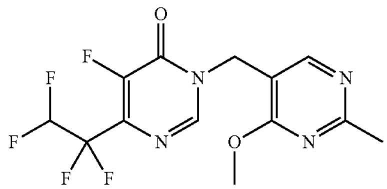 [SMILES: COc1nc(C)ncc1Cn1cnc(C(F)(F)C(F)F)c(F)c1=O] | 5-fluoro-3-((4-methoxy-2-methylpyrimidin-5-yl)methyl)-6-(1,1,2,2-tetrafluoroethyl)pyrimidin-4(3H)-one | 351.2 |
| BC04 | 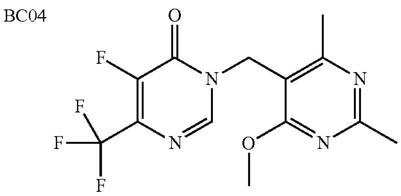 | 5-fluoro-3-((4-methoxy-2,6-dimethylpyrimidin-5-yl)methyl)-6-(trifluoromethyl)pyrimidin-4(3H)-one | 333.2 |
| BC05 | 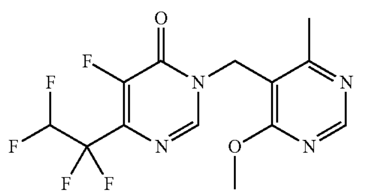 [SMILES: COc1ncnc(C)c1Cn1cnc(C(F)(F)C(F)F)c(F)c1=O] | 5-fluoro-3-((4-methoxy-6-methylpyrimidin-5-yl)methyl)-6-(1,1,2,2-tetrafluoroethyl)pyrimidin-4(3H)-one | 351.2 |

Intermediate BC06

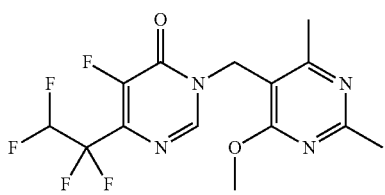 [SMILES: COc1nc(C)nc(C)c1Cn1cnc(C(F)(F)C(F)F)c(F)c1=O]

5-fluoro-3-((4-methoxy-2,6-dimethylpyrimidin-5-yl)methyl)-6-(1,1,2,2-tetrafluoroethyl)pyrimidin-4 (3H)-one A mixture of 5-fluoro-6-(1,1,2,2-tetrafluoroethyl)pyrimidin-4 (3H)-one, B01 (123 mg, 0.57 mmol), 5-(chloromethyl)-4-methoxy-2,6-dimethylpyrimidine, C15 (107 mg, 0.57 mmol) and potassium carbonate (238 mg, 1.72 mmol) in NMP (1147 µl) was stirred at 23° C. for 16 h. LC-MS showed the reaction is complete. The reaction mixture was filtered and purified with reverse phase HPLC (ACN/water with 0.1% TFA modifier) to afford the title compound. MS: 365.1 (M+1).

Example 1

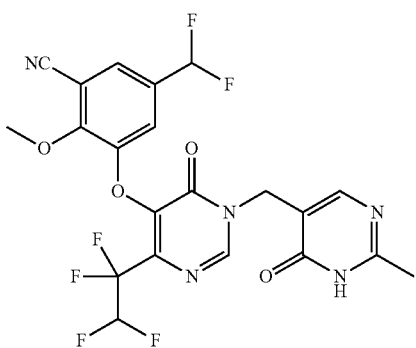

5-(difluoromethyl)-2-methoxy-3-((1-((2-methyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile Step 1: 5-(difluoromethyl)-2-methoxy-3-((1-((4-((4-methoxybenzyl)oxy)-2-methylpyrimidin-5-yl)methyl)-6-oxo-4-(1,1,2,2-tetrafluoroethyl)-1,6-dihydropyrimidin-5-yl)oxy)benzonitrile To a solution of 5-(difluoromethyl)-2-methoxy-3-((6-oxo-4-(1,1,2,2-tetrafluoroethyl)-1,6-dihydropyrimidin-5-yl)oxy) benzonitrile, AB18 (46 mg, 0.12 mmol) in DMF (1 mL) was added 5-(chloromethyl)-4-((4-methoxybenzyl)oxy)-2-methylpyrimidine, C15 (48.9 mg, 0.175 mmol), K₂CO₃ (48.5 mg, 0.351 mmol) and LiBr (10.16 mg, 0.117 mmol). The resulting reaction mixture was stirred at 50° C. for 2 h. LC-MS showed the reaction was complete. The reaction was concentrated under reduced pressure. The residue was purified by column chromatography on silica (66% EtOAc/P.E.) to give the title compound. MS: 634.4 (M–1).

Step 2: 5-(difluoromethyl)-2-methoxy-3-((1-((2-methyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile To a solution of 5-(difluoromethyl)-2-methoxy-3-((1-((4-((4-methoxybenzyl)oxy)-2-methylpyrimidin-5-yl)methyl)-6-oxo-4-(1,1,2,2-tetrafluoroethyl)-1,6-dihydropyrimidin-5-yl)oxy)benzonitrile (15 mg, 0.024 mmol) in DCM (1 mL) was added TFA (1 mL, 12.98 mmol). And the resulting mixture was stirred under N₂ at 25° C. for 1 h. LC-MS showed the starting material was consumed completely. The reaction mixture was concentrated under reduced pressure. The residue was purified by reverse phase HPLC (ACN/water with 0.1% TFA modifier) to afford the title compound.

MS: 516.2 (M+1). ¹H NMR (400 MHz, DMSO-d₆) δ 8.75 (s, 1H), 7.90 (s, 1H), 7.74 (s, 1H), 7.40 (s, 1H), 6.69-7.03 (m, 2H), 4.85 (s, 2H), 4.02 (s, 3H), 2.26 (s, 3H).

Example 2

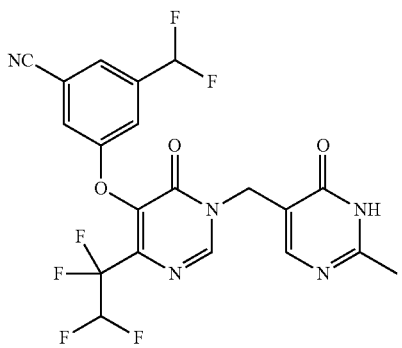 [SMILES: Cc1ncc(Cn2cnc(C(F)(F)C(F)F)c(Oc3cc(C#N)cc(C(F)F)c3)c2=O)c(=O)[nH]1]

3-(difluoromethyl)-5-((1-((2-methyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile This compound was prepared in an analogous manner to that described above for the synthesis of Example 1 using an appropriate intermediate AB01 and intermediate C15. MS: 486 (M+1)

Example 3

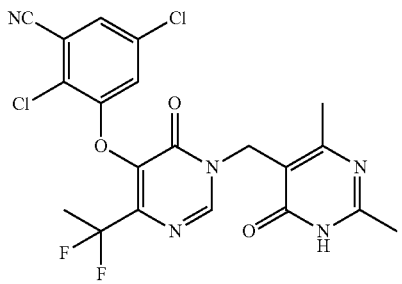 [SMILES: Cc1nc(C)c(Cn2cnc(C(C)(F)F)c(Oc3cc(Cl)cc(C#N)c3Cl)c2=O)c(=O)[nH]1]

2,5-dichloro-3-((4-(1,1-difluoroethyl)-1-((2,4-dimethyl-6-oxo-1,6-dihydropyrimidin-5-yl)methyl)-6-oxo-1,6-dihydropyrimidin-5-yl)oxy)benzonitrile Step 1: 5-chloro-3-((4-(1,1-difluoroethyl)-1-((4-methoxy-2,6-dimethylpyrimidin-5-yl)methyl)-6-oxo-1,6-dihydropyrimidin-5-yl)oxy)-2-methylbenzonitrile A mixture of 2, 5-dichloro-3-((6-oxo-4-(1,1,2,2-tetrafluoroethyl)-1, 6-dihydropyrimidin-5-yl) oxy) benzonitrile, AB01 (30 mg, 0.079 mmol), 5-(chloromethyl)-4-methoxy-2,6-dimethylpyrimidine, C14 (29.3 mg, 0.157 mmol), lithium bromide (13.64 mg, 0.157 mmol) and K₂CO₃ (76 mg, 0.550 mmol) in DMF (4 mL) was stirred at 50° C. for 2 h. TLC shows that the reaction was complete. The reaction mixture was diluted with saturated NaHCO₃ aqueous solution (20 mL) and extracted with EtOAc (2×10 mL). The combined organic layers were dried over anhydroud Na₂SO₄, filtered and concentrated under the reduced pressure to afford the title compound. MS: 532 (M+1).

Step 2: 2,5-dichloro-3-((4-(1,1-difluoroethyl)-1-((2, 4-dimethyl-6-oxo-1,6-dihydropyrimidin-5-yl) methyl)-6-oxo-1,6-dihydropyrimidin-5-yl)oxy)benzonitrile To a solution of 2, 5-dichloro-3-((4-(1,1-difluoroethyl)-1-((4-methoxy-2, 6-dimethylpyrimidin-5-yl) methyl)-6-oxo-1, 6-dihydropyrimidin-5-yl)oxy) benzonitrile (40 mg, 0.081 mmol) in ACN (3.0 mL) was added KI (40.1 mg, 0.242 mmol) and TMS-Cl (0.031 mL, 0.242 mmol). The resulting mixture was stirred at 70° C. for 1.5 h. LC-MS showed the reaction was completed. The reaction mixture was diluted with water (5 mL), and extracted with EtOAc (3×10 mL). The combined organic layers were washed with brine, dried over anhydroud Na₂SO₄, filtrated and concentrated under reduced pressure. The residue was purified by reverse phase HPLC (ACN/water with 0.1% TFA as modifier) to afford the title compound. MS: 548.2 (M+1). ¹H NMR (400 MHz, CHLOROFORM-d) δ ppm 8.70 (s, 1H) 7.37 (d, J=2.20 Hz, 1H) 6.79 (d, J=2.21 Hz, 1H) 5.02 (s, 2H) 2.60 (s, 3H) 2.50 (s, 3H) 1.97 (t, J=18.85 Hz, 3H).

The following examples in Table 12 were prepared in an analogous manner as that described above for the synthesis of Example 3 using an appropriate intermediate AB and intermediate C.

TABLE 12

| Ex# (AB#, C#) | Structure | IUPAC Name | MS (M + 1) |
| --- | --- | --- | --- |
| 4 (AB01, C14) | 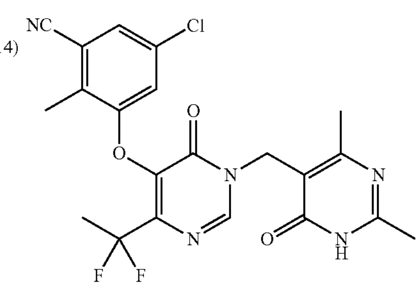 | 5-chloro-3-((4-(1,1-difluoroethyl)-1-((2,4-dimethyl-6-oxo-1,6-dihydropyrimidin-5-yl)methyl)-6-oxo-1,6-dihydropyrimidin-5-yl)oxy)-2-methylbenzonitrile | 462 |

TABLE 12-continued

| Ex# (AB#, C#) | Structure | IUPAC Name | MS (M + 1) |
|---|---|---|---|
| 5 (AB04, C14) | 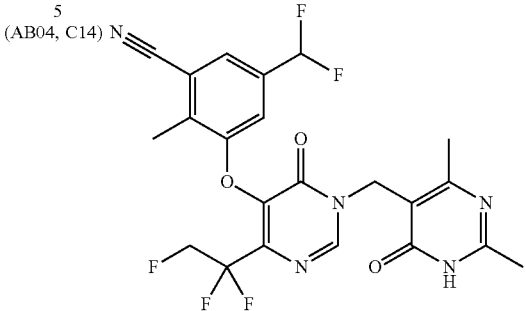 | 5-(difluoromethyl)-3-((1-((2,6-dimethyl-4-oxo-4,5-dihydropyrimidin-5-yl)methyl)-6-oxo-4-(1,1,2-trifluoroethyl)-1,6-dihydropyrimidin-5-yl)oxy)-2-methylbenzonitrile | 496.2 |
| 6 (AB03, C14) | 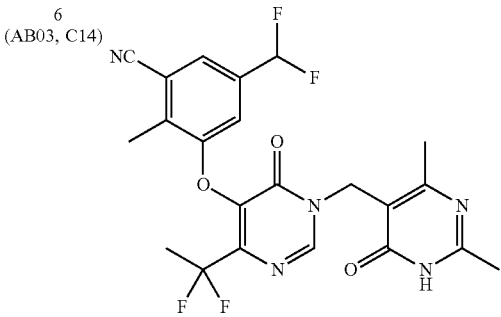 | 3-((4-(1, 1-difluoroethyl)-1-((2,4-dimethyl-6-oxo-1,6-dihydropyrimidin-5-yl)methyl)-6-oxo-1,6-dihydropyrimidin-5-yl)oxy)-5-(difluoromethyl)-2-methylbenzonitrile | 478 |
| 7 (AB13, C14) | 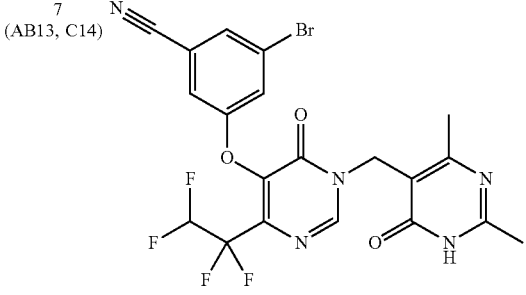 | 3-bromo-5-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile | 529 and 530 |
| 8 (AB05, C14) | 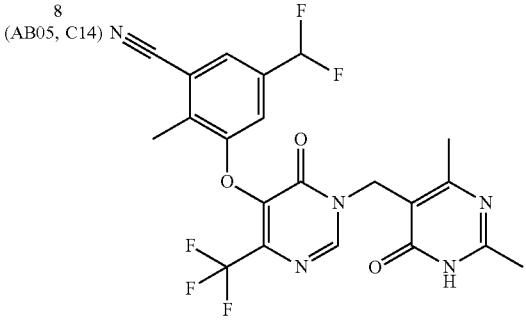 | 5-(difluoromethyl)-3-((1-((2,4-dimethyl-6-oxo-1,6-dihydropyrimidin-5-yl)methyl)-6-oxo-4-(trifluoromethyl)-1,6-dihydropyrimidin-5-yl)oxy)-2-methylbenzonitrile | 482.1 |
| 9 (AB20, C14) | 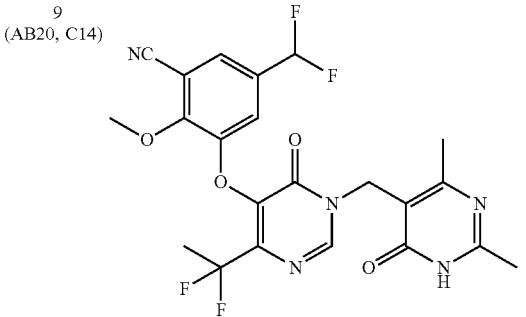 | 3-((4-(1,1-difluoroethyl)-1-((2,4-dimethyl-6-oxo-1,6-dihydropyrimidin-5-yl)methyl)-6-oxo-1,6-dihydropyrimidin-5-yl)oxy)-5-(difluoromethyl)-2-methoxybenzonitrile | 494.0 |

TABLE 12-continued

| Ex# (AB#, C#) | Structure | IUPAC Name | MS (M + 1) |
|---|---|---|---|
| 10 (AB18, C14) | 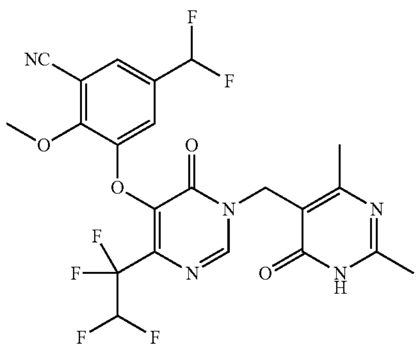 | 5-(difluoromethyl)-3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-2-methoxybenzonitrile | 530.2 |
| 11 (AB17, C14) | 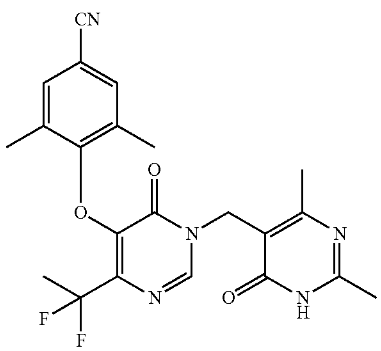 | 4-((4-(1,1-difluoroethyl)- 1 -((2,4-dimethyl- 6 -oxo-1, 6-dihydropyrimidin-5-yl)methyl)- 6 -oxo-1,6-dihydropyrimidin-5-yl)oxy)-3, 5-dimethylbenzonitrile | 442.1 |
| 12 (AB21, C14) | 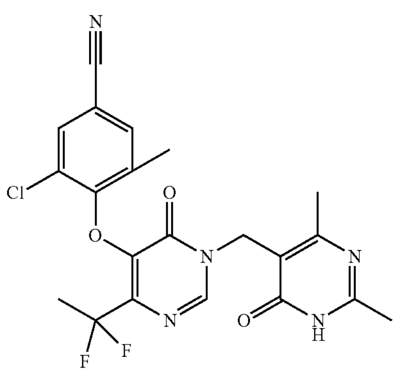 [SMILES: Cc1nc(C)c(Cn2cnc(C(C)(F)F)c(Oc3c(C)cc(C#N)cc3Cl)c2=O)c(=O)[nH]1] | 3-chloro-4-((4-(1,1-difluoroethyl)-1-((2,4-dimethyl-6-oxo-1,6-dihydropyrimidin-5-yl)methyl)-6-oxo-1,6-dihydropyrimidin-5-yl)oxy)-5-methylbenzonitrile | 462.2 |
| 13 (AB19, C14) | 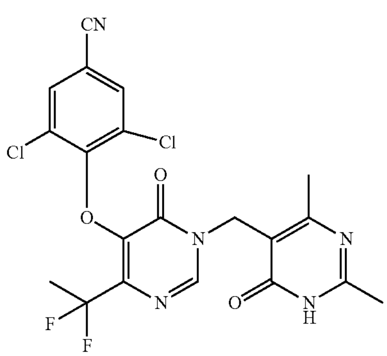 [SMILES: Cc1nc(C)c(Cn2cnc(C(C)(F)F)c(Oc3c(Cl)cc(C#N)cc3Cl)c2=O)c(=O)[nH]1] | 3,5-dichloro-4-((4-(1,1-difluoroethyl)-1-((2,4-dimethyl-6-oxo-1,6-dihydropyrimidin-5-yl)methyl)-6-oxo-1,6-dihydropyrimidin-5-yl)oxy) benzonitrile | 482 |

TABLE 12-continued

| Ex# (AB#, C#) | Structure | IUPAC Name | MS (M + 1) |
|---|---|---|---|
| 14 (AB23, C14) | 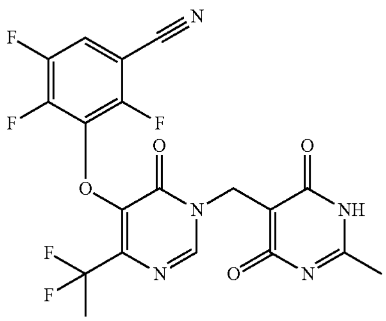 | 3-((4-(1, 1-difluoroethyl)-1-((2,4-dimethyl-6-oxo-1,6-dihydropyrimidin-5-yl)methyl)-6-oxo-1,6-dihydropyrimidin-5-yl)oxy)-2,4,5-trifluorobenzonitrile | 468.1 |
| 15 (AB15, C14) | 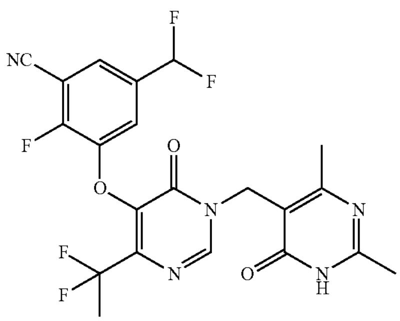 [SMILES: Cc1nc(C)c(Cn2cnc(C(C)(F)F)c(Oc3cc(C(F)F)cc(C#N)c3F)c2=O)c(=O)[nH]1] | 3-((4-(1, 1-difluoroethyl)-1-((2,4-dimethyl-6-oxo-1,6-dihydropyrimidin-5-yl)methyl)-6-oxo-. 1,6-dihydropyrimidin-5-yl)oxy)-5-(difluoromethyl)-2-fluorobenzonitrile | 482.1 |
| 16 (AB22, C14) | 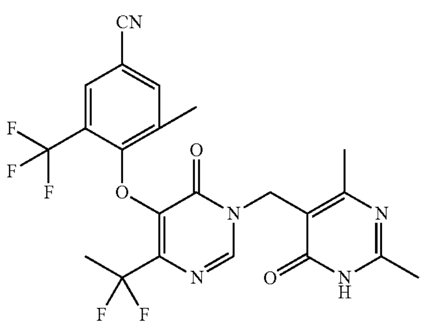 [SMILES: Cc1nc(C)c(Cn2cnc(C(C)(F)F)c(Oc3c(C)cc(C#N)cc3C(F)(F)F)c2=O)c(=O)[nH]1] | 4-((4-(1, 1-difluoroethyl)-1-((4-hydroxy-2,6-dimethylpyrimidin-5-yl)methyl)-6-oxo-1,6-dihydropyrimidin-5-yl)oxy)-3-methyl-5-(trifluoromethyl)benzonitrile | 496.2 |
| 17 (AB25, C14) | 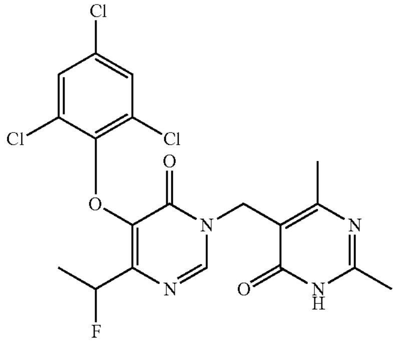 [SMILES: Cc1nc(C)c(Cn2cnc(C(C)F)c(Oc3c(Cl)cc(Cl)cc3Cl)c2=O)c(=O)[nH]1] | (S) or (R)-3,5-dichloro-4-((1-((2,4-dimethyl-6-oxo-1,6-dihydropyrimidin-5-yl)methyl)-4-(1-fluoroethyl)-6-oxo-1,6-dihydropyrimidin-5-yl)oxy) benzonitrile single enantiomer (faster eluting isomer A) | 464.0 |

TABLE 12-continued

| Ex# (AB#, C#) | Structure | IUPAC Name | MS (M + 1) |
|---|---|---|---|
| 18 (AB28, C14) | 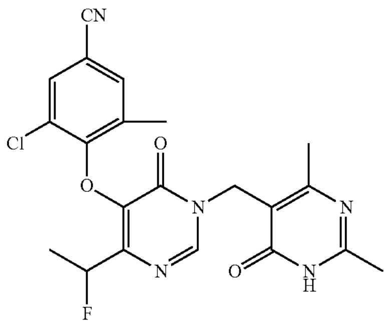 [SMILES: Cc1nc(C)c(Cn2cnc(C(C)F)c(Oc3c(C)cc(C#N)cc3Cl)c2=O)c(=O)[nH]1] | (S) or (R)-3-chloro-4-((1-((2,4-dimethyl-6-oxo-1,6-dihydropyrimidin-5-yl)methyl)-4-(1-fluoroethyl)-6-oxo-1,6-dihydropyrimidin-5-yl)oxy)-5-methylbenzonitrile single enantiomer (faster eluting isomer A) | 444.2 |
| 19 (AB30, C14) | 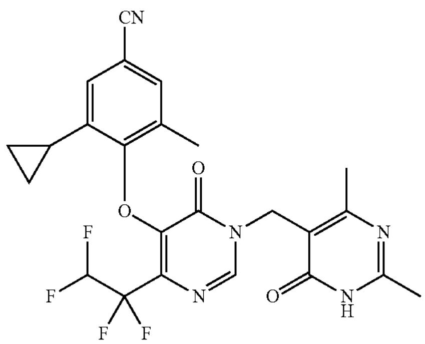 [SMILES: Cc1nc(C)c(Cn2cnc(C(F)(F)C(F)F)c(Oc3c(C)cc(C#N)cc3C3CC3)c2=O)c(=O)[nH]1] | 3-cyclopropyl-4-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-5-methylbenzonitrile | 504.0 |
| 20 (AB31, C14) | 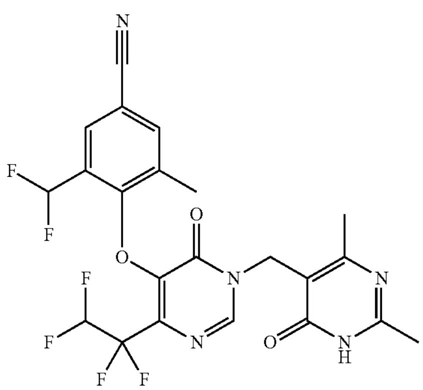 [SMILES: Cc1nc(C)c(Cn2cnc(C(F)(F)C(F)F)c(Oc3c(C)cc(C#N)cc3C(F)F)c2=O)c(=O)[nH]1] | 3-(difluoromethyl)-4-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-5-methylbenzonitrile | 514 |
| 21 (AB14, C14) | 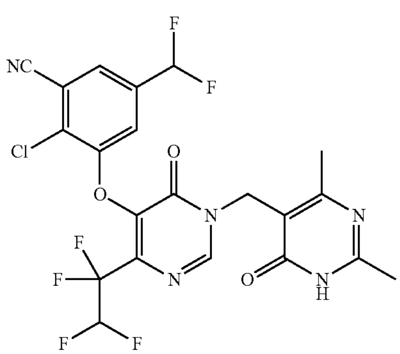 [SMILES: Cc1nc(C)c(Cn2cnc(C(F)(F)C(F)F)c(Oc3cc(C(F)F)cc(C#N)c3Cl)c2=O)c(=O)[nH]1] | 2-chloro-5-(difluoromethyl)-3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile | 534.2 |

Example 22

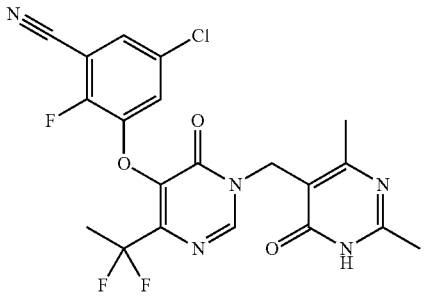 [SMILES: Cc1nc(C)c(Cn2cnc(C(C)(F)F)c(Oc3cc(Cl)cc(C#N)c3F)c2=O)c(=O)[nH]1]

5-(difluoromethyl)-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-methylbenzonitrile Step 1: 5-Chloro-3-((4-(1,1-difluoroethyl)-1-((4-methoxy-2,6-dimethylpyrimidin-5-yl)methyl)-6-oxo-1,6-dihydropyrimidin-5-yl)oxy)-2-fluorobenzonitrile To a stirred solution of 5-chloro-3-((4-(1,1-difluoroethyl)-6-oxo-1,6-dihydropyrimidin-5-yl)oxy)-2-fluorobenzonitrile, AB34 (50 mg, 0.152 mmol) and 5-(chloromethyl)-4-methoxy-2,6-dimethylpyrimidine, C14 (31.1 mg, 0.167 mmol) in DMF (758 µL), was added $K_2CO_3$ (41.9 mg, 0.303 mmol). The resulting mixture was stirred at RT overnight. The mixture was filtered to give the title compound, which was used directly in the next step.

Step 2: 5-Chloro-3-((4-(1,1-difluoroethyl)-1-((2,4-dimethyl-6-oxo-1,6-dihydropyrimidin-5-yl)methyl)-6-oxo-1,6-dihydropyrimidin-5-yl)oxy)-2-fluorobenzonitrile To a solution of 5-Chloro-3-((4-(1,1-difluoroethyl)-1-((4-methoxy-2,6-dimethylpyrimidin-5-yl)methyl)-6-oxo-1,6-dihydropyrimidin-5-yl)oxy)-2-fluorobenzonitrile (72.9 mg, 0.152 mmol) in NMP (758 µL), was added pyridine hydrochloride (88 mg, 0.76 mmol). The resulting mixture was heated at 120° C. in a microwave oven for 20 min. LC-MS showed desired product. The reaction mixture was diluted with water (100 uL) and DMSO (300 uL) and purified by reverse phase HPLC (ACN/water with 0.1% TFA as modifier) to afford the title compound. MS: 466.0 (M+1). $^1$H NMR (600 MHz, DMSO-$d_6$): δ 8.72 (s, 1H), 7.81 (dd, J=4.3, 2.3 Hz, 1H), 7.61 (dd, J=7.4, 2.3 Hz, 1H), 4.90 (s, 2H), 2.35 (s, 3H), 2.27 (s, 3H), 1.92 (t, J=19.6 Hz, 3H).

The following examples in Table 13 were prepared in an analogous manner to that described above for the synthesis of Example 22 using an appropriate intermediate AB and intermediate C.

TABLE 13

| Ex# (AB#, C#) | Structure | IUPAC Name | MS (M + 1) |
|---|---|---|---|
| 23 (AB08, C14) | 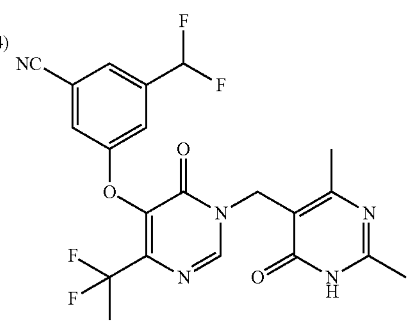 | 3-((4-(1, 1-difluoroethyl)-1-((2,4-dimethyl-6-oxo-1,6-dihydropyrimidin-5-yl)methyl)-6-oxo-1,6-dihydropyrimidin-5-yl)oxy)-5-(difluoromethyl)benzonitrile | 464.1 |
| 24 (AB34, C25) | 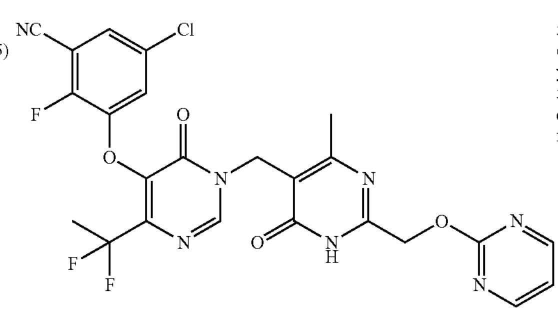 | 5-chloro-3-((4-(1,1-difluoroethyl)-1-((4-methyl-6-oxo-2-((pyrimidin-2-yloxy)methyl)-1,6-dihydropyrimidin-5-yl)methyl)-6-oxo-1,6-dihydropyrimidin-5-yl)oxy)-2-fluorobenzonitrile | 559.9 |

TABLE 13-continued

| Ex# (AB#, C#) | Structure | IUPAC Name | MS (M + 1) |
|---|---|---|---|
| 25 (AB03, C25) | 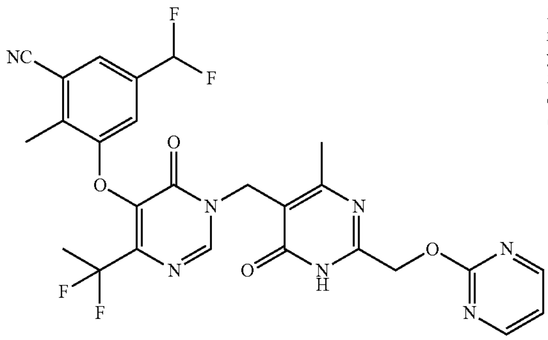 [SMILES: Cc1nc(COc2ncccn2)[nH]c(=O)c1Cn1cnc(C(C)(F)F)c(Oc2cc(C(F)F)cc(C#N)c2C)c1=O] | 3-((4-(1,1-difluoroethyl)-1-((4-methyl-6-oxo-2-((pyrimidin-2-yloxy)methyl)-1,6-dihydropyrimidin-5-yl)methyl)-6-oxo-1,6-dihydropyrimidin-5-yl)oxy)-5-(difluoromethyl)-2-methylbenzonitrile | 572.0 |
| 26 (AB35, C14) | 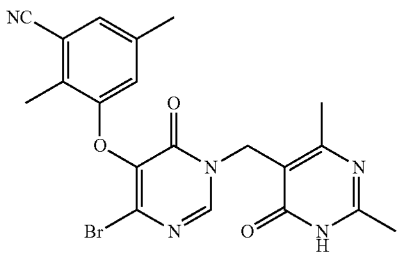 | 3-((4-bromo-1-((2,4-dimethyl-6-oxo-1,6-dihydropyrimidin-5-yl)methyl)-6-oxo-1,6-dihydropyrimidin-5-yl)oxy)-2,5-dimethylbenzonitrile | 458.1 |

Example 27

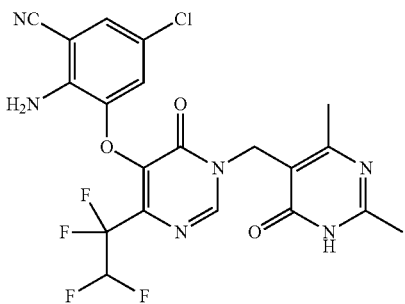 [SMILES: Cc1nc(C)c(Cn2cnc(C(F)(F)C(F)F)c(Oc3cc(Cl)cc(C#N)c3N)c2=O)c(=O)[nH]1]

2-amino-5-chloro-3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile A solution of 5-chloro-3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-2-fluorobenzonitrile, Example 23 (800 mg, 1.594 mmol) in EtOH (280 mL) was stirred at 60° C. under $NH_3$ for 30 h, and then concentrated by blowing under $N_2$ to give the crude residue. The residue was purified by reverse phase HPLC (ACN/water with 0.1% TFA as modifier) to afford the title compound. MS: 499.1 (M+1).

Examples 28 (Isomer A) and 29 (Isomer B)

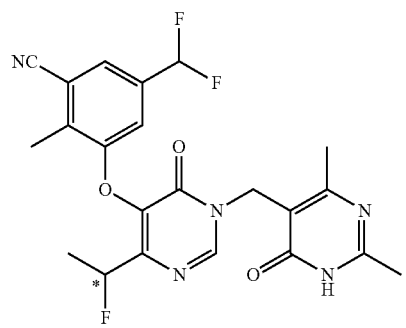

(S)-5-(difluoromethyl)-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-methylbenzonitrile, and (R)-5-(difluoromethyl)-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-methylbenzonitrile Step 1: 5-(difluoromethyl)-3-((4-(1-fluoroethyl)-1-((4-methoxy-2,6-dimethylpyrimidin-5-yl)methyl)-6-oxo-1,6-dihydropyrimidin-5-yl)oxy)-2-methylbenzonitrile To a stirred solution of 5-(difluoromethyl)-3-((4-(1-fluoroethyl)-6-oxo-1,6-dihydropyrimidin-5-yl)oxy)-2-methylbenzonitrile, AB27 (200 mg, 0.619 mmol) in DMF (2 mL) was added 5-(chloromethyl)-4-methoxy-2,6-dimethylpyrimidine, C14 (115 mg, 0.619 mmol), $K_2CO_3$ (171 mg, 1.237 mmol) and lithium bromide (53.7 mg, 0.619 mmol).

The resulting mixture was stirred at 25° C. for 1 h. TLC (50% EtOAc/P.E.) showed the reaction was complete. The reaction mixture was diluted with water (20 mL) and extracted with EtOAc (3×20 mL). The combined organic layers were washed with brine, dried over anydrous Na$_2$SO$_4$, filtered and concentrated under reduced pressure. The residue was purified by preparative TLC plates (50% EtOAc/P.E.) to give a racemic mixture of the title compound. MS: 474.1, (M+1).

Step 2: 5-(difluoromethyl)-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-methylbenzonitrile To a stirred solution of 5-(difluoromethyl)-3-((4-(1-fluoroethyl)-1-((4-methoxy-2,6-dimethylpyrimidin-5-yl)methyl)-6-oxo-1,6-dihydropyrimidin-5-yl)oxy)-2-methylbenzonitrile (180 mg, 0.380 mmol) in ACN (4 mL) was added KI (189 mg, 1.141 mmol) and TMS-Cl (0.146 mL, 1.141 mmol). The resulting reaction mixture was stirred at 70° C. for 12 h. TLC (66% EtOAc/P.E.) showed the reaction was complete. The reaction mixture was concentrated under reduced pressure. The residue was purified by reverse phase HPLC (ACN/water with 0.1% TFA as modifier) to afford a racemate of the title compound. MS: 460.2 (M+1).

The racemic mixture was purified by chiral SFC (IC-H column, 25% EtOH/CO$_2$ with 0.1% NH$_4$OH as modifier) to afford Example 28 isomer A (faster eluting): MS: 460.2 (M+1), and Example 29 isomer B (slower eluting): MS: 460.2 (M+1).

Examples 30 (Isomer A) and 31 (Isomer B)

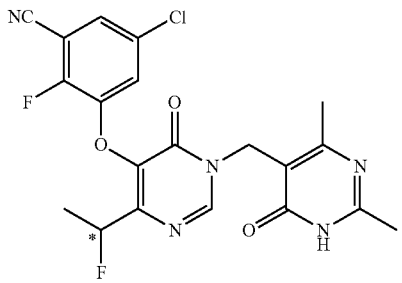 [SMILES: Cc1nc(C)c(Cn2cnc(C(C)F)c(Oc3cc(Cl)cc(C#N)c3F)c2=O)c(=O)[nH]1]

(S)-5-chloro-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-fluorobenzonitrile, and (R)-5-chloro-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-fluorobenzonitrile Step 1: 5-chloro-2-fluoro-3-((4-(1-fluoroethyl)-1-((4-methoxy-2,6-dimethylpyrimidin-5-yl)methyl)-6-oxo-1,6-dihydropyrimidin-5-yl)oxy)benzonitrile To a solution of 5-chloro-2-fluoro-3-((4-(1-fluoroethyl)-6-oxo-1,6-dihydropyrimidin-5-yl)oxy)benzonitrile, AB24 (152 mg, 0.488 mmol) in DMF (5 mL), was added K$_2$CO$_3$ (202 mg, 1.46 mmol), lithium bromide (85 mg, 0.98 mmol), and then 5-(chloromethyl)-4-methoxy-2,6-dimethylpyrimidine, C14 (202 mg, 0.975 mmol). The resulting reaction mixture was stirred at 20° C. for 30 min. TLC (33% EtOAc/P.E.) and LC-MS showed the reaction was complete. The mixture was diluted with water (5.0 mL), and extracted with EtOAc (3×5 mL). The combined organic layers were washed with brine, dried over anhydrous Na$_2$SO$_4$, filtered and concentrated under reduced pressure to give the title compound. MS: 462.2 (M+1).

Step 2: 5-chloro-2-fluoro-3-((4-(1-fluoroethyl)-1-((4-hydroxy-2,6-dimethylpyrimidin-5-yl)methyl)-6-oxo-1,6-dihydropyrimidin-5-yl)oxy)benzonitrile To a solution of 5-chloro-2-fluoro-3-((4-(1-fluoroethyl)-1-((4-methoxy-2,6-dimethylpyrimidin-5-yl)methyl)-6-oxo-1,6-dihydropyrimidin-5-yl)oxy)benzonitrile (150 mg, 0.325 mmol) in ACN (3 mL), was added KI (67.9 mg, 0.409 mmol) and TMS-Cl (0.136 mL, 1.065 mmol). The resulting reaction mixture was stirred at 70° C. for 5 h. TLC (20% EtOAc/P.E.) showed the reaction was complete. The reaction mixture was concentrated under reduced pressure. Then residue was purified by reverse phase HPLC (ACN/water with 0.1% TFA as modifier) to give racemic mixture of the title compounds. MS: 448.2 (M+1). The mixture of the two stereoisomers was purified by chiral SFC (IC-H, 35% IPA/CO2) to afford Example 30 isomer A (faster eluting): MS: 448.2 (M+1), $^1$H NMR (400 MHz, DMSO-d$_6$) δ 8.67 (s, 1H), 7.81 (br d, J=2.3 Hz, 1H), 7.55-7.46 (m, 1H), 5.82-5.61 (m, 1H), 4.87 (br s, 2H), 2.33 (s, 3H), 2.23 (s, 3H), 1.59-1.47 (m, 3H), and Example 31 isomer B (slower eluting): MS: 448.2 (M+1), $^1$H NMR (400 MHz, DMSO-d$_6$) δ 8.67 (s, 1H), 7.81 (dd, J=2.3, 4.4 Hz, 1H), 7.51 (dd, J=2.3, 7.3 Hz, 1H), 5.83-5.62 (m, 1H), 4.87 (br s, 2H), 2.33 (s, 3H), 2.23 (s, 3H), 1.59-1.45 (m, 3H).

The following compounds in Table 14 were each prepared as a racemate followed by purification to obtain the noted isomer(s) in an analogous manner to that described above for the synthesis of Example 30 using, an appropriate intermediate AB and intermediate C which were described in the intermediate session.

TABLE 14

| Ex# (AB#, C#) | Structure | IUPAC Name | MS (M + 1) |
|---|---|---|---|
| 32 (AB33, C14) | 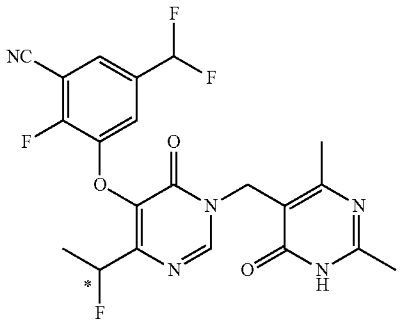 [SMILES: Cc1nc(C)c(Cn2cnc(C(C)F)c(Oc3cc(C(F)F)cc(C#N)c3F)c2=O)c(=O)[nH]1] | (S) or (R)-5-(difluoromethyl)-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-fluorobenzonitrile single enantiomer (faster eluting isomer A) | 464.1 |
| 33 (AB33, C14) | 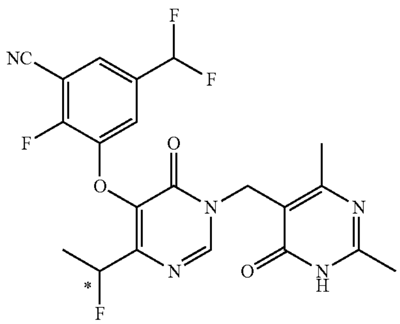 | (R) or (S)-5-(difluoromethyl)-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-fluorobenzonitrile single enantiomer (slower eluting isomer B) | 464.1 |
| 34 (AB26, C14) | 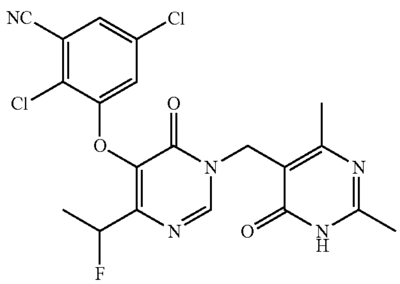 [SMILES: Cc1nc(C)c(Cn2cnc(C(C)F)c(Oc3cc(Cl)cc(C#N)c3Cl)c2=O)c(=O)[nH]1] | (S) or (R)-2,5-dichloro-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)benzonitrile single enantiomer (faster eluting isomer A) | 464.0 |
| 35 (AB32, C14) | 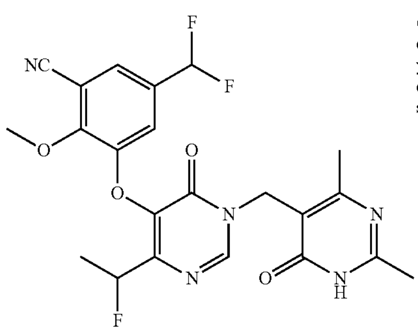 | (S)or (R)-5-(difluoromethyl)-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-methoxybenzonitrile single enantiomer (faster eluting isomer A) | 476.0 |
| 36 (AB32, C14) | 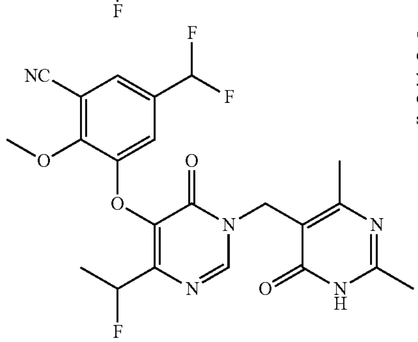 | (R)or (S)-5-(difluoromethyl)-3-((1-((2,4-dimethyl-6-oxo-1,6-dihydropyrimidin-5-yl)methyl)-4-(1-fluoroethyl)-6-oxo-1,6-dihydropyrimidin-5-yl)oxy)-2-methoxybenzonitrile single enantiomer (slower eluting isomer B) | 476.0 |

Example 37

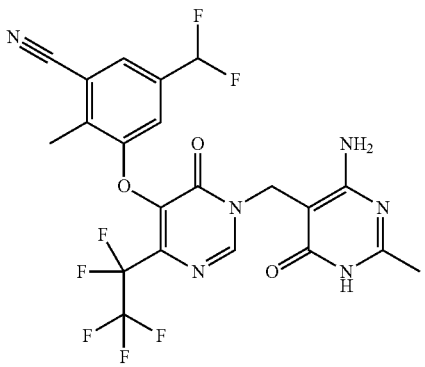 [SMILES: Cc1nc(N)c(Cn2cnc(C(F)(F)C(F)(F)F)c(Oc3cc(C(F)F)cc(C#N)c3C)c2=O)c(=O)[nH]1]

3-((1-((4-amino-2-methyl-6-oxo-1,6-dihydropyrimidin-5-yl)methyl)-6-oxo-4-(perfluoroethyl)-1,6-dihydropyrimidin-5-yl)oxy)-5-(difluoromethyl)-2-methylbenzonitrile Step 1: 3-((1-((4-(bis(4-methoxybenzyl)amino)-6-methoxy-2-methylpyrimidin-5-yl)methyl)-6-oxo-4-(perfluoroethyl)-1,6-dihydropyrimidin-5-yl)oxy)-5-(difluoromethyl)-2-methylbenzonitrile To a chilled (0° C.) solution of 5-(difluoromethyl)-2-methyl-3-((6-oxo-4-(perfluoroethyl)-1,6-dihydropyrimidin-5-yl)oxy)benzonitrile, AB06 (100 mg, 0.253 mmol) and (4-(Bis(4-methoxybenzyl)amino)-6-methoxy-2-methylpyrimidin-5-yl)methanol, C13 (104 mg, 0.253 mmol) in DCM (1265 μl), was added triphenylphosphine (66.4 mg, 0.253 mmol) and DIAD (49.2 μl, 0.253 mmol). The resulting solution was stirred at 23° C. for 16 h, then purified directly by column chromatography on silica (0-50% EtOAc/hexanes) to afford title compound. MS: 787.2 (M+1).

Step 2: 3-((1-((4-amino-6-methoxy-2-methylpyrimidin-5-yl)methyl)-6-oxo-4-(perfluoroethyl)-1,6-dihydropyrimidin-5-yl)oxy)-5-(difluoromethyl)-2-methylbenzonitrile 3-((1-((4-(bis(4-methoxybenzyl)amino)-6-methoxy-2-methylpyrimidin-5-yl)methyl)-6-oxo-4-(perfluoroethyl)-1,6-dihydropyrimidin-5-yl)oxy)-5-(difluoromethyl)-2-methylbenzonitrile (130 mg, 0.165 mmol) was dissolved in TFA (2 mL) and was heated to 100° C. for 1 h. The solution was concentrated under reduced pressure. The residue was further dried via azotropic evaporation with toluene to isolate the title compound. MS: 547.1 (M+1).

Step 3: 3-((1-((4-amino-2-methyl-6-oxo-1,6-dihydropyrimidin-5-yl)methyl)-6-oxo-4-(perfluoroethyl)-1,6-dihydropyrimidin-5-yl)oxy)-5-(difluoromethyl)-2-methylbenzonitrile To a chilled (0° C.) solution of 3-((1-((4-amino-6-methoxy-2-methylpyrimidin-5-yl)methyl)-6-oxo-4-(perfluoroethyl)-1,6-dihydropyrimidin-5-yl)oxy)-5-(difluoromethyl)-2-methylbenzonitrile (90 mg, 0.165 mmol) in ACN (824 μL), was added TMS-I (448 μL, 3.29 mmol). The resulting reaction mixture was stirred at 23° C. for 1 h. The reaction is neutralized with $Na_2SO_3$ (500 uL), then concentrated under reduced pressure. The residue was purified by reverse phase HPLC (ACN/water with 0.05% $NH_4OH$ modifier) to afford the title compound. MS: 410.3 (M+1). $^1H$ NMR (600 MHz, DMSO-$d_6$) δ 11.66 (s, 1H), 8.57 (s, 1H), 7.74 (s, 1H), 7.35 (s, 1H), 6.88 (t, J=55.3 Hz, 1H), 6.58 (s, 2H), 4.74 (s, 2H), 3.28 (s, 3H), 2.10 (s, 3H).

The following examples in Table 15 were prepared in an analogous manner to that described in Example 37 with appropriate intermediate AB described in the intermediate section.

TABLE 15

| Ex# (AB#, C#) | Structure | IUPAC Name | MS (M + 1) |
|---|---|---|---|
| 38 (AB12, C13) | (structure) | 3-((1-((4-amino-2-methyl-6-oxo-1,6-dihydropyrimidin-5-yl)methyl)-6-oxo-4-(perfluoroethyl)-1,6-dihydropyrimidin-5-yl)oxy)-5-chloro-2-fluorobenzonitrile | 521.1 |

TABLE 15-continued

| Ex# (AB#, C# | Structure | IUPAC Name | MS (M + 1) |
|---|---|---|---|
| 39 (AB10, C13) | 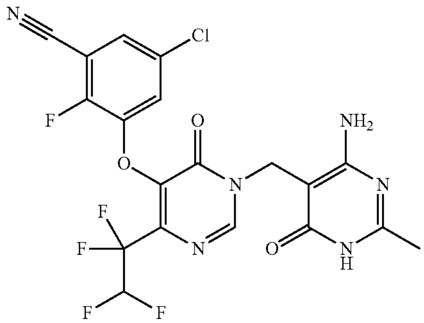 [SMILES: Cc1nc(N)c(Cn2cnc(C(F)(F)C(F)F)c(Oc3cc(Cl)cc(C#N)c3F)c2=O)c(=O)[nH]1] | 3-((1-((4-amino-2-methyl-6-oxo-1,6-dihydropyrimidin-5-yl)methyl)-6-oxo-4-(1,1,2,2-tetrafluoroethyl)-1,6-dihydropyrimidin-5-yl)oxy)-5-chloro-2-fluorobenzonitrile | 503.1 |

Example 40

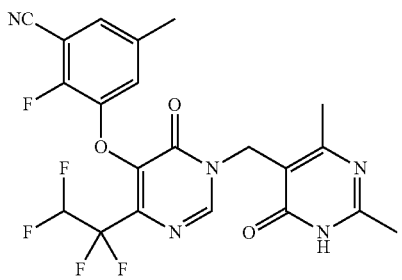 [SMILES: Cc1cc(C#N)c(F)c(Oc2c(C(F)(F)C(F)F)ncn(Cc3c(C)nc(C)[nH]c3=O)c2=O)c1]

3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-2-fluoro-5-methylbenzonitrile Step 1: 5-chloro-2-fluoro-3-((1-((4-methoxy-2,6-dimethylpyrimidin-5-yl)methyl)-6-oxo-4-(1,1,2,2-tetrafluoroethyl)-1,6-dihydropyrimidin-5-yl)oxy)benzonitrile To a mixture of 5-chloro-2-fluoro-3-((6-oxo-4-(1,1,2,2-tetrafluoroethyl)-1,6-dihydropyrimidin-5-yl)oxy)benzonitrile, AB10 (153 mg, 0.418 mmol), K$_2$CO$_3$ (133 mg, 0.964 mmol) and LiBr (27.9 mg, 0.321 mmol) in DMF (3 mL) was added 5-(chloromethyl)-4-methoxy-2,6-dimethylpyrimidine, C14 (60 mg, 0.321 mmol). The resulting reaction mixture was stirred at 20° C. for 3 h, and then concentrated under reduced pressure. The residue was purified by column chromatography on silica (0-33% EtOAc/P.E.) to give the title compound. $^1$HNMR (400 MHz, DMSO-d$_6$) δ 8.70 (s, 1H) 7.85 (dd, J=4.82, 2.63 Hz, 1H) 7.69 (dd, J=7.24, 2.41 Hz, 1H) 6.68-7.01 (m, 2H) 5.06 (s, 2H) 3.88 (s, 3H) 2.48 (br s, 3H) 2.45 (s, 3H).

Step 2: 2-fluoro-3-((1-((4-methoxy-2,6-dimethylpyrimidin-5-yl)methyl)-6-oxo-4-(1,1,2,2-tetrafluoroethyl)-1,6-dihydropyrimidin-5-yl)oxy)-5-methylbenzonitrile To a mixture of 5-chloro-2-fluoro-3-((1-((4-methoxy-2,6-dimethylpyrimidin-5-yl)methyl)-6-oxo-4-(1,1,2,2-tetrafluoroethyl)-1,6-dihydropyrimidin-5-yl)oxy)benzonitrile (180 mg, 348.96 umol) in 1,4-dioxane (4 mL) and H$_2$O (0.5 mL) were added K$_2$CO$_3$ (144.68 mg, 1.05 mmol), 2,4,6-trimethyl-1,3,5,2,4,6-trioxatriborinane (131.42 mg, 1.05 umol), X-Phos (83.18 mg, 174.48 umol) and Pd(OAc)$_2$ (7.83 mg, 34.9 umol). The resulting mixture was stirred at 110° C. under N$_2$ for 2 h, and then purified by column chromatography on silica (0-33% EtOAc/P.E.) to give the title compound. MS: 496.2 (M+1).

Step 3: 3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-2-fluoro-5-methylbenzonitrile To a solution of 2-fluoro-3-((1-((4-methoxy-2,6-dimethylpyrimidin-5-yl)methyl)-6-oxo-4-(1,1,2,2-tetrafluoroethyl)-1,6-dihydropyrimidin-5-yl)oxy)-5-methylbenzonitrile (100 mg, 201.85 umol) in ACN (5 mL) were added TMS-Cl (65.79 mg, 605.56 umol) and KI (100.52 mg, 605.56 umol). The resulting reaction mixture was stirred at 70° C. for 2 h, and then concentrated under reduced pressure. The residue was purified by reverse phase HPLC (ACN/water with 0.1% TFA as modifier) to afford the title compound. MS: 482.1 (M+1). $^1$H NMR (400 MHz, DMSO-d$_6$) δ 8.77 (s, 1H) 7.42 (br d, J=3.75 Hz, 1H) 7.21-7.27 (m, 1H) 6.70-7.01 (m, 1H) 4.91 (s, 2H) 2.35 (s, 3H) 2.28 (s, 3H) 2.23 (s, 3H).

The following examples in Table 16 were prepared in an analogous manner to that described in Example 40 with an appropriate intermediate AB described in the intermediate section.

TABLE 16

| Ex# (AB#, C#) | Structure | IUPAC Name | MS (M + 1) |
|---|---|---|---|
| 41 (AB34, C14) | 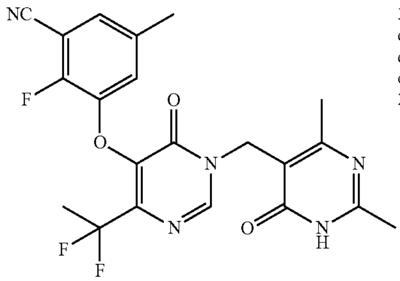 | 3-((4-(1, 1-difluoroethyl)-1 -((2,4-dimethyl-6-oxo-1,6-dihydropyrimidin-5-yl)methyl)-6-oxo-1,6-dihydropyrimidin-5-yl)oxy)-2-fluoro-5-methylbenzonitrile | 446.2 |
| 42 (AB10, C14) | 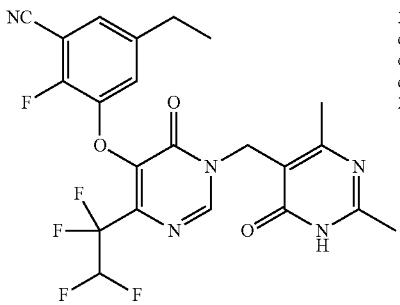 | 3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-5-ethyl-2-fluorobenzonitrile | 496.2 |

Example 43 (Isomer A)

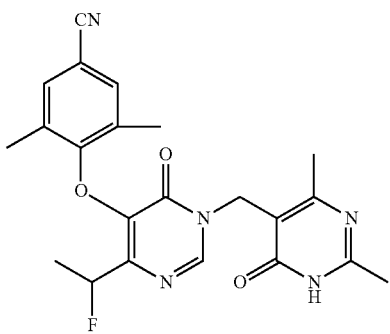

(S) or (R)-4-((1-((2,4-dimethyl-6-oxo-1,6-dihydropyrimidin-5-yl)methyl)-4-(1-fluoroethyl)-6-oxo-1,6-dihydropyrimidin-5-yl)oxy)-3,5-dimethylbenzonitrile Step 1: 4-((4-acetyl-6-oxo-1,6-dihydropyrimidin-5-yl)oxy)-3,5-dimethylbenzonitrile To a solution of 4-((4-acetyl-1-(4-methoxybenzyl)-6-oxo-1, 6-dihydropyrimidin-5-yl) oxy)-3, 5-dimethylbenzonitrile, AB16 (650 mg, 1.45 mmol) in TFA (5 mL, 64.9 mmol) was added TFAA (2.5 mL, 17.70 mmol). The resulting reaction mixture was stirred at 110° C. for 6 h. Then the reaction mixture was concentrated under reduced pressure, then basified to pH~9 with saturated NaHCO₃ aq. solution (10.0 mL), and extracted with EtOAc (3×20 mL). The combined organic layers were washed with brine, dried over anhydrous Na₂SO₄, filtrated and concentrated under reduced pressure to give the title compound. MS: 284.1 (M+1), 589.1 (2M+23), and used directly without further purification.

Step 2: 4-((4-acetyl-1-((4-methoxy-2,6-dimethylpyrimidin-5-yl)methyl)-6-oxo-1,6-dihydropyrimidin-5-yl)oxy)-3,5-dimethylbenzonitrile To a solution of 4-((4-acetyl-6-oxo-1,6-dihydropyrimidin-5-yl)oxy)-3,5-dimethylbenzonitrile (500 mg)(crude), lithium bromide (307 mg, 3.53 mmol) in DMA (5 mL) was added 5-(chloromethyl)-4-methoxy-2,6-dimethylpyrimidine, C14 (366 mg, 1.765 mmol) and K₂CO₃ (488 mg, 3.53 mmol). The resulting reaction mixture was stirred at 20° C. for 30 min. Upon completion of the reaction, water (5.0 mL) was added. And the reaction mixture was extracted with EtOAc (3×5 mL). The combined organic layers were washed with brine, dried over anhydrous Na₂SO₄, filtrated and concentrated under reduced pressure. The residue was purified with preparative TLC plates (10% MeOH/DCM) to give the title compound.

Step 3: 4-((4-(1-hydroxyethyl)-1-((4-methoxy-2,6-dimethylpyrimidin-5-yl)methyl)-6-oxo-1,6-dihydropyrimidin-5-yl)oxy)-3,5-dimethylbenzonitrile To a solution of 4-((4-acetyl-1-((4-methoxy-2, 6-dimethylpyrimidin-5-yl) methyl)-6-oxo-1, 6-dihydropyrimidin-5-yl)oxy)-3,5-dimethylbenzonitrile (200 mg, 0.438 mmol) in MeOH (1.0 mL) was added 1M Zn(BH₄)₂ solution in THF (0.110 mL, 0.110 mmol) at −10-0° C. The resulting reaction mixture was stirred at −10-0° C. for 0.5 h. TLC (10% MeOH/DCM) showed the reaction was complete. The reaction mixture was diluted with water (5 mL) and extracted with EtOAc (4×10 mL). The combined organic layers were washed with brine, dried over anhydrous Na₂SO₄, filtrated and concentrated under reduced pressure to afford the title compound.

Step 4: 4-((4-(1-fluoroethyl)-1-((4-methoxy-2,6-dimethylpyrimidin-5-yl)methyl)-6-oxo-1,6-dihydropyrimidin-5-yl)oxy)-3,5-dimethylbenzonitrile To a solution of 4-((4-(1-hydroxyethyl)-1-((4-methoxy-2,6-dimethylpyrimidin-5-yl)methyl)-6-oxo-1, 6-dihydropyrimidin-5-yl) oxy)-3,5-dimethylbenzonitrile (130 mg, 0.269 mmol) in DCM (5 mL) was added DAST (0.082 mL, 0.618 mmol) at 0° C. and the resulting mixture was stirred at 0° C. for 1 h. TLC (10% MeOH/DCM) and showed the reaction was complete. The reaction mixture was diluted with water (5 mL), and extracted with DCM (3×10 mL). The combined organic layers were washed with brine, dried over anhydrous Na$_2$SO$_4$, filtrated and concentrated under reduced pressure to give the title compound. MS: 438.1 (M+1).

Step 5:4-((1-((2,4-dimethyl-6-oxo-1,6-dihydropyrimidin-5-yl)methyl)-4-(1-fluoroethyl)-6-oxo-1,6-dihydropyrimidin-5-yl)oxy)-3,5-dimethylbenzonitrile To a solution of 4-((4-(1-fluoroethyl)-1-((4-methoxy-2,6-dimethylpyrimidin-5-yl) methyl)-6-oxo-1, 6-dihydropyrimidin-5-yl) oxy)-3,5-dimethylbenzonitrile (150 mg, 0.261 mmol) in ACN (2 mL) was added KI (216 mg, 1.303 mmol) and TMS-Cl (0.167 mL, 1.303 mmol). The resulting reaction mixture was stirred at 70° C. for 1 h, and then concentrated under reduced pressure. The residue was purified by reverse phase HPLC (ACN/water with 0.1% TFA as modifier) to give racemic mixture of the title compound. MS: 424.1 (M+1). The racemic mixture was purified by chiral SFC (IC-H column, 40% IPA/CO$_2$ with 0.1% NH$_4$OH as modifier) to give Example 43 isomer A (faster eluting) MS: 424.1 (M+1). $^1$H NMR (400 MHz, DMSO-d$_6$): δ 12.44 (s, 1H), 8.42 (s, 1H), 7.49 (d, J=7.24, 2H), 6.06 (d, J=6.00, 0.5H), 5.94 (d, J=6.80, 0.5H) 4.77 (s, 2H). 2.22 (d, J=10.4, 6H), 2.06 (s, J=7.2, 6H), 1.58 (m, 3H).

Example 44 (Isomer B)

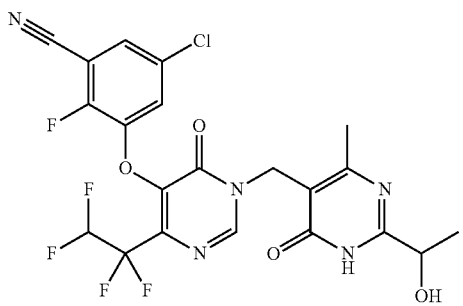 [SMILES: Cc1nc(C(C)O)[nH]c(=O)c1Cn1cnc(C(F)(F)C(F)F)c(Oc2cc(Cl)cc(C#N)c2F)c1=O]

(S) or (R)-5-chloro-2-fluoro-3-((1-((2-(1-hydroxyethyl)-4-methyl-6-oxo-1,6-dihydropyrimidin-5-yl)methyl)-2-oxo-4-(1,1,2,2-tetrafluoroethyl)-1,2-dihydropyridin-3-yl)oxy)benzonitrile Step 1: 3-((1-((2-acetyl-4-methoxy-6-methylpyrimidin-5-yl)methyl)-6-oxo-4-(1,1,2,2-tetrafluoroethyl)-1,6-dihydropyrimidin-5-yl)oxy)-5-chloro-2-fluorobenzonitrile To a stirred solution of 5-chloro-2-fluoro-3-((6-oxo-4-(1,1,2,2-tetrafluoroethyl)-1,6-dihydropyrimidin-5-yl)oxy)benzonitrile, AB10 (307 mg, 0.839 mmol) in DMF (10 mL) was added K$_2$CO$_3$ (193 mg, 1.398 mmol), lithium bromide (91 mg, 1.048 mmol) and 1-(5-(chloromethyl)-4-methoxy-6-methylpyrimidin-2-yl)ethanone, C21 (150 mg, 0.00 mmol). And the resulting mixture was stirred at 20° C. for 16 h. TLC (50% EtOAc/P.E.) showed the completion of the reaction. The reaction mixture was diluted with water (15 mL) and extracted with EtOAc (3×20 mL). The combined organic layers were washed with brine, dried over anhydrous Na$_2$SO$_4$, filtered and concentrated under reduced pressure. The residue was purified by column chromatography on silica (10-66% EtOAc/P.E.) to afford the title compound. MS: 544 (M+1).

Step 2: 5-chloro-2-fluoro-3-((1-((2-(1-hydroxyethyl)-4-methoxy-6-methylpyrimidin-5-yl)methyl)-6-oxo-4-(1,1,2,2-tetrafluoroethyl)-1,6-dihydropyrimidin-5-yl)oxy)benzonitrile To a stirred solution of 3-((1-((2-acetyl-4-methoxy-6-methylpyrimidin-5-yl)methyl)-6-oxo-4-(1,1,2,2-tetrafluoroethyl)-1,6-dihydropyrimidin-5-yl)oxy)-5-chloro-2-fluorobenzonitrile (95 mg, 0.175 mmol) in DCM (5 mL) was added a solution of zinc borohydride (0.175 mL, 0.175 mmol) in DCM (1 mL). And the resulting mixture was stirred at 20° C. for 5 min. TLC (25% EtOAc/P.E.) showed the completion of the reaction. The reaction mixture was quenched with 1N HCl aqueous solution (5 mL) and water (20 mL), extracted with DCM (3×50 mL). The combined organic layers were dried over anhydrous Na$_2$SO$_4$, filtered and concentrated under reduced pressure to afford the title compound, which was used directly into next step without purification. MS: 546 (M+1).

Step 3: 5-chloro-2-fluoro-3-((1-((2-(1-hydroxyethyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile To a stirred solution of 5-chloro-2-fluoro-3-((1-((2-(1-hydroxyethyl)-4-methoxy-6-methylpyrimidin-5-yl)methyl)-2-oxo-4-(1,1,2,2-tetrafluoroethyl)-1,2-dihydropyridin-3-yl)oxy)benzonitrile (80 mg, 0.147 mmol) in ACN (0.5 mL) was added KI (73.1 mg, 0.440 mmol) and TMS-Cl (0.056 mL, 0.440 mmol). And the resulting mixture was stirred at 70° C. for 2 h, and then concentrated under reduced pressure. The residue was purified by reverse phase HPLC (ACN/water with 0.1% TFA as modifier) to give a racemic mixture of the title compound. MS: 532 (M+1). The racemic mixture was purified by chiral SFC (IC-H column, 25% IPA/CO$_2$ with 0.1% NH$_4$OH as modifier) to afford Example 44 isomer B (slower eluting) as the title compound. MS: 532 (M+1). $^1$H NMR (400 MHz, DMSO-d$_6$): δ ppm 8.82 (s, 1H), 7.83-7.90 (m, 1H), 7.72 (dd, J=7.40, 2.38 Hz, 1H), 6.72-7.02 (m, 1H), 5.67 (br s, 1H), 4.91 (s, 2H), 4.41-4.51 (m, 1H), 2.38 (s, 3H), 1.33 (d, J=6.72 Hz, 3H).

Example 45

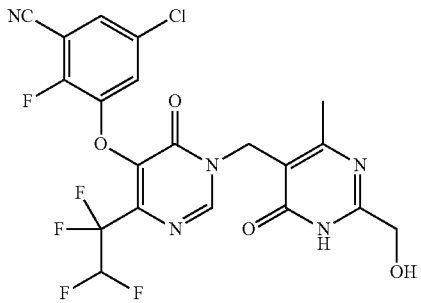 [SMILES: Cc1nc(CO)[nH]c(=O)c1Cn1cnc(C(F)(F)C(F)F)c(Oc2cc(Cl)cc(C#N)c2F)c1=O]

5-chloro-2-fluoro-3-((1-((2-(hydroxymethyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile Step 1: 5-chloro-2-fluoro-3-((1-(4-methoxy-6-methyl-2-vinylpyrimidin-5-yl)methyl)-6-oxo-4-(1,1,2,2-tetrafluoroethyl)-1,6-dihydropyrimidin-5-yl)oxy)benzonitrile To a stirred solution of 5-chloro-2-fluoro-3-((6-oxo-4-(1,1,2,2-tetrafluoroethyl)-1,6-dihydropyrimidin-5-yl)oxy)benzonitrile, AB10 (442 mg, 0.967 mmol), 5-(chloromethyl)-4-methoxy-6-methyl-2-vinylpyrimidine, C24 (240 mg, 0.967 mmol) in DMF (8 mL) was added $K_2CO_3$ (267 mg, 1.933 mmol) and lithium bromide (126 mg, 1.450 mmol). The resulting mixture was stirred at 15° C. for 1 h. TLC (50% EtOAc/P.E.) showed the reaction was complete. The reaction mixture was diluted with $H_2O$ (10 mL) and extracted with EtOAc (3×10 mL). The combined organic layers were washed with brine, dried over anhydrous $Na_2SO_4$, filtered and concentrated under reduced pressure. The residue was purified by column chromatography on silica (10-50% EtOAc/P.E.) to give the title compound. MS: 528 (M+1).

Step 2: 5-chloro-2-fluoro-3-((1-((2-formyl-4-methoxy-6-methylpyrimidin-5-yl)methyl)-6-oxo-4-(1,1,2,2-tetrafluoroethyl)-1,6-dihydropyrimidin-5-yl)oxy)benzonitrile To a stirred solution of 5-chloro-2-fluoro-3-((1-((4-methoxy-6-methyl-2-vinylpyrimidin-5-yl)methyl)-6-oxo-4-(1,1,2,2-tetrafluoroethyl)-1,6-dihydropyrimidin-5-yl)oxy)benzonitrile (270 mg, 0.512 mmol) in 1,4-dioxane (10 mL) and water (3 mL), was added 2,6-dimethylpyridine (110 mg, 1.023 mmol), osmium(VIII) oxide (6.50 mg, 0.026 mmol) and sodium periodate (328 mg, 1.535 mmol). The resulting mixture was stirred at 15° C. for 30 min. TLC (50% EtOAc/P.E.) showed the reaction was complete. The reaction mixture was quenched with saturated aqueous solution of $Na_2SO_3$ (15 mL) and extracted with EtOAc (3×10 mL). The combined organic layers were washed with brine, dried over anhydrous $Na_2SO_4$, filtered and concentrated under reduced pressure to afford the title compound, which was used directly into the next step. MS: 529.9 (M+1).

Step 3: 5-chloro-2-fluoro-3-((1-((2-(hydroxymethyl)-4-methoxy-6-methylpyrimidin-5-yl)methyl)-6-oxo-4-(1,1,2,2-tetrafluoroethyl)-1,6-dihydropyrimidin-5-yl)oxy)benzonitrile To a solution of 5-chloro-2-fluoro-3-((1-((2-formyl-4-methoxy-6-methylpyrimidin-5-yl)methyl)-6-oxo-4-(1,1,2,2-tetrafluoroethyl)-1,6-dihydropyrimidin-5-yl)oxy)benzonitrile (80 mg, 0.151 mmol) in EtOAc (3 mL) was added 1M $Zn(BH_4)_2$ solution in DCM (0.151 mL, 0.151 mmol). The resulting mixture was stirred at 15° C. for 3 min. TLC (66% EtOAc/P.E.) showed the completion of the reaction. The reaction mixture was quenched with $H_2O$ (10 mL), extracted with EtOAc (3×10 mL). The combined the organic layers were dried over anhydrous $Na_2SO_4$, filtrated and concentrated under reduced pressure to obtain the title compound, which was used directly in the next step. MS: 532 (M+1).

Step 4: 5-chloro-2-fluoro-3-((1-((2-(hydroxymethyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile To a stirred solution of 5-chloro-2-fluoro-3-((1-((2-(hydroxymethyl)-4-methoxy-6-methylpyrimidin-5-yl)methyl)-6-oxo-4-(1,1,2,2-tetrafluoroethyl)-1,6-dihydropyrimidin-5-yl)oxy)benzonitrile (70 mg, 0.132 mmol) in ACN (1.5 mL) was added KI (65.5 mg, 0.395 mmol) and TMS-Cl (0.050 mL, 0.395 mmol) under $N_2$ atmosphere. The resulting mixture was stirred at 70° C. for 2 h, and then purified directly by reverse phase HPLC (ACN/water with 0.1% TFA as modifier) to give the title compound. MS: 518 (M+1). $^1H$ NMR (400 MHz, DMSO-$d_6$): 8.81 (s, 1H), 7.85 (dd, J=4.52, 2.54 Hz, 1H), 7.71 (dd, J=7.28, 2.43 Hz, 1H), 6.69-7.03 (m, 1H), 4.92 (s, 2H), 4.29 (s, 2H), 2.38 (s, 3H).

Example 46

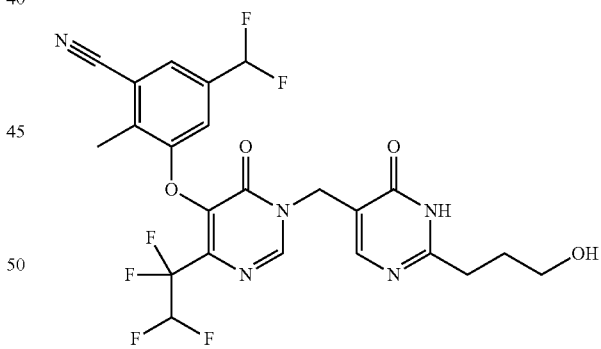

5-(difluoromethyl)-3-((1-((2-(3-hydroxypropyl)-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile Step 1: 3-((1-((2-chloro-4-methoxypyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile To a solution of 5-(difluoromethyl)-2-methyl-3-((6-oxo-4-(1,1,2,2-tetrafluoroethyl)-1,6-dihydropyrimidin-5-yl)oxy)

benzonitrile, AB07 (1 g, 2.65 mmol) in NMP (8.84 mL) was added K₂CO₃ (0.733 g, 5.30 mmol), and 2-chloro-5-(chloromethyl)-4-methoxypyrimidine, C19 (0.537 g, 2.78 mmol). The resulting mixture was stirred at RT overnight. LC-MS analysis showed the desired product and no starting material. The reaction mixture was diluted with water, and stirred at RT for 30 minutes. The white precipitate was collected on top of a filter, and washed with water (3×), then air-dried to give the title compound. MS: 534.2 (M+1).

Step 2: 5-(difluoromethyl)-3-((1-((2-(3-hydroxypropyl)-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile A mixture of 3-((1-((2-chloro-4-methoxypyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile (30 mg, 0.056 mmol), potassium trifluoro(3-hydroxypropyl)borate (37.3 mg, 0.225 mmol), cesium carbonate (18.31 mg, 0.056 mmol), and chloro[(di(1-adamantyl)-N-butylphosphine)-2-(2-aminobiphenyl)]palladium(II)(cataCXimum A Pd G2 precatalyst (3.76 mg, 5.62 μmol) was purged with N₂ and then added 1,4-dioxane (1.6 mL) and water (0.4 mL). The reaction mixture was heated at 120° C. in a microwave oven for 10 min. LC-MS showed desired product. The reaction mixture was diluted with Et₂O, dried over anhydrous Na₂SO₄, filtered and concentrated under reduced pressure. The residue was retaken up with ACN (1.5 mL), and then treated with potassium iodide (28.0 mg, 0.169 mmol), and chlorotrimethylsilane (0.071 mL, 0.562 mmol). The resulting reaction mixture was heated at 100° C. for 10 min, then purified by reverse phase HPLC (ACN/water with 0.1% TFA as modifier) to afford the title compound. MS: 544.2 (M+1).

Example 47

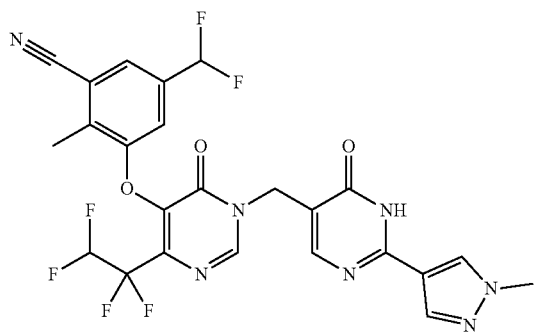 [SMILES: Cc1c(C#N)cc(C(F)F)cc1Oc1c(C(F)(F)C(F)F)ncn(Cc2cnc(-c3cnn(C)c3)[nH]c2=O)c1=O]

5-(difluoromethyl)-2-methyl-3-((1-((2-(1-methyl-1H-pyrazol-4-yl)-6-oxo-1,6-dihydropyrimidin-5-yl)methyl)-6-oxo-4-(1,1,2,2-tetrafluoroethyl)-1,6-dihydropyrimidin-5-yl)oxy)benzonitrile This compound was prepared in an analogous manner to that described in Example 46 with (1-methyl-1H-pyrazol-4-yl)boronic acid. MS: 566.3 (M+1)

Example 48

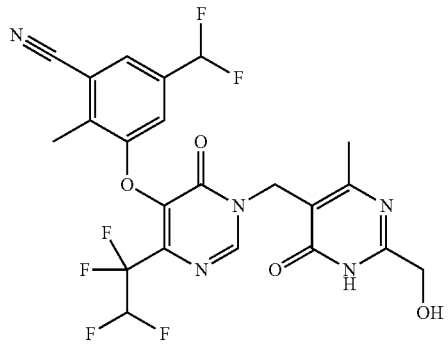 [SMILES: Cc1nc(CO)[nH]c(=O)c1Cn1cnc(C(F)(F)C(F)F)c(Oc2cc(C(F)F)cc(C#N)c2C)c1=O]

5-(difluoromethyl)-3-((1-((2-(hydroxymethyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile Step 1: 3-((1-((2-chloro-4-methoxy-6-methylpyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile To a stirred solution of 5-(difluoromethyl)-2-methyl-3-((6-oxo-4-(1,1,2,2-tetrafluoroethyl)-1,6-dihydropyrimidin-5-yl)oxy)benzonitrile, AB07 (1.5 g, 3.98 mmol) and (2-chloro-4-methoxy-6-methylpyrimidin-5-yl)methanol, C20 (0.750 g, 3.98 mmol) in toluene (30 mL) at 0° C., was added triphenylphosphine (1.564 g, 5.96 mmol), and then DIAD (1.160 mL, 5.96 mmol) dropwise. The resulting reaction mixture was stirred at RT for 2 h, and then diluted with water (100 mL), extracted with EtOAc (3×80 mL). The combined organic layers were washed with brine, dried over anhydrous Na₂SO₄, filtered and concentrated under reduced pressure. The residue was purified by column chromatography on silica (10-35% EtOAc/P.E.) to obtain the title compound. MS: 548.2 (M+1).

Step 2: 5-(difluoromethyl)-3-((1-((2-(hydroxymethyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile To a N₂ purged mixture of 3-((1-((2-chloro-4-methoxy-6-methylpyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile (50 mg, 0.091 mmol), potassium trifluoro(((4-methoxybenzyl) oxy)methyl)borate (47.1 mg, 0.183 mmol) and cataCXium A Pd G2 precatalyst (12.20 mg, 0.018 mmol) in 1,4-dioxane (1 mL) and water (500 μL), was added 2M aqueous solution of cesium carbonate (500 μL, 1.000 mmol). The resulting reaction mixture was heated at 150° C. in a microwave oven for 10 min. LC-MS showed the desired product. The reaction mixture was extracted with Et₂O (2×). The combined organic layers were concentrated under reduced pressure. The residue was taken up by ACN (1 mL), and then treated with potassium iodide (45.5 mg, 0.274 mmol) and chlorotrimethylsilane (116 μL, 0.913 mmol). The mixture was heated at 100° C. for 10 min. LC-MS showed the desired product. The mixture was purified by reverse phase HPLC (ACN/water with 0.1% TFA as modifier) to afford the title compound. MS: 530.3 (M+1).

The following examples in Table 17 were prepared in an analogous manner to that described in Example 48 with an appropriate intermediate AB and intermediate C using a corresponding boronic acid or potassium trifluoroborate for Step 2.

TABLE 17

| Ex# (AB#, C#) | Structure | IUPAC Name | MS (M + 1) |
|---|---|---|---|
| 49 (AB07, C20) | 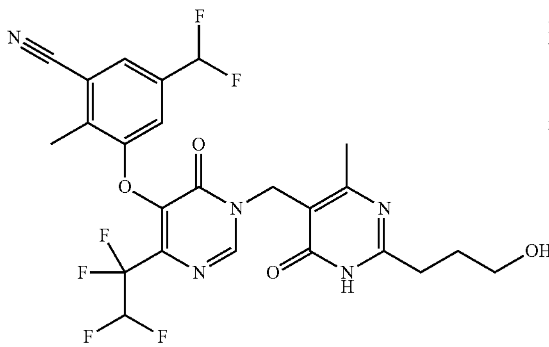 [SMILES: Cc1nc(CCCO)[nH]c(=O)c1Cn1cnc(C(F)(F)C(F)F)c(Oc2cc(C(F)F)cc(C#N)c2C)c1=O] | 5-(difluoromethyl)-3-((1-((2-(3-hydroxypropyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile | 558.2 |
| 50 (AB11, C20) | 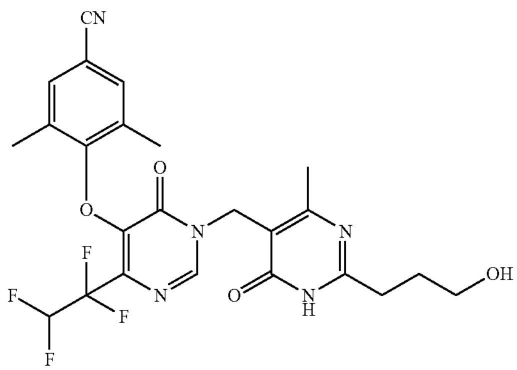 [SMILES: Cc1cc(C#N)cc(C)c1Oc1c(C(F)(F)C(F)F)ncn(Cc2c(C)nc(CCCO)[nH]c2=O)c1=O] | 4-((1-((2-(3-hydroxypropyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)-3,5-dimethylbenzonitrile | 522.2 |
| 51 (AB07, C20) | 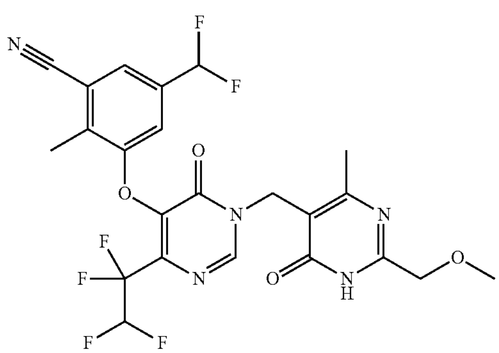 [SMILES: COCc1nc(C)c(Cn2cnc(C(F)(F)C(F)F)c(Oc3cc(C(F)F)cc(C#N)c3C)c2=O)c(=O)[nH]1] | 5-(difluoromethyl)-3-((1-((2-(methoxymethyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile | 544.3 |
| 52 (AB07, C20) | 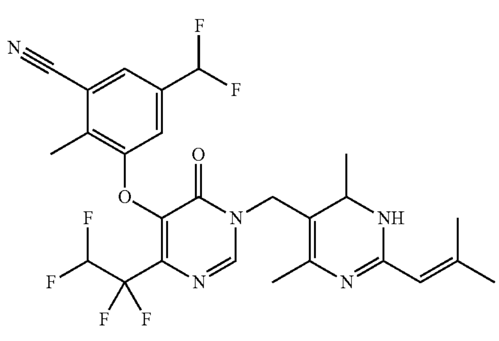 [SMILES: CC(C)=CC1=NC(C)=C(Cn2cnc(C(F)(F)C(F)F)c(Oc3cc(C(F)F)cc(C#N)c3C)c2=O)C(C)N1] | 5-(difluoromethyl)-2-methyl-3-((1-((4-methyl-2-(2-methylprop-1-en-1-yl)-6-oxo-1,6-dihydropyrimidin-5-yl)methyl)-6-oxo-4-(1,1,2,2-tetrafluoroethyl)-1,6-dihydropyrimidin-5-yl)oxy)benzonitrile | 554.3 |

Examples 53 (Isomer Mixture) and 54 (Isomer A)

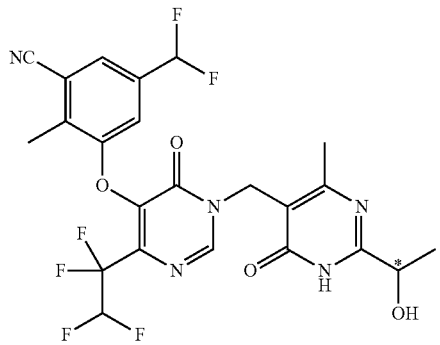 [SMILES: Cc1nc(C(C)O)[nH]c(=O)c1Cn1cnc(C(F)(F)C(F)F)c(Oc2cc(C(F)F)cc(C#N)c2C)c1=O]

5-(difluoromethyl)-3-((1-((2-(1-hydroxyethyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile (53, Racemic Mixture) and 5-(difluoromethyl)-3-((1-((2-(1-hydroxyethyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile (54, Single S or R Isomer)

Step 1: 5-(difluoromethyl)-3-((1-((4-methoxy-6-methyl-2-vinylpyrimidin-5-yl)methyl)-6-oxo-4-(1,1,2,2-tetrafluoroethyl)-1,6-dihydropyrimidin-5-yl)oxy)-2-methylbenzonitrile A mixture of 3-((1-((2-chloro-4-methoxy-6-methylpyrimidin-5-yl)methyl)-6-oxo-4-(1,1,2,2-tetrafluoroethyl)-1,6-dihydropyrimidin-5-yl)oxy)-5-(difluoromethyl)-2-methyl benzonitrile (title compound from step 1 of Example 48) (230 mg, 0.420 mmol), potassium vinyltrifluoroborate (169 mg, 1.259 mmol), PdCl$_2$(dppf) (92 mg, 0.126 mmol) and cesium carbonate (850 mg, 2.61 mmol) in 1,4-dioxane (1679 µL) and water (420 µL) was purged with N$_2$, and heated at 150° C. in a microwave oven for 15 min. LC-MS showed the desired product as the major peak. The reaction mixture was partitioned between water and EtOAc (2×). The combined organic layers were dried over anhydrous Na$_2$SO$_4$, filtered and concentrated under reduced pressure. The residue was purified with column chromatography on silica (40-100% EtOAc/hexanes) to afford the title compound. MS: 540.2 (M+1).

Step 2: 5-(difluoromethyl)-3-((1-((2-formyl-4-methoxy-6-methylpyrimidin-5-yl)methyl)-6-oxo-4-(1,1,2,2-tetrafluoroethyl)-1,6-dihydropyrimidin-5-yl)oxy)-2-methylbenzonitrile To a 20 mL of vial was added 5-(difluoromethyl)-3-((1-((4-methoxy-6-methyl-2-vinylpyrimidin-5-yl)methyl)-6-oxo-4-(1,1,2,2-tetrafluoroethyl)-1,6-dihydropyrimidin-5-yl)oxy)-2-methylbenzonitrile (118 mg, 0.219 mmol), osmium tetroxide (274 µL, 0.022 mmol), 2,6-dimethylpyridine (51.0 µL, 0.437 mmol), and sodium periodate (140 mg, 0.656 mmol) in 1,4-dioxane (1641 µL) and water (547 µL). The resulting reaction mixture was stirred at RT for 48 h. The reaction solution was diluted with EtOAc (50 mL), then washed with saturated aqueous solution of NH$_4$Cl (2×20 mL), water (20 mL), brine (20 mL), then dried over anhydrous MgSO$_4$ and filtered, and concentrated under reduced pressure. The residue was purified by column chromatography on silica (0-100% EtOAc/hexanes) to afford the title compound. MS: 542.2 (M+1).

Step 3: 5-(difluoromethyl)-3-((1-((2-(1-hydroxyethyl)-4-methoxy-6-methylpyrimidin-5-yl)methyl)-6-oxo-4-(1,1,2,2-tetrafluoroethyl)-1,6-dihydropyrimidin-5-yl)oxy)-2-ethylbenzonitrile To a chilled (−78° C.) solution of 5-(difluoromethyl)-3-((1-(2-formyl-4-methoxy-6-methylpyrimidin-5-yl)methyl)-6-oxo-4-(1,1,2,2-tetrafluoroethyl)-1,6-dihydropyrimidin-5-yl)oxy)-2-methylbenzonitrile (38 mg, 0.070 mmol) in THF (351 µL) was added 3M solution of methylmagnesium bromide in Et$_2$O (28.1 µl, 0.084 mmol) dropwise. The resulting mixture was stirred at −78 C till LC-MS showed complete consumption of the starting material. The reaction mixture was diluted with water, then extracted with EtOAc (2×). The combined organic layers were dried over anhydrous Na$_2$SO$_4$, filtered and concentrated under reduced pressure to give the title compound, which was used as is for the following step without further purification. MS: 558.3 (M+1).

Step 4: 5-(difluoromethyl)-3-((1-((2-(1-hydroxyethyl)-4-methyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile To a mixture of 5-(difluoromethyl)-3-((1-((2-(1-hydroxyethyl)-4-methoxy-6-methylpyrimidin-5-yl)methyl)-6-oxo-4-(1,1,2,2-tetrafluoroethyl)-1,6-dihydropyrimidin-5-yl)oxy)-2-methylbenzonitrile (34 mg, 0.061 mmol) in ACN (2 mL), was added KI (10 mg, 0.060 mmol) and TMS-Cl (66 µL, 0.516 mmol). The resulting mixture was heated at 100° C. for 10 min in a microwave oven. LC-MS showed reaction was complete. The reaction mixture was diluted with water, then filtered and purified by reverse phase HPLC (CN/water with 0.1% TFA as modifier) to afford the title compound, Example 53 (racemic mixture) MS: 544.2 (M+1). This racemic mixture was purified by chiral SFC (AD-H column, 15% MeOH/CO$_2$ with 0.1% DEA as modifier) to afford the title compound, Example 54 isomer A (faster eluting isomer). MS: 544.4 (M+1). $^1$H NMR (600 MHz, Acetone-d$_6$) δ 8.77 (s, 1H), 7.64 (s, 1H), 7.21 (s, 1H), 6.80 (t, J=48 Hz, 1H), 5.02 (s, 2H), 2.56 (s, 3H), 2.43 (s, 3H), 1.44 (d, J=6.7 Hz, 3H).

Example 55

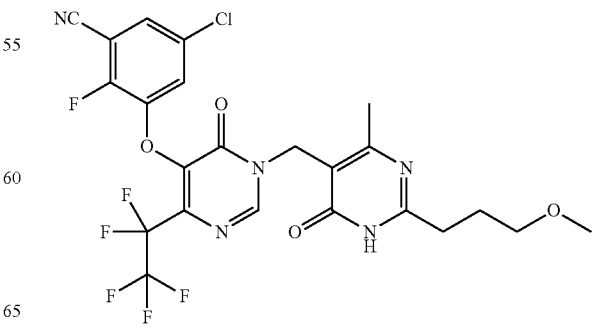

5-chloro-2-fluoro-3-((1-((2-(3-methoxypropyl)-4-methyl-6-oxo-1,6-dihydropyrimidin-5-yl)methyl)-6-oxo-4-(perfluoroethyl)-1,6-dihydropyrimidin-5-yl)oxy)benzonitrile Step 1: 5-chloro-3-((1-((2-chloro-4-methoxy-6-methylpyrimidin-5-yl)methyl)-6-oxo-4-(perfluoroethyl)-1,6-dihydropyrimidin-5-yl)oxy)-2-fluorobenzonitrile To a stirred solution of 5-chloro-2-fluoro-3-((6-oxo-4-(perfluoroethyl)-1,6-dihydropyrimidin-5-yl)oxy)benzonitrile, AB12 (0.73 g, 1.903 mmol) and 2-chloro-5-(chloromethyl)-4-methoxy-6-methylpyrimidine, C20 (0.433 g, 2.093 mmol) in NMP (9.51 mL) was added $K_2CO_3$ (0.526 g, 3.81 mmol). The resulting mixture was stirred at RT overnight. LC-MS showed desired product. The reaction mixture was diluted with water (20 mL) and extracted with EtOAc (10 mL). The organic layer was dried over anhydrous $Na_2SO_4$, filtered and concentrated under reduced pressure. The resulting mixture was purified by column chromatography on silica (0-100% EtOAc/hexanes) to provide the title compound. MS: 554.1 (M+1).

Step: 5-chloro-2-fluoro-3-((1-((2-(3-methoxypropyl)-4-methyl-6-oxo-1,6-dihydropyrimidin-5-yl)methyl)-6-oxo-4-(perfluoroethyl)-1,6-dihydropyrimidin-5-yl)oxy)benzonitrile Degassed DME (474 μL) was added to a vial containing 5-chloro-3-((1-((2-chloro-4-methoxy-6-methylpyrimidin-5-yl)methyl)-6-oxo-4-(perfluoroethyl)-1,6-dihydropyrimidin-5-yl)oxy)-2-fluorobenzonitrile (35 mg, 0.063 mmol), tris(trimethylsilyl)silane (21.43 μL, 0.069 mmol), [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate, $(Ir[dF(CF_3)ppy]_2(dtbpy))PF_6$ (0.708 mg, 0.632 μmol), 1-bromo-3-methoxypropane (6.00 mg, 0.063 mmol) and anhydrous $Na_2CO_3$ (13.39 mg, 0.126 mmol). The resulting vial was placed under $N_2$ and 250 uL of the nickel stock solution [prepared by sonicating a mixture of $NiCl_2DME$ (35 mg) and 4,4'-di-tert-butyl-2,2'-dipyridyl (40 mg) in degassed DME (10 mL) under $N_2$ for 10 min]. The resulting mixture was sealed and irradiated with a 34 W Kessil® LED lamp (7 cm away, with cooling fan to keep the temperature at 25° C.) overnight. The reaction was quenched by exposure to air. The reaction mixture was diluted with water (2 mL) and EtOAc (2 mL). The organic layer was separated and concentrated under reduced pressure. The resulting crude was dissolved in DMF (1 mL) and pyridine hydrochloride (36.2 mg) was added. The resulting mixture was stirred at 120° C. for 30 min. The reaction was diluted with DMSO (1 mL) and purified by reverse phase HPLC (ACN/water with 0.1% TFA as modifier) to afford the title compound. MS: 578.2 (M+1). $^1$H NMR (600 MHz, DMSO-$d_6$): δ 8.81 (d, J=5.6 Hz, 1H), 7.85 (m, 1H), 7.81 (m, 1H), 4.92 (s, 2H), 4.43 (t, J=6.1 Hz, 1H), 3.42 (t, J=6.1 Hz, 1H), 2.63 (t, J=7.4 Hz, 1H), 2.57 (t, J=7.4 Hz, 1H), 2.36 (s, 3H), 2.35 (s, 3H), 2.08 (m, 1H), 1.78 (m, 1H).

Example 56

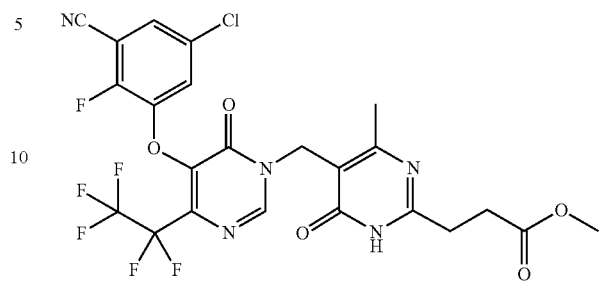

Methyl 3-(5-((5-(5-chloro-3-cyano-2-fluorophenoxy)-6-oxo-4-(perfluoroethyl)pyrimidin-1 (6H)-yl)methyl)-4-methyl-6-oxo-1,6-dihydropyrimidin-2-yl)propanoate This compound was prepared in an analogous manner to that described in Example 56 with methyl 3-bromopropanoate. MS: 592.2 (M+1).

Example 57

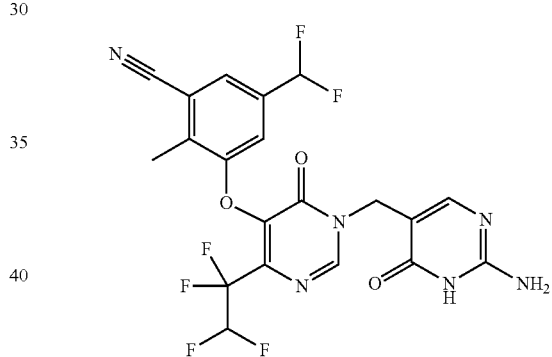

3-((1-((2-amino-6-oxo-1,6-dihydropyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile Step 1: 3-((1-((2-chloro-4-methoxypyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile To a chilled (0° C.) suspension of 5-(difluoromethyl)-2-methyl-3-((6-oxo-4-(1,1,2,2-tetrafluoroethyl)-1,6-dihydropyrimidin-5-yl)oxy)benzonitrile, AB07 (1.4 g, 3.71 mmol) and $K_2CO_3$ (0.513 g, 3.71 mmol) in DMF (18.56 mL), was added 2-chloro-5-(chloromethyl)-4-methoxypyrimidine, C19 (0.860 g, 4.45 mmol). The resulting suspension was stirred at RT for 10 min. when LC-MS showed completion of reaction. The reaction mixture was concentrated under reduced pressure. The residue was purified by column chromatography on silica (0-80% EtOAc/hexanes) to afford the title compound. MS: 534.1 (M+1).

Step 2: 5-(difluoromethyl)-3-((1-((4-methoxy-2-((4-methoxybenzyl)amino)pyrimidin-5-yl)methyl)-6-oxo-4-(1,1,2,2-tetrafluoroethyl)-1,6-dihydropyrimidin-5-yl)oxy)-2-methylbenzonitrile To a solution of 3-((1-((2-chloro-4-methoxypyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile (95 mg, 0.178 mmol) in THF (890 µL) was added 4-methoxybenzylamine (48.8 mg, 0.356 mmol). The resulting reaction mixture was stirred at 60° C. overnight. LC-MS indicates the reaction was complete. The reaction mixture was concentrated under reduced pressure. The residue was taken up in EtOAc (10 mL), washed with saturated aqueous NaHCO₃ solution, and dried over anhydrous MgSO₄, filtered and concentrated under reduced pressure. The residue was purified by column chromatography on silica (0-100% EtOAc/hexanes) to afford the title compound. MS: 635.2 (M+1).

Step 3: 3-((1-((2-amino-4-methoxypyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile To a solution of 5-(difluoromethyl)-3-((1-((4-methoxy-2-((4-methoxybenzyl) amino)pyrimidin-5-yl)methyl)-6-oxo-4-(1,1,2,2-tetrafluoroethyl)-1,6-dihydropyrimidin-5-yl)oxy)-2-methylbenzonitrile 0389804-0171 (110 mg, 0.173 mmol) in DCM (867 was added TFA (134 µL, 1.734 mmol) and TFAA (24.49 µL, 0.173 mmol). The resulting reaction mixture was heated to 100° C. for 1 h. LC-MS indicates reaction was complete. The mixture was concentrated under reduced pressure to give the title compound, which was used directly in the following step with purification. MS: 515.2 (M+1).

Step 4: 3-((1-((2-amino-6-oxo-1,6-dihydropyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile To a solution of 3-((1-((2-amino-4-methoxypyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile (85 mg, 0.165 mmol) in ACN (826 µL) was added TMS-I (225 µL, 1.652 mmol). The resulting reaction mixture was heated to 110° C. in a microwave oven till LC-MS showed the reaction was at completion. The reaction solution was diluted with EtOAc (10 mL), and washed with saturated aqueous Na₂SO₃, filtered and purified by reverse phase HPLC (ACN/water with 0.1% TFA as modifier) to afford the title compound. MS: 501.2 (M+1).

Example 58

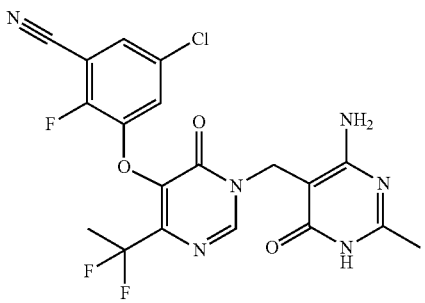 [SMILES: Cc1nc(N)c(Cn2cnc(C(C)(F)F)c(Oc3cc(Cl)cc(C#N)c3F)c2=O)c(=O)[nH]1]

3-((1-((4-amino-2-methyl-6-oxo-1,6-dihydropyrimidin-5-yl)methyl)-4-(1,1-difluoroethyl)-6-oxo-1,6-dihydropyrimidin-5-yl)oxy)-5-chloro-2-fluorobenzonitrile Step 1: 5-chloro-3-((1-((4-chloro-6-methoxy-2-methylpyrimidin-5-yl)methyl)-4-(1,1-difluoroethyl)-6-oxo-1,6-dihydropyrimidin-5-yl)oxy)-2-fluorobenzonitrile To a solution of 5-chloro-3-((4-(1,1-difluoroethyl)-6-oxo-1,6-dihydropyrimidin-5-yl)oxy)-2-fluorobenzonitrile, AB34 (100 mg, 0.303 mmol) in DMF (3 mL) were added 4-chloro-5-(chloromethyl)-6-methoxy-2-methylpyrimidine, C22 (69.1 mg, 0.334 mmol), potassium carbonate (126 mg, 0.910 mmol) and lithium bromide (26.3 mg, 0.303 mmol). The resulting mixture was stirred at 25° C. for 8 h, and then concentrated under reduced pressure. The residue was purified by preparative TLC plates (50% EtOAc/P.E.) to give the title compound. MS: 500.1 (M+1)

Step 2: 5-chloro-3-((9-(1,1-difluoroethyl)-4-methoxy-11-(4-methoxybenzyl)-2-methyl-7-oxo-7,10,10a,11-tetrahydro-5H-dipyrimido[1,2-a:4',5'-d]pyrimidin-8-yl)oxy)-2-fluorobenzonitrile To a solution of 5-chloro-3-((1-((4-chloro-6-methoxy-2-methylpyrimidin-5-yl)methyl)-4-(1,1-difluoroethyl)-6-oxo-1,6-dihydropyrimidin-5-yl)oxy)-2-fluorobenzonitrile (60 mg, 0.120 mmol) and (4-methoxyphenyl)methanamine (16.45 mg, 0.120 mmol) in DMA (2 mL) was added TEA (0.033 mL, 0.240 mmol). The resulting mixture was stirred at 80° C. for 4 h, and then concentrated under reduced pressure. The residue was purified by column chromatography on silica (0-20% EtOAc/P.E.) to afford the title compound. MS: 601. (2M+1).

Step 3: 3-((1-((4-amino-6-methoxy-2-methylpyrimidin-5-yl)methyl)-4-(1,1-difluoroethyl)-6-oxo-1,6-dihydropyrimidin-5-yl)oxy)-5-chloro-2-fluorobenzonitrile To a solution of 5-chloro-3-((4-(1,1-difluoroethyl)-1-((4-methoxy-6-((4-methoxybenzyl)amino)-2-methylpyrimidin-5-yl)methyl)-6-oxo-1,6-dihydropyrimidin-5-yl)oxy)-2-fluorobenzonitrile (30 mg, 0.050 mmol) in TFA (3 mL) was added TFAA (7.05 µl, 0.050 mmol). The resulting solution was stirred at 80° C. for 0.5 h, and then concentrated under reduced pressure to afford the title compound. MS: 481.1 (M+1).

Step 4: 3-((1-((4-amino-2-methyl-6-oxo-1,6-dihydropyrimidin-5-yl)methyl)-4-(1,1-difluoroethyl)-6-oxo-1,6-dihydropyrimidin-5-yl)oxy)-5-chloro-2-fluorobenzonitrile To a solution of 3-((1-((4-amino-6-methoxy-2-methylpyrimidin-5-yl)methyl)-4-(1,1-difluoroethyl)-6-oxo-1,6-dihydropyrimidin-5-yl)oxy)-5-chloro-2-fluorobenzonitrile (15 mg, 0.031 mmol) in ACN (3 mL) were added KI (15.54 mg, 0.094 mmol) and TMS-Cl (0.012 mL, 0.094 mmol). The resulting mixture was stirred at 70° C. for 2 h. LC-MS showed the reaction was complete. The reaction mixture was concentrated under reduced pressure. The residue was purified by reverse phase HPLC (ACN/water with 0.1% TFA as modifier) to afford the title compound. MS: 481.1 (M+1). ¹H NMR (400 MHz, DMSO-d₆) δ 11.72 (br s, 1H) 8.58 (s, 1H) 7.79-7.89 (m, 1H) 7.66 (dd, J=7.34, 2.32 Hz, 1H) 6.65 (br s, 2H) 4.78 (s, 2H) 2.15 (s, 3H) 1.93 (t, J=19.44 Hz, 3H).

The following examples in Table 18 were prepared in an analogous manner to that described in Example 58 with a corresponding intermediate AB.

TABLE 18

| Ex# (AB#) | Structure | IUPAC Name | MS (M + 1) |
|---|---|---|---|
| 59 (AB07) | 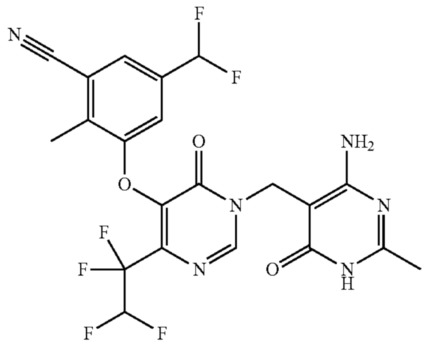 [SMILES: Cc1nc(N)c(Cn2cnc(C(F)(F)C(F)F)c(Oc3cc(C(F)F)cc(C#N)c3C)c2=O)c(=O)[nH]1] | 3-((1-((4-amino-2-methyl-6-oxo-1,6-dihydropyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile | 515.2 |
| 60 (AB05) | 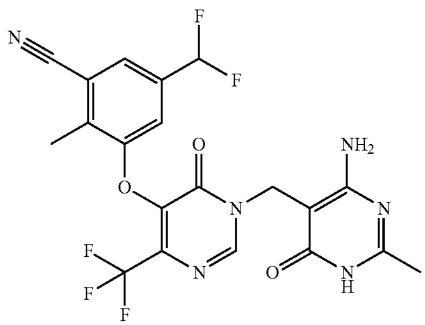 [SMILES: Cc1nc(N)c(Cn2cnc(C(F)(F)F)c(Oc3cc(C(F)F)cc(C#N)c3C)c2=O)c(=O)[nH]1] | 3-((1-((4-amino-2-methyl-6-oxo-1,6-dihydropyrimidin-5-yl)methyl)-6-oxo-4-(trifluoromethyl)-1,6-dihydropyrimidin-5-yl)oxy)-5-(difluoromethyl)-2-methylbenzonitrile | 483.2 |

Example 61

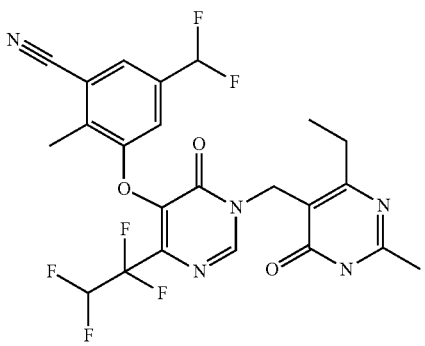 [SMILES: CCc1nc(C)[nH]c(=O)c1Cn1cnc(C(F)(F)C(F)F)c(Oc2cc(C(F)F)cc(C#N)c2C)c1=O]

5-(difluoromethyl)-3-((1-((4-ethyl-2-methyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile Step 1: 3-((1-((4-chloro-6-methoxy-2-methylpyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile To a solution of 5-(difluoromethyl)-2-methyl-3-((6-oxo-4-(1,1,2,2-tetrafluoroethyl)-1,6-dihydropyrimidin-5-yl)oxy)benzonitrile, AB07 (392 mg, 1.039 mmol) and 4-chloro-5-(chloromethyl)-6-methoxy-2-methylpyrimidine, C22 (323 mg, 1.56 mmol) in DMF (3464 µL) was added $K_2CO_3$ (287 mg, 2.078 mmol). The resulting reaction mixture was stirred at RT overnight. LC-MS showed the reaction was complete. The reaction mixture was diluted with water, and then extracted with EtOAc (3×). The combined organic layers were concentrated under reduced pressure. The residue was purified with column chromatography on silica (0-100% EtOAc/hexanes) to afford the title compound. MS: 548.2 (M+1).

Step 2: 5-(difluoromethyl)-3-((1-((4-ethyl-2-methyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile A mixture of 3-((1-((4-chloro-6-methoxy-2-methylpyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile (10.9 mg, 0.020 mmol), ethylboronic acid (21 mg, 0.284 mmol), $Cs_2CO_3$ (19.45 mg, 0.060 mmol), and cataCXium A Pd G2 precatalyst (5.32 mg, 7.96 µmol) was flushed with $N_2$, then treated with 1,4-dioxane (500 µL) and water (50 µL). The resulting mixture was heated at 150° C. in a microwave oven for 10 min. LC-MS showed the reaction was complete. The reaction mixture was extracted with $Et_2O$ (2×). The combined organic layers were dried over anhydrous Na2SO4, filtered and concentrated under reduced pressure. The residue was taken up in ACN (1 mL), and KI (9.91 mg, 0.060 mmol) and TMS-Cl (25.4 µL, 0.199 mmol) was added. The resulting mixture was heated at 100° C. for 2 h. The reaction mixture was filtered and purified with reverse phase HPLC (ACN/water with 0.1% TFA as modifier) to afford the title compound. MS: 528.2 (M+1).

Example 62

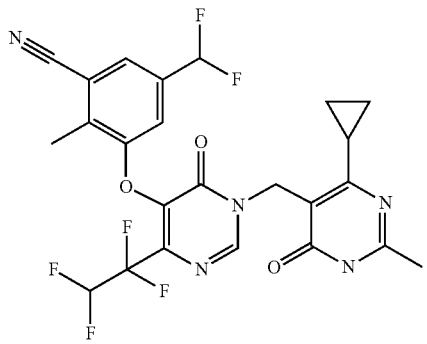 [SMILES: Cc1nc(C2CC2)c(Cn2cnc(C(F)(F)C(F)F)c(Oc3cc(C(F)F)cc(C#N)c3C)c2=O)c(=O)[nH]1]

2-((1-((4-cyclopropyl-6-methoxy-2-methylpyrimidin-5-yl)methyl)-6-oxo-4-(1,1,2,2-tetrafluoroethyl)-1,6-dihydropyrimidin-5-yl)oxy)-5-(difluoromethyl)-2-methylbenzonitrile This compound was prepared in an analogous manner to that described in Example 61 with cyclopropylboronic acid. MS: 540.2 (M+1)

Example 63

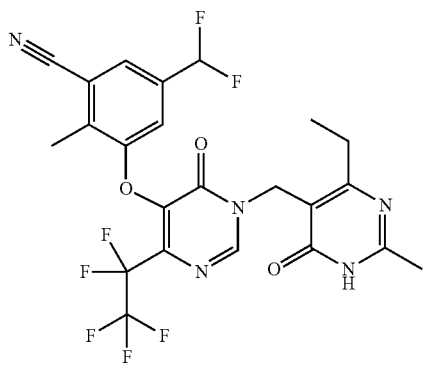 [SMILES: CCc1nc(C)[nH]c(=O)c1Cn1cnc(C(F)(F)C(F)(F)F)c(Oc2cc(C(F)F)cc(C#N)c2C)c1=O]

5-(difluoromethyl)-3-((1-((4-ethyl-2-methyl-6-oxo-1,6-dihydropyrimidin-5-yl)methyl)-6-oxo-4-(perfluoroethyl)-1,6-dihydropyrimidin-5-yl)oxy)-2-methylbenzonitrile

Step 1: 3-((1-((4-chloro-6-methoxy-2-methylpyrimidin-5-yl)methyl)-6-oxo-4-(perfluoroethyl)-1,6-dihydropyrimidin-5-yl)oxy)-5-difluoromethyl)-2-methylbenzonitrile To a solution of 5-(difluoromethyl)-2-methyl-3-((6-oxo-4-(perfluoroethyl)-1,6-dihydropyrimidin-5-yl)oxy)benzonitrile, AB06 (1200 mg, 3.04 mmol) and 4-chloro-5-(chloromethyl)-6-methoxy-2-methylpyrimidine, C22 (711 mg, 3.43 mmol) in DMF (15.2 mL) was added $K_2CO_3$ (839 mg, 6.07 mmol). The resulting reaction mixture was stirred at RT overnight. LC-MS indicated the reaction was complete. The reaction mixture was poured into EtOAc (20 mL) and washed with water (2×10 mL) and brine. The organic layer was dried over anhydrous $MgSO_4$, filtered and concentrated under reduced pressure. The residue was purified by column chromatography on silica (0-75% EtOAc/hexanes) to afford the title compound. MS: 566.0 (M+1).

Step 2: 5-(difluoromethyl)-3-((1-((4-ethyl-6-methoxy-2-methylpyrimidin-5-yl)methyl)-6-oxo-4-(perfluoroethyl)-1,6-dihydropyrimidin-5-yl)oxy)-2-methylbenzonitrile A mixture of 3-((1-((4-chloro-6-methoxy-2-methylpyrimidin-5-yl)methyl)-6-oxo-4-(perfluoroethyl)-1,6-dihydropyrimidin-5-yl)oxy)-5-difluoromethyl)-2-methylbenzonitrile (50 mg, 0.088 mmol), ethylboronic acid (9.79 mg, 0.133 mmol), chloro[(di(1-adamantyl)-n-butylphosphine)-2-(2-aminobiphenyl)]palladium(II) (5.91 mg, 8.84 µmol) ad $Cs_2CO_3$ (86 mg, 0.265 mmol) was purged with $N_2$, then dissolved in water (80 µL) and 1,4-dioxane (803 The resulting mixture was heated to 100° C. for 16 h, and then filtered over CELITE®. The filtrate was diluted with EtOAc (10 mL), and washed with water (2×3 mL). The organic layer was dried over anhydrous $MgSO_4$ and concentrated under reduced pressure. The residue was purified on column chromatography on silica (0-100% EtOAc/hexanes) to afford the title compound. MS: 560.1 (M+1).

Step 3: 5-(difluoromethyl)-3-((1-((4-ethyl-2-methyl-6-oxo-1,6-dihydropyrimidin-5-yl)methyl)-6-oxo-4-(perfluoroethyl)-1,6-dihydropyrimidin-5-yl)oxy)-2-methylbenzonitrile To a solution of 5-(difluoromethyl)-3-((1-((4-ethyl-6-methoxy-2-methylpyrimidin-5-yl)methyl)-6-oxo-4-(perfluoroethyl)-1,6-dihydropyrimidin-5-yl)oxy)-2-methylbenzonitrile (18 mg, 0.032 mmol) in DMF (1000 µL) was added pyridine hydrochloride (18.59 mg, 0.161 mmol). The resulting mixture was heated to 120° C. for 15 min. LC-MS showed the reaction was complete. The reaction mixture was diluted with DMSO (1 mL) and purified by reverse phase HPLC (ACN/water with 0.1% TFA modifier) to afford the title compound. MS: 546.1 (M+1)

Example 64

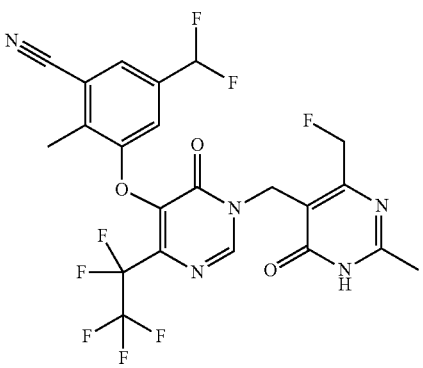

5-(difluoromethyl)-3-((1-((4-(fluoromethyl)-2-methyl-6-oxo-1,6-dihydropyrimidin-5-yl)methyl)-6-oxo-4-(perfluoroethyl)-1,6-dihydropyrimidin-5-yl)oxy)-2-methylbenzonitrile Step 1: 3-((1-((4-chloro-6-methoxy-2-methylpyrimidin-5-yl)methyl)-6-oxo-4-(perfluoroethyl)-1,6-dihydropyrimidin-5-yl)oxy)-5-(difluoromethyl)-2-methylbenzonitrile To a solution of 5-(difluoromethyl)-2-methyl-3-((6-oxo-4-(perfluoroethyl)-1,6-dihydropyrimidin-5-yl)oxy)benzonitrile, AB06 (1750 mg, 4.43 mmol) and 4-chloro-5-(chloromethyl)-6-methoxy-2-methylpyrimidine, C22 (1 g, 4.83 mmol) in DMF (22.14 mL) was added $K_2CO_3$ (1.224 g, 8.86 mmol). The resulting reaction mixture was stirred at RT for 16 h. The solution was poured into EtOAc (20 mL) and washed with water (2×10 mL) and brine. The organic layer was dried over anhydrous $MgSO_4$, filtered and concentrated under reduced pressure. The residue was purified by column chromatography on silica (0-75% EtOAc:hexanes) to afford title compound. MS: 566.1 (M+1).

Step 2: 5-(difluoromethyl)-3-((1-((4-methoxy-6-(((4-methoxybenzyl)oxy)methyl)-2-methylpyrimidin-5-yl)methyl)-6-oxo-4-(perfluoroethyl)-1,6-dihydropyrimidin-5-yl)oxy)-2-methylbenzonitrile 3-((1-((4-chloro-6-methoxy-2-methylpyrimidin-5-yl)methyl)-6-oxo-4-(perfluoroethyl)-1,6-dihydropyrimidin-5-yl)oxy)-5-(difluoromethyl)-2-methylbenzonitrile (150 mg, 0.265 mmol) was dissolved in water (241 µL) and 1,4-dioxane (2410 µL) and degassed. And then CataCXium A Pd G2 precatalyst (17.73 mg, 0.027 mmol), potassium trifluoro(((4-methoxy benzyl)oxy)methyl)borate (103 mg, 0.398 mmol) ad $Cs_2CO_3$ (259 mg, 0.795 mmol) were added to the reaction. The resulting reaction mixture was degassed and heated to 100° C. for 1 h, and then filtered and concentrated under reduced pressure. The residue was purified by column chromatography on silica (0-100% EtOAc/hexanes) to afford title compound. MS: 682.1 (M+1).

Step 3: 5-(difluoromethyl)-3-((1-((4-(hydroxymethyl)-6-methoxy-2-methylpyrimidin-5-yl)methyl)-6-oxo-4-(perfluoroethyl)-1,6-dihydropyrimidin-5-yl)oxy)-2-methylbenzonitrile To a solution of 5-(difluoromethyl)-3-((1-((4-methoxy-6-(((4-methoxybenzyl)oxy) methyl)-2-methylpyrimidin-5-yl)methyl)-6-oxo-4-(perfluoroethyl)-1,6-dihydropyrimidin-5-yl)oxy)-2-methylbenzonitrile (123 mg, 0.180 mmol) in $CH_2Cl_2$ (1805 µL), was added TFA (139 µL, 1.805 mmol). The resulting reaction mixture was stirred at RT for 16 h. The material was concentrated under reduced pressure to isolate the title compound. MS: 562.1 (M+1).

Step: 4 5-(difluoromethyl)-3-((1-((4-(fluoromethyl)-6-methoxy-2-methylpyrimidin-5-yl)methyl)-6-oxo-4-(perfluoroethyl)-1,6-dihydropyrimidin-5-yl)oxy)-2-methylbenzonitrile A solution of 5-(difluoromethyl)-3-((1-((4-(hydroxymethyl)-6-methoxy-2-methylpyrimidin-5-yl)methyl)-6-oxo-4-(perfluoroethyl)-1,6-dihydropyrimidin-5-yl)oxy)-2-methylbenzonitrile (101 mg, 0.180 mmol) in DCM (900 µl) was treated with DAST (59.4 µL, 0.450 mmol) and stirred at 55° C. for 72 h. The solution was diluted with DCM (10 mL) and quenched slowly with saturated aqueous $NaHCO_3$ solution until pH~7. The organic layer was then dried over anhydrous $Na_2SO_4$, filtered and concentrated under reduced pressure to isolate the title compound. MS: 564.1 (M+1).

Step 5: 5-(difluoromethyl)-3-((1-((4-(fluoromethyl)-2-methyl-6-oxo-1,6-dihydropyrimidin-5-yl)methyl)-6-oxo-4-(perfluoroethyl)-1,6-dihydropyrimidin-5-yl)oxy)-2-methylbenzonitrile A solution of 5-(difluoromethyl)-3-((1-((4-(fluoromethyl)-6-methoxy-2-methylpyrimidin-5-yl)methyl)-6-oxo-4-(perfluoroethyl)-1,6-dihydropyrimidin-5-yl)oxy)-2-methylbenzonitrile (100 mg, 0.177 mmol) in DMF (1775 µL) was treated with pyridine hydrochloride (103 mg, 0.887 mmol). The resulting reaction mixture was heated to 120° C. in a microwave oven for 15 min. The reaction mixture was filtered and purified by reverse phase HPLC (ACN/water with 0.05% $NH_4OH$ as modifier) to isolate the title compound. MS: 550.1 (M+1). $^1$H NMR (500 MHz, DMSO-$d_6$) δ 8.78 (s, 1H), 7.73 (s, 1H), 7.25 (s, 1H), 6.86 (t, J=55.3 Hz, 1H), 5.38 (d, J=46.8 Hz, 2H), 4.96 (s, 2H), 2.43 (s, 3H), 2.27 (s, 3H).

Example 65

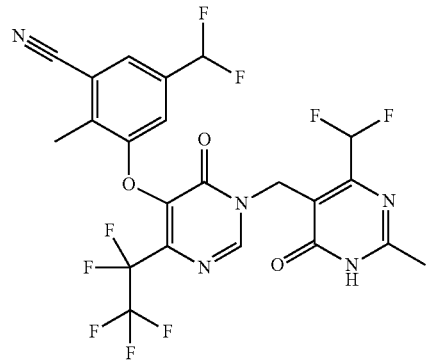 [SMILES: Cc1nc(C(F)F)c(Cn2cnc(C(F)(F)C(F)(F)F)c(Oc3cc(C(F)F)cc(C#N)c3C)c2=O)c(=O)[nH]1]

5-(difluoromethyl)-3-((1-((4-(difluoromethyl)-2-methyl-6-oxo-1,6-dihydropyrimidin-5-yl)methyl)-6-oxo-4-(perfluoroethyl)-1,6-dihydropyrimidin-5-yl)oxy)-2-methylbenzonitrile Step 1: 5-(difluoromethyl)-3-((1-(((6-methoxy-2-methyl-4-vinyl-1,6-dihydropyrimidin-5-yl)methyl)-6-oxo-4-(perfluoroethyl)-1,6-dihydropyrimidin-5-yl)oxy)-2-methylbenzonitrile A mixture of 3-((1-((4-chloro-6-methoxy-2-methylpyrimidin-5-yl)methyl)-6-oxo-4-(perfluoroethyl)-1,6-dihydropyrimidin-5-yl)oxy)-5-(difluoromethyl)-2-methylbenzonitrile, the title compound from Step 1 of Example 63) (200 mg, 0.353 mmol), tributyl(vinyl)stannane (208 uL, 0.707 mmol), and bis(triphenylphosphone)palladium(II) dichloride (49.6 mg, 0.071 mmol) in toluene (3535 µL) was stirred at 100° C. for 16 h. The mixture was partitioned between EtOAc and saturated KF solution. The resulting solution was stirred for 30 min then filtered and the organic layer was separated and concentrated under reduced pressure. The residue was purified by column chromatography on silica (0-80% EtOAc/hexanes) to afford the title compound. MS: 558.1 (M+1).

Step 2: 5-(difluoromethyl)-3-((1-((4-formyl-6-methoxy-2-methylpyrimidin-5-yl)methyl)-6-oxo-4-(perfluoroethyl)-1,6-dihydropyrimidin-5-yl)oxy)-2-methylbenzonitrile To a solution of 5-(difluoromethyl)-3-((1-(6-methoxy-2-methyl-4-vinyl-1,6-dihydropyrimidin-5-yl)methyl)-6-oxo-4-(perfluoroethyl)-1,6-dihydropyrimidin-5-yl)oxy)-2-methylbenzonitrile (100 mg, 0.179 mmol) in dioxane (1345 µL):water (448 µL), was added 2.5% (by weight) solution of osmium(VIII) oxide in t-butanol (225 µL, 0.018 mmol), 2,6-dimethylpyridine (41.6 µL, 0.359 mmol), and sodium periodate (115 mg, 0.538 mmol). The resulting reaction mixture was stirred at 25° C. for 24 h. The mixture was diluted with EtOAc (50 mL) and washed with saturated aqueous NH$_4$Cl (2×20 mL), water (20 mL), brine (20 mL), dried over anhydrous MgSO$_4$ and concentrated under reduced pressure. The residue was purified by column chromatography on silica (0-60% EtOAc/hexanes) to afford the title compound. MS: 560.1 (M+1).

Step 3: 5-(difluoromethyl)-3-((1-((4-(difluoromethyl)-2-methyl-6-oxo-1,6-dihydropyrimidin-5-yl)methyl)-6-oxo-4-(perfluoroethyl)-1,6-dihydropyrimidin-5-yl)oxy)-2-methylbenzonitrile A solution of 5-(difluoromethyl)-3-((1-((4-formyl-6-methoxy-2-methylpyrimidin-5-yl)methyl)-6-oxo-4-(perfluoroethyl)-1,6-dihydropyrimidin-5-yl)oxy)-2-methylbenzonitrile (40 mg, 0.072 mmol) in DCM (358 µl) was treated with DAST (23.62 µl, 0.179 mmol). The resulting reaction solution was stirred at RT for 2 h, and then concentrated under reduced pressure. The residue was taken up with f DMF (1 mL), treated with pyridine hydrochloride (83 mg, 0.715 mmol), and heated to 120° C. for 15 min increments until all starting material was consumed. The reaction mixture was filtered and purified by reverse phase HPLC (ACN/water with 0.1% TFA as modifier) to afford the title compound. MS: 568.1 (M+1). $^1$H NMR (500 MHz, DMSO-d$_6$) δ 12.98 (s, 1H), 8.80 (s, 1H), 7.75 (s, 1H), 7.48-6.65 (m, 3H), 5.05 (s, 2H), 2.49 (p, J=1.8 Hz, 3H), 2.31 (s, 3H).

Example 66

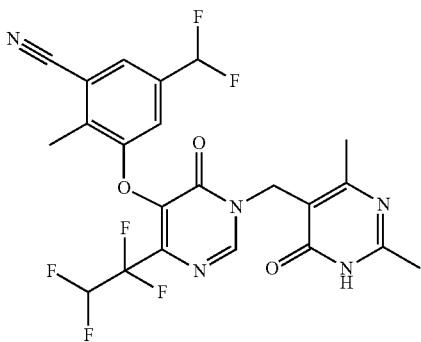 [SMILES: Cc1nc(C)c(Cn2cnc(C(F)(F)C(F)F)c(Oc3cc(C(F)F)cc(C#N)c3C)c2=O)c(=O)[nH]1]

5-(difluoromethyl)-3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile Step 1: 5-(difluoromethyl)-3-((1-((4-methoxy-2,6-dimethylpyrimidin-5-yl)methyl)-6-oxo-4-(1,1,2,2-tetrafluoroethyl)-1,6-dihydropyrimidin-5-yl)oxy)-2-methylbenzonitrile A mixture of 5-fluoro-3-((4-methoxy-2,6-dimethylpyrimidin-5-yl)methyl)-6-(1,1,2,2-tetrafluoroethyl)pyrimidin-4(3H)-one, BC05 (23 mg, 0.063 mmol), 5-(difluoromethyl)-3-hydroxy-2-methylbenzonitrile, A02 (11.56 mg, 0.063 mmol), and potassium carbonate (26.2 mg, 0.189 mmol) in NMP (210 µL) was heated at 80° C. till LC-MS showed complete conversion. The reaction mixture was diluted with water, and the precipitate was collected on top of a filter and washed with water (3×), then air-dried to afford the title compound. MS: 528.2 (M+1).

Step 2: 5-(difluoromethyl)-3-((1-(2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-2-methylbenzonitrile A mixture of 5-(difluoromethyl)-3-((1-(4-methoxy-2,6-dimethylpyrimidin-5-yl)methyl)-6-oxo-4-(1,1,2,2-tetrafluoroethyl)-1,6-dihydropyrimidin-5-yl)oxy)-2-methylbenzonitrile and potassium iodide (10.48 mg, 0.063 mmol) in ACN (2 mL) was treated with TMS-Cl (48.4 µL, 0.379 mmol), then heated at 100° C. for 10 minutes. The reaction mixture was filtered and purified by reverse phase HPLC (ACN/water with 0.1% TFA as modifier) to afford the title compound. MS: 514.2 (M+1). $^1$H NMR (600 MHz, CDCl$_3$) δ 8.65 (s, 1H), 7.44 (s, 1H), 6.73 (s, 1H), 4.99 (s, 2H), 2.59 (s, 3H), 2.55 (s, 3H), 2.49 (s, 3H).

Example 67

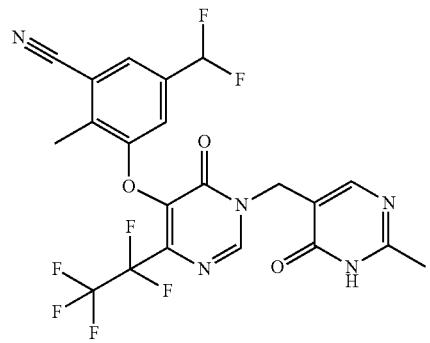 [SMILES: Cc1ncc(Cn2cnc(C(F)(F)C(F)(F)F)c(Oc3cc(C(F)F)cc(C#N)c3C)c2=O)c(=O)[nH]1]

5-(difluoromethyl)-2-methyl-3-((1-((2-methyl-6-oxo-1,6-dihydropyrimidin-5-yl)methyl)-6-oxo-4-(perfluoroethyl)-1,6-dihydropyrimidin-5-yl)oxy) benzonitrile Step 1: 5-(difluoromethyl)-3-((1-((4-methoxy-2-methylpyrimidin-5-yl)methyl)-6-oxo-4-(perfluoroethyl)-1,6-dihydropyrimidin-5-yl)oxy)-2-methylbenzonitrile A mixture of 5-fluoro-3-((4-methoxy-2-methylpyrimidin-5-yl)methyl)-6-(perfluoroethyl)pyrimidin-4(3H)-one, BC02

(16 mg, 0.043 mmol), 5-(difluoromethyl)-3-hydroxy-2-methylbenzonitrile, A02 (7.96 mg, 0.043 mmol), and potassium carbonate (18.02 mg, 0.130 mmol) in NMP (145 µL) was heated at 80° C. for 1 h. The reaction mixture was diluted with water and the precipitate was collected on top of a filter and washed with water (2×), and air-dried to obtain the title compound, which was used as is for the next step. MS: 532.2 (M+1).

Step 2: 5-(difluoromethyl)-2-methyl-3-((1-((2-methyl-6-oxo-1,6-dihydropyrimidin-5-yl)methyl)-6-oxo-4-(perfluoroethyl)-1,6-dihydropyrimidin-5-yl)oxy)benzonitrile The above crude material and KI (21.64 mg, 0.130 mmol) in ACN (2 mL) was treated with TMS-Cl (70 µL, 0.548 mmol), then heated to 100° C. till LC-MS showed the reaction was complete. The reaction mixture was purified by reverse phase HPLC (ACN/water with 0.1% TFA as modifier) to afford the title compound. MS: 518.2 (M+1). $^1$H NMR (600 MHz, Methanol-$d_4$) δ 8.67 (s, 2H), 8.04 (s, 2H), 7.60 (s, 2H), 7.03 (s, 2H), 6.68 (s, 1H), 3.30 (s, 19H), 2.54 (s, 6H), 2.45 (s, 6H), 1.93 (s, 1H).

The following examples in Table 19 were prepared in an analogous manner to that described in Example 67 with an appropriate intermediate BC and intermediate A.

TABLE 19

| Ex# (BC#, A#) | Structure | IUPAC Name | MS (M + 1) |
|---|---|---|---|
| 68 (BC05, A10) | 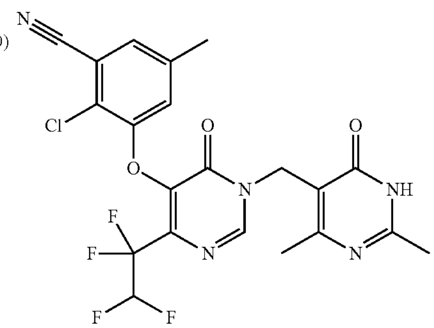 | 2-chloro-3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-5-methylbenzonitrile | 498.0 |
| 69 (BC05, A01) | 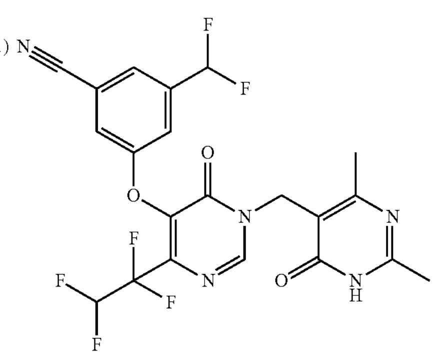 | 3-(difluoromethyl)-5-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile | 500.1 |
| 70 (BC03, A02) | 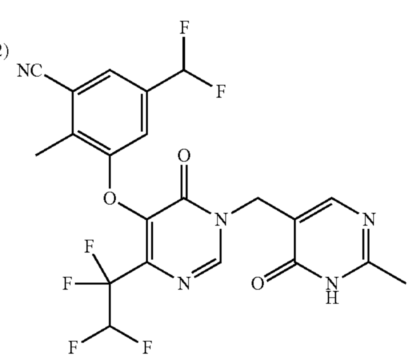 | 5-(difluoromethyl)-2-methyl-3-((1-((2-methyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile | 500.2 |

TABLE 19-continued

| Ex# (BC#, A#) | Structure | IUPAC Name | MS (M + 1) |
|---|---|---|---|
| 71 (BC0, A17) | 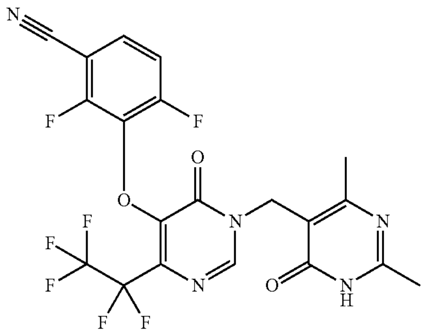 [SMILES: Cc1nc(C)c(Cn2cnc(C(F)(F)C(F)(F)F)c(Oc3c(F)ccc(C#N)c3F)c2=O)c(=O)[nH]1] | 3-((1-((2,4-dimethyl-6-oxo-1,6-dihydropyrimidin-5-yl)methyl)-6-oxo-4-(perfluoroethyl)-1,6-dihydropyrimidin-5-yl)oxy)-2,4-difluorobenzonitrile | 504.2 |
| 72 (BC01, A07) | 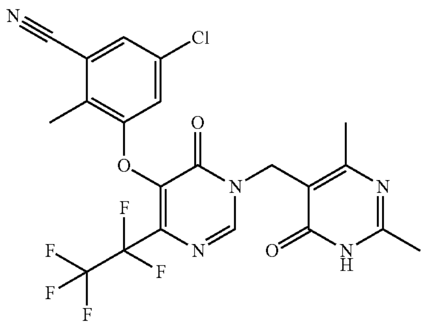 [SMILES: Cc1nc(C)c(Cn2cnc(C(F)(F)C(F)(F)F)c(Oc3cc(Cl)cc(C#N)c3C)c2=O)c(=O)[nH]1] | 5-chloro-3-((1-((2,4-dimethyl-6-oxo-1,6-dihydropyrimidin-5-yl)methyl)-6-oxo-4-(perfluoroethyl)-1,6-dihydro-pyrimidin-5-yl)oxy)-2-methylbenzonitrile | 516.2 |
| 73 (BC01, A18) | 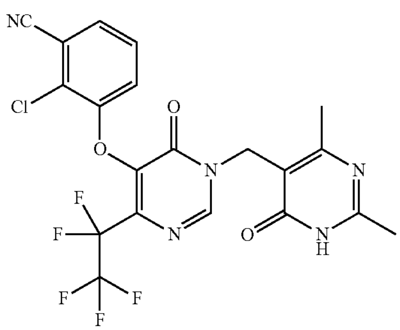 [SMILES: Cc1nc(C)c(Cn2cnc(C(F)(F)C(F)(F)F)c(Oc3cccc(C#N)c3Cl)c2=O)c(=O)[nH]1] | 3-((1-((2,4-dimethyl-6-oxo-1,6-dihydropyrimidin-5-yl)methyl)-6-oxo-4-(perfluoroethyl)-1,6-dihydropyrimidin-5-yl)oxy)-2-methylbenzonitrile | 502.1 |
| 74 (BC01, A19) | 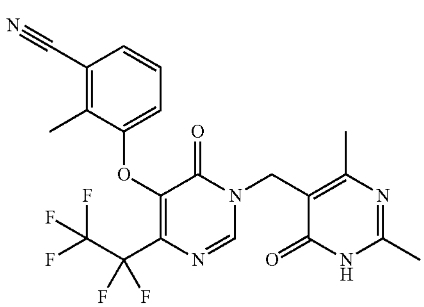 [SMILES: Cc1nc(C)c(Cn2cnc(C(F)(F)C(F)(F)F)c(Oc3cccc(C#N)c3C)c2=O)c(=O)[nH]1] | 3-((1-((2,4-dimethyl-6-oxo-1,6-dihydropyrimidin-5-yl)methyl)-6-oxo-4-(perfluoroethyl)-1,6-dihydropyrimidin-5-yl)oxy)-2-methylbenzonitrile | 482.2 |

TABLE 19-continued

| Ex# (BC#, A#) | Structure | IUPAC Name | MS (M + 1) |
|---|---|---|---|
| 75 (BC05, A20) | 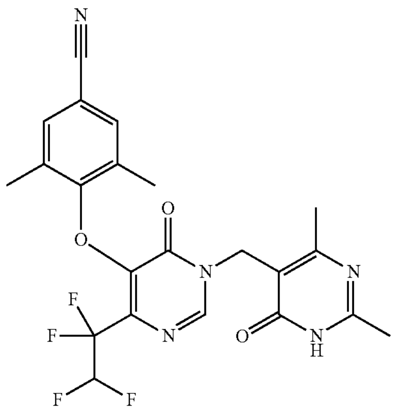 | 4-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-3,5-dimethylbenzonitrile | 477 |
| 76 (BC01, A21) | 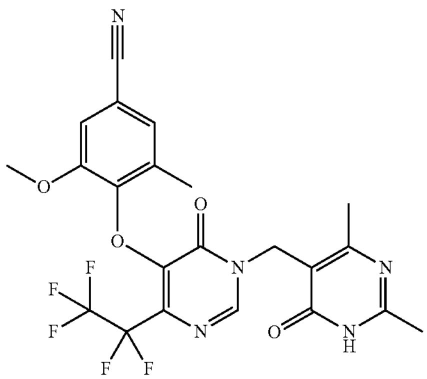 | 4-((1-((2,4-dimethyl-6-oxo-1,6-dihydropyrimidin-5-yl)methyl)-6-oxo-4-(perfluoroethyl)-1,6-dihydropyrimidin-5-yl)oxy)-3-methoxy-5-methylbenzonitrile | 512.3 |
| 77 (BC04, A20) | 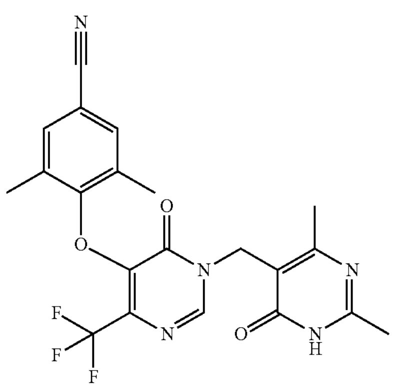 | 4-((1-((2,4-dimethyl-6-oxo-1,6-dihydropyrimidin-5-yl)methyl)-6-oxo-4-(trifluoromethyl)-1,6-dihydropyrimidin-5-yl)oxy)-3,5-dimethylbenzonitrile | 446.2 |
| 78 (BC01, A20) | 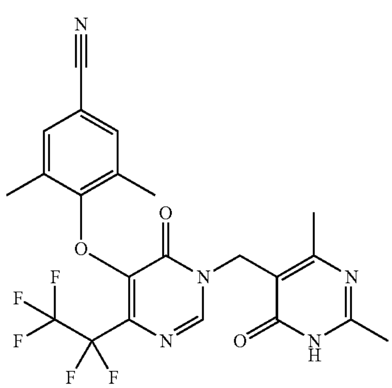 | 4-((1-((2,4-dimethyl-6-oxo-1,6-dihydropyrimidin-5-yl)methyl)-6-oxo-4-(perfluoroethyl)-1,6-dihydropyrimidin-5-yl)oxy)-3,5-dimethylbenzonitrile | 496.2 |

TABLE 19-continued

| Ex# (BC#, A#) | Structure | IUPAC Name | MS (M + 1) |
|---|---|---|---|
| 79 (BC06, A02) | 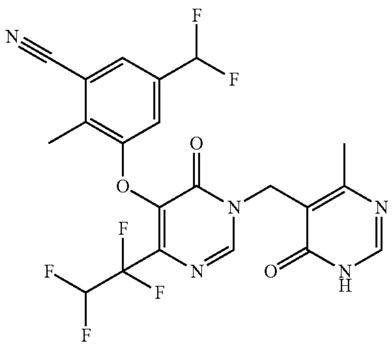 [SMILES: Cc1nc[nH]c(=O)c1Cn1cnc(C(F)(F)C(F)F)c(Oc2cc(C(F)F)cc(C#N)c2C)c1=O] | 5-(difluoromethyl)-2-methyl-3-((1-((4-methyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile | 500.2 |

Example 80

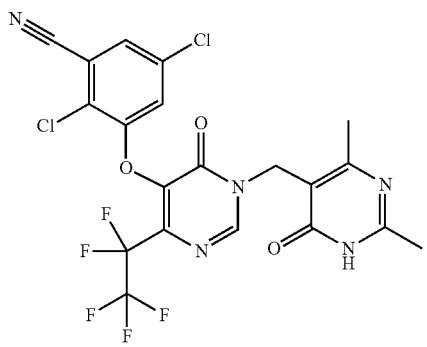 [SMILES: Cc1nc(C)c(Cn2cnc(C(F)(F)C(F)(F)F)c(Oc3cc(Cl)cc(C#N)c3Cl)c2=O)c(=O)[nH]1]

2,5-dichloro-3-((1-((2,4-dimethyl-6-oxo-1,6-dihydropyrimidin-5-yl)methyl)-6-oxo-4-(perfluoroethyl)-1,6-dihydropyrimidin-5-yl)oxy)benzonitrile Step 1: 2,5-dichloro-3-((1-((4-methoxy-2,6-dimethylpyrimidin-5-yl)methyl)-6-oxo-4-(perfluoroethyl)-1,6-dihydropyrimidin-5-yl)oxy)benzonitrile To a solution of 5-(difluoromethyl)-2-methyl-3-((6-oxo-4-(perfluoroethyl)-1,6-dihydropyrimidin-5-yl)oxy)benzonitrile, BC01 (200 mg, 0.523 mmol) in ACN (2616 was added potassium carbonate (72.3 mg, 0.523 mmol) and 2,5-dichloro-3-hydroxybenzonitrile, A04 (118 mg, 0.628 mmol). The reaction mixture was stirred at 100° C. for 16 h, and then filtered. The filtrate was diluted with EtOAc (200 mL) and hexanes (20 mL), and washed with water (3×50 mL), brine (50 mL), dried over anhydrous MgSO₄, filtered and concentrated under reduced pressure. The residue was purified with column chromatography on silica (0-70% EtOAc/hexanes) to afford the title compound. MS: 550.2 (M+1).

Step 2: 2,5-dichloro-3-((1-((2,4-dimethyl-6-oxo-1,6-dihydropyrimidin-5-yl)methyl)-6-oxo-4-(perfluoroethyl)-1,6-dihydropyrimidin-5-yl)oxy)benzonitrile To a solution of 2,5-dichloro-3-((1-((4-methoxy-2,6-dimethylpyrimidin-5-yl)methyl)-6-oxo-4-(perfluoroethyl)-1,6-dihydropyrimidin-5-yl)oxy)benzonitrile (154 mg, 0.280 mmol) in ACN (2799 µL) was added TMS-I (381 µl, 2.80 mmol). The resulting reaction mixture was stirred at RT for 2 days. LC-MS showed complete conversion. The reaction is quenched with saturated aqueous Na₂SO₃ (300 uL) and purified by reverse phase HPLC (ACN/water with 0.05% NH₄OH as modifier) to afford the title compound. MS: 536.1 (M+1). ¹H NMR (600 MHz, DMSO-d₆) δ 8.79 (s, 1H), 7.92 (d, J=2.1 Hz, 1H), 7.73 (d, J=2.1 Hz, 1H), 4.89 (s, 2H), 2.31 (s, 3H), 2.22 (s, 3H).

The following examples in Table 20 were prepared in an analogous manner to that described in Example 80 with appropriate intermediate BC and intermediate A.

TABLE 20

| Ex# (BC#, A#) | Structure | IUPAC Name | MS (M + 1) |
|---|---|---|---|
| 81 (BC05, A06) | 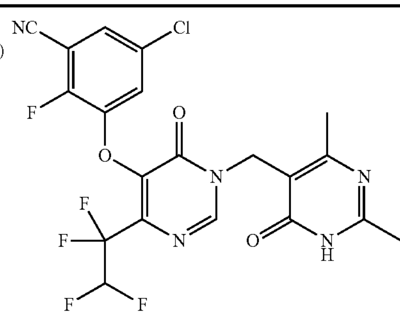 | 5-chloro-3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-2-fluorobenzonitrile | 502.1 |

TABLE 20-continued

| Ex# (BC#, A#) | Structure | IUPAC Name | MS (M + 1) |
|---|---|---|---|
| 82 (BC01, A03) | 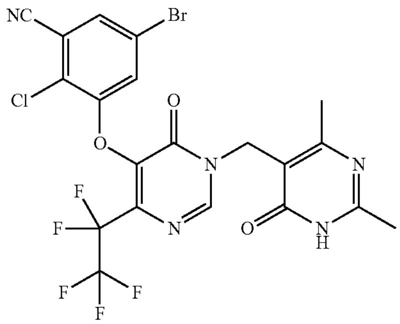 [SMILES: Cc1nc(C)c(Cn2cnc(C(F)(F)C(F)(F)F)c(Oc3cc(Br)cc(C#N)c3Cl)c2=O)c(=O)[nH]1] | 5-bromo-2-chloro-3-((1-((2,4-dimethyl-6-oxo-1,6-dihydro-pyrimidin-5-yl)methyl)-6-oxo-4-(perfluoroethyl)-1,6-dihydro-pyrimidin-5-yl)oxy)benzonitrile | 580.1 and 582.1 |
| 83 (BC01, A02) | 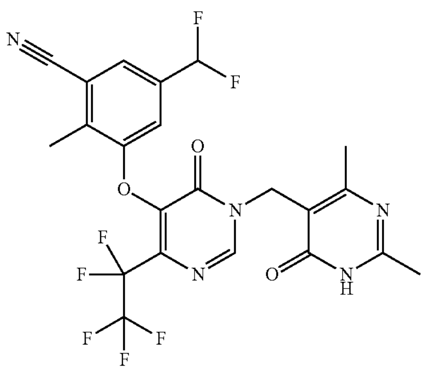 [SMILES: Cc1nc(C)c(Cn2cnc(C(F)(F)C(F)(F)F)c(Oc3cc(C(F)F)cc(C#N)c3C)c2=O)c(=O)[nH]1] | 5-(difluoromethyl)-3-((1-((4-methoxy-2,6-dimethylpyrimidin-5-yl)methyl)-6-oxo-4-(perfluoroethyl)-1,6-dihydropyrimidin-5-yl)oxy)-2-methylbenzonitrile | 532.2 |
| 84 (BC01, A01) | 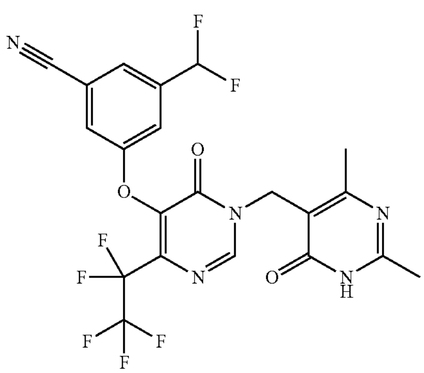 [SMILES: Cc1nc(C)c(Cn2cnc(C(F)(F)C(F)(F)F)c(Oc3cc(C#N)cc(C(F)F)c3)c2=O)c(=O)[nH]1] | 3-(difluoromethyl)-5-((1-((4-methoxy-2,6-dimethylpyrimidin-5-yl)methyl)-6-oxo-4-(perfluoroethyl)-1,6-dihydropyrimidin-5-yl)oxy)benzonitrile | 518.2 |
| 85 (BC01, A11) | 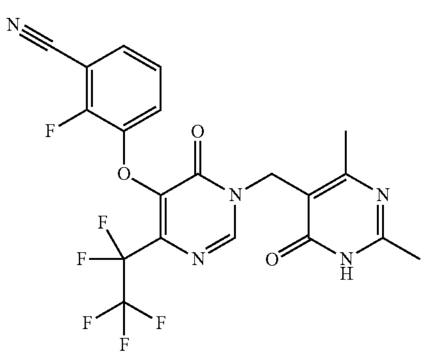 [SMILES: Cc1nc(C)c(Cn2cnc(C(F)(F)C(F)(F)F)c(Oc3cccc(C#N)c3F)c2=O)c(=O)[nH]1] | 3-((1-((2,4-dimethyl-6-oxo-1,6-dihydropyrimidin-5-yl)methyl)-6-oxo-4-(perfluoroethyl)-1,6-dihydropyrimidin-5-yl)oxy)-2-fluorobenzonitrile | 486.1 |

TABLE 20-continued

| Ex# (BC#, A#) | Structure | IUPAC Name | MS (M + 1) |
|---|---|---|---|
| 86 (BC01, A12) | 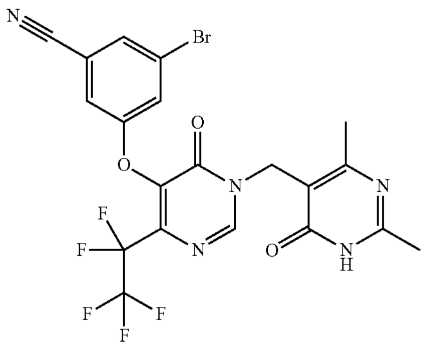 [SMILES: Cc1nc(C)c(Cn2cnc(C(F)(F)C(F)(F)F)c(Oc3cc(Br)cc(C#N)c3)c2=O)c(=O)[nH]1] | 3-bromo-5-((1-((2,4-dimethyl-6-oxo-1,6-dihydropyrimidin-5-yl)methyl)-6-oxo-4-(perfluoroethyl)-1,6-dihydro-pyrimidin-5-yl)oxy)benzonitrile | 546.1 and 548.1 |
| 87 (BC01, A06) | 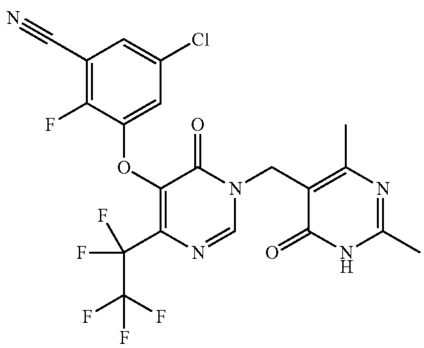 [SMILES: Cc1nc(C)c(Cn2cnc(C(F)(F)C(F)(F)F)c(Oc3cc(Cl)cc(C#N)c3F)c2=O)c(=O)[nH]1] | 5-chloro-3-((1-((2,4-dimethyl-6-oxo-1,6-dihydropyrimidin-5-yl)methyl)-6-oxo-4-(perfluoroethyl)-1,6-dihydropyrimidin-5-yl)oxy)-2-fluorobenzonitrile | 520.2 |
| 88 (BC01, A13) | 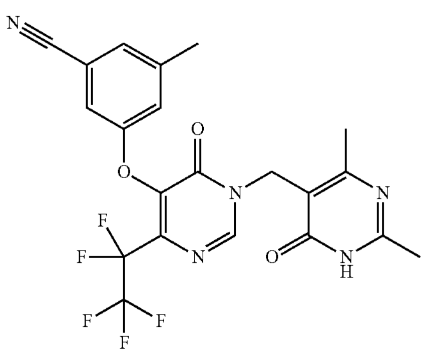 | 3-((1-((4-methoxy-2,6-dimethylpyrimidin-5-yl)methyl)-6-oxo-4-(perfluoroethyl)-1,6-dihydropyrimidin-5-yl)oxy)-5-methylbenzonitrile | 482.1 |
| 89 (BC04, A03) | 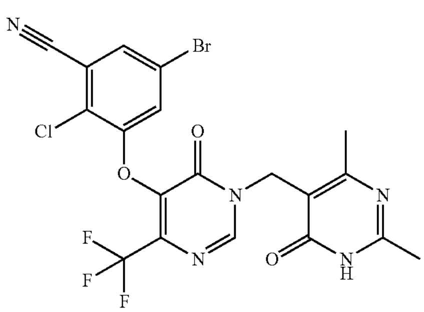 [SMILES: Cc1nc(C)c(Cn2cnc(C(F)(F)F)c(Oc3cc(Br)cc(C#N)c3Cl)c2=O)c(=O)[nH]1] | 5-bromo-2-chloro-3-((1-((2,4-dimethyl-6-oxo-1,6-dihydro-pyrimidin-5-yl)methyl)-6-oxo-4-(trifluoromethyl)-1,6-dihydropyrimidin-5-yl)oxy)benzonitrile | 530.1 and 532.1 |

TABLE 20-continued

| Ex# (BC#, A#) | Structure | IUPAC Name | MS (M + 1) |
|---|---|---|---|
| 90 (BC04, A04) | 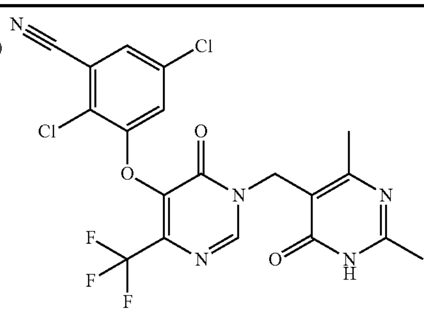 | 2,5-dichloro-3-((1-((2,4-dimethyl-6-oxo-1,6-dihydropyrimidin-5-yl)methyl)-6-oxo-4-(trifluoromethyl)-1,6-dihydropyrimidin-5-yl)oxy)benzonitrile | 486.1 |
| 91 (BC05, A14) | 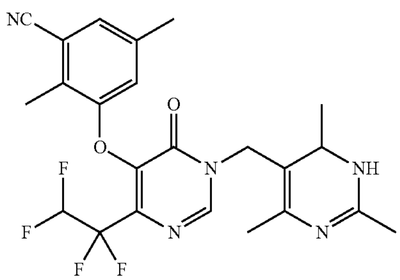 | 3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-2,5-dimethylbenzonitrile | 477.2 |
| 92 (BC04, A06) | 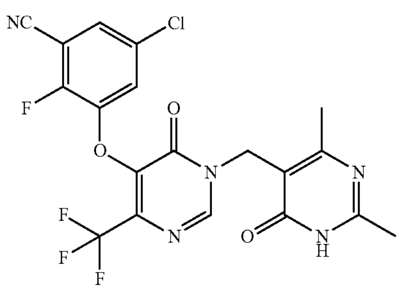 [SMILES: Cc1nc(C)c(Cn2cnc(C(F)(F)F)c(Oc3cc(Cl)cc(C#N)c3F)c2=O)c(=O)[nH]1] | 5-chloro-3-((1-((2,4-dimethyl-6-oxo-1,6-dihydropyrimidin-5-yl)methyl)-6-oxo-4-(trifluoromethyl)-1,6-dihydropyrimidin-5-yl)oxy)-2-fluorobenzonitrile | 470.1 |

Example 93

3-((1-((2,4-dimethyl-6-oxo-1,6-dihydropyrimidin-5-yl)methyl)-6-oxo-4-(perfluoroethyl)-1,6-dihydropyrimidin-5-yl)oxy)-2-fluoro-5-methylbenzonitrile

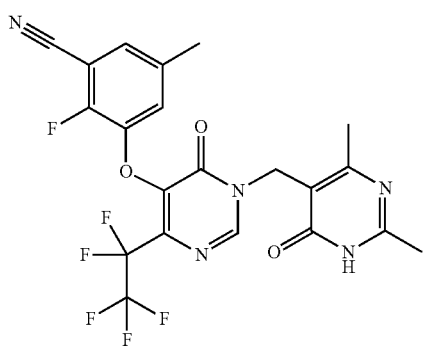 [SMILES: Cc1cc(C#N)c(F)c(Oc2c(C(F)(F)C(F)(F)F)ncn(Cc3c(C)nc(C)[nH]c3=O)c2=O)c1]

Step 1: 5-chloro-2-fluoro-3-((1-((4-methoxy-2,6-dimethylpyrimidin-5-yl)methyl)-6-oxo-4-(perfluoroethyl)-1,6-dihydropyrimidin-5-yl)oxy)benzonitrile To a solution of 5-fluoro-3-((4-methoxy-2,6-dimethylpyrimidin-5-yl)methyl)-6-(perfluoroethyl)pyrimidin-4 (3H)-one, BC01 (115 mg, 0.301 mmol) in ACN (1504 µL) was added potassium carbonate (83 mg, 0.602 mmol) and 5-chloro-2-fluoro-3-hydroxybenzonitrile, A05 (61.9 mg, 0.361 mmol). The resulting reaction mixture was stirred at r.t. for 16 h, and then filtered. The filtrate was diluted with EtOAc (200 mL) and hexanes (20 mL), then washed with water (3×50 mL), brine (50 mL), dried over anhydrous MgSO₄, filtered and concentrated under reduced pressure.

153

The residue was purified with column chromatography on silica (0-70% EtOAc/hexanes) to afford the title compound. MS: 534.2 (M+1).

Step 2: 5-methyl-2-fluoro-3-((1-((4-methoxy-2,6-dimethylpyrimidin-5-yl)methyl)-6-oxo-4-(perfluoroethyl)-1,6-dihydropyrimidin-5-yl)oxy)benzonitrile To a degassed mixture of 5-chloro-2-fluoro-3-((1-(4-methoxy-2,6-dimethylpyrimidin-5-yl)methyl)-6-oxo-4-(perfluoroethyl)-1,6-dihydropyrimidin-5-yl)oxy)benzonitrile (90 mg, 0.169 mmol) in water (211 µL) and 1,4-dioxane (632 was added chloro[(di(1-adamantyl)-n-butylphosphine)-2-(2-aminobiphenyl)]palladium(II) (11.27 mg, 0.017 mmol), potassium methyltrifluoroborate (30.8 mg, 0.253 mmol) ad Cs$_2$CO$_3$ (165 mg, 0.506 mmol). The resulting reaction mixture was heated to 130° C. for 30 minutes. LC-MS showed that the reaction was complete. The reaction mixture was concentrated under reduced pressure. The residue was purified on column chromatography on silica (0-80% EtOAc/hexanes) to afford the title compound. MS: 514.2 (M+1).

Step 3: 3-((1-((2,4-dimethyl-6-oxo-1,6-dihydropyrimidin-5-yl)methyl)-6-oxo-4-(perfluoroethyl)-1,6-dihydropyrimidin-5-yl)oxy)-2-fluoro-5-methylbenzonitrile A solution of 3-((1-((2,4-dimethyl-6-oxo-1,6-dihydropyrimidin-5-yl)methyl)-6-oxo-4-(perfluoroethyl)-1,6-dihydropyrimidin-5-yl)oxy)-2-fluoro-5-methylbenzonitrile (32 mg, 0.062 mmol) was dissolved in ACN (312 µL) was treated with TMS-I (42.4 µL, 0.312 mmol). The resulting reaction mixture was heated to 40° C. for 4 h. LC-MS showed the reaction was complete. The reaction was quenched with saturated aqueous Na$_2$SO$_3$ (100 uL) and stirred for 30 minutes. DMSO (2 mL) was added to the solution was purified by reverse phase HPLC (ACN/water with 0.05% NH$_4$OH as modifier) to afford the title compound. MS: 500.2 (M+1). $^1$H NMR (600 MHz, DMSO-d$_6$) δ 8.76 (s, 1H), 7.41 (d, J=3.9 Hz, 1H), 7.32 (d, J=7.5 Hz, 1H), 5.05 (s, 2H), 2.30 (s, 3H), 2.22 (s, 3H), 2.21 (s, 3H).

Example 94

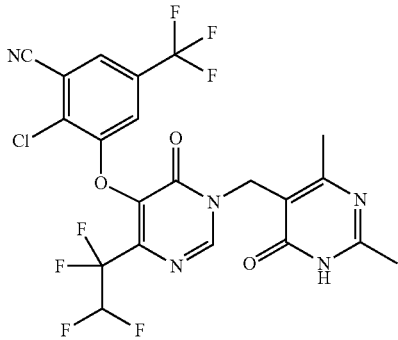 [SMILES: Cc1nc(C)c(Cn2cnc(C(F)(F)C(F)F)c(Oc3cc(C(F)(F)F)cc(C#N)c3Cl)c2=O)c(=O)[nH]1]

154

2-chloro-3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-5-(trifluoromethyl)benzonitrile Step 1: 5-(3-bromo-2-chloro-5-(trifluoromethyl)phenoxy)-3-((4-methoxy-2,6-dimethylpyrimidin-5-yl)methyl)-6-(1,1,2,2-tetrafluoroethyl)pyrimidin-4(3H)-one To a stirred solution of 5-fluoro-3-((4-methoxy-2,6-dimethylpyrimidin-5-yl)methyl)-6-(1,1,2,2-tetrafluoroethyl)pyrimidin-4 (3H)-one, BC05 (50 mg, 0.137 mmol) and 3-bromo-2-chloro-5-(trifluoromethyl)phenol (41.6 mg, 0.151 mmol) in DMF (1 mL) was added K$_2$CO$_3$ (37.9 mg, 0.275 mmol) at RT. The resulting mixture was stirred at 120° C. overnight. LC-MS showed desired product. The reaction mixture was diluted with water (5 mL) and extracted with EtOAc (5 mL). The organic layer was concentrated under reduced pressure. The residue was purified by column chromatography on silica (0-100% EtOAc/hexanes) to afford the title compound. MS: 621.0 (M+1).

Step 2: 2-chloro-3-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-5-(trifluoromethyl)benzonitrile A mixture of 5-(3-bromo-2-chloro-5-(trifluoromethyl)phenoxy)-3-((4-methoxy-2,6-dimethylpyrimidin-5-yl)methyl)-6-(1,1,2,2-tetrafluoroethyl)pyrimidin-4 (3H)-one (37 mg, 0.060 mmol), Zn(CN)$_2$ (4.21 mg, 0.036 mmol) and Pd(PPh$_3$)$_4$ (6.90 mg, 5.97 µmol) in DMF (600 µL) was degassed for 5 min and then heated at 120° C. overnight. LC-MS showed desired product. The reaction mixture was diluted with DMF (1 mL), and then filtered and treated with pyridine hydrochloride (20.70 mg, 0.179 mmol). The resulting mixture was stirred at 120° C. for 20 min. LC-MS showed the final product. The residue was purified by reverse phase HPLC (ACN/water with 0.1% TFA as modifier) to afford the title compound. MS: 552.1 (M+1). $^1$H NMR (500 MHz, DMSO-d$_6$) δ 8.81 (s, 1H), 8.23 (s, 1H), 7.78 (s, 1H), 3.84 (s, 2H), 2.32 (s, 3H), 2.27 (s, 3H).

Example 95

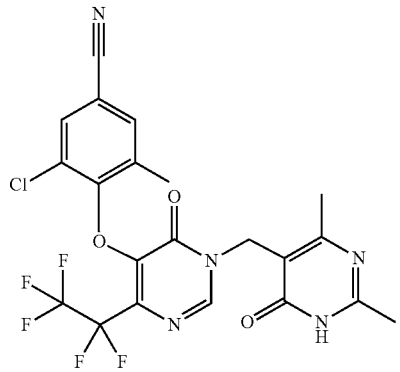 [SMILES: Cc1nc(C)c(Cn2cnc(C(F)(F)C(F)(F)F)c(Oc3c(C)cc(C#N)cc3Cl)c2=O)c(=O)[nH]1]

3-chloro-4-((1-((2,4-dimethyl-6-oxo-1,6-dihydropyrimidin-5-yl)methyl)-6-oxo-4-(perfluoroethyl)-1,6-dihydropyrimidin-5-yl)oxy)-5-methylbenzonitrile Step 1: 5-(2-chloro-4-methoxy-6-methylphenoxy)-3-((4-methoxy-2,6-dimethylpyrimidin-5-yl)methyl)-6-(perfluoroethyl)pyrimidin-4 (3H)-one To a vial was added 2-chloro-4-methoxy-6-methylphenol (45.2 mg, 0.262 mmol), 5-fluoro-3-((4-methoxy-2,6-dimethylpyrimidin-5-yl)methyl)-6-(perfluoroethyl)pyrimidin-(3H)-one, BC01 (100 mg, 0.26 mmol), potassium carbonate (90 mg, 0.65 mmol) and DMF (2.6 mL). The resulting reaction mixture was heated to 100° C. for 15 h, cooled to ambient temperature and then filtered through a syringe filter. The crude solution was purified by reverse phase HPLC (ACN/water with 0.1% TFA as modifier) to afford the title compound. MS: 535.3 (M+1).

Step 2: 5-(2-chloro-4-hydroxy-6-methylphenoxy)-3-((4-methoxy-2,6-dimethylpyrimidin-5-yl)methyl)-6-(perfluoroethyl)pyrimidin-4 (3H)-one To a ice-cooled solution of 5-(2-chloro-4-methoxy-6-methylphenoxy)-3-((4-methoxy-2,6-dimethylpyrimidin-5-yl)methyl)-6-(perfluoroethyl)pyrimidin-4 (3H)-one (87 mg, 0.16 mmol) in DCM (3 mL) was added 1M solution of $BBr_3$ in DCM (0.34 mL, 0.34 mmol) dropwise. The resulting reaction mixture was allowed to warm to ambient temperature, stirred for 15 h, and then quenched by the addition of methanol (2 mL). The resulting mixture was concentrated under reduced pressure. The residue was purified by column chromatography on silica (0-100% EtOAc/hexanes, and then 10% MeOH/DCM) to afford the title compound. MS: 521.2 (M+1).

Step 3: 3-chloro-4-((1-((4-methoxy-2,6-dimethylpyrimidin-5-yl)methyl)-6-oxo-4-(perfluoroethyl)-1,6-dihydropyrimidin-5-yl)oxy)-5-methylphenyl trifluoromethanesulfonate To a solution of 5-(2-chloro-4-hydroxy-6-methylphenoxy)-3-((4-methoxy-2,6-dimethylpyrimidin-5-yl)methyl)-6-(perfluoroethyl)pyrimidin-4 (3H)-one (100 mg, 0.19 mmol) in DCM (3 mL) was added triethylamine (0.04 mL, 0.29 mmol) and N,N-bis(trifluoromethyl sulfonyl) aniline (82 mg, 0.23 mmol). The resulting reaction mixture was allowed to stir at ambient temperature for 2 h and then quenched by the addition of saturated aqueous sodium bicarbonate (10 mL). The reaction mixture was extracted by DCM (3×10 mL). The combined organic layers were dried over anhydrous $MgSO_4$, filtered and concentrated under reduced pressure. The residue was purified by column chromatography on silica (0-100% EtOAc/hexanes) to afford the title compound. MS: 653.2 (M+1).

Step 4: 3-chloro-4-((1-((4-methoxy-2,6-dimethylpyrimidin-5-yl)methyl)-6-oxo-4-(perfluoroethyl)-1,6-dihydropyrimidin-5-yl)oxy)-5-methylbenzonitrile A mixture of 3-chloro-4-((1-(4-methoxy-2,6-dimethylpyrimidin-5-yl)methyl)-6-oxo-4-(perfluoroethyl)-1,6-dihydropyrimidin-5-yl)oxy)-5-methylphenyl trifluoromethanesulfonate (62 mg, 0.10 mmol), tbuXPhos Pd G3 precatalyst (30.2 mg, 0.038 mmol), and zinc cyanide (7.36 mg, 0.063 mmol) was purged with nitrogen three times before water (1.5 mL) and THF (0.38 mL) were added. The resulting reaction mixture was heated to 65° C. for 15 h, cooled to ambient temperature, filtered over a pad of CELITE® and concentrated under reduced pressure. The residue was purified by column chromatography on silica (0-100% EtOAc/hexanes) to afford the title compound. MS: 530.2 (M+1).

Step 5: 3-chloro-4-((1-((2,4-dimethyl-6-oxo-1,6-dihydropyrimidin-5-yl)methyl)-6-oxo-4-(perfluoroethyl)-1,6-dihydropyrimidin-5-yl)oxy)-5-methylbenzonitrile To a stirred solution of 3-chloro-4-((1-(4-methoxy-2,6-dimethylpyrimidin-5-yl)methyl)-6-oxo-4-(perfluoroethyl)-1,6-dihydropyrimidin-5-yl)oxy)-5-methylbenzonitrile (16 mg, 0.030 mmol) and potassium iodide (15.04 mg, 0.091 mmol) in ACN (302 was added TMS-Cl (11.58 µl, 0.091 mmol). The resulting mixture was heated to 50° C. overnight. LC-MS showed complete and clean conversion. The reaction mixture was cooled, and quenched with MeOH (1 mL), and concentrated under reduced pressure. The residue was purified by reverse phase HPLC (ACN/water with 0.1% TFA as modifier) to give fractions containing desired product, which were combined, diluted with saturated aqueous $NaHCO_3$ solution, and extracted with DCM (3×). The combined organic layers were dried over anhydrous $MgSO_4$, filtered and concentrated under reduced pressure to afford the title compound. MS: 516.2 (M+1). $^1H$ NMR (500 MHz, $CDCl_3$): δ 8.5 (s, 1H), 7.4 (s, 2H), 5.0-4.8 (dd, 2H), 2.55 (s, 3H), 2.5 (s, 3H), 2.3 (s, 3H).

The following examples in Table 21 were prepared in an analogous manner to that described in Example 95 with appropriate intermediate BC and intermediate A.

TABLE 21

| Ex# (BC#, A#) | Structure | IUPAC Name | MS (M + 1) |
|---|---|---|---|
| 96 (BC01, A15) | 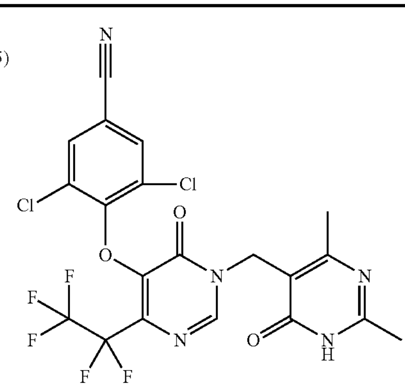 | 3,5-dichloro-4-((1-((2,4-dimethyl-6-oxo-1,6-dihydropyrimidin-5-yl)methyl)-6-oxo-4-(perfluoroethyl)-1,6-dihydropyrimidin-5-yl)oxy)benzonitrile | 536.2 |

TABLE 21-continued

| Ex# (BC#, A#) | Structure | IUPAC Name | MS (M + 1) |
|---|---|---|---|
| 97 (BC05, A15) | 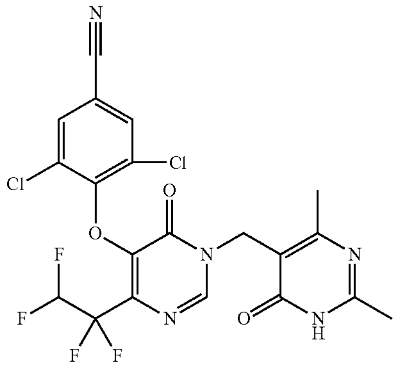 [SMILES: Cc1nc(C)c(Cn2cnc(C(F)(F)C(F)F)c(Oc3c(Cl)cc(C#N)cc3Cl)c2=O)c(=O)[nH]1] | 3,5-dichloro-4-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)benzonitrile | 518.2 |
| 98 (BC05, A16) | 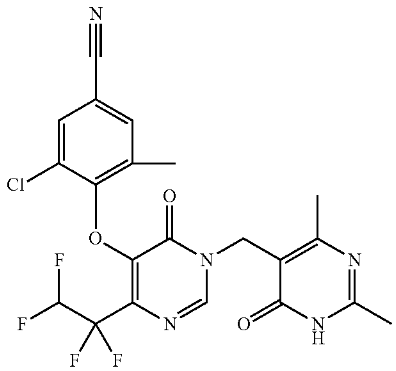 [SMILES: Cc1nc(C)c(Cn2cnc(C(F)(F)C(F)F)c(Oc3c(C)cc(C#N)cc3Cl)c2=O)c(=O)[nH]1] | 3-chloro-4-((1-((2,4-dimethyl-6-oxo-1,6-dihydropyrimidin-5-yl)methyl)-6-oxo-4-(1,1,2,2-tetrafluoroethyl)-1,6-dihydropyrimidin-5-yl)oxy)-5-methylbenzonitrile | 498.2 |

Determination of Cell Kill (HIV-TACK) Activity:

PBMCs derived from healthy donors were grown in complete media (RPMI 1640 with L-glutamine; 10% heat inactivated Fetal Bovine Serum; 100 U/mL Penicillin-Streptomycin) containing 5 μg/mL Phytohemagglutinin at about $2.5 \times 10^6$ cells/mL for 3 days at 5% $CO_2$, 37° C., and 90% humidity. On day 4, PHA stimulated cells were washed and resuspended at about $20 \times 10^6$ cells/mL in complete media with IL-2 (10 U/mL) with VSV-G pseudotyped HIV virus stock (VSV-G/pNLG1-P2A-ΔEnv—20 μg/mL p24) and incubated for 4 hours at 37° C., 5% $CO_2$ and 90% humidity. VSV-G/pNLG1-P2A-ΔEnv is a VSV-G pseudotyped virus derived from pNL43 with egn) inserted 5' of nef and eGFP expression driven off normal spliced RNA transcripts. Virus contained Vif truncated by 50 amino acids due to deletion of a single nucleotide causing a frameshift and does not express Nef due to a stop codon after gfp. HIV Env is not expressed due to a frameshift resulting in multiple stop codons. Infected cells were then washed with complete media plus 10 U/mL IL-2 3-times with centrifuging at 200×g for 3 minutes at 22° C. Cells were resuspended at $5 \times 10^6$ cells/mL in complete media plus 10 U/mL IL-2 and incubated overnight at 37° C., 5% $CO_2$ and 90% humidity. For compound treatment infected PBMCs were diluted to $4 \times 10^5$ cells/mL with RPMI 1640 with L-glutamine, 50% Normal Human Serum (NETS), 100 U/mL Penicillin-Streptomycin plus IL-2 (10 U/mL) and 20,000 cells were transferred to each well in a 384-well poly-D-lysine coated compound plate containing compounds with final DMSO<0.5%. Compounds were tested with 10-point 3-fold titration. Plates were analyzed on an Acumen ex3 imager using the Blue Laser 488 nm and the number of GFP positive objects were collected with loss of GFP representing death of infected cells. Titration curves and $EC_{50}$ values were calculated using a four-parameter logistic fit. Results are shown in Table 22.

TABLE 22

| Ex. No. | TACK $EC_{50}$ (nM) |
|---|---|
| 1 | 431.0 |
| 2 | 411.4 |
| 3 | 416.9 |
| 4 | 411.5 |
| 5 | 186.8 |
| 6 | 201.2 |
| 7 | 353.3 |
| 8 | 251.7 |
| 9 | 287.0 |
| 10 | 146.2 |
| 11 | 267.0 |
| 12 | 199.5 |
| 13 | 395.0 |
| 14 | 343.0 |
| 15 | 244.7 |
| 16 | 199.4 |
| 17 | 282.4 |
| 18 | 128.6 |
| 19 | 315.3 |
| 20 | 364.9 |
| 21 | 131.8 |
| 22 | 181.0 |
| 23 | 428.7 |
| 24 | 338.8 |
| 25 | 353.2 |
| 26 | 413.0 |
| 27 | 450.7 |

TABLE 22-continued

| Ex. No. | TACK EC$_{50}$ (nM) |
|---|---|
| 28 | 208.4 |
| 29 | 312.0 |
| 30 | 205.7 |
| 31 | 396.8 |
| 32 | 170.8 |
| 33 | 208.1 |
| 34 | 474.0 |
| 35 | 350.8 |
| 36 | 72.3 |
| 37 | 114.1 |
| 38 | 480.6 |
| 39 | 265.1 |
| 40 | 198.4 |
| 41 | 363.1 |
| 42 | 307.8 |
| 43 | 437.7 |
| 44 | 333.3 |
| 45 | 257.2 |
| 46 | 303.3 |
| 47 | 393.9 |
| 48 | 341.8 |
| 49 | 277.8 |
| 50 | 249.6 |
| 51 | 394.8 |
| 52 | 456.0 |
| 53 | 391.5 |
| 54 | 212.9 |
| 55 | 276.0 |
| 56 | 161.4 |
| 57 | 493.3 |
| 58 | 252.1 |
| 59 | 134.6 |
| 60 | 227.9 |
| 61 | 485.2 |
| 62 | 406.3 |
| 63 | 276.5 |
| 64 | 162.0 |
| 65 | 382.3 |
| 66 | 262.5 |
| 67 | 174.4 |
| 68 | 477.9 |
| 69 | 340.5 |
| 70 | 202.6 |
| 71 | 148.6 |
| 72 | 377.2 |
| 73 | 450.0 |
| 74 | 483.8 |
| 75 | 208.6 |
| 76 | 498.0 |
| 77 | 409.4 |
| 78 | 155.9 |
| 79 | 459.8 |
| 80 | 340.0 |
| 81 | 156.3 |
| 82 | 530.9 |
| 83 | 251.8 |
| 84 | 291.0 |
| 85 | 440.7 |
| 86 | 472.8 |
| 87 | 217.5 |
| 88 | 397.1 |
| 89 | 433.7 |
| 90 | 489.1 |
| 91 | 325.3 |
| 92 | 283.6 |
| 93 | 172.0 |
| 94 | 491.9 |
| 95 | 179.2 |
| 96 | 366.6 |
| 97 | 182.4 |
| 98 | 183.0 |

What is claimed is:

1. A compound which is:
5-(difluoromethyl)-2-methyl-3((1-((2-methyl-6-oxo-1,6-dihydropyrimidin-5-yl)methyl)-6-oxo-4-(perfluoroethyl)-1,6-dihydropyrimidin-5-yl)oxy)benzonitrile;
or a pharmaceutically acceptable salt thereof.

2. The compound of claim 1 that is

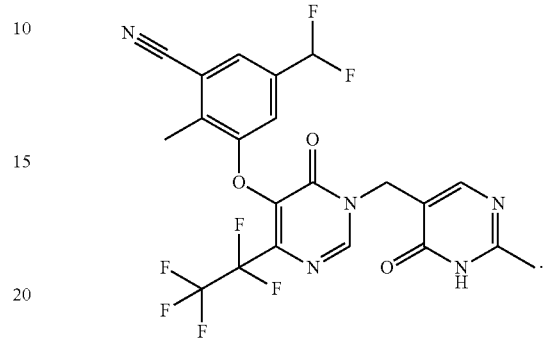

3. A pharmaceutical composition comprising an effective amount of the compound of claim 1, or a pharmaceutically acceptable salt thereof, and a pharmaceutically acceptable carrier.

4. The pharmaceutical composition of claim 3 further comprising an effective amount of one or more additional nucleoside or nucleotide HIV reverse transcriptase inhibitors, nucleoside or nucleotide reverse transcriptase translocation inhibitors, non-nucleoside HIV reverse transcriptase inhibitors, HIV integrase inhibitors, HIV fusion inhibitors, HIV entry inhibitors, HIV maturation inhibitors and post-attachment inhibitors.

5. A method for the treatment or prophylaxis of infection by HIV, or for the treatment, prophylaxis or delay in the onset or progression of AIDS or ARC in a human subject in need thereof which comprises administering to the human subject an effective amount of the compound of claim 1, or a pharmaceutically acceptable salt thereof.

6. A method for eliciting GAG-POL dimerization in HIV-infected cells in a human subject in need thereof which comprises administering to the human subject an effective amount of the compound of claim 1, or a pharmaceutically acceptable salt thereof.

7. A method for selectively killing HIV infected GAG-POL expressing cells without concomitant cytotoxicity to HIV naïve cells in a human subject which comprises administering to the human subject an effective amount of the compound of claim 1, or a pharmaceutically acceptable salt thereof.

8. The method of claim 5 further comprising administering to the human subject an effective amount of one or more additional compatible HIV antiviral agent selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors and post-attachment inhibitors.

9. A method for augmenting the suppression of HIV viremia in a human subject whose viremia is being suppressed by administration of one or more compatible HIV antiviral agents, which comprises additionally administering to the human subject an effective amount of the compound of claim 1, or a pharmaceutically acceptable salt thereof.

* * * * *